United States Patent
Bavetsias et al.

(10) Patent No.: US 9,371,319 B2
(45) Date of Patent: Jun. 21, 2016

(54) PYRROLOPYRIDINEAMINO DERIVATIVES AS MPS1 INHIBITORS

(75) Inventors: Vassilios Bavetsias, Sutton (GB); Butrus Atrash, Sutton (GB); Sebastien Gaston Andre Naud, Sutton (GB); Peter William Sheldrake, Sutton (GB); Julian Blagg, Sutton (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 313 days.

(21) Appl. No.: 14/004,515

(22) PCT Filed: Mar. 14, 2012

(86) PCT No.: PCT/GB2012/050564
§ 371 (c)(1),
(2), (4) Date: Sep. 11, 2013

(87) PCT Pub. No.: WO2012/123745
PCT Pub. Date: Sep. 20, 2012

(65) Prior Publication Data
US 2013/0345181 A1    Dec. 26, 2013

(30) Foreign Application Priority Data
Mar. 14, 2011 (GB) .................................. 1104267.8

(51) Int. Cl.
*C07D 471/04* (2006.01)
(52) U.S. Cl.
CPC .................................. *C07D 471/04* (2013.01)
(58) Field of Classification Search
None
See application file for complete search history.

(56) References Cited

U.S. PATENT DOCUMENTS

| | | | |
|---|---|---|---|
| 2,697,710 A | 12/1954 | Hitchings et al. | |
| 3,021,332 A | 2/1962 | Hitchings et al. | |
| 2003/0073668 A1 | 4/2003 | Booth et al. | |
| 2003/0105115 A1 | 6/2003 | Metcalf et al. | |
| 2004/0092521 A1 | 5/2004 | Altenbach et al. | |
| 2005/0256118 A1 | 11/2005 | Altenbach et al. | |
| 2005/0272728 A1 | 12/2005 | Altenbach et al. | |
| 2011/0212975 A1 | 9/2011 | Kao et al. | |
| 2011/0257196 A1 | 10/2011 | Lu et al. | |
| 2015/0031672 A1 | 1/2015 | Ren et al. | |

FOREIGN PATENT DOCUMENTS

| | | | |
|---|---|---|---|
| JP | 2009-051827 A | 3/2009 | |
| WO | WO 96/15128 A2 | 5/1996 | |
| WO | WO 00/25780 A1 | 5/2000 | |
| WO | WO 00/68203 A1 | 11/2000 | |
| WO | WO 01/19788 A2 | 3/2001 | |
| WO | WO 01/55147 A1 | 8/2001 | |
| WO | WO 01/64642 A1 | 9/2001 | |
| WO | WO 01/64643 A2 | 9/2001 | |
| WO | WO 02/00647 A1 | 1/2002 | |
| WO | WO 02/090360 A1 | 11/2002 | |
| WO | WO 03/007955 A2 | 1/2003 | |
| WO | WO 03/074530 A1 | 9/2003 | |
| WO | WO 2004/007472 A1 | 1/2004 | |
| WO | WO 2004/043458 A1 | 5/2004 | |
| WO | WO 2004/065378 A1 | 8/2004 | |
| WO | WO 2004/085385 A2 | 10/2004 | |
| WO | WO 2006/001463 A1 | 1/2006 | |
| WO | WO 2007/000240 A1 | 1/2007 | |
| WO | WO 2007/011759 A2 | 1/2007 | |
| WO | WO 2007/088996 A1 | 8/2007 | |
| WO | WO 2007/088999 A1 | 8/2007 | |
| WO | WO 2007/125405 A2 | 11/2007 | |
| WO | WO 2007/140222 A2 | 12/2007 | |
| WO | WO 2008/073670 A2 | 6/2008 | |
| WO | WO 2008/135232 | 11/2008 | |

(Continued)

OTHER PUBLICATIONS

PCT/GB2012/050564 International Search Report and Written Opinion Dated Jun. 28, 2012.

(Continued)

*Primary Examiner* — Timothy R Rozof
(74) *Attorney, Agent, or Firm* — Wilson Sonsini Goodrich & Rosati

(57) ABSTRACT

The present invention relates to the use of certain pyrrolopyridineamino derivatives (hereinafter referred to as "PPA derivatives"), particularly 1H-pyrrolo[3,2-c]pyridine-6-amino derivatives, to inhibit the spindle checkpoint function of Monospindle 1 (Mps1—also known as TTK) kinases either directly or indirectly via interaction with the Mps kinase itself. In particular, the present invention relates to PPA derivatives for use as therapeutic agents for the treatment and/or prevention of proliferative diseases, such as cancer. The present invention also relates to processes for the preparation of the PPA derivatives, and pharmaceutical compositions comprising them. Formula (I)

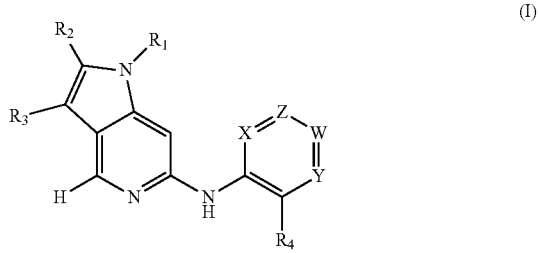

(I)

18 Claims, No Drawings

(56) References Cited

FOREIGN PATENT DOCUMENTS

| | | |
|---|---|---|
| WO | WO 2008/135232 A1 | 11/2008 |
| WO | WO 2009/010455 A2 | 1/2009 |
| WO | WO 2009/010871 A2 | 1/2009 |
| WO | WO 2009/026717 A1 | 3/2009 |
| WO | WO 2009/032694 A1 | 3/2009 |
| WO | WO 2009/076618 A2 | 6/2009 |
| WO | WO 2009/103966 A1 | 8/2009 |
| WO | WO 2010/048149 A2 | 4/2010 |
| WO | WO 2010/080537 A1 | 7/2010 |
| WO | WO 2010/129816 A2 | 11/2010 |
| WO | WO 2011/015037 A1 | 2/2011 |
| WO | WO 2011/159297 A1 | 12/2011 |
| WO | WO 2012/028756 A1 | 3/2012 |
| WO | WO 2012/064973 A2 | 5/2012 |
| WO | WO 2012/079032 A2 | 6/2012 |
| WO | WO 2012/080284 A2 | 6/2012 |
| WO | WO 2012/080729 A2 | 6/2012 |
| WO | WO 2012/088438 A1 | 6/2012 |
| WO | WO 2012/092471 A1 | 7/2012 |
| WO | WO 2012/123745 A1 | 9/2012 |
| WO | WO 2014/037750 A1 | 3/2014 |

OTHER PUBLICATIONS

Balog et al., "Novel fluorescent isoquinoline derivatives obtained via Buchwald-Hartwig coupling of isoquinolin-3-amines", Arkivoc, vol. 5, 109-119 (2012).

Bathini et al., "2-Aminoquinazoline inhibitors of cyclin-dependent kinases", Bioorg. Med. Chem. Lett. vol. 15(17), 3881-3885 (Jun. 29, 2005).

Cabarello et al., "2D Autocorrelation, CoMFA, and CoMSIA modeling of protein tyrosine kinases' inhibition by substituted pyrido[2,3-d]pyrimidine derivatives", Bioorg. Med. Chem., vol. 16(2), 810-821 (Oct. 13, 2007).

Database PubChem Compounds [Online] Dec. 1, 2012, XP002714058, Database accession No. CID 70113665, abstract.
Database PubChem Compounds [Online] Jul. 13, 2005, XP002714054, Database accession No. CID 2000835, abstract.
Database PubChem Compounds [Online] Jul. 13, 2005, XP002714055, Database accession No. CID 2004801, abstract.
Database PubChem Compounds [Online] Jul. 13, 2005, XP002714056, Database accession No. CID 2019230, abstract.
Database PubChem Compounds [Online] Jul. 9, 2005, XP002714051, Database accession No. CID 940974, abstract.
Database PubChem Compounds [Online] Jul. 9, 2005, XP002714052, Database accession No. CID 945107, abstract.
Database PubChem Compounds [Online] Jul. 9, 2005, XP002714053, Database accession No. CID 945815, abstract.
Database PubChem Compounds [Online] NCBI; Dec. 1, 2012, XP002714059, Database accession No. CID 69975764, abstract.
Database PubChem Compounds [Online] NCBI; Sep. 13, 2005, XP002714057, Database accession No. CID 4000352, abstract.
Database Registry [Online] Chemical Abstracts Service, Columbus, Ohio, US; Jan. 19, 2004, XP002714050, Database accession No. 639005-15-5, abstract.

Lainchbury et al., "Discovery of 3-Alkoxyamino-5-(pyridin-2-ylamino)pyrazine-2-carbonitriles as Selective, Orally Bioavailable CHK1 Inhibitors", J. Med. Chem., vol. 55(22), 10229-10240 (Oct. 19, 2012).

Ranjitkar et al., "Affinity-Based Probes Based on Type II Kinase Inhibitors", J. Am. Chem. Soc. vol. 134(46), 19017-19025 (Nov. 21, 2012).

Thompson et al., "Synthesis and Structure—Activity Relationships of 7-Substituted 3-(2,6-Dichlorophenyl)-1,6-naphthyridin-2(1$H$)-ones as Selective Inhibitors of pp60$^{c\text{-}src}$", J. Med. Chem., vol. 43(16), 3134-3147 (Jul. 13, 2000).

Trumpp-Kallmeyer et al., "Development of a Binding Model to Protein Tyrosine Kinases for Substituted Pyrido[2,3-d]pyrimidine Inhibitors", J. Med. Chem., vol. 41(11), 1752-1763 (Apr. 28, 1998).

Walton et al., "The Preclinical Pharmacology and Therapeutic Activity of the Novel CHK1 Inhibitor SAR-020106", Mol. Cancer Ther., vol. 9, No. 1, 89-100 (Jan. 12, 2010).

PYRROLOPYRIDINEAMINO DERIVATIVES AS MPS1 INHIBITORS

RELATED APPLICATIONS

This application is the National Stage Entry of PCT/GB2012/050564 filed on Mar. 14, 2012, which claims priority to GB Application No. 1104267.8 filed on Mar. 14, 2011, both of which are incorporated herein by reference in their entireties.

INTRODUCTION

The present invention relates to the use of certain pyrrolopyridineamino derivatives (hereinafter referred to as "PPA derivatives"), particularly pyrrolo[3,2-c]pyridine-6-amino derivatives, to inhibit the spindle checkpoint function of monopolar spindle 1 (Mps1—also known as TTK) kinases either directly or indirectly via interaction with the Mps1 kinase itself. In particular, the present invention relates to PPA derivatives for use as therapeutic agents for the treatment and/or prevention of proliferative diseases, such as cancer. The present invention also relates to processes for the preparation of these PPA derivatives, and to pharmaceutical compositions comprising them.

BACKGROUND OF THE INVENTION

Cancer is caused by uncontrolled and unregulated cellular proliferation. Precisely what causes a cell to become malignant and proliferate in an uncontrolled and unregulated manner has been the focus of intense research over recent decades. This research has led to the targeting of surveillance mechanisms, such as those responsible for regulating the cell cycle, with anticancer agents. For example, published patent application WO 2009/103966 (CANCER RESEARCH TECHNOLOGY LIMITED) relates to the inhibition of checkpoint kinase 1 (CHK1) kinase function, with bicyclylaryl-arylamine compounds, in the treatment of cancer.

The main role of the cell cycle is to enable error-free DNA replication, chromosome segregation and cytokinesis. Surveillance mechanisms, the so-called checkpoint pathways, monitor passage through mitosis at several stages. One of the best characterised is the spindle assembly checkpoint that prevents anaphase onset until the appropriate tension and attachment across kinetochores is achieved (HARDWICK KG, 1998, "The spindle checkpoint", *Trends Genet* 14, 1-4). The majority of proteins involved in the checkpoint exert their functions through protein binding interactions with the involvement of only a small number of kinases (MUSACCHIO A et al, 2007, "The spindle-assembly checkpoint in space and time", *Nature Reviews, Molecular and Cell Biology*, 8, 379-393). A mitotic checkpoint complex (MCC) that contains three checkpoint proteins (Mad2, BubR1/Mad3, Bub3) and the APC/C co-factor, CDC20, concentrates at the kinetochores and acts as a spindle checkpoint effector. Other core proteins required to amplify the checkpoint signal include Mad1 and the kinases Bub1, Mps1 (also known as TTK) and Aurora-B (MUSACCHIO, referenced above).

One of the first components of the spindle assembly checkpoint signal, identified by a genetic screen in budding yeast, was dubbed Mps1 (monopolar spindle 1) for the monopolar spindles produced by Mps1 mutant cells (WEISS E, 1996, "The *Saccharomyces cerevisiae* spindle pole body duplication gene MPS1 is part of a mitotic checkpoint", *J Cell Biol* 132, 111-123), however, it still remains one of the least studied checkpoint components in higher eukaryotes. Subsequently, the Mps1 gene was shown to encode an essential dual-specificity kinase (LAUZE et al, 1995, "Yeast spindle pole body duplication gene MPS1 encodes an essential dual specificity protein kinase", *EMBO J* 14, 1655-1663 and also POCH et al, 1994, "RPK1, an essential yeast protein kinase involved in the regulation of the onset of mitosis, shows homology to mammalian dual-specificity kinases", *Mol Gen Genet* 243, 641-653) conserved from yeast to humans (MILLS et al, 1992, "Expression of TTK, a novel human protein kinase, is associated with cell proliferation", *J Biol Chem* 267, 16000-16006). Mps1 activity peaks at the $G_2$/M transition and is enhanced upon activation of the spindle checkpoint with nocodazole (STUCKE et al, 2002, "Human Mps1 kinase is required for the spindle assembly checkpoint but not for centrosome duplication", *EMBO J* 21, 1723-1732 and also LIU et al, 2003, "Human MPS1 kinase is required for mitotic arrest induced by the loss of CENP-E from kinetochores", *Mol Biol Cell* 14, 1638-1651). The autophosphorylation of Mps1 at Thr676 in the activation loop has been identified and is essential for Mps1 function (MATTISON et al, 2007, "Mps1 activation loop autophosphorylation enhances kinase activity", *J Biol Chem* 282, 30553-30561).

Given the importance of Mps1 in spindle checkpoint activation, the development of Mps1 inhibitors would be an asset, not only as a tool to further investigate its cell cycle-related functions, but also as a form of anticancer treatment. The first generation inhibitors of Mps1 have been described. Cincreasin, caused chromosome mis-segregation and death in yeast cells (DORER et al, 2005, "A small-molecule inhibitor of Mps1 blocks the spindle-checkpoint response to a lack of tension on mitotic chromosomes", *Curr Biol* 15, 1070-1076) and SP600125, a JNK (c-Jun amino-terminal kinase) inhibitor, also disrupts spindle checkpoint function in a JNK-independent manner via the inhibition of Mps1 (SCHMIDT et al, 2005, "Ablation of the spindle assembly checkpoint by a compound targeting Mps1", *EMBO Rep* 6, 866-872). Recently, three small molecule inhibitors of Mps1 were identified (KWIATOWSKI et al, 2010, "Small-molecule kinase inhibitors provide insight into Mps1 cell cycle function", *Nat Chem Biol* 6, 359-368; HEWITT et al, 2010, "Sustained Mps1 activity is required in mitosis to recruit O-Mad2 to the Mad1-C-Mad2 core complex", *J Cell Biol* 190, 25-34; and SANTAGUIDA et al, 2010, "Dissecting the role of MPS1 in chromosome biorientation and the spindle checkpoint through the small molecule inhibitor reversine", *J Cell Biol* 190, 73-87). Chemical inhibition of Mps1 induced premature mitotic exit, gross aneuploidy and death to human cancer cell lines (KWIATOWSKI above). Mps1 inhibitors AZ3146 and reversine, severely impaired recruitment of Mad1, Mad2 and CENP-E to kinetochores (HEWITT, and SANTAGUIDA above).

Dysregulation of the mitotic checkpoint is recognised as a feature of the malignant transformation process. Mitotic checkpoint dysfunction in tumors provides an opportunity for developing a therapeutic strategy using small molecules. This is based on the proposition that pharmacologic disruption of an already compromised mitotic checkpoint may selectively sensitize tumors. This observation has led to the hypothesis that inhibition of Mps1 may be of therapeutic benefit.

SUMMARY OF THE INVENTION

In one aspect, the present invention provides a compound, or a pharmaceutically acceptable salt or solvate thereof, or a pharmaceutical composition as defined herein.

In one aspect, the present invention provides a compound, or a pharmaceutically acceptable salt or solvate thereof, or a pharmaceutical composition as defined herein, for use in the treatment of a proliferative condition.

In another aspect, the present invention provides a compound, or a pharmaceutically acceptable salt or solvate thereof, or a pharmaceutical composition as defined herein, for use in the treatment of cancer. In a particular embodiment, the cancer is a human cancer.

In another aspect, the present invention provides a compound, or a pharmaceutically acceptable salt or solvate thereof, or a pharmaceutical composition as defined herein, for use in the production of a Mps1 kinase inhibitory effect.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of an Mps1 kinase inhibitory effect.

In another aspect, the present invention provides a method of inhibiting Mps1 kinase in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound, or a pharmaceutically acceptable salt or solvate thereof, or a pharmaceutical composition as defined herein.

In another aspect, the present invention provides a compound, or a pharmaceutically acceptable salt or solvate thereof, or a pharmaceutical composition as defined herein for use in therapy.

In another aspect, the present invention provides a pharmaceutical composition comprising a compound, or a pharmaceutically acceptable salt or solvate thereof, as defined herein, in admixture with a pharmaceutically acceptable diluent or carrier.

The present invention further provides a method of synthesising a compound, or a pharmaceutically acceptable salt or solvate thereof, as defined herein.

In another aspect, the present invention provides a compound, or a pharmaceutically acceptable salt or solvate thereof, obtainable by, or obtained by, or directly obtained by a method of synthesis as defined herein.

In another aspect, the present invention provides novel intermediates as defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C) alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1] heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" refers to fluoro, chloro, bromo and iodo.

The term "fluoroalkyl" is used herein to refer to an alkyl group in which one or more hydrogen atoms have been replaced by fluorine atoms. Examples of fluoroalkyl groups include —$CHF_2$, —$CH_2CF_3$, or perfluoroalkyl groups such as —$CF_3$ or —$CF_2CF_3$.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzothienyl, dihydrobenzofuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
  a) a benzene ring fused to a 5- or 6-membered ring containing 1, 2 or 3 ring heteroatoms;
  b) a pyridine ring fused to a 5- or 6-membered ring containing 1, 2 or 3 ring heteroatoms;
  c) a pyrimidine ring fused to a 5- or 6-membered ring containing 1 or 2 ring heteroatoms;
  d) a pyrrole ring fused to a 5- or 6-membered ring containing 1, 2 or 3 ring heteroatoms;
  e) a pyrazole ring fused to a 5- or 6-membered ring containing 1 or 2 ring heteroatoms;

f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered heteroaromatic ring containing 1, 2 or 3 ring heteroatoms; and
o) a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like This specification also makes use of several composite terms to describe groups comprising more than one functionality. Such terms will be understood by a person skilled in the art. For example heterocyclyl(m-nC)alkyl comprises (m-nC) alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Pyrrolopyridineamino (PPA) Derivatives
(i) Pyrrolopyridineamino (PPA) Derivatives for Use in the Treatment of Diseases and/or Conditions in which Mps1 Kinase Activity is Implicated (e.g. Proliferative Conditions)

The present invention provides compounds useful for the treatment of diseases and/or conditions in which Mps1 kinase activity is implicated.

In one aspect, the present invention provides a compound of formula I shown below for use in the treatment of a proliferative condition (such as cancer):

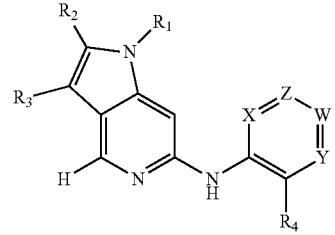

Formula I wherein:
R$_1$ is hydrogen, (1-5C)alkyl, (1-5C)fluoroalkyl, (3-8C)cycloalkyl, (3-8C)cycloalkyl-(1-4C)alkyl, aryl, aryl-(1-4C)alkyl, heteroaryl, heteroaryl-(1-4C)alkyl, —S(O)$_2$—R$^a$, —C(O)—R$^a$, or —C(O)—O—R$^a$, wherein R$^a$ is (1-5C)alkyl, (3-8C)cycloalkyl, (3-8C)cycloalkyl-(1-4C)alkyl, aryl, aryl-(1-4C)alkyl, heteroaryl or heteroaryl-(1-4C)alkyl, and wherein any (1-5C)alkyl, (3-8C)cycloalkyl, (3-8C)cycloalkyl-(1-4C)alkyl, aryl, aryl-(1-4C)alkyl, heteroaryl, heteroaryl-(1-4C)alkyl group present in a R$_1$ substituent group is optionally substituted by methyl, trifluoromethyl, methoxy, trifluoromethoxy, halo, cyano, nitro, hydroxy, mercapto, amino, carboxy, carbamoyl, or sulphamoyl;

R$_2$ is an aryl, aryl(1-2C)alkyl, 5- or 6-membered heteroaryl or a 5- or 6-membered heteroaryl(1-2C)alkyl,
wherein R$_2$ is optionally substituted by one or more substituents selected from halogeno, trifluoromethyl, trifluoromethoxy, cyano, nitro, hydroxy, mercapto, amino, carboxy, carbamoyl, sulphamoyl,
or a group of the formula:

L-L$^0$-R$^b$ wherein
L is absent or a linker group of the formula —[CR$_g$R$_h$]$_n$— in which n is an integer selected from 1, 2, 3 or 4, and R$_g$ and R$_h$ are each independently selected from hydrogen or (1-2C)alkyl;
L$^0$ is absent or is selected from O, S, SO, SO$_2$, N(R$^c$), C(O), C(O)O, OC(O), CH(OR$^c$), C(O)N(R$^c$), N(R$^c$)C(O), N(R$^c$)C(O)N(R$^d$), SO$_2$N(R$^c$), or N(R$^c$) SO$_2$, wherein R$^c$ and R$^d$ are each independently selected from hydrogen or (1-2C)alkyl; and
R$^b$ is (1-4C)alkyl, aryl, aryl-(1-4C)alkyl, (3-6C)cycloalkyl, (3-6C)cycloalkyl-(1-4C)alkyl, heteroaryl, heteroaryl-(1-4C)alkyl, heterocyclyl, or heterocyclyl-(1-4C)alkyl;
and wherein R$^b$ is optionally further substituted by one or more substituents independently selected from oxo, halogeno, cyano, nitro, hydroxy, NR$^e$R$^f$, (1-5C)alkyl, (1-5C)alkoxy, (1-5C)alkanoyl, (1-5C) sulphonyl or aryl; and wherein R$^e$ and R$^f$ are each independently selected from hydrogen or (1-4C) alkyl or (3-6C)cycloalkyl-(1-4C)alkyl; or R$^e$ and R$^f$ can be linked such that, together with the nitrogen atom to which they are attached, they form a 4-7 membered heterocyclic, heteroaryl or carbocyclic ring;

$R_3$ is H, (1-3C)alkyl, halogeno or $CF_3$;

$R_4$ is H, cyano, (1-3C)alkyl, (1-3C)fluoroalkyl, (1-3C)alkoxy, (1-3C)perfluoroalkoxy, halo, (1-3C)alkanoyl, $C(O)NR^iR^j$, or $S(O)_2NR^iR^j$; wherein $R^i$ and $R^j$ are each independently selected from H or (1-3C)alkyl;

X is CH or $CR_5$;

W, Y and Z are each independently selected from N, CH, or $CR_5$;

$R_5$ is halogeno, trifluoromethyl, trifluoromethoxy, cyano, nitro, hydroxy, mercapto, amino, carboxy, carbamoyl, sulphamoyl, ureido, (1-6C)alkyl, (2-6C)alkenyl, (2-6C)alkynyl, or $R_5$ is a group of the formula:

-L¹-L²-R₇ wherein
$L^1$ is absent or a linker group of the formula —$[CR_8R_9]_n$— in which n is an integer selected from 1, 2, 3 or 4, and $R_8$ and $R_9$ are each independently selected from hydrogen or (1-2C)alkyl;

$L^2$ is absent or is selected from O, S, SO, $SO_2$, $N(R_{10})$, C(O), C(O)O, OC(O), $CH(OR_{10})$, $C(O)N(R_{10})$, $N(R_{10})C(O)$, $N(R_{10})C(O)N(R_{11})$, $S(O)_2N(R_{10})$, or $N(R_{13})SO_2$, wherein $R_{10}$ and $R_{11}$ are each independently selected from hydrogen or (1-2C)alkyl; and $R_7$ is (1-6C)alkyl, aryl, aryl-(1-6C)alkyl, (3-6C)cycloalkyl, (3-6C)cycloalkyl-(1-6C)alkyl, heteroaryl, heteroaryl-(1-6C)alkyl, heterocyclyl, heterocyclyl-(1-6C)alkyl, and wherein $R_7$ is optionally further substituted by one or more substituents independently selected from hydrogen, oxo, halogeno, cyano, nitro, hydroxy, $NR_{12}R_{13}$, (1-4C)alkoxy, (1-5C)alkyl, (3-8C)cycloalkyl, (3-8C)cycloalkyl-(1-5C)alkyl, aryl, aryl-(1-5C)alkyl, (1-5C)alkanoyl, (1-5C)alkylsulphonyl, heterocyclyl, heterocyclyl-(1-5C)alkyl, heteroaryl, heteroaryl-(1-5C)alkyl, $CONR_{12}R_{13}$ and $SO_2NR_{12}R_{13}$;

$R_{12}$ and $R_{13}$ are each independently selected from hydrogen or (1-2C)alkyl; or $R_{12}$ and $R_{13}$ can be linked such that, together with the nitrogen atom to which they are attached, they form a 4-7 membered heterocyclic or heteroaryl ring;

or either W and Z, W and Y or Z and X are both $CR_5$ and the $R_5$ groups on the adjacent carbon atoms are linked such that, together with the carbon atoms to which they are attached, they form a fused 4-7 membered heterocyclic, heteroaryl or carbocyclic ring;

or a pharmaceutically acceptable salt or solvate thereof.

In another aspect, the present invention provides a compound of formula I for use in the treatment of a proliferative condition (such as cancer);

wherein:
$R_1$ is hydrogen, (1-5C)alkyl, (1-5C)fluoroalkyl, (3-8C)cycloalkyl, (3-8C)cycloalkyl-(1-4C)alkyl, aryl-(1-4C)alkyl, heteroaryl-(1-4C)alkyl, —$S(O)_2$—$R^a$, —C(O)—$R^a$, or —C(O)—O—$R^a$, wherein $R^a$ is (1-5C)alkyl, aryl, or heteroaryl;

$R_2$ is an aryl or a 5- or 6-membered heteroaryl,
wherein $R_2$ is optionally substituted by one or more substituents selected from halogeno, fluoroalkyl, trifluoromethoxy, cyano, nitro, hydroxy, mercapto, amino, carboxy, carbamoyl, or sulphamoyl, or $R_2$ is substituted by a group of the formula:

L-L⁰-R^b wherein
L is absent or a linker group of the formula —$[CR_gR_h]_n$— in which n is an integer selected from 1, 2, 3 or 4, and $R_g$ and $R_h$ are each independently selected from hydrogen or (1-2C)alkyl;

$L^0$ is absent or is selected from O, S, SO, $SO_2$, $N(R^c)$, C(O), C(O)O, OC(O), $CH(OR^c)$, $C(O)N(R^c)$, $N(R^c)C(O)$, $N(R^c)C(O)N(R^d)$, $SO_2N(R^c)$, or $N(R^c)SO_2$, wherein $R^c$ and $R^d$ are each independently selected from hydrogen or (1-2C)alkyl; and $R^b$ is (1-4C)alkyl, aryl, aryl-(1-4C)alkyl, (3-6C)cycloalkyl, (3-6C)cycloalkyl-(1-4C)alkyl, heteroaryl, heteroaryl-(1-4C)alkyl, heterocyclyl, or heterocyclyl-(1-4C)alkyl;

and wherein $R^b$ is optionally further substituted by one or more substituents independently selected from oxo, halogeno, cyano, nitro, hydroxy, $NR^eR^f$, (1-5C)alkyl, (1-5C)alkoxy, (1-5C)alkanoyl, (1-5C)sulphonyl or aryl; and wherein $R^e$ and $R^f$ are each independently selected from hydrogen or (1-4C)alkyl or (3-6C)cycloalkyl-(1-4C)alkyl; or $R^e$ and $R^f$ can be linked such that, together with the nitrogen atom to which they are attached, they form a 4-7 membered heterocyclic, heteroaryl or carbocyclic ring;

$R_3$ is H, (1-3C)alkyl, halogeno, or $CF_3$;

$R_4$ is H, cyano, (1-3C)alkyl, (1-3C)fluoroalkyl, (1-3C)alkoxy, (1-3C)perfluoroalkoxy, halo, $C(O)NR^iR^j$, or $S(O)_2NR^iR^j$; wherein $R^i$ and $R^j$ are each independently selected from H or (1-3C)alkyl;

W, X, Y and Z are each independently selected from N, CH, or $CR_5$;

$R_5$ is hydrogen, halogeno, trifluoromethyl, trifluoromethoxy, cyano, nitro, hydroxy, mercapto, amino, carboxy, carbamoyl, sulphamoyl, ureido, (1-6C)alkyl, (2-6C)alkenyl, (2-6C)alkynyl, or $R_5$ is a group of the formula:

-L¹-L²-R₇ wherein
$L^1$ is absent or a linker group of the formula —$[CR_8R_9]_n$— in which n is an integer selected from 1, 2, 3 or 4, and $R_8$ and $R_9$ are each independently selected from hydrogen or (1-2C)alkyl;

$L^2$ is absent or is selected from O, S, SO, $SO_2$, $N(R_{10})$, C(O), C(O)O, OC(O), $CH(OR_{10})$, $C(O)N(R_{10})$, $N(R_{10})C(O)$, $N(R_{10})C(O)N(R_{11})$, $S(O)_2N(R_{10})$, or $N(R_{13})SO_2$, wherein $R_{10}$ and $R_{11}$ are each independently selected from hydrogen or (1-2C)alkyl; and $R_7$ is (1-6C)alkyl, aryl, aryl-(1-6C)alkyl, (3-6C)cycloalkyl, (3-6C)cycloalkyl-(1-6C)alkyl, heteroaryl, heteroaryl-(1-6C)alkyl, heterocyclyl, heterocyclyl-(1-6C)alkyl, and wherein $R_7$ is optionally further substituted by one or more substituents independently selected from hydrogen, oxo, halogeno, cyano, nitro, hydroxy, $NR_{12}R_{13}$, (1-4C)alkoxy, (1-5C)alkyl, (3-8C)cycloalkyl, (3-8C)cycloalkyl-(1-5C)alkyl, aryl, aryl-(1-5C)alkyl, (1-5C)alkanoyl, (1-5C)alkylsulphonyl, heterocyclyl, heterocyclyl-(1-5C)alkyl, heteroaryl, heteroaryl-(1-5C)alkyl, $CONR_{12}R_{13}$ and $SO_2NR_{12}R_{13}$;

$R_{12}$ and $R_{13}$ are each independently selected from hydrogen or (1-2C)alkyl; or $R_{12}$ and $R_{13}$ can be linked such that, together with the nitrogen atom to which they are attached, they form a 4-7 membered heterocyclic or heteroaryl ring;

or either W and Z, W and Y or Z and X are both CR$_5$ and the R$_5$ groups on the adjacent carbon atoms are linked such that, together with the carbon atoms to which they are attached, they form a fused 4-7 membered heterocyclic, heteroaryl or carbocyclic ring;
or a pharmaceutically acceptable salt or solvate thereof.

Particular compounds of the invention include, for example, compounds of the formula I, or pharmaceutically acceptable salts thereof, wherein, unless otherwise stated, each of R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, W, X, Y, Z, L$^1$ or L$^2$ has any of the meanings defined hereinbefore or in any of paragraphs (1) to (70) hereinafter:—

(1) R$_1$ is hydrogen, (1-5C)alkyl, (1-5C)fluoroalkyl, (3-8C)cycloalkyl, (3-8C)cycloalkyl-(1-4C)alkyl, aryl, aryl-(1-4C)alkyl, heteroaryl, heteroaryl-(1-4C)alkyl, —S(O)$_2$—R$^a$, —C(O)—R$^a$, or —C(O)—O—R$^a$, wherein R$^a$ is (1-5C)alkyl, (3-8C)cycloalkyl, (3-8C)cycloalkyl-(1-2C)alkyl, aryl, aryl-(1-2C)alkyl, heteroaryl or heteroaryl-(1-2C)alkyl, and wherein any (1-5C)alkyl, (3-8C)cycloalkyl, (3-8C)cycloalkyl-(1-4C)alkyl, aryl, aryl-(1-4C)alkyl, heteroaryl, heteroaryl-(1-4C)alkyl group present in a R$_1$ substituent group is optionally substituted by methyl, trifluoromethyl, methoxy, trifluoromethoxy, halo, cyano, hydroxy or amino;

(2) R$_1$ is hydrogen, (1-5C)alkyl, (3-8C)cycloalkyl, (3-8C)cycloalkyl-(1-2C)alkyl, aryl, aryl-(1-2C)alkyl, heteroaryl, heteroaryl-(1-2C)alkyl, —S(O)$_2$—R$^a$, —C(O)—R$^a$ or —C(O)—O—R$^a$, wherein R$^a$ is (1-5C)alkyl, (3-8C)cycloalkyl, (3-8C)cycloalkyl-(1-2C)alkyl, and wherein any (1-5C)alkyl, (3-8C)cycloalkyl, (3-8C)cycloalkyl-(1-2C)alkyl, aryl, aryl-(1-2C)alkyl, heteroaryl, heteroaryl-(1-2C)alkyl group present in a R$_1$ substituent group is optionally substituted by methyl, trifluoromethyl, methoxy, trifluoromethoxy, halo, cyano, hydroxy or amino;

(3) R$_1$ is hydrogen or —C(O)—O—R$^a$, wherein R$^a$ is (1-5C)alkyl, (3-8C)cycloalkyl, (3-8C)cycloalkyl-(1-2C)alkyl, and wherein any (1-5C)alkyl, (3-8C)cycloalkyl, (3-8C)cycloalkyl-(1-2C)alkyl group is optionally substituted by methyl, trifluoromethyl, methoxy, trifluoromethoxy, halo, cyano, hydroxy or amino;

(4) R$_1$ is hydrogen or —C(O)—O—R$^a$, wherein R$^a$ is (1-5C)alkyl, (3-6C)cycloalkyl, (3-6C)cycloalkyl-(1-2C)alkyl, and wherein any (1-5C)alkyl, (3-6C)cycloalkyl, (3-6C)cycloalkyl-(1-2C)alkyl group is optionally substituted by methyl, trifluoromethyl, methoxy, trifluoromethoxy, halo, cyano, hydroxy or amino;

(5) R$_1$ is hydrogen or —C(O)—O—R$^a$, wherein R$^a$ is (1-5C)alkyl, (3-6C)cycloalkyl, (3-6C)cycloalkyl-(1-2C)alkyl;

(6) R$_1$ is —C(O)—O—R$^a$, wherein R$^a$ is (1-5C)alkyl, (3-6C)cycloalkyl, (3-6C)cycloalkyl-(1-2C)alkyl;

(7) R$_1$ is H, (1-5C)alkyl, (1-5C)fluoroalkyl, aryl-(1-4C)alkyl, —S(O)$_2$—R$^a$, —C(O)—R$^a$ or —C(O)—O—R$^a$, wherein R$^a$ is (1-5C)alkyl;

(8) R$_1$ is H, (1-5C)alkyl, benzyl, —S(O)$_2$—R$^a$ or —C(O)—O—R$^a$, wherein R$^a$ is (1-4C)alkyl;

(9) R$^a$ is (1-5C)alkyl, (3-6C)cycloalkyl, (3-6C)cycloalkyl-(1-2C)alkyl;

(10) R$^a$ is (1-5C)alkyl or (3-6C)cycloalkyl;

(11) R$^a$ is isopropyl, tert-butyl, cyclobutyl, cyclopentyl, cyclohexyl, cyclopropylmethyl, cyclobutylmethyl, or cyclopentylmethyl;

(12) R$^a$ is isopropyl, tert-butyl or cyclobutyl;

(13) R$^a$ is methyl or tert-butyl;

(14) R$_1$ is H, methyl, benzyl, —S(O)$_2$—R$^a$ or —C(O)—O—R$^a$, wherein R$^a$ is (1-4C)alkyl;

(15) R$_1$ is H;

(16) R$_2$ is an aryl or a 5- or 6-membered heteroaryl, wherein R$_2$ is optionally substituted by one or more substituents selected from trifluoromethyl, cyano, amino, or a group of the formula:

L-L$^0$-R$^b$ wherein

L is absent or a linker group of the formula —[CR$_g$R$_h$]$_n$— in which n is 1 or 2, and R$_g$ and R$_h$ are each independently selected from hydrogen;

L$^0$ is absent or is selected from O, SO$_2$, N(R$^c$), C(O)O, C(O)N(R$^c$), or SO$_2$N(R$^c$), wherein R$^c$ is selected from hydrogen or (1-2C)alkyl; and R$^b$ is (1-4C)alkyl, heteroaryl, or heterocyclyl-(1-4C)alkyl;

and wherein R$^b$ is optionally further substituted by one or more substituents independently selected from oxo, and NR$^e$R$^f$; and wherein R$^e$ and R$^f$ can be linked such that, together with the nitrogen atom to which they are attached, they form a 4-7 membered heterocyclic ring;

(17) R$_2$ is a 5- or 6-membered heteroaryl optionally substituted by a substituent group as defined in paragraph (16) above;

(18) R$_2$ is a 5- or 6-membered heteroaryl optionally substituted by (1-4C)alkyl, (1-4C)fluoroalkyl or (1-4C)alkoxy;

(19) R$_2$ is a nitrogen-containing 5- or 6-membered heteroaryl optionally N-substituted by (1-4C)alkyl;

(20) R$_2$ is a 5- or 6-membered heteroaryl optionally substituted by methyl;

(21) R$_2$ is a nitrogen-containing 5- or 6-membered heteroaryl optionally N-substituted by methyl;

(22) R$_2$ is a 5-membered heteroaryl optionally substituted as defined hereinbefore;

(23) R$_2$ is a 5-membered heteroaryl selected from the group including the following structures:

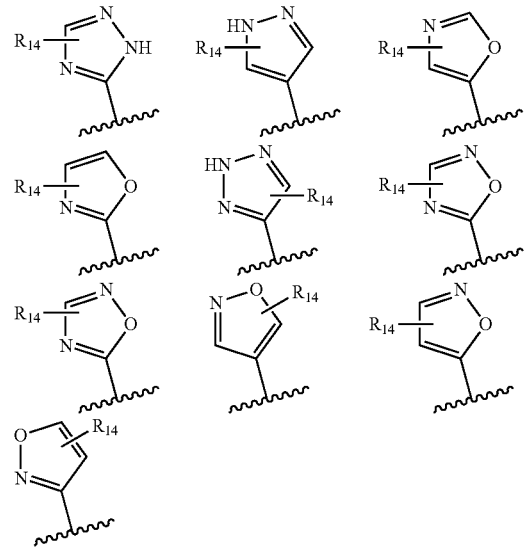

or R$_2$ is a 6-membered heteroaryl selected from any one of the following:

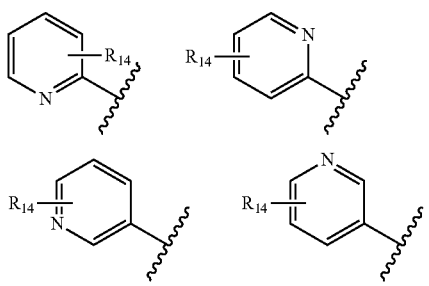

wherein R$_{14}$ is H, (1-5C)alkyl, or (1-5C)fluoroalkyl;

(24) R$_2$ is a 5-membered heteroaryl selected from the group including the following structures:

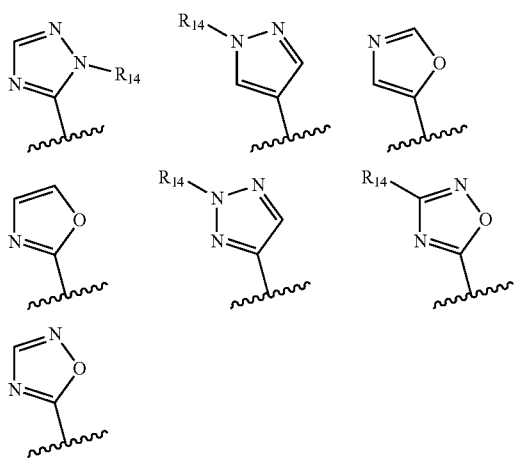

wherein R$_{14}$ is H or (1-3C)alkyl or (1-3C)fluoroalkyl;

(25) R$_2$ is a 5-membered heteroaryl selected from the group including the following structures:

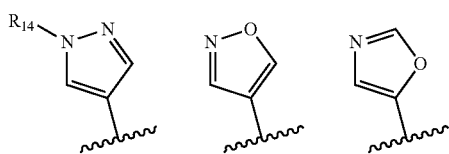

wherein R$_{14}$ is H, methyl or trifluoromethyl;

(26) R$_2$ is a 5-membered heteroaryl having the following structure:

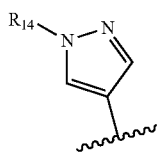

wherein R$_{14}$ is H or (1-3C)alkyl or (1-3C)fluoroalkyl;

(27) R$_2$ is a 5-membered heteroaryl having the following structure:

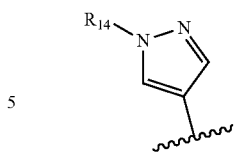

wherein R$_{14}$ is methyl;
(28) R$_{14}$ is H or CH$_3$;
(29) R$_{14}$ is CH$_3$;
(30) R$_2$ is a 6-membered heteroaryl selected from any one of the following:

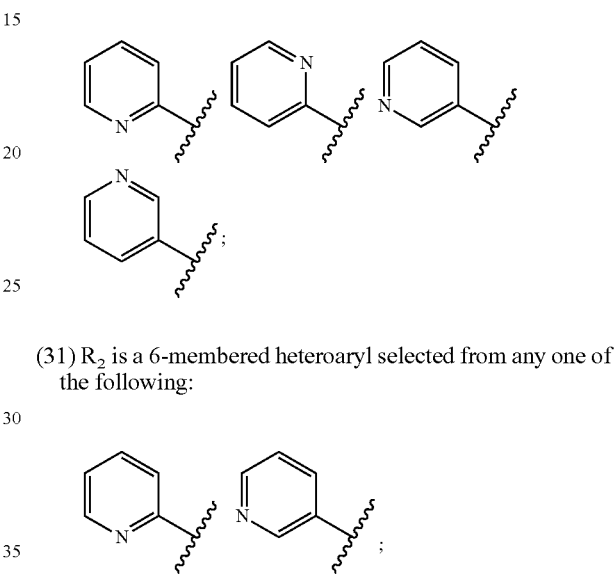

(31) R$_2$ is a 6-membered heteroaryl selected from any one of the following:

(32) R$_3$ is H or halo;
(33) R$_3$ is H or chloro;
(34) R$_3$ is H;
(35) R$_4$ is H, cyano, (1-3C)alkyl, (1-3C)perfluoroalkyl, (1-3C)alkoxy, (1-3C)perfluoroalkoxy or halo;
(36) R$_4$ is (1-3C)alkyl, CF$_3$, (1-3C)alkoxy, —OCF$_3$ or Cl;
(37) R$_4$ is OCH$_3$ or Cl;
(38) R$_4$ is CH$_3$;
(39) R$_4$ is OCH$_3$;
(40) R$_4$ is Cl;
(41) X is CH;
(42) One or two of W, Y or Z is N and the others are CH or CR$_5$;
(43) One of W, Y or Z is N and the others are CH or CR$_5$;
(44) Z is CH;
(45) One of either W or Y is CH whilst the other is N or CR$_5$;
(46) One of either W or Y is CH or N whilst the other is CR$_5$;
(47) One of either W or Y is CH whilst the other of either W or Y is CR$_5$;
(48) Both W and Y are CH;
(49) All of W, X, Y, and Z are CH;
(50) Y is N;
(51) Y is CH;
(52) W is CR$_5$ and X, Y and Z are all CH;
(53) Z is CR$_5$ and X, Y and W are all CH;
(54) Y is CR$_5$ and X, W and Z are all CH;
(55) R$_5$ is halogeno, trifluoromethyl, cyano, hydroxy, or R$_5$ is a group of formula:

-L$^1$-L$^2$-R$_7$ wherein
- L¹ is absent or a linker group of the formula —[CR$_8$R$_9$]$_n$— in which n is 1, and R$_8$ and R$_9$ are each independently selected from hydrogen or (1-2C)alkyl;
- L² is absent or is selected from O, SO$_2$, N(R$_{10}$), C(O), C(O)N(R$_{10}$), N(R$_{10}$)C(O), or S(O)$_2$N(R$_{10}$), or N(R$_{13}$)SO$_2$, wherein R$_{10}$ is selected from hydrogen or (1-2C)alkyl; and
- R$_7$ is (1-6C)alkyl, aryl, heteroaryl, heteroaryl-(1-6C)alkyl, heterocyclyl, or heterocyclyl-(1-6C)alkyl, wherein R$_7$ is optionally further substituted by one or more substituents independently selected from oxo, halogeno, cyano, NR$_{12}$R$_{13}$, (1-4C)alkoxy, (1-5C)alkyl, or (1-5C)alkanoyl; and wherein R$_{12}$, and R$_{13}$ are each independently selected from hydrogen or (1-2C)alkyl; or R$_{12}$ and R$_{13}$ can be linked such that, together with the nitrogen atom to which they are attached, they form a 4-7 membered heterocyclic ring;

(56) W and Z or W and Y are both CR$_5$ and the R$_5$ groups on the adjacent carbon atoms are linked such that, together with the carbon atoms to which they are attached, they form a fused 5 or 6-membered heterocyclic ring;

(57) L¹ is a linker group of the formula —[CR$_8$R$_9$]$_n$— in which n is an integer selected from 1 or 2, and R$_8$ and R$_9$ are each hydrogen;

(58) L¹ is absent;

(59) L² is O;

(60) R$_7$ is (1-6C)alkyl;

(61) R$_7$ is heterocyclyl;

(62) R$_7$ is further substituted by one or more (1-5C)alkyl;

(63) R$_7$ is further substituted upon a heteroatom by (1-5C)alkyl;

(64) R$_7$ is further substituted upon a nitrogen atom by (1-5C)alkyl;

(65) R$_5$ is -L¹-L²-R$_7$; wherein L¹ is absent; L² is O; and R$_7$ is heterocyclyl, wherein R$_7$ is optionally further substituted by (1-5C)alkyl;

(66) R$_5$ is selected from the group including the following structures:

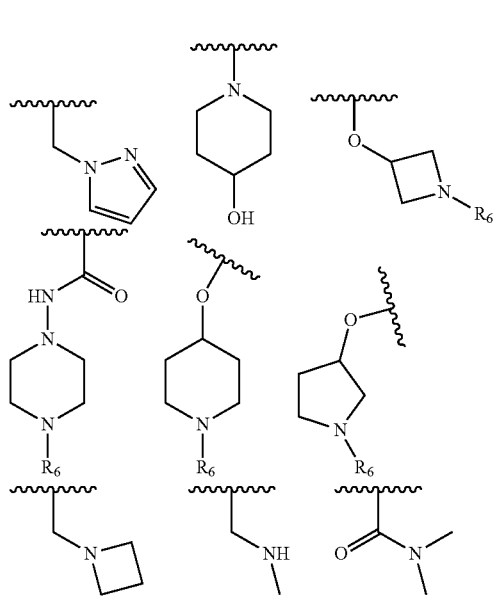

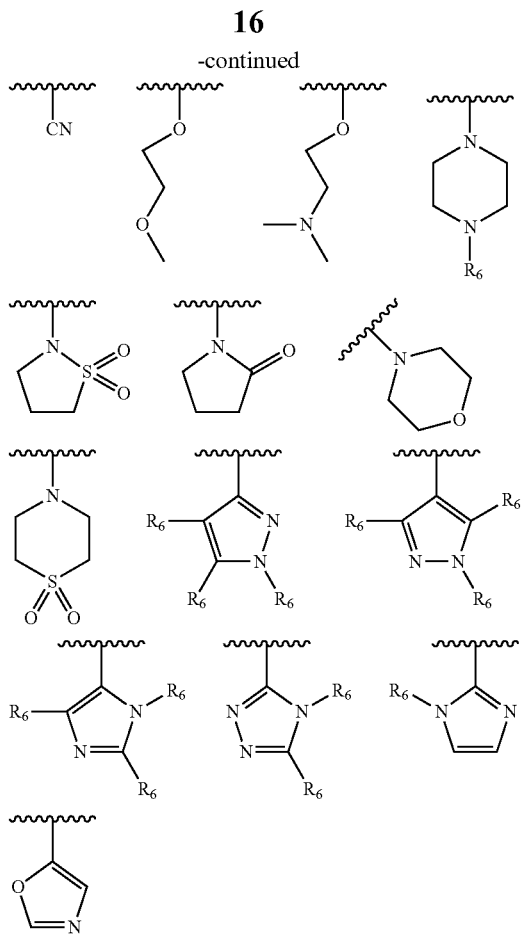

wherein R$_6$ is independently selected from the group including hydrogen, (1-5C)alkyl, (3-8C)cycloalkyl, (3-8C)cycloalkyl-(1-5C)alkyl, aryl, aryl-(1-5C)alkyl, (1-5C)alkanoyl, (1-5C)sulphonyl;

(67) R$_5$ has the following structure:

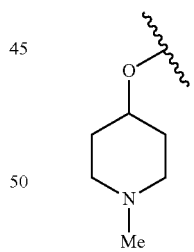

(68) R$_6$ is H or (1-5C)alkyl;

(69) R$_6$ is CH$_3$, or

(70) R$_5$ is selected from:

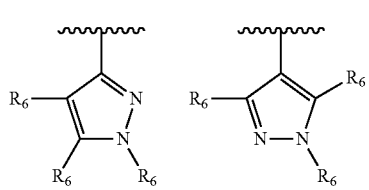

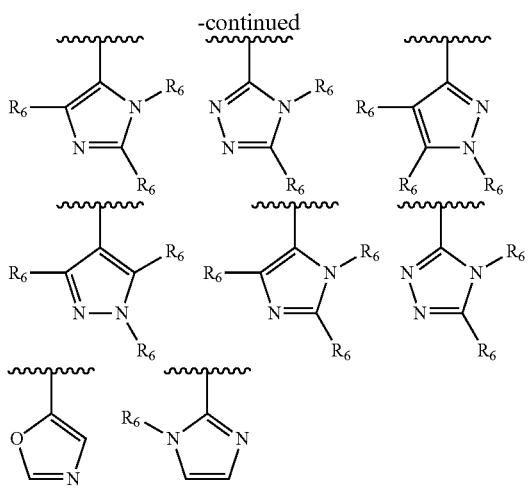

wherein $R_6$ is independently H or methyl.

Suitably, $R_2$ is an electron withdrawing aryl or 5- or 6-membered heteroaryl group which is optionally substituted as defined herein, especially an electron withdrawing 5-membered heteroaryl group.

In a particular group of compounds of the invention, $R_1$ is H, Y is CH, and W is $CR_5$, i.e. the compounds have the structural formula IIa shown below:

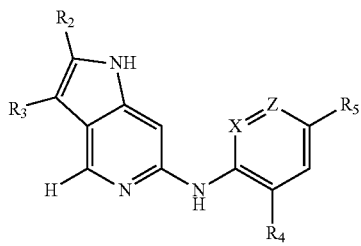

Formula IIa wherein $R_2$, $R_3$, $R_4$, $R_5$, X and Z have any one of the meanings defined herein, or a pharmaceutically acceptable salt or solvate thereof.

In a further group of compounds of the invention, $R_1$ is H, W is CH, and Y is $CR_5$, i.e. the compounds have the structural formula IIb shown below:

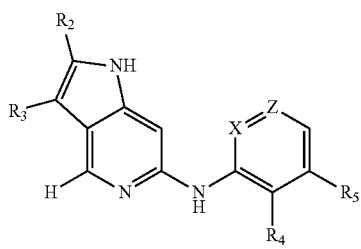

Formula IIb wherein $R_2$, $R_3$, $R_4$, $R_5$, X, and Z have any one of the meanings defined herein, or a pharmaceutically acceptable salt or solvate thereof.

In a further group of compounds of the invention, $R_1$ is H; X, Y and Z are CH; and W is $CR_5$, i.e. the compounds have the structural formula IIIa shown below:

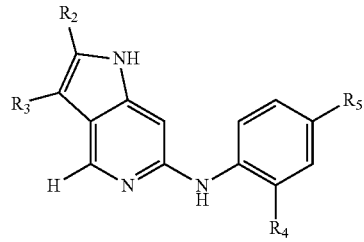

Formula IIIa wherein $R_2$, $R_3$, $R_4$ and $R_5$ have any one of the meanings defined herein, or a pharmaceutically acceptable salt or solvate thereof.

In a particular group of compounds of the invention, $R_1$ is H; W, X and Z are CH; and Y is $CR_5$, i.e. the compounds have the structural formula IIIb shown below:

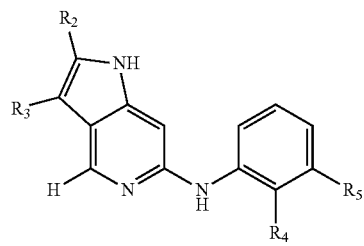

Formula IIIb wherein $R_2$, $R_3$, $R_4$ and $R_5$ have any one of the meanings defined herein, or a pharmaceutically acceptable salt or solvate thereof.

In a particular group of compounds of the invention, $R_1$ is H, and $R_2$ is an optionally substituted pyrazole group. In a particular embodiment, the compounds have the structural formula IV shown below:

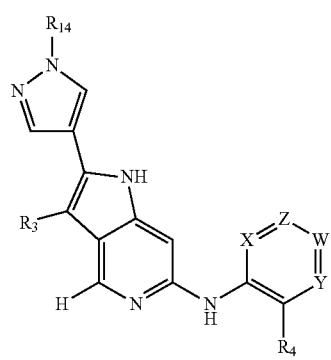

Formula IV wherein $R_3$, $R_4$, $R_{14}$, W, X, Y, and Z have any one of the meanings defined herein, or a pharmaceutically acceptable salt or solvate thereof.

In a particular group of compounds of the invention, $R_1$ is H, and $R_2$ is an optionally substituted pyrazole group, and X and Z are CH. In a particular embodiment, the compounds have the structural formula V shown below:

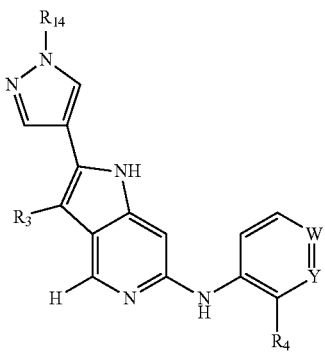

Formula V wherein R₃, R₄, R₁₄, W and Y have any one of the meanings defined herein, or a pharmaceutically acceptable salt or solvate thereof.

In a particular group of compounds of the invention, R₁ is H, R₂ is an optionally substituted pyrazole group, X and Z are CH, one of either W or Y is CH and the other of W or Y is CR₅. In a particular embodiment, the compounds have the structural formula VI shown below:

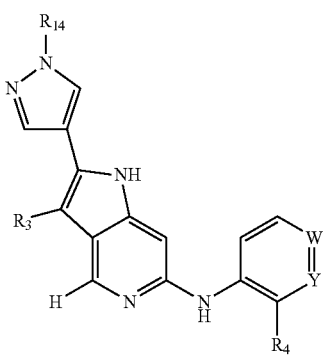

Formula VI wherein one of either W or Y is CH whilst the other of W or Y is CR₅, and R₃, R₄, R₅ and R₁₄ have any one of the meanings defined herein, or a pharmaceutically acceptable salt or solvate thereof. R₅ may suitably be H (i.e. both W and Y are CH).

In a particular group of compounds of the invention, R₁ is H, R₂ is an N-methyl substituted pyrazole group, R₃ is H, X and Z are CH, one of either W or Y is CH and the other of W or Y is CR₅. In a particular embodiment, the compounds have the structural formula VII shown below:

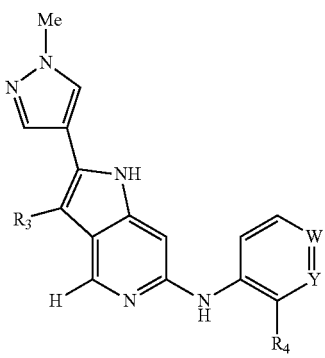

Formula VII wherein one of either W or Y is CH whilst the other of W or Y is CR₅, and R₄, and R₅ have any one of the meanings defined herein, or a pharmaceutically acceptable salt thereof.

In a particular group of compounds, R₁ is as defined in any one of paragraphs (1) to (6) above. Suitably, R₁ is as defined in either of paragraphs (5) or (6) above.

In a particular group of compounds, R₂ is as defined in any one of paragraphs (16) to (27) above. Suitably, R₂ is as defined in any one of paragraphs (25), (26) or (27) above.

Suitably, R₃ is hydrogen or chloro, especially hydrogen.

In a particular group of compounds of the invention, R₄ is a substituent group as defined hereinbefore, other than hydrogen. In particular, R₄ is a substituent other than hydrogen selected from those defined in any one of paragraphs (35), (36), (38), (39) or (40) above. Suitably, R₄ is chloro or methoxy.

Suitably, X is CH.

Suitably, only one of W, X, Y and Z is CR₅.

Suitably, only one of W, X, Y and Z is CR₅ and the others are CH.

In a particular group of compounds, W is CR₅, and X, Y and Z are all CH or one of Y and Z is N and the others are CH. In a further group of compounds, W is CR₅, and X is CH and Y and Z are both CH or one of Y and Z is N and the other is CH.

In a particular group of compounds, Z is CR₅, and W, X and Y are all CH or one of W and Y is N and the others are CH. In a further group of compounds, Z is CR₅, X is CH, W and Y are both CH or one of W and Y is N and the other is CH.

In a particular group of compounds, W is CR₅ and X, Y and Z are all CH.

In a further group of compounds, Z is CR₅ and W, X and Y are all CH.

Suitably, R₅ has any one of the definitions set out hereinbefore. In a particular group of compounds, R₅ has any one of the definitions set out in paragraphs (55) to (71) above. In a particular group of compounds, R₅ is as defined in paragraph (71) above.

A particular group of compounds have the structural formula VIII:

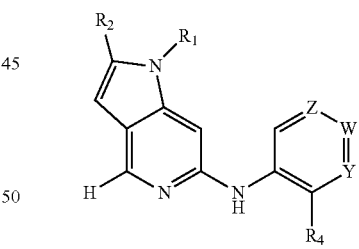

VIII wherein:
R₁ has any one of the definitions set out herein, and in particular is as defined in paragraph (5) or (6) above;
R₂ has any one of the definitions set out herein, and in particular is as defined in any one of paragraphs (25), (26) or (27) above;
R₄ has any one of the definitions set out herein, and in particular is as defined in paragraphs (35), (36), (38), (39) or (40) above (and especially is chloro or methoxy);
one of W, Y and Z is CR₅ and the others are selected from CH or N;
R₅ has any one of the definitions set out herein, and in particular is as defined in paragraphs (55) to (71) above, and is especially as defined in paragraph (71) above;

or a pharmaceutically acceptable salt or solvate thereof.

In a particular group of compounds of formula VIII:
R₁ is as defined in paragraph (5) above;
R₂ is as defined in any one of paragraphs (25), (26) or (27) above;
R₄ is chloro or methoxy;
one of W, Y and Z is CR₅ and the others are selected from CH or N;
R₅ has any one of the definitions set out herein, and in particular is as defined in paragraphs (55) to (71), and is especially as defined in paragraph (71) above.

In a further group of compounds of formula VIII:
R₁ is as defined in paragraph (5) above;
R₂ is as defined in any one of paragraphs (25), (26) or (27) above;
R₄ is chloro or methoxy;
one of W, Y and Z is CR₅ and the others are selected from CH or N;
R₅ is as defined in paragraph (71) above.

In a further group of compounds of formula VIII:
R₁ is as defined in paragraph (5) above;
R₂ is as defined in any one of paragraphs (25), (26) or (27) above;
R₄ is chloro or methoxy;
one of W, Y and Z is CR₅ and the others are CH;
R₅ is especially as defined in paragraph (71) above.

Particular compounds of the present invention include any one of the compounds exemplified in the present application, or a pharmaceutically acceptable salt or solvate thereof, and/ or any one of the following:

N-(3-((1-benzyl-2-(1-methyl-1H-pyrazol-4-yl)-1H-pyrrolo[3,2-c]pyridin-6-yl)amino)phenyl)acetamide;
1-benzyl-N-(4-methoxy-2-methylphenyl)-2-(1-methyl-1H-pyrazol-4-yl)-1H-pyrrolo[3,2-c]pyridin-6-amine;
N¹-(1-benzyl-2-(1-methyl-1H-pyrazol-4-yl)-1H-pyrrolo[3,2-c]pyridin-6-yl)-N^β,N^β-dimethylbenzene-1,3-diamine;
1-benzyl-N-(2,4-dimethoxyphenyl)-2-(1-methyl-1H-pyrazol-4-yl)-1H-pyrrolo[3,2-c]pyridin-6-amine;
4-(6-((2,4-dimethoxyphenyl)amino)-1H-pyrrolo[3,2-c]pyridin-2-yl)-N,N-dimethylbenzamide;
1-benzyl-N-(2,4-dimethoxyphenyl)-2-(pyridin-3-yl)-1H-pyrrolo[3,2-c]pyridin-6-amine;
1-benzyl-N-(3,4-dimethoxyphenyl)-2-(pyridin-3-yl)-1H-pyrrolo[3,2-c]pyridin-6-amine;
1-benzyl-2-(1-methyl-1H-pyrazol-4-yl)-N-(4-(methylsulfonyl)phenyl)-1H-pyrrolo[3,2-c]pyridin-6-amine;
N-(3-((1-benzyl-2-(1-methyl-1H-pyrazol-4-yl)-1H-pyrrolo[3,2-c]pyridin-6-yl)amino)phenyl)methanesulfonamide;
5-((1-benzyl-2-(1-methyl-1H-pyrazol-4-yl)-1H-pyrrolo[3,2-c]pyridin-6-yl)amino)-2-methoxyphenol;
3-((1-benzyl-2-(1-methyl-1H-pyrazol-4-yl)-1H-pyrrolo[3,2-c]pyridin-6-yl)amino)phenol;
N-(benzo[d][1,3]dioxol-5-yl)-1-benzyl-2-(1-methyl-1H-pyrazol-4-yl)-1H-pyrrolo[3,2-c]pyridin-6-amine;
1-benzyl-2-(1-methyl-1H-pyrazol-4-yl)-N-(3-(methylsulfonyl)phenyl)-1H-pyrrolo[3,2-c]pyridin-6-amine;
1-benzyl-N-(4-methoxyphenyl)-2-(1-methyl-1H-pyrazol-4-yl)-1H-pyrrolo[3,2-c]pyridin-6-amine;
1-benzyl-N-(6-methoxypyridin-3-yl)-2-(1-methyl-1H-pyrazol-4-yl)-1H-pyrrolo[3,2-c]pyridin-6-amine;
1-benzyl-N-(3,4-dimethoxyphenyl)-2-(1-methyl-1H-pyrazol-4-yl)-1H-pyrrolo[3,2-c]pyridin-6-amine;
N-(4-((1-benzyl-2-(1-methyl-1H-pyrazol-4-yl)-1H-pyrrolo[3,2-c]pyridin-6-yl)amino)phenyl)acetamide;
1-benzyl-2-(1-methyl-1H-pyrazol-4-yl)-N-(3,4,5-trimethoxyphenyl)-1H-pyrrolo[3,2-c]pyridin-6-amine;
1-benzyl-2-(pyridin-3-yl)-N-(3,4,5-trimethoxyphenyl)-1H-pyrrolo[3,2-c]pyridin-6-amine;
1-benzyl-N-(4-(methylsulfonyl)phenyl)-2-(pyridin-3-yl)-1H-pyrrolo[3,2-c]pyridin-6-amine;
4-((1-benzyl-2-(pyridin-3-yl)-1H-pyrrolo[3,2-c]pyridin-6-yl)amino)-N,N-dimethylbenzamide;
1-benzyl-N-(4-morpholinophenyl)-2-(pyridin-3-yl)-1H-pyrrolo[3,2-c]pyridin-6-amine;
N-(4-Isopropoxyphenyl)-1-methyl-2-(pyridin-3-yl)-1H-pyrrolo[3,2-c]pyridin-6-amine;
1-Methyl-2-(1-methyl-1H-pyrazol-4-yl)-N-(3-(trifluoromethoxy)phenyl)-1H-pyrrolo[3,2-c]pyridin-6-amine;
N-(3-Methoxy-5-(trifluoromethyl)phenyl)-1-methyl-2-(1-methyl-1H-pyrazol-4-yl)-1H-pyrrolo[3,2-c]pyridin-6-amine;
4-((1-Benzyl-2-(1-methyl-1H-pyrazol-4-yl)-1H-pyrrolo[3,2-c]pyridin-6-yl)amino)-N,N-dimethylbenzamide;
4-(1-Benzyl-2-(1-methyl-1H-pyrazol-4-yl)-1H-pyrrolo[3,2-c]pyridin-6-yl)morpholine;
1-Benzyl-2-(1-methyl-1H-pyrazol-4-yl)-N-(pyridin-2-yl)-1H-pyrrolo[3,2-c]pyridin-6-amine;
1-Benzyl-2-(1-methyl-1H-pyrazol-4-yl)-N-(pyridin-4-yl)-1H-pyrrolo[3,2-c]pyridin-6-amine;
4-((1-Benzyl-2-(1-methyl-1H-pyrazol-4-yl)-1H-pyrrolo[3,2-c]pyridin-6-yl)amino)benzamide;
N-(4-Isopropoxyphenyl)-2-(1-methyl-1H-imidazol-5-yl)-1H-pyrrolo[3,2-c]pyridin-6-amine;
1-(3-((2-(1-Methyl-1H-imidazol-5-yl)-1H-pyrrolo[3,2-c]pyridin-6-yl)amino)phenyl)ethanone;
N-(4-Isopropylphenyl)-2-(1-methyl-1H-imidazol-5-yl)-1H-pyrrolo[3,2-c]pyridin-6-amine;
2-(1-Methyl-1H-imidazol-5-yl)-N-(4-(trifluoromethoxy)phenyl)-1H-pyrrolo[3,2-c]pyridin-6-amine;
2-(1-Methyl-1H-imidazol-5-yl)-N-(3-(trifluoromethoxy)phenyl)-1H-pyrrolo[3,2-c]pyridin-6-amine;
N-(4-Fluorophenyl)-2-(1-methyl-1H-imidazol-5-yl)-1H-pyrrolo[3,2-c]pyridin-6-amine;
N¹,N¹-Dimethyl-N^β-(2-(1-methyl-1H-imidazol-5-yl)-1H-pyrrolo[3,2-c]pyridin-6-yl)benzene-1,3-diamine;
N-(3,4-Dimethoxyphenyl)-2-(1-methyl-1H-imidazol-5-yl)-1H-pyrrolo[3,2-c]pyridin-6-amine;
N-(3-Methoxyphenyl)-2-(1-methyl-1H-imidazol-5-yl)-1H-pyrrolo[3,2-c]pyridin-6-amine;
N-(3-Phenoxyphenyl)-2-(1H-pyrazol-4-yl)-1H-pyrrolo[3,2-c]pyridin-6-amine;
N¹-(2-(1H-Pyrazol-4-yl)-1H-pyrrolo[3,2-c]pyridin-6-yl)-N^β,N^β-dimethylbenzene-1,3-diamine;
N-(3-Methoxyphenyl)-2-(1H-pyrazol-4-yl)-1H-pyrrolo[3,2-c]pyridin-6-amine;
4-(6-((3-Acetamidophenyl)amino)-1H-pyrrolo[3,2-c]pyridin-2-yl)-N,N-dimethylbenzamide;
N,N-Dimethyl-4-(6-((3-(methylsulfonamido)phenyl)amino)-1H-pyrrolo[3,2-c]pyridin-2-yl)benzamide;
4-(6-((3-Hydroxyphenyl)amino)-1H-pyrrolo[3,2-c]pyridin-2-yl)-N,N-dimethylbenzamide;
N,N-Dimethyl-4-(6-((3-(methylsulfonyl)phenyl)amino)-1H-pyrrolo[3,2-c]pyridin-2-yl)benzamide;
N,N-Dimethyl-4-(6-((4-(4-methylpiperazin-1-yl)phenyl)amino)-1H-pyrrolo[3,2-c]pyridin-2-yl)benzamide;
4-(1-Benzyl-6-(pyrimidin-4-ylamino)-1H-pyrrolo[3,2-c]pyridin-2-yl)-N,N-dimethylbenzamide;
4-(1-Benzyl-6-morpholino-1H-pyrrolo[3,2-c]pyridin-2-yl)-N,N-dimethylbenzamide;
N-(3-Isopropoxyphenyl)-1-methyl-2-(1-methyl-1H-pyrazol-4-yl)-1H-pyrrolo[3,2-c]pyridin-6-amine;
1-(3-((1-Methyl-2-(1-methyl-1H-pyrazol-4-yl)-1H-pyrrolo[3,2-c]pyridin-6-yl)amino)phenyl)ethanone;

N-(4-Isopropylphenyl)-1-methyl-2-(1-methyl-1H-pyrazol-4-yl)-1H-pyrrolo[3,2-c]pyridin-6-amine;

1-Methyl-2-(1-methyl-1H-pyrazol-4-yl)-N-(m-tolyl)-1H-pyrrolo[3,2-c]pyridin-6-amine;

N-(2,4-Dimethoxyphenyl)-1-methyl-2-(1-methyl-1H-pyrazol-4-yl)-1H-pyrrolo[3,2-c]pyridin-6-amine;

N-(3-Methoxyphenyl)-1-methyl-2-(1-methyl-1H-pyrazol-4-yl)-1H-pyrrolo[3,2-c]pyridin-6-amine;

N-(3-((2-(Pyridin-3-yl)-1H-pyrrolo[3,2-c]pyridin-6-yl)amino)phenyl)acetamide;

N-(6-Methoxypyridin-3-yl)-2-(pyridin-3-yl)-1H-pyrrolo[3,2-c]pyridin-6-amine;

N-(3,4-Dimethoxyphenyl)-2-(1-methyl-1H-pyrazol-4-yl)-1H-pyrrolo[3,2-c]pyridin-6-amine;

2-(3-Aminophenyl)-N-(pyridin-3-yl)-1H-pyrrolo[3,2-c]pyridin-6-amine;

N-(3-((1-Methyl-2-(pyridin-3-yl)-1H-pyrrolo[3,2-c]pyridin-6-yl)amino)phenyl)acetamide;

1-Methyl-N-(3-(methylsulfonyl)phenyl)-2-(pyridin-3-yl)-1H-pyrrolo[3,2-c]pyridin-6-amine;

N-(4-Methoxyphenyl)-1-methyl-2-(pyridin-3-yl)-1H-pyrrolo[3,2-c]pyridin-6-amine;

$N^1,N^1$-Dimethyl-$N^\beta$-(1-methyl-2-(pyridin-3-yl)-1H-pyrrolo[3,2-c]pyridin-6-yl)benzene-1,3-diamine;

1-Methyl-N-phenyl-2-(pyridin-3-yl)-1H-pyrrolo[3,2-c]pyridin-6-amine;

N-(6-Methoxypyridin-3-yl)-1-methyl-2-(pyridin-3-yl)-1H-pyrrolo[3,2-c]pyridin-6-amine;

N-(3,4-Dimethoxyphenyl)-1-methyl-2-(pyridin-3-yl)-1H-pyrrolo[3,2-c]pyridin-6-amine;

N-(2,3-Dihydrobenzo[b][1,4]dioxin-6-yl)-1-methyl-2-(pyridin-3-yl)-1H-pyrrolo[3,2-c]pyridin-6-amine;

N-(2,4-Dimethoxyphenyl)-1-methyl-2-(pyridin-3-yl)-1H-pyrrolo[3,2-c]pyridin-6-amine;

N-(3-Methoxyphenyl)-1-methyl-2-(pyridin-3-yl)-1H-pyrrolo[3,2-c]pyridin-6-amine;

1-Methyl-2-(pyridin-3-yl)-N-(3,4,5-trimethoxyphenyl)-1H-pyrrolo[3,2-c]pyridin-6-amine;

N-(4-isopropoxyphenyl)-1-methyl-2-(1-methyl-1H-pyrazol-4-yl)-1H-pyrrolo[3,2-c]pyridin-6-amine;

1-methyl-2-(1-methyl-1H-pyrazol-4-yl)-N-(4-(methylthio)phenyl)-1H-pyrrolo[3,2-c]pyridin-6-amine;

N,N-dimethyl-4-((1-methyl-2-(1-methyl-1H-pyrazol-4-yl)-1H-pyrrolo[3,2-c]pyridin-6-yl)amino)benzamide;

N-(2-chlorophenyl)-1-methyl-2-(1-methyl-1H-pyrazol-4-yl)-1H-pyrrolo[3,2-c]pyridin-6-amine;

N-(3-isopropylphenyl)-1-methyl-2-(1-methyl-1H-pyrazol-4-yl)-1H-pyrrolo[3,2-c]pyridin-6-amine;

N-(benzo[d][1,3]dioxol-5-yl)-1-methyl-2-(1-methyl-1H-pyrazol-4-yl)-1H-pyrrolo[3,2-c]pyridin-6-amine;

1-methyl-2-(1-methyl-1H-pyrazol-4-yl)-N-(pyridin-2-yl)-1H-pyrrolo[3,2-c]pyridin-6-amine;

N-(4-methoxyphenyl)-1-methyl-2-(1-methyl-1H-pyrazol-4-yl)-1H-pyrrolo[3,2-c]pyridin-6-amine;

N-(4-methoxy-2-methylphenyl)-1-methyl-2-(1-methyl-1H-pyrazol-4-yl)-1H-pyrrolo[3,2-c]pyridin-6-amine;

1-methyl-2-(1-methyl-1H-pyrazol-4-yl)-N-phenyl-1H-pyrrolo[3,2-c]pyridin-6-amine;

N-(3,4-dimethoxyphenyl)-1-methyl-2-(1-methyl-1H-pyrazol-4-yl)-1H-pyrrolo[3,2-c]pyridin-6-amine;

N-(2,3-dihydrobenzo[b][1,4]dioxin-6-yl)-1-methyl-2-(1-methyl-1H-pyrazol-4-yl)-1H-pyrrolo[3,2-c]pyridin-6-amine;

N-(4-methoxyphenyl)-2-(pyridin-2-yl)-1H-pyrrolo[3,2-c]pyridin-6-amine;

1-(3-((2-(1-methyl-1H-pyrazol-4-yl)-1H-pyrrolo[3,2-c]pyridin-6-yl)amino)phenyl)ethanone;

2-(1-methyl-1H-pyrazol-4-yl)-N-(4-(trifluoromethyl)phenyl)-1H-pyrrolo[3,2-c]pyridin-6-amine;

N-(2,3-dihydrobenzo[b][1,4]dioxin-6-yl)-2-(1-methyl-1H-pyrazol-4-yl)-1H-pyrrolo[3,2-c]pyridin-6-amine;

N-(2-fluoro-5-(trifluoromethyl)phenyl)-2-phenyl-1H-pyrrolo[3,2-c]pyridin-6-amine;

N-(3-methoxy-5-(trifluoromethyl)phenyl)-2-phenyl-1H-pyrrolo[3,2-c]pyridin-6-amine;

N-(4-morpholinophenyl)-2-phenyl-1H-pyrrolo[3,2-c]pyridin-6-amine;

or a pharmaceutically acceptable salt or solvate thereof.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

(ii) Novel Pyrrolopyridineamino (PPA) Derivatives

In a further aspect, there is provided a compound of formula I as defined herein.

In another aspect, the present invention relates to a compound of formula I as defined herein before, wherein $R_1$ is a substituent group as defined in paragraph (5) or (6) above, and $R_2, R_3, R_4, X, W, Y$ and $Z$ each have any one of the definitions set out hereinbefore, or a pharmaceutically acceptable salt or solvate thereof.

In another aspect, the present invention relates to a compound of formula I as defined herein before, wherein $R_4$ is a substituent group as defined hereinbefore other than hydrogen; and $R_1, R_2, R_3, X, W, Y$ and $Z$ each have any one of the definitions set out hereinbefore, or a pharmaceutically acceptable salt or solvate thereof.

In another aspect, the present invention relates to a compound of formula I as defined herein before, wherein $R_2$ is a substituent group as defined in any one of paragraphs (25), (26) or (27) above; and $R_1, R_3, R_4, X, W, Y$ and $Z$ each have any one of the definitions set out hereinbefore, or a pharmaceutically acceptable salt or solvate thereof.

Compounds of the present aspect may also be defined by formulas IIa, IIb, IIIa, IIIb, IV, V, VI, VII and VIII described above in relation to the earlier aspect of the invention.

A particular group of novel compounds are the compounds of formula VIII defined above.

In a particular aspect, the present invention provides any one of the compounds exemplified herein, or a pharmaceutically acceptable salt thereof.

In a particular aspect, the present invention provides any one of the following novel compounds:

isopropyl 6-((4-methoxy-2-(1-methyl-1H-pyrazol-4-yl)pyrimidin-5-yl)amino)-2-(1-methyl-1H-pyrazol-4-yl)-1H-pyrrolo[3,2-c]pyridine-1-carboxylate;

isopropyl 6-((4-(1,2-dimethyl-1H-imidazol-5-yl)phenyl)amino)-2-(1-methyl-1H-pyrazol-4-yl)-1H-pyrrolo[3,2-c]pyridine-1-carboxylate;

isopropyl 6-(4-(1,3-dimethyl-1H-pyrazol-4-yl)-2-methoxyphenylamino)-2-(1-methyl-1H-pyrazol-4-yl)-1H-pyrrolo[3,2-c]pyridine-1-carboxylate;

N-(2-chloro-5-(1-methyl-1H-pyrazol-4-yl)phenyl)-2-(1-methyl-1H-pyrazol-4-yl)-1H-pyrrolo[3,2-c]pyridin-6-amine;

tert-butyl 6-((2-chloro-5-(1-methyl-1H-pyrazol-4-yl)phenyl)amino)-2-(1-methyl-1H-pyrazol-4-yl)-1H-pyrrolo[3,2-c]pyridine-1-carboxylate;

N-(2-chloro-4-(1,2-dimethyl-1H-imidazol-5-yl)phenyl)-2-(oxazol-5-yl)-1H-pyrrolo[3,2-c]pyridin-6-amine;

tert-butyl 6-(2-chloro-4-(1,2-dimethyl-1H-imidazol-5-yl)phenylamino)-2-(oxazol-5-yl)-1H-pyrrolo[3,2-c]pyridine-1-carboxylate;
isopropyl 6-(2-chloro-4-(1,2-dimethyl-1H-imidazol-5-yl)phenylamino)-2-(oxazol-5-yl)-1H-pyrrolo[3,2-c]pyridine-1-carboxylate;
isopropyl 6-(2-methoxy-4-(1-methyl-1H-pyrazol-4-yl)phenylamino)-2-(1-methyl-1H-pyrazol-4-yl)-1H-pyrrolo[3,2-c]pyridine-1-carboxylate;
isopropyl 6-((2-chloro-5-(1-methyl-1H-pyrazol-4-yl)phenyl)amino)-2-(1-methyl-1H-pyrazol-4-yl)-1H-pyrrolo[3,2-c]pyridine-1-carboxylate;
N-(2-chloro-4-(1,2-dimethyl-1H-imidazol-5-yl)phenyl)-1-(2-methoxyethyl)-2-(1-methyl-1H-pyrazol-4-yl)-1H-pyrrolo[3,2-c]pyridin-6-amine;
tert-butyl 6-(2-chloro-4-(1,4-dimethyl-1H-imidazol-5-yl)phenylamino)-2-(1-methyl-1H-pyrazol-4-yl)-1H-pyrrolo[3,2-c]pyridine-1-carboxylate;
N-(2-chloro-4-(1,2-dimethyl-1H-imidazol-5-yl)phenyl)-1-(cyclopropylmethyl)-2-(1-methyl-1H-pyrazol-4-yl)-1H-pyrrolo[3,2-c]pyridin-6-amine;
N-(2-chloro-4-(1-methyl-1H-imidazol-5-yl)phenyl)-2-(oxazol-5-yl)-1H-pyrrolo[3,2-c]pyridin-6-amine;
tert-butyl 6-((2-chloro-4-(3,3-difluoroazetidine-1-carbonyl)phenyl)amino)-2-(1-methyl-1H-pyrazol-4-yl)-1H-pyrrolo[3,2-c]pyridine-1-carboxylate;
(3-chloro-4-((2-(1-methyl-1H-pyrazol-4-yl)-1H-pyrrolo[3,2-c]pyridin-6-yl)amino)phenyl)(3,3-difluoroazetidin-1-yl)methanone;
propyl-6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
ethyl-6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
methyl-6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
isopropyl 6-(4-(1,2-dimethyl-1H-imidazol-5-yl)-2-methoxyphenylamino)-2-(1-methyl-1H-pyrazol-4-yl)-1H-pyrrolo[3,2-c]pyridine-1-carboxylate;
tert-butyl 6-(2-chloro-4-(oxazol-5-yl)phenylamino)-2-(1-methyl-1H-pyrazol-4-yl)-1H-pyrrolo[3,2-c]pyridine-1-carboxylate;
tert-butyl 6-(2-chloro-4-(thiazol-5-yl)phenylamino)-2-(1-methyl-1H-pyrazol-4-yl)-1H-pyrrolo[3,2-c]pyridine-1-carboxylate;
tert-butyl 6-(2-chloro-4-(5-methylisoxazol-4-yl)phenylamino)-2-(1-methyl-1H-pyrazol-4-yl)-1H-pyrrolo[3,2-c]pyridine-1-carboxylate;
tert-butyl 6-((2-chloro-4-(pyrazin-2-yl)phenyl)amino)-2-(1-methyl-1H-pyrazol-4-yl)-1H-pyrrolo[3,2-c]pyridine-1-carboxylate;
cyclobutyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
cyclopentyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
isopropyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
tert-butyl 6-(2-chloro-4-(6-methylpyridin-3-yl)phenylamino)-2-(1-methyl-1H-pyrazol-4-yl)-1H-pyrrolo[3,2-c]pyridine-1-carboxylate;
tert-butyl 6-(2-chloro-4-(1-methyl-1H-imidazol-2-yl)phenylamino)-2-(1-methyl-1H-pyrazol-4-yl)-1H-pyrrolo[3,2-c]pyridine-1-carboxylate;
tert-butyl 6-(2-chloro-4-(1,3-dimethyl-1H-pyrazol-4-yl)phenylamino)-2-(1-methyl-1H-pyrazol-4-yl)-1H-pyrrolo[3,2-c]pyridine-1-carboxylate;
tert-butyl 6-(2-chloro-4-(1,5-dimethyl-1H-pyrazol-4-yl)phenylamino)-2-(1-methyl-1H-pyrazol-4-yl)-1H-pyrrolo[3,2-c]pyridine-1-carboxylate;
tert-butyl 6-(2-chloro-4-(pyridin-3-yl)phenylamino)-2-(1-methyl-1H-pyrazol-4-yl)-1H-pyrrolo[3,2-c]pyridine-1-carboxylate;
tert-butyl 6-(2-chloro-4-(4-methyl-4H-1,2,4-triazol-3-yl)phenylamino)-2-(1-methyl-1H-pyrazol-4-yl)-1H-pyrrolo[3,2-c]pyridine-1-carboxylate;
tert-butyl 6-((2-chloro-4-(pyrimidin-5-yl)phenyl)amino)-2-(1-methyl-1H-pyrazol-4-yl)-1H-pyrrolo[3,2-c]pyridine-1-carboxylate;
tert-butyl-6-(2-chloro-4-(6-methoxypyridin-3-yl)phenylamino)-2-(1-methyl-1H-pyrazol-4-yl)-1H-pyrrolo[3,2-c]pyridine-1-carboxylate;
cyclobutyl-6-(2-chloro-4-(1-methyl-1H-imidazol-5-yl)phenylamino)-2-(1-methyl-1H-pyrazol-4-yl)-1H-pyrrolo[3,2-c]pyridine-1-carboxylate;
cyclobutyl-6-(2-chloro-4-(dimethylcarbamoyl)phenylamino)-2-(1-methyl-1H-pyrazol-4-yl)-1H-pyrrolo[3,2-c]pyridine-1-carboxylate;
N-(2-chloro-4-(1-methyl-1H-imidazol-5-yl)phenyl)-1-cyclopentyl-2-(1-methyl-1H-pyrazol-4-yl)-1H-pyrrolo[3,2-c]pyridin-6-amine;
isopropyl 6-(2-chloro-4-(1-methyl-1H-imidazol-5-yl)phenylamino)-2-(1-methyl-1H-pyrazol-4-yl)-1H-pyrrolo[3,2-c]pyridine-1-carboxylate;
tert-butyl 6-(2-chloro-4-(1-methyl-1H-imidazol-5-yl)phenylamino)-2-(oxazol-5-yl)-1H-pyrrolo[3,2-c]pyridine-1-carboxylate;
cyclopentyl 6-((2-chloro-4-(1-methyl-1H-imidazol-5-yl)phenyl)amino)-2-(1-methyl-1H-pyrazol-4-yl)-1H-pyrrolo[3,2-c]pyridine-1-carboxylate;
tert-butyl 6-((4-(azetidine-1-carbonyl)-2-chlorophenyl)amino)-2-(1-methyl-1H-pyrazol-4-yl)-1H-pyrrolo[3,2-c]pyridine-1-carboxylate;
N-(2-chloro-4-(1,2-dimethyl-1H-imidazol-5-yl)phenyl)-2-(1-methyl-1H-pyrazol-4-yl)-1H-pyrrolo[3,2-c]pyridin-6-amine;
tert-butyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
3-chloro-N,N-dimethyl-4-(2-(1-methyl-1H-pyrazol-4-yl)-1-(5-methylpyridin-2-yl)-1H-pyrrolo[3,2-c]pyridin-6-ylamino)benzamide;
3-chloro-N,N-dimethyl-4-(2-(1-methyl-1H-pyrazol-4-yl)-1-(pyrimidin-2-yl)-1H-pyrrolo[3,2-c]pyridin-6-ylamino)benzamide;
3-chloro-N,N-dimethyl-4-(2-(1-methyl-1H-pyrazol-4-yl)-1-(pyridin-2-yl)-1H-pyrrolo[3,2-c]pyridin-6-ylamino)benzamide;
N-(2-chloro-4-(2-methoxypyridin-4-yl)phenyl)-2-(1-methyl-1H-pyrazol-4-yl)-1H-pyrrolo[3,2-c]pyridin-6-amine;
tert-butyl 6-(2-chloro-4-(2-methoxypyridin-4-yl)phenylamino)-2-(1-methyl-1H-pyrazol-4-yl)-1H-pyrrolo[3,2-c]pyridine-1-carboxylate;
N-(2-chloro-4-(2,4-dimethylthiazol-5-yl)phenyl)-2-(1-methyl-1H-pyrazol-4-yl)-1H-pyrrolo[3,2-c]pyridin-6-amine;
tert-butyl 6-(2-chloro-4-(2,4-dimethylthiazol-5-yl)phenylamino)-2-(1-methyl-1H-pyrazol-4-yl)-1H-pyrrolo[3,2-c]pyridine-1-carboxylate;

N-(2-chloro-4-(1-methyl-1H-pyrazol-5-yl)phenyl)-2-(1-methyl-1H-pyrazol-4-yl)-1H-pyrrolo[3,2-c]pyridin-6-amine;
tert-butyl 6-(2-chloro-4-(1-methyl-1H-pyrazol-5-yl)phenylamino)-2-(1-methyl-1H-pyrazol-4-yl)-1H-pyrrolo[3,2-c]pyridine-1-carboxylate;
isopropyl 6-(2-chloro-4-(dimethylcarbamoyl)phenylamino)-2-(1-methyl-1H-pyrazol-4-yl)-1H-pyrrolo[3,2-c]pyridine-1-carboxylate;
isopropyl 6-(2-chloro-4-(1-methyl-1H-pyrazol-4-yl)phenylamino)-2-(1-methyl-1H-pyrazol-4-yl)-1H-pyrrolo[3,2-c]pyridine-1-carboxylate;
N-(2-chloro-4-(1-methyl-1H-imidazol-5-yl)phenyl)-2-(1-methyl-1H-pyrazol-4-yl)-1H-pyrrolo[3,2-c]pyridin-6-amine;
N-(2-chloro-4-(1-methyl-1H-pyrazol-3-yl)phenyl)-2-(1-methyl-1H-pyrazol-4-yl)-1H-pyrrolo[3,2-c]pyridin-6-amine;
(3-chloro-4-(2-(1-methyl-1H-pyrazol-4-yl)-1H-pyrrolo[3,2-c]pyridin-6-ylamino)phenyl)(4-(dimethylamino)piperidin-1-yl)methanone;
tert-butyl-6-(2-chloro-4-(4-(dimethylamino)piperidine-1-carbonyl)phenylamino)-2-(1-methyl-1H-pyrazol-4-yl)-1H-pyrrolo[3,2-c]pyridine-1-carboxylate;
cyclopentyl 6-(2-chloro-4-(1-methyl-1H-pyrazol-4-yl)phenylamino)-2-(1-methyl-1H-pyrazol-4-yl)-1H-pyrrolo[3,2-c]pyridine-1-carboxylate;
(3-chloro-4-(2-(1-methyl-1H-pyrazol-4-yl)-1H-pyrrolo[3,2-c]pyridin-6-ylamino)phenyl)(4-methoxypiperidin-1-yl)methanone;
tert-butyl 6-(2-chloro-4-(4-methoxypiperidine-1-carbonyl)phenylamino)-2-(1-methyl-1H-pyrazol-4-yl)-1H-pyrrolo[3,2-c]pyridine-1-carboxylate;
tert-butyl 6-(2-chloro-4-(1-methyl-1H-imidazol-5-yl)phenylamino)-2-(1-methyl-1H-pyrazol-4-yl)-1H-pyrrolo[3,2-c]pyridine-1-carboxylate;
tert-butyl 6-(2-chloro-4-(1-methyl-1H-pyrazol-3-yl)phenylamino)-2-(1-methyl-1H-pyrazol-4-yl)-1H-pyrrolo[3,2-c]pyridine-1-carboxylate;
(3-chloro-4-(2-(1-methyl-1H-pyrazol-4-yl)-1H-pyrrolo[3,2-c]pyridin-6-ylamino)phenyl)(4-methylpiperazin-1-yl)methanone;
tert-butyl 6-(2-chloro-4-(4-methylpiperazine-1-carbonyl)phenylamino)-2-(1-methyl-1H-pyrazol-4-yl)-1H-pyrrolo[3,2-c]pyridine-1-carboxylate;
(3-chloro-4-(3-chloro-2-(1-methyl-1H-pyrazol-4-yl)-1H-pyrrolo[3,2-c]pyridin-6-ylamino)phenyl)(S,S-dioxo-thiomorpholino)methanone;
(3-chloro-4-(3-chloro-2-(1-methyl-1H-pyrazol-4-yl)-1H-pyrrolo[3,2-c]pyridin-6-ylamino)phenyl)(3-methoxyazetidin-1-yl)methanone;
(3-chloro-4-(2-(1-methyl-1H-pyrazol-4-yl)-1H-pyrrolo[3,2-c]pyridin-6-ylamino)phenyl)(pyrrolidin-1-yl)methanone;
tert-butyl 6-(2-chloro-4-(pyrrolidine-1-carbonyl)phenylamino)-2-(1-methyl-1H-pyrazol-4-yl)-1H-pyrrolo[3,2-c]pyridine-1-carboxylate;
3-chloro-N-ethyl-N-methyl-4-(2-(1-methyl-1H-pyrazol-4-yl)-1H-pyrrolo[3,2-c]pyridin-6-ylamino)benzamide;
tert-butyl 6-(2-chloro-4-(ethyl(methyl)carbamoyl)phenylamino)-2-(1-methyl-1H-pyrazol-4-yl)-1H-pyrrolo[3,2-c]pyridine-1-carboxylate;
(3-chloro-4-(2-(1-methyl-1H-pyrazol-4-yl)-1H-pyrrolo[3,2-c]pyridin-6-ylamino)phenyl)(S,S-dioxo-thiomorpholino)methanone;
tert-butyl 6-(2-chloro-4-(S,S-dioxo-thiomorpholine-4-carbonyl)phenylamino)-2-(1-methyl-1H-pyrazol-4-yl)-1H-pyrrolo[3,2-c]pyridine-1-carboxylate;
N-(2-chlorophenyl)-1-(cyclohexylmethyl)-2-(1-methyl-1H-pyrazol-4-yl)-1H-pyrrolo[3,2-c]pyridin-6-amine;
3-chloro-N-(2-chloro-4-(1-methyl-1H-pyrazol-4-yl)phenyl)-2-(1-methyl-1H-pyrazol-4-yl)-1H-pyrrolo[3,2-c]pyridin-6-amine;
3-chloro-N-(2-chlorophenyl)-2-(1-methyl-1H-pyrazol-4-yl)-1H-pyrrolo[3,2-c]pyridin-6-amine;
N-(2-chlorophenyl)-2-(1-methyl-1H-pyrazol-4-yl)-1H-pyrrolo[3,2-c]pyridin-6-amine;
N-(2-chlorophenyl)-2-(1-methyl-1H-pyrazol-4-yl)-1H-pyrrolo[3,2-c]pyridin-6-amine;
(3-chloro-4-(2-(1-methyl-1H-pyrazol-4-yl)-1H-pyrrolo[3,2-c]pyridin-6-ylamino)phenyl)(3-methoxyazetidin-1-yl)methanone;
tert-butyl 6-(2-chloro-4-(3-methoxyazetidine-1-carbonyl)phenylamino)-2-(1-methyl-1H-pyrazol-4-yl)-1H-pyrrolo[3,2-c]pyridine-1-carboxylate;
tert-butyl 6-(2-chloro-4-(1-methyl-1H-pyrazol-4-yl)phenylamino)-2-(1-methyl-1H-pyrazol-4-yl)-1H-pyrrolo[3,2-c]pyridine-1-carboxylate;
tert-butyl 6-(2-chlorophenylamino)-2-(1-methyl-1H-pyrazol-4-yl)-1H-pyrrolo[3,2-c]pyridine-1-carboxylate;
3-chloro-4-(1-isopropyl-2-(1-methyl-1H-pyrazol-4-yl)-1H-pyrrolo[3,2-c]pyridin-6-ylamino)-N,N-dimethylbenzamide;
3-chloro-4-(1-cyclopentyl-2-(1-methyl-1H-pyrazol-4-yl)-1H-pyrrolo[3,2-c]pyridin-6-ylamino)-N,N-dimethylbenzamide;
3-chloro-4-(3-chloro-1-(cyclopentylmethyl)-2-(1-methyl-1H-pyrazol-4-yl)-1H-pyrrolo[3,2-c]pyridin-6-ylamino)-N,N-dimethylbenzamide;
3-chloro-4-(3-chloro-1-(cyclopropylmethyl)-2-(1-methyl-1H-pyrazol-4-yl)-1H-pyrrolo[3,2-c]pyridin-6-ylamino)-N,N-dimethylbenzamide;
3,5-dichloro-N,N-dimethyl-4-(2-(1-methyl-1H-pyrazol-4-yl)-1H-pyrrolo[3,2-c]pyridin-6-ylamino)benzamide;
tert-butyl 6-(4-(dimethylcarbamoyl)-2-(trifluoromethoxy)phenylamino)-2-(1-methyl-1H-pyrazol-4-yl)-1H-pyrrolo[3,2-c]pyridine-1-carboxylate;
tert-butyl 6-(2,6-dichloro-4-(dimethylcarbamoyl)phenylamino)-2-(1-methyl-1H-pyrazol-4-yl)-1H-pyrrolo[3,2-c]pyridine-1-carboxylate;
3-chloro-4-(1-(cyclopropylmethyl)-2-(1-methyl-1H-pyrazol-4-yl)-1H-pyrrolo[3,2-c]pyridin-6-ylamino)-N,N-dimethylbenzamide;
cyclopentyl 6-(2-chloro-4-(dimethylcarbamoyl)phenylamino)-2-(1-methyl-1H-pyrazol-4-yl)-1H-pyrrolo[3,2-c]pyridine-1-carboxylate;
3-chloro-4-(1-(cyclohexylmethyl)-2-(1-methyl-1H-pyrazol-4-yl)-1H-pyrrolo[3,2-c]pyridin-6-ylamino)-N,N-dimethylbenzamide;
3-chloro-4-(1-(4-fluorobenzyl)-2-(1-methyl-1H-pyrazol-4-yl)-1H-pyrrolo[3,2-c]pyridin-6-ylamino)-N,N-dimethylbenzamide;
3-chloro-4-(1-(cyclopentylsulfonyl)-2-(1-methyl-1H-pyrazol-4-yl)-1H-pyrrolo[3,2-c]pyridin-6-ylamino)-N,N-dimethylbenzamide;
3-chloro-4-(3-chloro-2-(oxazol-5-yl)-1H-pyrrolo[3,2-c]pyridin-6-ylamino)-N,N-dimethylbenzamide;
tert-butyl 6-(2-methoxyphenylamino)-2-(oxazol-5-yl)-1H-pyrrolo[3,2-c]pyridine-1-carboxylate;
3-chloro-N,N-dimethyl-4-((2-(1-methyl-1H-pyrazol-4-yl)-1-((5-methylisoxazol-3-yl)methyl)-1H-pyrrolo[3,2-c]pyridin-6-yl)amino)benzamide;
(3-methoxy-4-(2-(oxazol-5-yl)-1H-pyrrolo[3,2-c]pyridin-6-ylamino)phenyl)(3-methoxyazetidin-1-yl)methanone;
tert-butyl 6-(2-methoxy-4-(3-methoxyazetidine-1-carbonyl)phenylamino)-2-(oxazol-5-yl)-1H-pyrrolo[3,2-c]pyridine-1-carboxylate;

3-chloro-N,N-dimethyl-4-(2-(oxazol-5-yl)-1H-pyrrolo[3,2-c]pyridin-6-ylamino)benzamide;
tert-butyl 6-(2-chloro-4-(dimethylcarbamoyl)phenylamino)-2-(oxazol-5-yl)-1H-pyrrolo[3,2-c]pyridine-1-carboxylate;
3-chloro-N-(2-chloro-4-(methylsulfonyl)phenyl)-2-(1-methyl-1H-pyrazol-4-yl)-1H-pyrrolo[3,2-c]pyridin-6-amine;
2-(3-(2-(1-methyl-1H-pyrazol-4-yl)-1H-pyrrolo[3,2-c]pyridin-6-ylamino)phenoxy)acetonitrile;
tert-butyl 6-(3-(cyanomethoxy)phenylamino)-2-(1-methyl-1H-pyrazol-4-yl)-1H-pyrrolo[3,2-c]pyridine-1-carboxylate;
tert-butyl 3-chloro-6-(2-chloro-4-(dimethylcarbamoyl)phenylamino)-2-(1-methyl-1H-pyrazol-4-yl)-1H-pyrrolo[3,2-c]pyridine-1-carboxylate;
3-chloro-4-(1-(cyclopentylmethyl)-2-(1-methyl-1H-pyrazol-4-yl)-1H-pyrrolo[3,2-c]pyridin-6-ylamino)-N,N-dimethylbenzamide;
N-(4-(aminomethyl)-2-methoxyphenyl)-2-(1-methyl-1H-pyrazol-4-yl)-1H-pyrrolo[3,2-c]pyridin-6-amine;
N-(4-((dimethylamino)methyl)-2-methoxyphenyl)-2-(1-methyl-1H-pyrazol-4-yl)-1H-pyrrolo[3,2-c]pyridin-6-amine;
tert-butyl 6-(4-((dimethylamino)methyl)-2-methoxyphenylamino)-2-(1-methyl-1H-pyrazol-4-yl)-1H-pyrrolo[3,2-c]pyridine-1-carboxylate;
N-(2-methoxy-4-((methylamino)methyl)phenyl)-2-(1-methyl-1H-pyrazol-4-yl)-1H-pyrrolo[3,2-c]pyridin-6-amine;
tert-butyl 6-(4-(((tert-butoxycarbonyl(methyl)amino)methyl)-2-methoxyphenylamino)-2-(1-methyl-1H-pyrazol-4-yl)-1H-pyrrolo[3,2-c]pyridine-1-carboxylate;
N-(2-methoxy-4-(pyrrolidin-1-ylmethyl)phenyl)-2-(1-methyl-1H-pyrazol-4-yl)-1H-pyrrolo[3,2-c]pyridin-6-amine;
tert-butyl 6-(2-methoxy-4-(pyrrolidin-1-ylmethyl)phenylamino)-2-(1-methyl-1H-pyrazol-4-yl)-1H-pyrrolo[3,2-c]pyridine-1-carboxylate;
tert-butyl 6-((2-cyanophenyl)amino)-2-(1-methyl-1H-pyrazol-4-yl)-1H-pyrrolo[3,2-c]pyridine-1-carboxylate;
tert-butyl 6-((2-chloro-4-(methylsulfonyl)phenyl)amino)-2-(1-methyl-1H-pyrazol-4-yl)-1H-pyrrolo[3,2-c]pyridine-1-carboxylate;
(3-methoxy-4-(2-(1-methyl-1H-pyrazol-4-yl)-1H-pyrrolo[3,2-c]pyridin-6-ylamino)phenyl)(3-methoxyazetidin-1-yl)methanone;
3-methoxy-N-(2-methoxyethyl)-4-(2-(1-methyl-1H-pyrazol-4-yl)-1H-pyrrolo[3,2-c]pyridin-6-ylamino)benzamide;
(3-methoxy-4-(2-(1-methyl-1H-pyrazol-4-yl)-1H-pyrrolo[3,2-c]pyridin-6-ylamino)phenyl)(morpholino)methanone;
tert-butyl 6-(2-methoxy-4-(3-methoxyazetidine-1-carbonyl)phenylamino)-2-(1-methyl-1H-pyrazol-4-yl)-1H-pyrrolo[3,2-c]pyridine-1-carboxylate;
tert-butyl 6-(2-methoxy-4-(2-methoxyethylcarbamoyl)phenylamino)-2-(1-methyl-1H-pyrazol-4-yl)-1H-pyrrolo[3,2-c]pyridine-1-carboxylate;
tert-butyl 6-(2-methoxy-4-(morpholine-4-carbonyl)phenylamino)-2-(1-methyl-1H-pyrazol-4-yl)-1H-pyrrolo[3,2-c]pyridine-1-carboxylate;
N-(2-methoxyphenyl)-2-(oxazol-5-yl)-1H-pyrrolo[3,2-c]pyridin-6-amine;
tert-butyl 6-(2-chloro-4-(dimethylcarbamoyl)phenylamino)-2-(1-methyl-1H-pyrazol-4-yl)-1H-pyrrolo[3,2-c]pyridine-1-carboxylate;
tert-butyl 6-(2-acetylphenylamino)-2-(1-methyl-1H-pyrazol-4-yl)-1H-pyrrolo[3,2-c]pyridine-1-carboxylate;
3-chloro-N,N-dimethyl-4-(2-(1-methyl-1H-pyrazol-4-yl)-1H-pyrrolo[3,2-c]pyridin-6-ylamino)benzenesulfonamide;
tert-butyl 6-(2-chloro-4-(N,N-dimethylsulfamoyl)phenylamino)-2-(1-methyl-1H-pyrazol-4-yl)-1H-pyrrolo[3,2-c]pyridine-1-carboxylate;
tert-butyl 6-(2-chloro-4-(2-oxopyrrolidin-1-yl)phenylamino)-2-(1-methyl-1H-pyrazol-4-yl)-1H-pyrrolo[3,2-c]pyridine-1-carboxylate;
2-(4-(6-(2,4-dimethoxyphenylamino)-1H-pyrrolo[3,2-c]pyridin-2-yl)-1H-pyrazol-1-yl)-N,N-dimethylacetamide;
3-chloro-4-(3-chloro-2-(1-methyl-1H-pyrazol-4-yl)-1H-pyrrolo[3,2-c]pyridin-6-ylamino)-N,N-dimethylbenzamide;
N-(2-methoxy-4-(thiomorpholinomethyl)phenyl)-2-(1-methyl-1H-pyrazol-4-yl)-1H-pyrrolo[3,2-c]pyridin-6-amine-S,S-dioxide;
(3-methoxy-4-(2-(1-methyl-1H-pyrazol-4-yl)-1H-pyrrolo[3,2-c]pyridin-6-ylamino)phenyl)(thiomorpholino)methanone-S,S-dioxide;
N-(2-chloro-4-(methylsulfonyl)phenyl)-2-(1H-pyrazol-4-yl)-1H-pyrrolo[3,2-c]pyridin-6-amine;
4-methoxy-N,N-dimethyl-3-(2-(1-methyl-1H-pyrazol-4-yl)-1H-pyrrolo[3,2-c]pyridin-6-ylamino)benzamide;
N,N-dimethyl-4-(2-(1-methyl-1H-pyrazol-4-yl)-1H-pyrrolo[3,2-c]pyridin-6-ylamino)-3-(trifluoromethoxy)benzamide
3-chloro-N-methyl-4-(2-(1-methyl-1H-pyrazol-4-yl)-1H-pyrrolo[3,2-c]pyridin-6-ylamino)benzamide;
3-methoxy-N-methyl-4-(2-(1-methyl-1H-pyrazol-4-yl)-1H-pyrrolo[3,2-c]pyridin-6-ylamino)benzamide;
N-(2-fluoro-4-methoxyphenyl)-2-(1-methyl-1H-pyrazol-4-yl)-1H-pyrrolo[3,2-c]pyridin-6-amine;
N-(2-methoxy-4-(trifluoromethyl)phenyl)-2-(1-methyl-1H-pyrazol-4-yl)-1H-pyrrolo[3,2-c]pyridin-6-amine;
N-(2-chloro-4-(difluoromethoxy)phenyl)-2-(1-methyl-1H-pyrazol-4-yl)-1H-pyrrolo[3,2-c]pyridin-6-amine;
N-(2-methoxypyridin-3-yl)-2-(1-methyl-1H-pyrazol-4-yl)-1H-pyrrolo[3,2-c]pyridin-6-amine;
N-(4-fluoro-2-methoxyphenyl)-2-(1-methyl-1H-pyrazol-4-yl)-1H-pyrrolo[3,2-c]pyridin-6-amine;
N-(2-methoxyphenyl)-2-(1-(2,2,2-trifluoroethyl)-1H-pyrazol-4-yl)-1H-pyrrolo[3,2-c]pyridin-6-amine;
N-(2-chloro-4-(methylsulfonyl)phenyl)-2-(1-methyl-1H-pyrazol-4-yl)-1H-pyrrolo[3,2-c]pyridin-6-amine;
3-methoxy-4-((2-(1-methyl-1H-pyrazol-4-yl)-1H-pyrrolo[3,2-c]pyridin-6-yl)amino)-N-(1-methylpiperidin-4-yl)benzamide;
N-(2-chloro-4-fluorophenyl)-2-(1-methyl-1H-pyrazol-4-yl)-1H-pyrrolo[3,2-c]pyridin-6-amine;
N-(2-chloro-4-(1H-1,2,4-triazol-1-yl)phenyl)-2-(1-methyl-1H-pyrazol-4-yl)-1H-pyrrolo[3,2-c]pyridin-6-amine;
2-(1-(difluoromethyl)-1H-pyrazol-4-yl)-N-(2-methoxyphenyl)-1H-pyrrolo[3,2-c]pyridin-6-amine;
3-methoxy-N,N-dimethyl-4-(2-(1-methyl-1H-pyrazol-4-yl)-1H-pyrrolo[3,2-c]pyridin-6-ylamino)benzamide;
3-chloro-N,N-dimethyl-4-(2-(1-methyl-1H-pyrazol-4-yl)-1H-pyrrolo[3,2-c]pyridin-6-ylamino)benzamide;
N-(2,4-dimethoxyphenyl)-2-(1-((5-methylisoxazol-3-yl)methyl)-1H-pyrazol-4-yl)-1H-pyrrolo[3,2-c]pyridin-6-amine;
1-(4-(4-(2-(1H-pyrazol-4-yl)-1H-pyrrolo[3,2-c]pyridin-6-ylamino)phenyl)piperazin-1-yl)ethanone;
N-(4-(morpholinomethyl)phenyl)-2-(1H-pyrazol-4-yl)-1H-pyrrolo[3,2-c]pyridin-6-amine;
N-(4-(2-methoxyethoxy)phenyl)-2-(1H-pyrazol-4-yl)-1H-pyrrolo[3,2-c]pyridin-6-amine;
N-(4-((1H-pyrazol-1-yl)methyl)phenyl)-2-(1H-pyrazol-4-yl)-1H-pyrrolo[3,2-c]pyridin-6-amine, N-(4-(2-morpholinoethoxy)phenyl)-2-(1H-pyrazol-4-yl)-1H-pyrrolo[3,2-c]pyridin-6-amine;
2-(1H-pyrazol-4-yl)-N-(4-(thiomorpholinomethyl)phenyl)-1H-pyrrolo[3,2-c]pyridin-6-amine-S,S-dioxide;
4-(2-(1H-pyrazol-4-yl)-1H-pyrrolo[3,2-c]pyridin-6-ylamino)benzonitrile;
N-(3,4-dimethoxyphenyl)-1-methyl-2-(1H-pyrazol-4-yl)-1H-pyrrolo[3,2-c]pyridin-6-amine;
N-(2-methoxyphenyl)-2-(1-methyl-1H-pyrazol-4-yl)-1H-pyrrolo[3,2-c]pyridin-6-amine;
4-(2-(1H-pyrazol-4-yl)-1H-pyrrolo[3,2-c]pyridin-6-ylamino)-N,N-dimethylbenzenesulfonamide;
N-(2-ethoxyphenyl)-2-(1H-pyrazol-4-yl)-1H-pyrrolo[3,2-c]pyridin-6-amine;
4-(2-(1H-pyrazol-4-yl)-1H-pyrrolo[3,2-c]pyridin-6-ylamino)-N,N-dimethylbenzamide;
2-(1H-pyrazol-4-yl)-N-(2-(trifluoromethyl)phenyl)-1H-pyrrolo[3,2-c]pyridin-6-amine;
N-(2-chloro-4-methoxyphenyl)-2-(1H-pyrazol-4-yl)-1H-pyrrolo[3,2-c]pyridin-6-amine;
N-(2,4-dimethoxyphenyl)-2-(1H-pyrazol-4-yl)-1H-pyrrolo[3,2-c]pyridin-6-amine;
N-(2-methoxyphenyl)-2-(1H-pyrazol-4-yl)-1H-pyrrolo[3,2-c]pyridin-6-amine;
N-(2-methoxy-4-(1-methylpiperidin-4-yloxy)phenyl)-2-(1H-pyrazol-4-yl)-1H-pyrrolo[3,2-c]pyridin-6-amine;
N-(4-methoxyphenyl)-2-(1H-pyrazol-4-yl)-1H-pyrrolo[3,2-c]pyridin-6-amine;
N-(5-fluoropyridin-2-yl)-2-(1H-pyrazol-4-yl)-1H-pyrrolo[3,2-c]pyridin-6-amine;
N-(4-fluorophenyl)-1-(methylsulfonyl)-2-(1H-pyrazol-4-yl)-1H-pyrrolo[3,2-c]pyridin-6-amine,
tert-butyl 2-(1-(tert-butoxycarbonyl)-1H-pyrazol-4-yl)-6-(p-tolylamino)-1H-pyrrolo[3,2-c]pyridine-1-carboxylate;
2-(1H-pyrazol-4-yl)-N-(4-(trifluoromethyl)phenyl)-1H-pyrrolo[3,2-c]pyridin-6-amine;
N-(4-fluorophenyl)-2-(1H-pyrazol-4-yl)-1H-pyrrolo[3,2-c]pyridin-6-amine;
N-(3,4-dimethoxyphenyl)-2-(1H-pyrazol-4-yl)-1H-pyrrolo[3,2-c]pyridin-6-amine;
tert-butyl-6-(2-chloro-4-(2-oxopyrrolidin-1-yl)phenylamino)-2-(1-methyl-1H-pyrazol-4-yl)-1H-pyrrolo[3,2-c]pyridine-1-carboxylate;
tert-butyl 6-(2-methoxy-4-(thiomorpholinomethyl)phenylamino)-2-(1-methyl-1H-pyrazol-4-yl)-1H-pyrrolo[3,2-c]pyridine-1-carboxylate-S,S-dioxide;
tert-butyl 6-(2-methoxy-4-(thiomorpholine-4-carbonyl)phenylamino)-2-(1-methyl-1H-pyrazol-4-yl)-1H-pyrrolo[3,2-c]pyridine-1-carboxylate-S,S-dioxide;
tert-butyl-6-(2-chloro-4-(methylcarbamoyl)phenylamino)-2-(1-methyl-1H-pyrazol-4-yl)-1H-pyrrolo[3,2-c]pyridine-1-carboxylate;
tert-butyl-6-(2-methoxy-4-(methylcarbamoyl)phenylamino)-2-(1-methyl-1H-pyrazol-4-yl)-1H-pyrrolo[3,2-c]pyridine-1-carboxylate;
tert-butyl 6-((2-fluoro-4-methoxyphenyl)amino)-2-(1-methyl-1H-pyrazol-4-yl)-1H-pyrrolo[3,2-c]pyridine-1-carboxylate;
tert-butyl 6-((2-methoxy-4-(trifluoromethyl)phenyl)amino)-2-(1-methyl-1H-pyrazol-4-yl)-1H-pyrrolo[3,2-c]pyridine-1-carboxylate;
tert-butyl-6-(2-chloro-4-(difluoromethoxy)phenylamino)-2-(1-methyl-1H-pyrazol-4-yl)-1H-pyrrolo[3,2-c]pyridine-1-carboxylate;
tert-butyl 6-(2-methoxypyridin-3-ylamino)-2-(1-methyl-1H-pyrazol-4-yl)-1H-pyrrolo[3,2-c]pyridine-1-carboxylate;
tert-butyl 6-((4-fluoro-2-methoxyphenyl)amino)-2-(1-methyl-1H-pyrazol-4-yl)-1H-pyrrolo[3,2-c]pyridine-1-carboxylate;
tert-butyl 6-(2-methoxyphenylamino)-2-(1-(2,2,2-trifluoroethyl)-1H-pyrazol-4-yl)-1H-pyrrolo[3,2-c]pyridine-1-carboxylate;
tert-butyl-6-(2-chloro-4-(methylsulfonyl)phenylamino)-2-(1-methyl-1H-pyrazol-4-yl)-1H-pyrrolo[3,2-c]pyridine-1-carboxylate;
tert-butyl 6-(2-methoxy-4-(1-methylpiperidin-4-ylcarbamoyl)phenylamino)-2-(1-methyl-1H-pyrazol-4-yl)-1H-pyrrolo[3,2-c]pyridine-1-carboxylate;
tert-butyl-6-(2-chloro-4-fluorophenylamino)-2-(1-methyl-1H-pyrazol-4-yl)-1H-pyrrolo[3,2-c]pyridine-1-carboxylate;
tert-butyl-6-(2-chloro-4-(1H-1,2,4-triazol-1-yl)phenylamino)-2-(1-methyl-1H-pyrazol-4-yl)-1H-pyrrolo[3,2-c]pyridine-1-carboxylate;
tert-butyl 2-(1-(difluoromethyl)-1H-pyrazol-4-yl)-6-(2-methoxyphenylamino)-1H-pyrrolo[3,2-c]pyridine-1-carboxylate;
or a pharmaceutically acceptable salt or solvate thereof.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl) amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess Mps1 kinase inhibitory activity.

The present invention also encompasses compounds of the invention as defined herein which comprise one or more isotopic substitutions. For example, H may be in any isotopic form, including $^1$H, $^2$H(D), and $^3$H (T); C may be in any isotopic form, including $^{12}$C, $^{13}$C, and $^{14}$C; and O may be in any isotopic form, including $^{16}$O and $^{18}$O; and the like.

It is also to be understood that certain compounds of the invention may exist in solvated as well as unsolvated forms such as, for example, hydrated forms. It is to be understood that the invention encompasses all such solvated forms that possess Mps1 kinase inhibitory activity.

It is also to be understood that certain compounds of the invention may exhibit polymorphism, and that the invention encompasses all such forms that possess Mps1 kinase inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

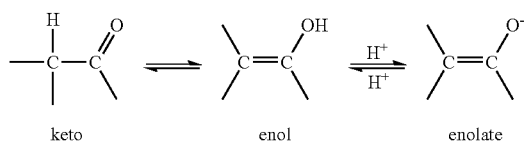

keto      enol      enolate

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenyl-methyl esters such as 5-methyl-2-oxo-1,3-dioxolen-4-ylm-ethyl esters and $C_{1-6}$alkoxycarbonyloxy-$C_{1-6}$alkyl esters such as methoxycarbonyloxymethyl and 1-methoxycarbonyloxy-ethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-$(C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-$(C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

In a particular aspect, the present invention provides a method of synthesising a compound of the formula I, or a pharmaceutically acceptable salt or solvate thereof, the method comprising:

a) reacting an intermediate of formula A:

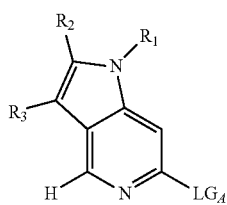

Formula A wherein $R_1$, $R_2$, and $R_3$ each have any one of the meanings as defined hereinbefore, and $LG_A$ is a suitable leaving group; with an intermediate of formula B:

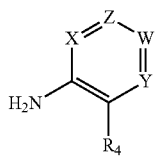

Formula B wherein $R_4$, X, Z, W, and Y have any one of the definitions set out hereinbefore; and b) optionally thereafter, and if necessary:
  i) removing any protecting groups present;
  ii) converting the compound formula I into another compound of formula I; and/or
  iii) forming a pharmaceutically acceptable salt or solvate thereof.

$LG_A$ may be any suitable leaving group. Suitably $LG_A$ is a halogen or any other suitable leaving group (e.g. trifluoromethylsulphonate etc.). Suitably $LG_A$ may be chlorine or bromine.

Suitably the coupling reaction between intermediate A and intermediate B may take place in the presence of a suitable solvent. Any suitable solvent or solvent mixture may be used for this reaction. A person skilled in the art will know how to select suitable solvents or solvent mixtures for use in these reactions. An example of a suitable solvent is dioxane or DMA.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 40 to 120° C. or, more suitably 60 to 100° C., for a suitable time period of, for example, 2 hours to 7 days, or more suitably 2 to 10 hours.

Suitably the coupling reaction between intermediate A and intermediate B may take place in the presence of a catalyst, suitably a palladium-derived catalyst, such as $Pd_2(dba)_3$.

Suitably the coupling reaction between intermediate A and intermediate B may take place in the presence of an organophosphorus compound, suitably an organophosphorus compound which serves as a suitable ligand to the catalyst. The organophosphorus compound may suitably be a phosphine-derivative, such as Xantphos.

Suitably the coupling reaction between intermediate A and intermediate B may take place in the presence of a base, for example a metal carbonate, such as cesium carbonate.

The resultant compound of formula I can be isolated and purified using techniques well known in the art.

The process defined herein may further comprise the step of subjecting the compound of formula I to a salt exchange, particularly in situations where the compound of formula I is formed as a mixture of different salt forms. The salt exchange suitably comprises immobilising the compound of formula I on a suitable solid support or resin, and eluting the compounds with an appropriate acid to yield a single salt of the compound of formula I.

The intermediate of formula A can be prepared by processes known in the art, suitably by processes described herein with reference to the examples.

The intermediate of formula B can be prepared by processes known in the art, suitably by processes described herein with reference to the examples.

In a particular embodiment, the intermediate of formula A is prepared by reacting an intermediate of formula C:

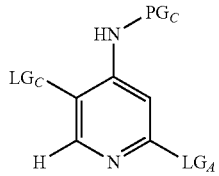

Formula C wherein $PG_C$ is a suitable protecting group or is $R_1$ has any one of the meanings as defined hereinbefore, and $LG_A$ and $LG_C$ are each suitable leaving groups;
with an intermediate of formula D:

Formula D wherein $R_2$ has any one of the meanings as defined hereinbefore.

$LG_C$ is suitably different to $LG_A$. $LG_C$ is suitably more reactive towards the compound of Formula D under appropriate reaction conditions than $LG_A$ such that the reaction between compounds of formula C and D gives selectivity for $LG_C$ in preference to $LG_A$ substitution. In an embodiment, $LG_C$ is a heavier halogen to that of $LG_A$. $LG_C$ is suitably iodo.

The reaction between intermediate C and intermediate D will take place in the presence of a suitable solvent. Any suitable solvent or solvent mixture may be used for this reaction. A person skilled in the art will know how to select suitable solvents or solvent mixtures for use in these reactions. Suitably the solvent is a polar solvent, such as N,N-dimethylformamide.

A person skilled in the art will also be able to select appropriate reaction conditions to use in order to facilitate this reaction. Suitably, the reaction is carried out in anhydrous conditions and in the presence of an inert atmosphere, such as argon or nitrogen. The reaction is also suitably carried out an elevated temperature, suitably within the range of 30 to 100°

C. or, more suitably 40 to 80° C. for a suitable time period of, for example, 2 hours to 7 days, or more suitably 2 to 10 hours.

Suitably the coupling reaction between intermediate C and intermediate D may take place in the presence of a catalyst, suitably a palladium-derived catalyst, suitably (PPh$_3$)$_2$PdCl$_2$.

Suitably the coupling reaction between intermediate C and intermediate D may take place in the presence of an additional metal compound, suitably an oxidisable metal compound, suitably copper(I) iodide.

Suitably the coupling reaction between intermediate C and intermediate D may take place in the presence of a base, suitably an organic base such as an amine, suitably triethylamine.

Preparing the intermediate of formula A may suitably additionally comprise an intramolecular cyclisation step to form an aza-indole. The cyclisation step may comprise treating the product of the reaction between intermediate C and intermediate D with a base, suitably an organic base, such as DBU or a base such as potassium tertiary butoxide (tBuOK), sodium hexamethyldisilazide (NaHMDS) or potassium hexamethyldisilazide (KHMDS).

The resultant compound of formula A can be isolated and purified using techniques well known in the art.

The intermediates defined by formulas A, B, C, and D, are suitably in structural conformity with those set forth above in relation to formulas I, IIa, IIb, IIIa, IIIb, IV, V, VI, VII and VIII, and R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, W, X, Y, and Z may be chosen accordingly.

In a further aspect of the invention, there is provided a compound of formula I obtainable by a process as defined herein.

In a further aspect of the invention, there is provided a compound of formula I obtained by process as defined herein.

In a further aspect of the invention, there is provided a compound of formula I directly obtained by process as defined herein.

By way of example, compounds of formula I (in which R$_1$, R$_3$ and R$_4$ are H; R$_2$ is pyrazol-4-yl; and one of W, X, Y and Z is CR$_5$ and the others are CH) are synthesised based on the synthetic methodology exemplified in Scheme I below, wherein intermediate 4 was prepared as per Scheme II.

In another approach, compounds of formula I are synthesised based on the synthetic methodology exemplified in Schemes IIIa and IIIb, again wherein intermediate 4 was prepared as per Scheme II.

In another approach, compounds of the formula I in which R2 is 1-methylpyrazol-4-yl are synthesised based upon the synthetic methodology to intermediate 23 exemplified in Scheme IV below, wherein intermediate 1 is prepared as per Scheme II and intermediate 8 is prepared as per Scheme IIIa.

In another approach, compounds of the formula I in which R1 is the group —C(O)—O—R$^a$ and R2 is 1-methylpyrazol-4-yl are synthesised based upon the synthetic methodology to intermediate of Formula E exemplified in Scheme V below, wherein intermediate 5 is prepared as per Scheme IIIa and intermediate 20 is prepared as per Scheme IV.

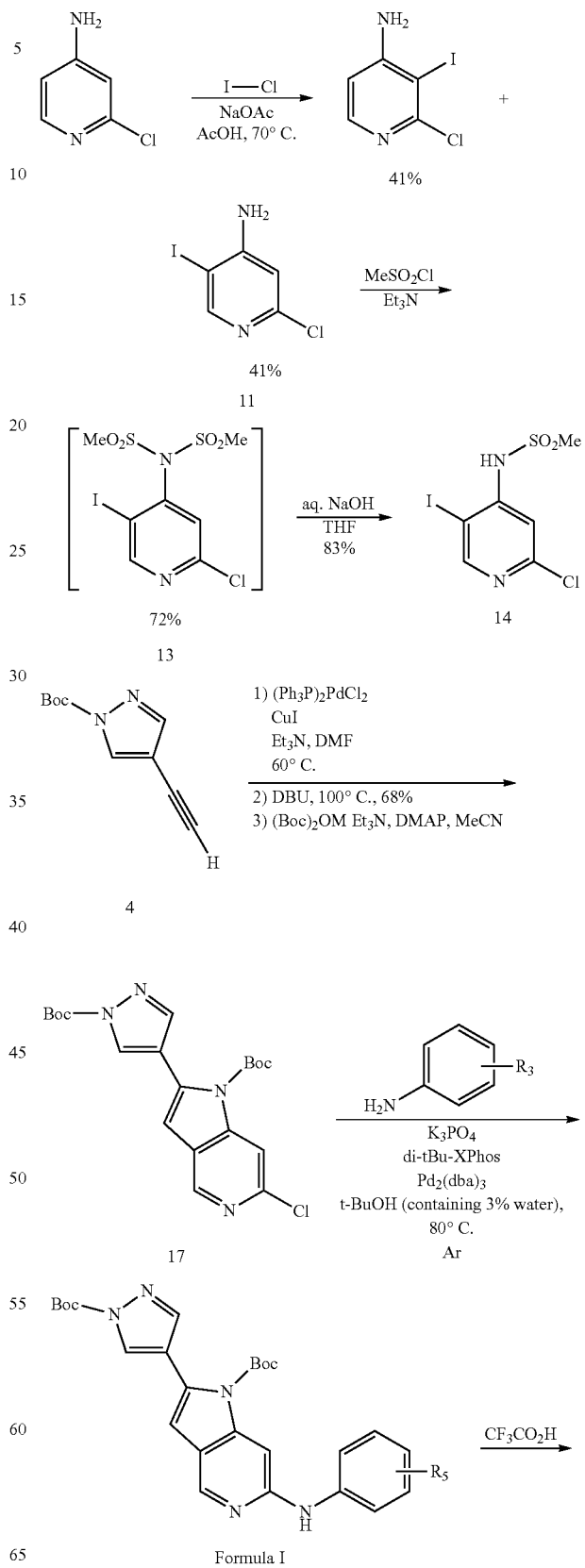

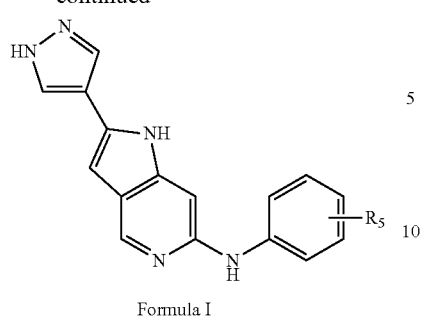

Scheme IIIb
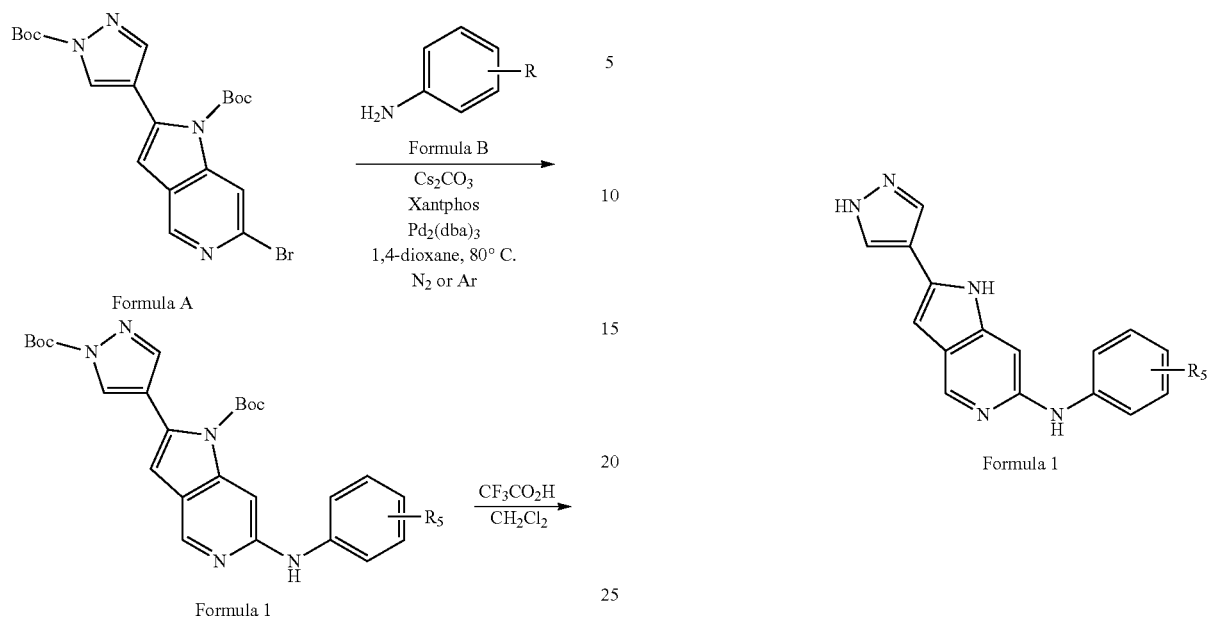
Scheme IV
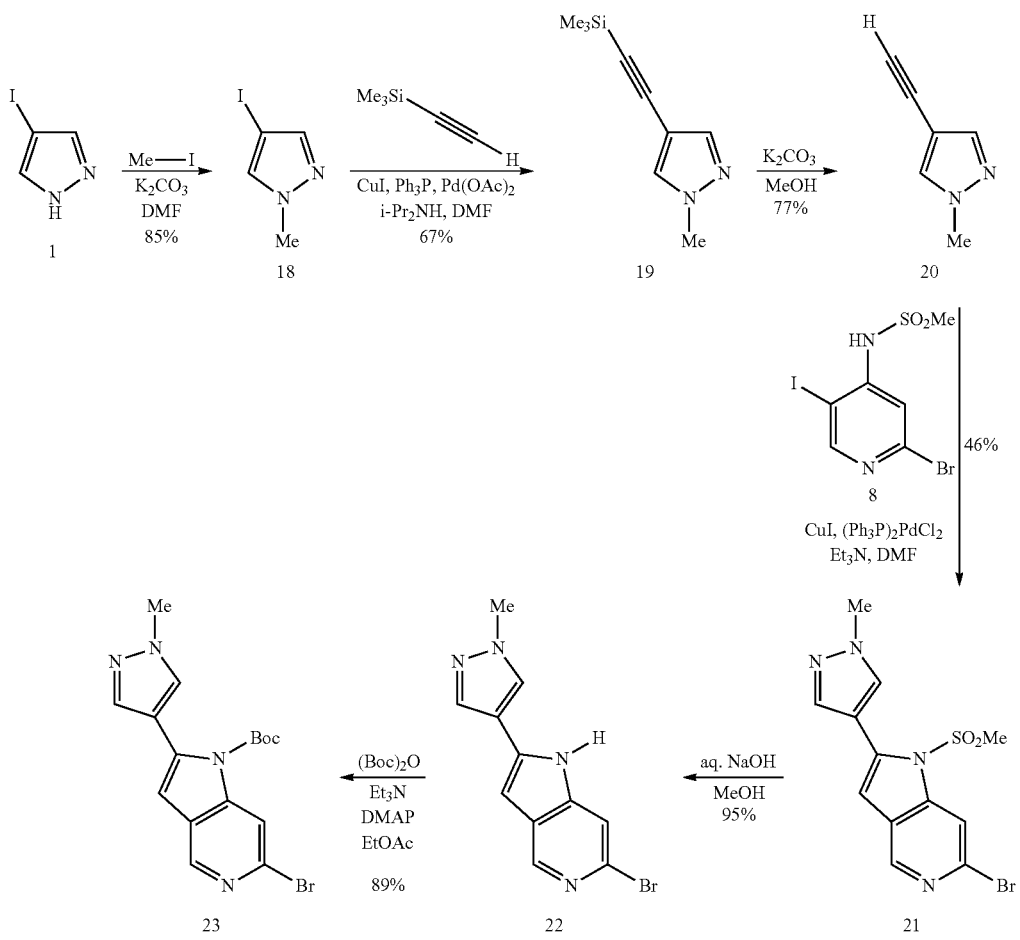

Scheme V

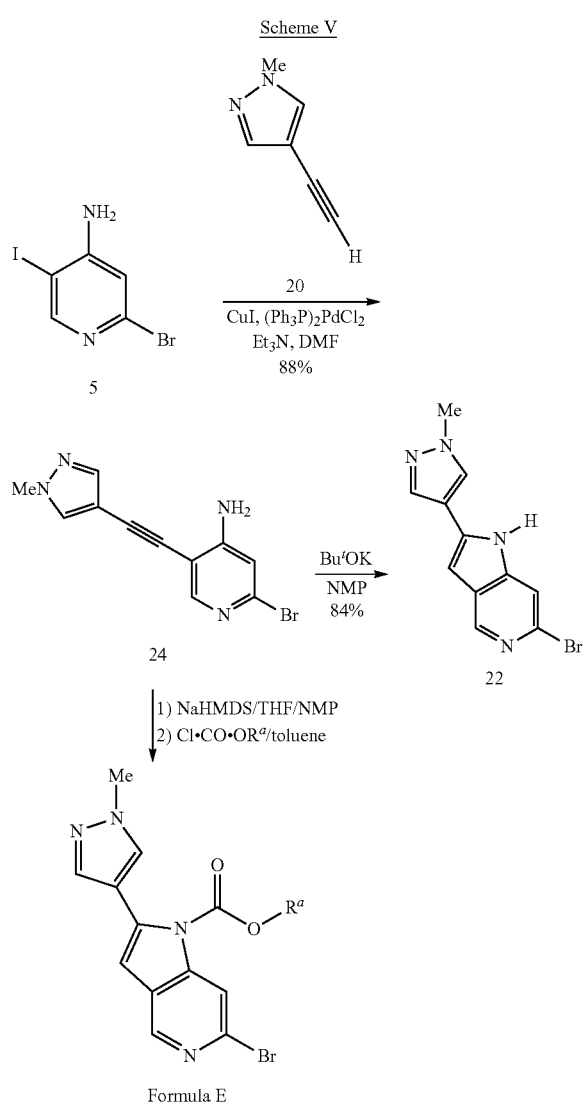

Formula E

Biological Activity

The following biological assays may be used to measure the pharmacological effects of the compounds of the present invention.

Measurement of Inhibition of MPS1 Kinase

The enzyme reaction (total volume 10 μl) was carried out in black 384-well low volume plates containing full length MPS1 (12.5 nM or 3 nM), fluorescent labelled peptide [known as H236, which has the sequence: 5FAM-DHTG-FLTEYVATR-CONH$_2$] (5 μM), ATP (10 μM), either DMSO (1% v/v) or the test compound (in the range 0.25 nM-100 μM in 1% DMSO) and assay buffer (50 mM HEPES (pH 7.0), 0.02% NaN$_3$, 0.01% BSA, 0.1 mM Orthovandate, 10 μM MgCl$_2$, 1 μM DTT, Roche protease inhibitor). The reaction was carried out for 60 min at room temperature and stopped by the addition of buffer (10 μl) containing 20 mM EDTA, 0.05% (v/v) Brij-35, in 0.1M HEPES-buffered saline (Free acid, Sigma, UK). The plate was read on a Caliper EZ reader II (Caliper Life Sciences).

The reader provides a Software package ('Reviewer') which converts the peak heights into % conversion by measuring both product and substrate peak and also allows selection of control well which represent 0% and 100% inhibition respectively. The % inhibition of the compounds is calculated relative to the means of selected control wells. IC$_{50}$s are determined by testing the compounds at a range of concentrations from 0.25 nM-100 μM. The % inhibitions at each concentration are then fitted to a 4 parameter logistic fit:

$$y=(a+((b-a)/(1+((c/x)^d))))$$

where a=asym min, b=asym max, c=IC$_{50}$ and d=hill coefficient

In general, activity possessed by compounds of the formula I, may be demonstrated in the inhibition assay by a IC$_{50}$ value of less than 15 μM. Suitably compounds have an IC$_{50}$ value of less than 10 μM, suitably less than 1 μM, suitably less than 0.1 μM, and suitably less than 0.01 μM (i.e. less than 10 nM).

The activities of compounds of the invention in the above assay are shown in the accompanying example section. Named compounds for which no example number is shown were purchased as a library of compounds (Libraries SFK01-57, FFK01-03, and SFK58-60) from BioFocus DPI (A Galapagos Company).

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In one aspect, the present invention provides a compound of Formula I, or a pharmaceutically acceptable salt or solvate thereof, or a pharmaceutical composition as defined herein for use in therapy.

The compounds of the invention are capable of inhibiting Mps1 kinase activity. Thus, in another aspect, the present invention provides a method of inhibiting Mps1 kinase activity in a cell, the method comprising administering to said cell compound of formula I as defined herein, or a pharmaceutically acceptable salt or solvate thereof.

In a further aspect, the present invention provides a method of inhibiting Mps1 kinase in vitro or in vivo, said method comprising contacting a cell with an effective amount of a compound, or a pharmaceutically acceptable salt or solvate thereof, as defined herein.

In another aspect, the present invention provides a method of inhibiting Mps1 kinase activity in a human or animal subject in need of such inhibition, the method comprising administering to said subject an effective amount of a compound of formula I as defined herein, or a pharmaceutically acceptable salt or solvate thereof.

In another aspect, the present invention provides a compound of formula I as defined herein, or a pharmaceutically acceptable salt or solvate thereof for use in the treatment of disease or condition associated with Mps1 kinase activity.

In another aspect, the present invention provides the use of a compound of formula I as defined herein, or a pharmaceutically acceptable salt or solvate thereof, in the manufacture of a medicament for use in the treatment of disease or condition associated with Mps1 kinase activity.

In yet another aspect, the present invention provides a method of treating a proliferative disorder in a human or animal subject, the method comprising administering to said subject a therapeutically acceptable amount of a compound of formula I as defined herein, or a pharmaceutically acceptable salt or solvate thereof.

In yet another aspect, the present invention provides a compound of formula I as defined herein, or a pharmaceutically acceptable salt or solvate thereof, for use in the treatment of a proliferative disorder.

In yet another aspect, the present invention provides the use of a compound of formula I as defined herein, or a pharmaceutically acceptable salt or solvate thereof, in the manufacture of a medicament for use in the treatment of a proliferative disorder.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers by virtue of their Mps1 kinase inhibitory properties.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Therefore, in another aspect, the present invention provides a compound, or a pharmaceutically acceptable salt or solvate thereof, or a pharmaceutical composition as defined herein for use in the treatment of cancer.

In yet another aspect, the present invention provides the use of a compound, or a pharmaceutically acceptable salt or solvate thereof, as defined herein in the manufacture of a medicament for use in the treatment of cancer.

In yet another aspect, the present invention provides a method of treating cancer in a patient in need of such treatment, said method comprising administering to said patient a therapeutically effective amount of a compound, or a pharmaceutically acceptable salt or solvate thereof, or a pharmaceutical composition as defined herein.

The invention further provides a method of treatment of the human or animal body, the method comprising administering to a subject in need of treatment a therapeutically-effective amount of an active compound, preferably in the form of a pharmaceutical composition.

Routes of Administration

The compounds of the invention or pharmaceutical composition comprising the active compound may be administered to a subject by any convenient route of administration, whether systemically/peripherally or topically (ie. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; and (x) immunotherapy approaches, including for example exvivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and another anti-tumour agent.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and any one of the anti-tumour agents listed under (i)-(ix) above.

In a further aspect of the invention there is provided a compound of the invention or a pharmaceutically acceptable salt or solvate thereof, in combination with an anti-tumour agent selected from one listed under (i)-(ix) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with an anti-tumour agent selected from one listed under (i)-(ix) herein above, in association with a pharmaceutically acceptable diluent or carrier.

EXAMPLES

General Experimental

Commercially available starting materials, reagents and dry solvents were used as supplied. Flash column chromatography was performed using Merck silica gel 60 (0.025-0.04 mm). Column chromatography was also performed on a FlashMaster personal unit using isolute Flash silica columns or a Biotage SP1 purification system using Merck or Biotage Flash silica cartridges. Preparative TLC was performed on Analtech or Merck plates. Ion exchange chromatography was performed using acidic Isolute Flash SCX-II columns, Isolute Si-carbonate columns or basic isolute Flash $NH_2$ columns. Preparative HPLC was conducted using a Phenomenex Luna column (5 μm, 250×21.2 mm, C18, Phenomenex, Torrance, USA) using a Gilson GX-281 Liquid Handler system combined with a Gilson 322 HPLC pump (Gilson, Middleton, USA), over a 15 minute gradient elution (Grad15mins20mls·m) from 10:90 to 100:0 methanol:water (both modified with 0.1% formic acid) at a flow rate of 20 mL/min. or over a 15 minute gradient elution (Grad15mins20 ml·m) from 40:60 to 100:0 methanol:water (both modified with 0.1% formic acid) at a flow rate of 20 mL/min. UV-Vis spectra were acquired at 254 nm on a Gilson 156 UV-Vis detector (Gilson, Middleton, USA). Collection was triggered by UV signal, and collected using a Gilson GX-281 Liquid Handler system (Gilson, Middleton, USA). Raw data was processed using Gilson Trilution Software. $^1$H NMR spectra were recorded on a Bruker Avance-500. Samples were prepared as solutions in a deuterated solvent and referenced to the appropriate internal non-deuterated solvent peak or tetramethylsilane. Chemical shifts were recorded in ppm (δ) downfield of tetramethylsilane. LC/MS and HRMS analyses were performed on an Agilent 1200 series HPLC and diode array detector coupled to a 6210 time of flight mass spectrometer with dual multimode APCI/ESI source. Analytical separation was carried out at 30° C. either on a Merck Chromolith SpeedROD column (RP-18e, 50×4.6 mm) using a flow rate of 2 mL/min in a 4 minute gradient elution with detection at 254 nm or on a Merck Purospher STAR column (RP-18e, 30×4 mm) using a flow rate of 1.5 mL/min in a 4 minute gradient elution with detection at 254 nm. The mobile phase was a mixture of methanol (solvent A) and water (solvent B) both containing formic acid at 0.1%. Gradient elution was either: 1:9 (A/B) to 9:1 (A/B) over 2.5 min, 9:1 (A/B) for 1 min, and then reversion back to 1:9 (A/B) over 0.3 min, finally 1:9 (A/B) for 0.2 min (Default method also referred to as ESI-HRMS Method B in the experimental) or: 1:9 (A/B) to 9:1 (A/B) over 1 min, 9:1 (A/B) for 2.5 min, and then reversion back to 1:9 (A/B) over 0.3 min, finally 1:9 (A/B) for 0.2 min (also referred to as ESI-HRMS Method D in the experimental). The following references masses were used for HRMS analysis: caffeine [M+H]$^+$ 195.087652; (hexakis(1H,1H,3H-tetrafluoropentoxy)phosphazene [M+H]$^+$ 922.009798) and hexakis(2,2-difluoroethoxy)phosphazene [M+H]$^+$ 622.02896 or reserpine [M+H]$^+$ 609.280657. LC/MS analysis was also performed on a Waters Alliance 2795 Separations Module and Waters 2487 dual wavelength absorbance detector coupled to a Waters/Micromass LCt time of flight mass spectrometer with ESI source. Analytical separation was carried out at 30° C. either on a Merck Chromolith SpeedROD column (RP-18e, 50×4.6 mm) using a flow rate of 2 mL/min in a 4 minute gradient elution with detection at 254 nm or on a Merck Purospher STAR column (RP-18e, 30×4 mm) using a flow rate of 1.5 mL/min in a 4 minute gradient elution with detection at 254 nm. The mobile phase was a mixture of methanol (solvent A) and water (solvent B) both containing formic acid at 0.1%. Gradient elution was as follows: 1:9 (A/B) to 9:1 (A/B) over 2.25 min, 9:1 (A/B) for 0.75 min, and then reversion back to 1:9 (A/B) over 0.3 min, finally 1:9 (A/B) for 0.2 min. (Also referred to ESI-HRMS Method A in the experimental). LC/MS and HRMS analysis were also performed on an Agilent 1200 series HPLC and diode array detector coupled to a 6520 Quadrupole-Time of flight mass spectrometer with dual multimode APCI/ESI source. Analytical separation was carried out at 30° C. on a Merck Purospher STAR column (RP-18e, 30×4 mm) using a flow rate of 1.5 mL/min in a 4 minute gradient elution with detection at 254 nm. The mobile phase was a mixture of methanol (solvent A) and water (solvent B) both containing formic acid at 0.1%. Gradient elution was as follows: 1:9 (A/B) to 9:1 (A/B) over 2.5 min, 9:1 (A/B) for 1 min, and then reversion back to 1:9 (A/B) over 0.3 min, finally 1:9 (A/B) for 0.2 min. The following references masses were used for HRMS analysis: caffeine [M+H]$^+$ 195.087652; (hexakis(1H,1H,3H-tetrafluoropentoxy)phosphazene [M+H]$^+$ 922.009798) and hexakis(2,2-difluoroethoxy)phosphazene [M+H]$^+$ 622.02896 or reserpine [M+H]$^+$ 609.280657 (Also referred to as ESI-HRMS Method C in the experimental).

General Synthetic Routes and Preparation of Intermediates

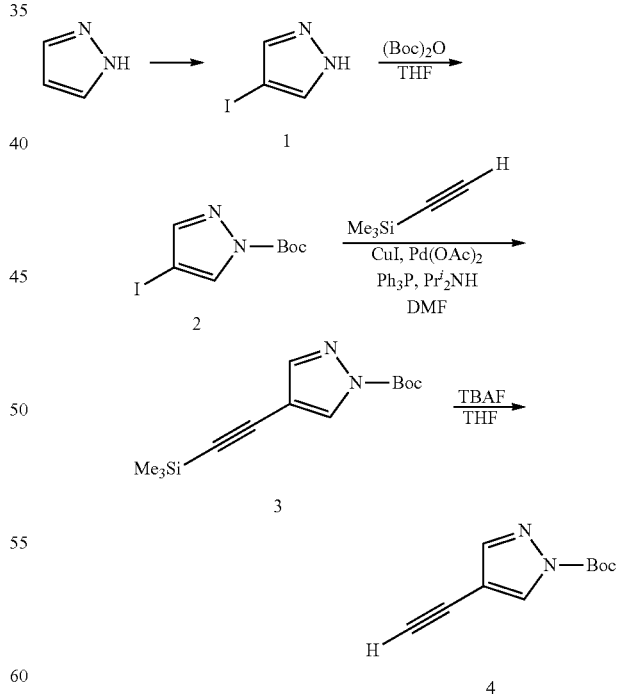

4-Iodopyrazole (1)

A mixture of iodic acid (3.6 g 20 mmole), iodine (10.2 g 40 mmole), 30% w/w sulfuric acid (4 mL) and acetic acid (30 mL) was stirred to give a solution/suspension. About half of this mix was added in portions to a solution of pyrazole (6.8 g, 100 mmole) in acetic acid (60 mL) maintained at 60° C. The colour was allowed to fade after each addition before adding the next aliquot. The rest of the solution/suspension was added in one portion and the mix stirred and heated at 60° C. for another 1.75 hours. The final mix still had an iodine colour. The reaction was cooled and added to saturated sodium hydrogen carbonate (100 mL). Sodium carbonate solution (200 ml of a 15% solution) was added carefully and then solid sodium carbonate was added until there was no more carbon dioxide evolved. The product was extracted with chloroform (3×60 mL) and the combined extracts were washed with water (50 mL). The extracts were dried and evaporated and the solid obtained was dried in vacuum over sodium hydroxide to give the title compound (17.4 g, 89%), spectroscopic data for which was consistent with data reported in G. Zoppellaro, A. Geiss, V. Enkelmann, M. Baumgarten, *Eur. J. Org. Chem.,* 2004, 2367-2374.

tert-Butyl 4-iodo-1H-pyrazole-1-carboxylate (2)

4-Iodopyrazole (1) (7.85 g 40.4 mmole) was dissolved in THF (120 mL) and triethylamine (8.5 mL, 6.12 g 60.5 mmole) and di-tert-butyl dicarbonate (9.7 g, 44.5 mmole) were added. The reaction was stirred at r.t. for 3 hours. The THF was evaporated and ethyl acetate (100 mL) was added. The solution was washed with water (2×50 mL) and with brine, then dried and evaporated to leave an oil (14.2 g). The crude product was purified by chromatography on a pad of silica in a sinter (10 cm diam, 6 cm thick) eluted with 10% ethyl acetate in cyclohexane (11×90 mL), then 20% ethyl acetate in cyclohexane (3×90 mL) to give the protected pyrazole 2 (11.66 g 98%). $^1$H-NMR (CDCl$_3$, 500 MHz): δ 1.68 (s, 9H), 7.73 (s, 1H), 8.17 (s, 1H).

tert-Butyl 4-((trimethylsilyl)ethynyl)-1H-pyrazole-1-carboxylate (3)

tert-Butyl 4-iodo-1H-pyrazole-1-carboxylate (2) (4.67 g 15.9 mmole) and trimethylsilyl acetylene (2.18 g, 22.2 mmole) were dissolved in DMF (22 mL) and placed under argon. Diisopropylamine (2.9 mL, 2.08 g, 20.7 mmole), copper(I) iodide (197 mg, 1.03 mmole), triphenylphosphine (832 mg, 3.18 mmole) and palladium acetate (239 mg, 1.06 mmole) were added and the flask was flushed again with argon. The reaction was heated at 60° C. for 1.25 hours. The reaction was cooled and added to water (220 mL). The product was extracted with ether (3×60 mL). The combined extracts were washed with water (3×50 mL) and with brine, then dried and evaporated. The crude product was flash chromatographed (silica, eluting with 10% ethyl acetate in cyclohexane) to give the title compound (3.88 g, 92%). $^1$H-NMR (CDCl$_3$, 500 MHz): δ 0.25 (s, 6H), 1.67 (s, 9H), 7.77 (d, J=0.63 Hz, 1H), 8.20 (d, J=0.63 Hz, 1H).

tert-Butyl 4-ethynyl-1H-pyrazole-1-carboxylate (4)

tert-Butyl 4-((trimethylsilyl)ethynyl)-1H-pyrazole-1-carboxylate (3) (3.88 g 14.69 mmole) was dissolved in THF (40 mL) and cooled to 0-5° C. A 1M solution of tetra-n-butylammonium fluoride in THF (16 mL, 16 mmole) was added and the reaction was stirred for 20 minutes. The THF was evaporated and the residue was taken up in ethyl acetate (50 mL) and washed with water (×2) and with brine, then dried and evaporated. The residue was purified on a flash column (silica, eluting with 15% ethyl acetate in cyclohexane) to give the title compound (1.765 g, 62%). $^1$H-NMR (CDCl$_3$, 500 MHz): δ 1.68 (s, 9H, 3.11 (s, 1H), 7.79 (s, 1H), 8.24 (s, 1H).

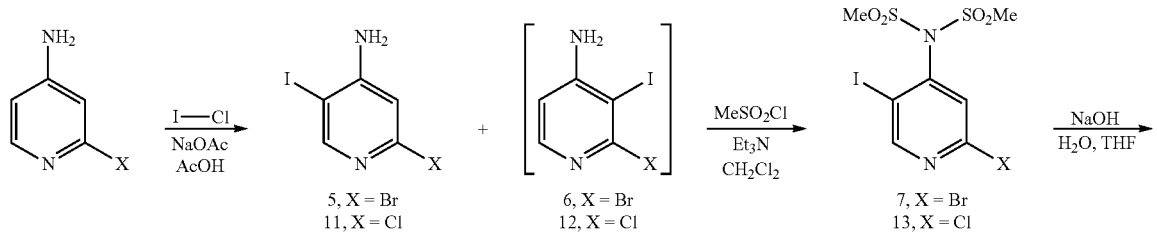

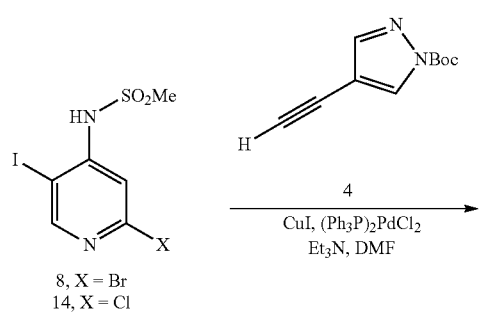

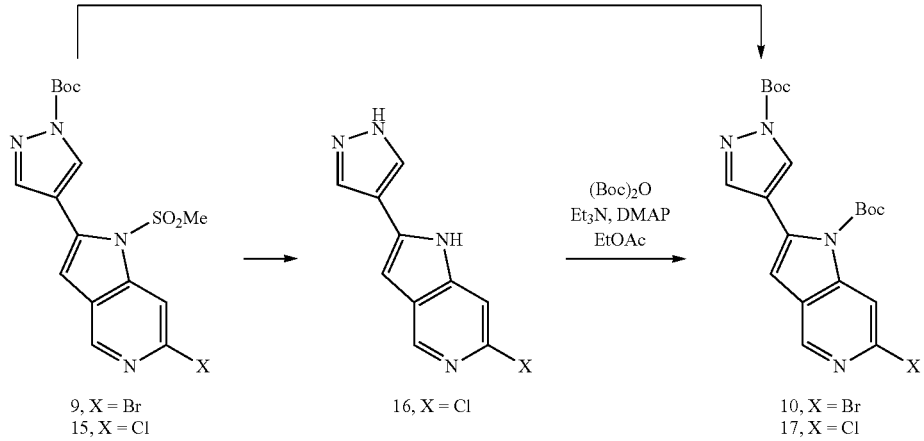

9, X = Br
15, X = Cl

16, X = Cl

10, X = Br
17, X = Cl

2-Bromo-5-iodopyridin-4-amine (5)

4-Amino-2-bromopyridine (22.8 g, 131.8 mmole) and sodium acetate (20.8 g 254 mmole) were stirred in acetic acid (82 mL) and a solution of iodine monochloride (1M in acetic acid, 134 mL, 134 mmole) was added. The mixture was stirred and heated at 75° C. for 3 hours. Most of the acetic acid was evaporated and the residue was partitioned between water (500 mL) and ethyl acetate (550 mL). The aqueous was again extracted with ethyl acetate (300 mL) The combined extracts were washed twice with 10% sodium carbonate solution (600, 300 mL), with 10% sodium thiosulfate solution (200 mL), with water and with brine, then dried and evaporated. This gave 40.3 g of a crude product mix. This was combined with the crude product from a reaction on 7.5 g of 4-amino-2-bromopyridine for purification. A large silica column (9 cm internal diameter with 28 cm bed of silica) was prepared in 5% ethyl acetate in dichloromethane. The crude material was applied in the same solvent. The column was eluted with 5% ethyl acetate in dichloromethane, with 10% ethyl acetate in dichloromethane and with 20% ethyl acetate in dichloromethane to give the desired isomer 5 (20.2 g, 38%): $^1$H-NMR (CDCl$_3$, 500 MHz): δ 4.74 (br s, 2H, NH$_2$), 6.80 (s, 1H), 8.34 (s, 1H); and subsequently with 1:1 ethyl acetate:dichloromethane to give 6 undesired isomer: 2-bromo-3-iodopyridin-4-amine 6 (19.3 g, 37%).

N-(2-Bromo-5-iodopyridin-4-yl)-N-(methylsulfonyl) methanesulfonamide (7)

4-Amino-2-bromo-5-iodopyridine (5) (3.055 g 10.2 mmol) was stirred in dichloromethane (34 mL) and triethylamine (6.9 mL, 4.97 g, 49.1 mmol) was added. The mix was cooled in ice. To the cold solution was added dropwise a solution of methanesulfonyl chloride (3.2 mL 4.66 g 40.6 mmol) in dichloromethane (11.5 mL) over a period of 14 minutes. The cold bath was removed and the reaction stirred at r.t. for 1.5 hours. The reaction was diluted with dichloromethane and washed twice with water. The solution was dried and evaporated. Trituration with ether gave a solid (5.01 g). The crude product was passed in 5% ethyl acetate in dichloromethane through a 2.5 cm pad of silica in a 10 cm diameter sinter to give the title compound (3.01 g, 64%). $^1$H-NMR (CDCl$_3$, 500 MHz): δ 3.60 (s, 6H), 7.53 (s, 1H), 8.89 (s, 1H).

N-(2-Bromo-5-iodopyridin-4-yl)methanesulfonamide (8)

N-(2-Bromo-5-iodopyridin-4-yl)-N-(methylsulfonyl) methanesulfonamide (7) (228 mg, 0.50 mmol) was stirred with THF (1.3 ml) and 10% sodium hydroxide in water (1.3 mL) at r.t. for 3 hours. The THF was evaporated and the aqueous was neutralised using 10% citric acid solution. The deposited white solid was filtered off and washed with water, then dried in a vacuum desiccator over sodium hydroxide to give the title compound (159 mg 84%). $^1$H-NMR (d$_6$-DMSO, 500 MHz): δ 3.29 (s, 3H), 7.54 (s, 1H), 8.64 (s, 1H)

tert-Butyl 4-(6-bromo-1-(methylsulfonyl)-1H-pyrrolo[3,2-c]pyridin-2-yl)-1H-pyrazole-1-carboxylate (9)

To a mixture of N-(2-bromo-5-iodopyridin-4-yl)methanesulfonamide (8) (419 mg, 1.11 mmol) and tert-butyl 4-ethynyl-1H-pyrazole-1-carboxylate (4) (277 mg, 1.44 mmol, 1.3 equiv) was added copper(I) iodide (7.4 mg 0.039 mmole) and DMF (4 mL), followed by triethylamine (0.69 mL, 497 mg, 4.92 mmole). The reaction was flushed twice with nitrogen. Bis(triphenylphosphine)palladium chloride (27 mg, 0.038 mmole) was added and the reaction flushed twice more with nitrogen, it was heated at 60° C. for 70 minutes. The reaction was added to water (40 mL) and extracted with ethyl acetate (3×20 mL). The combined extracts were washed with water (3×20 mL) and with brine, dried and evaporated. The residue was purified on four 2 mm 20×20 cm silica prep tlc plates, eluted with 3:1 ethyl acetate:cyclohexane. The product band was recovered with acetone giving the title compound (251 mg, 51%). $^1$H-NMR (CDCl$_3$, 500 MHz): δ 1.73 (s, 9H), 3.02 (s, 3H), 6.81 (s, 1H), 7.97 (s, 1H), 8.26 (s, 1H), 8.43 (s, 1H), 8.69 (s, 1H).

tert-Butyl 6-bromo-2-(1-(tert-butoxycarbonyl)-1H-pyrazol-4-yl)-1H-pyrrolo[3,2-c]pyridine-1-carboxylate (10)

tert-Butyl-4-(6-bromo-1-(methylsulfonyl)-1H-pyrrolo[3,2-c]pyridin-2-yl)-1H-pyrazole-1-carboxylate (9) (1.48 g 3.35 mmole) was stirred in THF (20 mL) and DBU (0.51 mL, 0.52 g 3.4 mmole) was added. The reaction was warmed at 40° C. for 1 hour. The reaction was cooled and THF evaporated. The residue was dissolved in ethyl acetate (50 mL) and washed with water (2×15 mL) and with brine, then dried and evaporated. ¹H-NMR of the residue revealed incomplete conversion. The material was redissolved in THF (20 mL) and DBU (0.3 ml) was added. The reaction was heated at 40° C. for 1.5 hours. Methanol (1 mL) was added and heating continued for 0.5 hour. The solution was evaporated and ethyl acetate (60 mL) added. The solution was washed with water (25 mL). The organic solution was washed again with water and with brine then dried and evaporated. ¹H-NMR of the residue revealed both demesylated and completely deprotected products. To this material was added ethyl acetate (20 mL), Di-t-butyl dicarbonate (1.11 g 5.1 mmole), followed by triethylamine (0.72 mL, 515 mg 5.1 mmole) and a crystal of DMAP. The reaction was stirred at r.t. for 1 hour, more di-t-butyl dicarbonate (414 mg 1.9 mmole) was added and stirring continued for 2 more hours. The solution was evaporated and residue kept at ambient temperature overnight. It was adsorbed from dichloromethane onto flash silica, packed onto a flash column made in 20% ethyl acetate in cyclohexane, eluted with this solvent then with 40% ethyl acetate in cyclohexane to give the title compound (1.2 g, 77%). ¹H-NMR (CDCl$_3$, 500 MHz): δ 1.58 (s, 9H), 1.69 (s, 9H), 6.67 (d, J=0.95 Hz, 1H), 7.84 (d, J=0.63 Hz, 1H), 8.24 (t, J=0.63 Hz, 1H), 8.27 (d, J=0.63 Hz, 1H), 8.61 (d, J=0.63 Hz, 1H).

4-Amino-2-chloro-5-iodopyridine (11)

4-Amino-2-chloropyridine (3.20 g 25 mmole) was stirred in acetic acid (20 mL) with sodium acetate (4.1 g 50 mmol) To the mixture was added a solution of iodine monochloride (4.1 g 25 mmol) in acetic acid (10 mL) and the reaction was heated at 70° C. for 3.5 h. Most of the acetic acid was evaporated and the reaction diluted with water (200 mL). The products were extracted with ethyl acetate (80, 70, 70 mL). The combined extracts were washed with 10% sodium carbonate solution (100 mL), with 5% sodium thiosulfate solution and with brine; then dried and evaporated. The crude product was purified by flash column chromatography on silica; eluting with 5% ethyl acetate in dichloromethane, with 10% ethyl acetate in dichloromethane and with 20% ethyl acetate in dichloromethane to give first a small amount of di-iodinated product (618 mg, 6.5%); then the desired product 4-amino-5-iodo-2-chloropyridine (11) (2.64 g, 41%) and then the isomeric 4-amino-4-chloro-3-iodopyridine (12) (2.61 g, 41%). 4-Amino-5-iodo-2-chloropyridine (11): ¹H-NMR (500 MHz, DMSO-d$_6$): 6.48 (br s, 2H), 6.63 (s, 1H), 8.19 (s, 1H). 4-Amino-2-chloro-3-iodopyridine (12): ¹H-NMR (500 MHz, DMSO-d$_6$): 6.50 (br s, 2H), 6.54 (d, J=5.36 Hz, 1H); 7.74 (d, J=5.68 Hz, 1H).

N-(2-Chloro-5-iodopyridin-4-yl)-N-(methylsulfonyl) methanesulfonamide (13)

4-Amino-2-chloro-5-iodopyridine (11) (1.01 g, 3.97 mmol) was dissolved in dichloromethane (8.5 mL) and triethylamine (2.48 mL, 1.78 g 17.6 mmol) was added. The suspension was cooled in an ice/water bath. A solution of methanesulfonyl chloride (1.56 mL, 2.31 g, 20.1 mmol) in dichloromethane (4.2 mL) was added dropwise. The reaction was stirred at room temperature for 100 min. More triethylamine (1.25 mL) was added to the reaction, which was then cooled in ice. To the cooled reaction was added dropwise a solution of methanesulfonyl chloride (0.78 mL, 1.15 g, 10 mmol) in dichloromethane (2.1 mL) and stirring at room temperature was continued for 16 h. The reaction was diluted with dichloromethane and washed twice with water. The residue was purified by flash chromatography eluting with dichloromethane, then 5% ethyl acetate in dichloromethane to give the title compound (13) (1.188 g 72%). ¹H-NMR (500 MHz, DMSO-d$_6$): 3.69 (s, 6H), 8.03 (s, 1H), 8.99 (s, 1H).

N-(2-Chloro-5-iodopyridin-4-yl)methanesulfonamide (14)

N-(2-chloro-5-iodopyridin-4-yl)-N-(methylsulfonyl) methanesulfonamide (13) (1.1 g) was stirred with THF (6.8 mL) and 10% sodium hydroxide (6.8 mL) at room temperature overnight. The THF was evaporated and the aqueous was brought to pH about 5 with 10% citric acid solution. Product was deposited—the mixture was cooled at 0-5° C. for 0.5 h and the product filtered off. It was washed with a little water and dried over sodium hydroxide in a vacuum desiccator to give the title compound (772 mg, 83%). ¹H-NMR (500 MHz, DMSO-d$_6$): 3.29 (s, 3H), 7.42 (s, 1H), 8.66 (s, 1H).

tert-Butyl 4-(6-chloro-1-(methylsulfonyl)-1H-pyrrolo[3,2-c]pyridin-2-yl)-1H-pyrazole-1-carboxylate (15)

Bis(triphenylphosphine)palladium dichloride (15.53 mg, 0.022 mmol) was added to a solution of N-(2-chloro-5-iodopyridin-4-yl)methanesulfonamide (14) (184.0 mg, 0.553 mmol), tert-butyl 4-ethynyl-1H-pyrazole-1-carboxylate (4) (160.0 mg, 0.830 mmol), triethylamine (347 μL, 2.49 mmol) and copper iodide (6.32 mg, 0.033 mmol) in anhydrous DMF (2.0 mL). The reaction mixture was heated at 60° C. for 1 h under microwave irradiation, then partitioned between water (60 mL) and EtOAc (60 mL). The aqueous layer was extracted with more EtOAc (2×60 mL), the combined extracts were washed with brine (2×40 mL), dried (Na$_2$SO$_4$) and concentrated in vacuo. The resulting residue was absorbed on silica gel (2.0 g) and the free-running powder was placed on a 20 g isolute silica column. Elution with dichloromethane and 1% ethanol in dichloromethane afforded the title compound (108 mg, 49%). ¹H-NMR (500 MHz, DMSO-d$_6$) 1.61 (s, 9H), 3.48 (s, 3H), 7.12 (d, J=0.6 Hz, 1H), 7.91 (br t, J=0.5 Hz, 1H), 8.07 (d, J=0.5 Hz, 1H), 8.61 (d, J=0.5 Hz, 1H), 8.78 (d, J=0.7 Hz, 1H).

6-Chloro-2-(1H-pyrazol-4-yl)-1H-pyrrolo[3,2-c]pyridine (16)

Bis(triphenylphosphine)palladium dichloride (23.30 mg, 0.033 mmol) was added to a solution of N-(2-chloro-5-iodopyridin-4-yl)methanesulfonamide (14) (276.0 mg, 0.83 mmol), tert-butyl 4-ethynyl-1H-pyrazole-1-carboxylate (4) (239.0 mg, 1.24 mmol), triethylamine (521 μL, 3.73 mmol) and copper iodide (7.90 mg, 0.041 mmol) in anhydrous DMF (3.0 mL). The reaction mixture was heated at 60° C. for 1 h under microwave irradiation (absorption:normal). To this reaction mixture, DBU (0.51 mL, 3.36 mmol) was added and the microwave vial was placed in an oil-bath preheated at 100° C., and then stirred at this temperature for 2.5 h. More DBU (0.08 mL) was added and stirring was continued at this temperature for an additional 45 min. The reaction mixture was poured in to 1M aqueous NH$_4$Cl (30 mL), extracted with EtOAc (3×50 mL). The combined organics were washed with brine (2×30 mL), dried (Na$_2$SO$_4$), filtered and concentrated under reduced pressure. The residue was triturated with dichloromethane (8.0 mL); the precipitate was collected by filtration and washed with dichloromethane to afford the product as a light brown solid, (0.129 g, 71%). ¹H-NMR (500

MHz, DMSO-d₆) 6.72 (dd, J=0.5, 1.5 Hz, 1H), 7.33 (t, J=0.85 Hz, 1H), 8.00 (br s, 1H), 8.24 (br s, 1H), 8.51 (s, 1H), 11.87 (s, 1H), 13.09 (s, 1H).

tert-Butyl-2-(1-(tert-butoxycarbonyl)-1H-pyrazol-4-yl)-6-chloro-1H-pyrrolo[3,2-c]pyridine-1-carboxylate (17)

To a mixture of 6-chloro-2-(1H-pyrazol-4-yl)-1H-pyrrolo[3,2-c]pyridine (16) (0.068 g, 0.31 mmol) in anhydrous acetonitrile (2.5 mL) was added di-tert-butyl dicarbonate (0.170 g, 0.78 mmol) followed by triethylamine (0.079 g, 0.11 mL, 0.78 mmol) and a crystal of DMAP (1.5 mg), a clear solution was obtained after a few minutes. The reaction mixture was stirred at room temperature for 1.5 h under argon. The solvent was removed in vacuo, the residue absorbed on silica (1.2 g) and the free-running powder was placed on a 10 g isolute silica column which was eluted with hexane and then 5%, 10%, 15%, and 20% EtOAc in hexane. The title compound was obtained as an oily residue which was solidified on standing (white solid; 77 mg, 52%). $^1$H-NMR (500 MHz, DMSO-d₆) 1.48 (s, 9H), 1.60 (s, 9H), 7.00 (d, J=0.4 Hz, 1H), 7.97 (s, 1H), 8.08 (s, 1H), 8.56 (s, 1H), 8.71 (d, J=0.5 Hz, 1H).

1-Methyl-4-iodopyrazole (18)

4-Iodopyrazole (1) (5.0 g 25.7 mmole) was dissolved in DMF (50 mL), potassium carbonate (4.26 g 30.9 mmoles) was added and stirred (2 mins) before iodomethane (1.76 mL, 4.01 g 28.3 mmole) was added. The reaction was stirred rapidly at r.t. for 17 hrs. It was filtered through a Celite pad. The filtrate was evaporated to a small volume, about 10 mL, using a rotary evaporator with a high vac. pump and the water bath at 60° C. Water (120 mL) was added to the residue. The filtered solids on the Celite pad were washed with ethyl acetate (50 ml) and these washings were used to extract the product from the aqueous. The aqueous was extracted with more ethyl acetate (2×50 mL). The combined organics were washed with water (3×30 mL) and with brine; dried and evaporated to give the title compound as a solid 4.56 g, 85%. $^1$H-NMR (CDCl₃, 500 MHz): δ 3.93 (s, 3H) 7.42 (s, 1H), 7.50 (s, 1H).

1-Methyl-4-((trimethylsilyl)ethynyl)-1H-pyrazole (19)

1-Methyl-4-iodo-pyrazole (18) (5.0 g 24.04 mmole) was dissolved in DMF (32 mL) and ethynyltrimethylsilane (4.76 mL, 3.31 g, 33.7 mmole) was added followed by diisopropylamine (4.46 mL, 3.21 g 31.78 mmole), copper(I) iodide (304 mg 1.59 mmole) and triphenylphosphine (1.26 g 4.81 mmole). The reaction was flushed with argon. Palladium acetate (351 mg 1.56 mmole) was added and the reaction was again flushed with argon. It was heated at 60° C. for 60 mins. The reaction was cooled, added to water (350 ml) and extracted with ether (3×100 mL). The organic solution was filtered from a brown solid which was washed with a little more ether. The organic solution was washed with water (3×80 mL), brine, dried and evaporated. The crude product was flash chromatographed (silica) using 1:4 ethyl acetate:cyclohexane and then 1:3 ethyl acetate:cyclohexane to give the title compound as a solid (2.85 g 67%). $^1$H-NMR (CDCl₃, 500 MHz): δ 0.24 (s, 9H), 3.87 (s, 3H), 7.50 (s, 1H), 7.58 (s, 1H).

4-Ethynyl-1-methyl-1H-pyrazole (20)

1-Methyl-4-((trimethylsilyl)ethynyl)-1H-pyrazole (19) (6.86 g, 38.5 mmole) was dissolved in methanol (77 mL) and potassium carbonate (385 mg) was added. The reaction was stirred at r.t. for 2 hours. Methanol was evaporated to a small volume. Ethyl acetate (100 mL) was added and the solution washed with water (70 mL, 40 mL) and brine. Each aqueous was backwashed with a single 40 mL portion of ethyl acetate. The ethyl acetate solution was dried and evaporated; the residue was chromatographed (silica) and eluted with 1:3 ethyl acetate:cyclohexane and 1:1 ethyl acetate:cyclohexane to give the title compound as a solid. (3.18 g 77%. $^1$H-NMR (CDCl₃, 500 MHz): δ 3.00 (s, 1H), 3.88 (s, 3H), 7.52 (s, 1H), 7.59 (s, 1H).

6-Bromo-2-(1-methyl-1H-pyrazol-4-yl)-1-(methylsulfonyl)-1H-pyrrolo[3,2-c]pyridine, (21)

4-Ethynyl-1-methyl-1H-pyrazole (20) (4.11 g, 38.7 mmole) was dissolved in DMF (95 mL) and N-(2-bromo-5-iodopyridin-4-yl)methanesulfonamide 8 (12.18 g 32.3 mmole) was added. To the solution was added triethylamine (19.6 mL, 14.1 g 139 mmole) and copper(I) iodide (214 mg 1.12 mmole). The reaction was sealed and flushed with nitrogen. Bis(triphenylphosphine)palladium dichloride (797 mg 1.13 mmole) was added and the reaction was again flushed with nitrogen and heated at 60° C. for 105 minutes. Most of the DMF was evaporated and the residue taken up in ethyl acetate (350 ml). The solution was washed with water (3×100 mL) and brine. Each aqueous fraction was backwashed with the same 100 mL portion of ethyl acetate. The combined organics were dried and evaporated. The residue was flash chromatographed (silica) eluting with dichloromethane, 1:4 ethyl acetate:dichloromethane, 1:1 ethyl acetate:dichloromethane and ethyl acetate to give the title compound (5.19 g 45.9%). $^1$H-NMR (CDCl₃, 500 MHz): δ 2.98 (s, 3H), 4.01 (s, 3H), 6.69 (d, J=0.95 Hz, 1H), 7.73 (s, 1H), 7.78 (s, 1H), 8.25 (t, J=0.95 Hz, 1H), 8.64 (d, J=0.95 Hz, 1H).

6-Bromo-2-(1-methyl-1H-pyrazol-4-yl)-1H-pyrrolo[3,2-c]pyridine, (22)

6-Bromo-2-(1-methyl-1H-pyrazol-4-yl)-1-(methylsulfonyl)-1H-pyrrolo[3,2-c]pyridine (21) (11.07 g 31.2 mmole) was stirred in methanol (105 mL) at 25° C. and 1M sodium hydroxide (35.3 mL) added. The reaction was stirred at 25° C. for 6 hours. Solvent (85 mL) was removed and water (40 mL) added. The mix was left to cool in ice-water for about 1 hour. The product was filtered off, washed with water (×3) and dried in a vacuum desiccator over potassium hydroxide, overnight. The resulting solid was azeotroped with toluene (100 mL) to give the title compound (8.22 g 95%). $^1$H-NMR (d₆-DMSO, 500 MHz): δ 3.90 (s, 3H), 6.69 (d, J=0.95 Hz, 1H), 7.47 (t, J=0.95 Hz, 1H), 7.94 (d, J=0.63 Hz, 1H), 8.18 (s, 1H), 8.50 (d, J=0.95 Hz, 1H), 11.92 (br s, 1H, NH).

6-Bromo-2-(1-methyl-1H-pyrazol-4-yl)-1H-pyrrolo[3,2-c]pyridine (22) can also be Prepared According to the Following Method Potassium t-butoxide (315 mg 2.81 mmole) was dissolved in NMP (3 mL) and 2-bromo-5-((1-methyl-1H-pyrazol-4-yl)ethynyl)pyridin-4-amine (24) (375 mg 1.35 mmole) was added to the stirred solution. The reaction was placed under nitrogen and warmed at 50° C. for 3 hours. The reaction was cooled and 10% ammonium chloride (3 mL) added. Water (21 mL) was heated to about 60° C. and the product solution in NMP/water was added to the water; a solid immediately crashes out. The suspension was allowed to cool to r.t., filtered and the solid washed with water. Drying in a vac desiccator over KOH for 3 days gave product (347 mg) which was azeotroped with ethanol (2×15 mL) and toluene (2×15 mL) to give the title compound (315 mg, 84%). $^1$H-NMR (d6-DMSO, 500 MHz): δ 3.90 (s, 3H), 6.69 (d, J=0.95 Hz, 1H), 7.47 (t, J=0.95 Hz, 1H), 7.94 (d, J=0.63 Hz, 1H), 8.18 (s, 1H), 8.50 (d, J=0.95 Hz, 1H), 11.92 (br s, 1H, NH).

t-Butyl 6-bromo-2-(1-methyl-1H-pyrazol-4-yl)-1H-pyrrolo[3,2-c]pyridine-1-carboxylate, (23)

6-Bromo-2-(1-methyl-1H-pyrazol-4-yl)-1H-pyrrolo[3,2-c]pyridine (22) (7.22 g 26.1 mmole) was stirred in ethyl acetate (93 mL) and triethylamine (5.3 mL, 3.82 g 37.8 mmole). To the suspension was added DMAP (622 mg, 5.1 mmole) and di-t-butyl dicarbonate (8.30 g, 38.1 mmole). After 25 minutes, solid deposited from solution and the suspension was evaporated to dryness. The residue was chromatographed (silica, 1:1 ethyl acetate:cyclohexane then 3:1 ethyl acetate:cyclohexane then pure ethyl acetate) to give the desired product (8.8 g, 89%). $^1$H-NMR (CDCl$_3$, 500 MHz): δ 1.57 (s, 9H), 3.98 (s, 3H), 6.57 (d, J=0.63 Hz, 1H), 7.59 (s, 1H), 7.63 (d, J=0.63 Hz, 1H), 8.19 (t, J=0.63 Hz), 8.58 (d, J=0.63 Hz, 1H).

2-Bromo-5-((1-methyl-1H-pyrazol-4-yl)ethynyl) pyridin-4-amine, (24)

4-Amino-2-bromo-5-iodopyridine (5) (2.58 g 8.63 mmole), copper(I) iodide (164 mg 0.86 mmole) and bis(triphenylphosphine)palladium dichloride (216 mg 0.432 mmole) were weighed into a 100 mL flask and DMF (25 mL) with triethylamine (22 mL) was added. The mixture was stirred at r.t. for 15 minutes under nitrogen. 4-Ethynyl-1-methyl-1H-pyrazole (20) (945 mg at 100%, 8.91 mmole) in DMF (10 mL) and triethylamine (5 mL) was added to the flask. The reaction was stirred at r.t. for 1.75 hrs. The reaction was diluted with ethyl acetate (450 mL) and the solution was washed with water (3×240 mL), brine (120 mL), dried and evaporated. The residue was flash chromatographed (silica/ethyl acetate) to give the title compound (2.11 g, 88%). $^1$H-NMR (CDCl$_3$, 500 MHz): δ 3.94 (s, 3H), 4.80 (br s, 2H), 6.79 (s, 1H), 7.59 (s, 1H), 7.66 (s, 1H), 8.15 (s, 1H).

tert-Butyl 2-(1-(tert-butoxycarbonyl)-1H-pyrazol-4-yl)-6-(p-tolylamino)-1H-pyrrolo[3,2-c]pyridine-1-carboxylate (25)

tert-Butyl-2-(1-(tert-butoxycarbonyl)-1H-pyrazol-4-yl)-6-chloro-1H-pyrrolo[3,2-c]pyridine-1-carboxylate (17) (44 mg 0.105 mmole) and 4-methylaniline (13 mg 0.12 mmole) were placed in a microwave vial and potassium phosphate (53 mg 0.25 mmole), XantPhos (10.5 mg 0.022 mmole) and Pd$_2$(dba)$_3$ (10.1 mg 0.011 mmole) were added. NMP containing water (3%) (1.2 mL) was then added and the vial sealed under argon. It was microwaved at 80° C. for 1.5 hrs. The reaction was added to water (10 mL) and extracted with ethyl acetate (3×6 mL). The combined organics were washed with water (3×5 mL) and with brine, dried and evaporated. The residue was applied to three 1 mm 20×20 cm silica prep tlc plates, which were twice eluted with 1:2 ethyl acetate:cyclohexane. The product band was recovered using acetone to give the product (17 mg). $^1$H-NMR (CDCl$_3$, 500 MHz): δ 1.51 (s, 9H), 1.70 (s, 9H), 2.36 (s, 3H), 6.58 (m, 1H), 6.68 (br s, 1H, NH), 7.18 (d, J=8.20 Hz, 1H), 7.25 (d, J=8.51 Hz, 2H), 7.54 (m, 1H), 7.83 (d, J=0.63 Hz, 1H), 8.23 (s, 1H), 8.44 (m, 1H). ESI-HRMS Found 490.2452, calculated for C$_{27}$H$_{32}$N$_5$O$_4$ [M+H]$^+$: 490.2449.

Isopropyl 6-bromo-2-(1-methyl-1H-pyrazol-4-yl)-1H-pyrrolo[3,2-c]pyridine-1-carboxylate, (26)

2-Bromo-5-((1-methyl-1H-pyrazol-4-yl)ethynyl)pyridin-4-amine (24) (134 mg 0.48 mmole) was dissolved in NMP (1.3 mL) and a 1M solution of sodium bis(trimethylsilyl) amide (0.87 mL, 0.87 mmole, 1.8 equiv) in THF was added. The reaction was placed under nitrogen and heated at 65° C. for 2.25 hours, then cooled to r.t. The reaction was quenched with 1M isopropyl chloroformate in toluene (0.90 mL) and stirred at r.t. for 2 hours. The reaction was diluted with ethyl acetate (40 mL) and washed with water (3×12 mL), brine, then dried and evaporated. The residue was applied to four 1 mm 20×20 cm silica prep tlc plates which were eluted with ethyl acetate. The product band was recovered with acetone to give the title compound (136 mg, 77%). $^1$H-NMR (CDCl$_3$, 500 MHz): δ 1.40 (d, J=6.3 Hz, 6H), 3.98 (s, 3H), 5.23 (sept, J=6.31 Hz, 1H), 6.60 (d, J=0.63 Hz, 1H), 7.62 (s, 1H), 7.65 (s, 1H), 8.19 (s, 1H), 8.59 (s, 1H).

Isopropyl 6-bromo-2-(1-methyl-1H-pyrazol-4-yl)-1H-pyrrolo[3,2-c]pyridine-1-carboxylate can also be Prepared According to the Following Preparation 6-bromo-2-(1-methyl-1H-pyrazol-4-yl)-1H-pyrrolo[3,2-c]pyridine (22, 100 mg, 0.36 mmol) was dissolved in dry DMF (1 ml). The solution was degassed and a solution of sodium bis(trimethylsilyl)amide (0.54 ml of a 1M solution in THF, 0.54 mmol) was added. After 20 minutes reaction, isopropylchloroformate (0.55 ml of a 1M solution in THF, 0.55 mmol)) was added. The reaction was stirred for 3 hr at room temperature, then diluted with ethyl acetate and water. The organic solution was extracted, washed with brine, dried over sodium sulphate and concentrated in vacuum. The crude product was purified using silica column chromatography eluting with 20% hexane in ethyl acetate. The pure fractions afforded the title compound as a white powder (110 mg, 84%). $^1$H-NMR (500 MHz, CDCl$_3$): δ 1.40 (d, J=6.3 Hz, 6H), 3.96 (s, 3H), 5.21 (sept, J=6.3 Hz, 1H), 6.60 (s, 1H), 7.61 (s, 1H), 7.63 (s, 1H), 8.16 (s. 1H), 8.55 (s, 1H)

tert-Butyl 4-(6-bromo-1H-pyrrolo[3,2-c]pyridin-2-yl)-1H-pyrazole-1-carboxylate (27)

DBU (0.193 mL, 1.289 mmol) was added to a solution of tert-butyl 4-(6-bromo-1-(methylsulfonyl)-1H-pyrrolo[3,2-c]pyridin-2-yl)-1H-pyrazole-1-carboxylate (9) (0.517 g, 1.172 mmol) and tert-butanol (0.224 mL, 2.343 mmol) in THF (11.7 mL). The reaction mixture was stirred at 40° C. for 1 hr. It was then diluted with water and the aqueous layer was extracted with EtOAc. The combined organic layers were dried over Na$_2$SO$_4$, filtered and concentrated under reduced pressure. The crude mixture was adsorbed on silica and purified via Biotage (DCM/EtOAc, 95/5 to 85/15, 25+M column) to afford the title compound as a white solid (271 mg, 58%). $^1$H NMR (500 MHz, CDCl$_3$) 1.71 (s, 9H), 6.75 (s, 1H), 7.50 (s, 1H), 8.02 (s, 1H), 8.38 (s, 1H), 8.50 (s, 1H), 8.66 (s, 1H).

tert-Butyl 4-(6-bromo-1-methyl-1H-pyrrolo[3,2-c]pyridin-2-yl)-1H-pyrazole-1-carboxylate (28)

Sodium hydride (60% in mineral oil, 7.1 mg, 0.178 mmol) was added to a solution of tert-butyl 4-(6-bromo-1H-pyrrolo[3,2-c]pyridin-2-yl)-1H-pyrazole-1-carboxylate (27) (43 mg, 0.118 mmol) in DMF (515 µL) at 0° C. The reaction mixture was then stirred for 30 min at 0° C. before the addition of iodomethane (18 µL, 0.237 mmol). After stirring for 30 min, it was diluted with water and EtOAc. The layers were separated and the aqueous layer was extracted with EtOAc. The combined organic layers were dried (MgSO$_4$), filtered and concentrated under reduced pressure. The crude was purified via Biotage (DCM/EtOAc 99/1 to 90/10; 12+M column) to afford the title compound as a white solid (35 mg, 78%). $^1$H NMR (500 MHz, CDCl$_3$) 1.71 (s, 9H), 3.78 (s, 1H), 6.68 (d, J=0.6 Hz, 1H), 7.46 (m, 1H), 7.94 (d, J=0.6 Hz, 1H), 8.32 (d, J=0.6 Hz, 1H), 8.64 (s, 1H).

4-Amino-3-methoxy-N,N-dimethylbenzamide (29)

HATU (0.296 g, 0.778 mmol) was added to a solution of 4-amino-3-methoxybenzoic acid (0.1 g, 0.598 mmol), DIPEA (0.156 mL, 0.897 mmol) and dimethylamine (2M in THF, 0.598 mL, 1.196 mmol) in THF (1.617 ml). The reaction mixture was stirred overnight. It was then partitioned between EtOAc and water. The separated organic phase was washed with water, dried over Na$_2$SO$_4$ and evaporated in vacuum. The crude was purified via Biotage (DCM/EtOAc 60/40 to 40/60; 25 g column) and was then filtered on SCX-2 column to afford the title compound as a colourless oil (69 mg, 59%). $^1$H NMR (500 MHz, CDCl$_3$) 3.06 (s, 6H), 3.87 (s, 1H), 3.99 (br s, 2H), 6.65 (d, J=7.9 Hz, 1H), 6.89 (dd, J=7.9, 1.7 Hz, 1H), 6.96 (d, J=1.7 Hz).

3-((4-Iodo-1H-pyrazol-1-yl)methyl)-5-methylisoxazole (30)

4-Iodo-1H-pyrazole (0.826 g, 4.26 mmol) (1), 3-(bromomethyl)-5-methylisoxazole (0.75 g, 4.26 mmol) and potassium carbonate (1.18 g, 8.52 mmol) were added to dry DMF (8 ml) and stirred at room temperature for 16 h. The reaction was diluted with ethyl acetate (20 ml) and washed with water, brine and dried. The organic solution was concentrated in vacuo and the residue purified by flash silica chromatography (20% ethyl acetate in hexane). The pure fractions provided the title compound as a white powder (0.7 g, 56.8%). $^1$H-NMR (500 MHz, CDCl$_3$) 2.4 (s, 3H), 5.33 (s, 2H), 5.92 (s, 1H), 7.51 (s, 1H), 7.55 (s, 1H).

5-Methyl-3-((4-((trimethylsilyl)ethynyl)-1H-pyrazol-1-yl)methyl)isoxazole (31)

3-((4-Iodo-1H-pyrazol-1-yl)methyl)-5-methylisoxazole (30) (0.7 g, 2.42 mmol) and trimethylsilylacetylene (0.326 g, 3.32 mmol) were dissolved in DMF (5 ml) and placed under argon. Diisopropylamine (0.47 ml, 3.3 mmol), copper(I) iodide (30 mg, 0.16 mmol), triphenylphosphine (126 mg, 0.242 mmol) and palladium acetate (40 mg, 0.16 mmol) were added and the flask was flushed with argon. The reaction was heated at 60° C. for 1 hour. It was cooled to room temperature and diluted with water (20 ml) and ethyl acetate (30 ml). The organic layer was collected, dried and concentrated. The crude product was purified by flash silica chromatography eluting with 5% ethyl acetate in DCM. The pure fractions provided the title compound as a brown oil which solidified on standing (550 mg, 88%). $^1$H-NMR (500 MHz, CDCl$_3$): 0.21 (s, 9H), 2.38 (s, 3H), 5.29 (s, 2H), 5.88 (s, 1H), 7.58 (s, 1H), 7.61 (s, 1H).

3-((4-Ethynyl-1H-pyrazol-1-yl)methyl)-5-methyl-isoxazole (32)

5-Methyl-3-((4-((trimethylsilyl)ethynyl)-1H-pyrazol-1-yl)methyl)isoxazole (31) (0.55 g, 2.12 mmol) was dissolved in 3 ml THF and stirred at RT. To the stirred solution was then added a 1M solution of TBAF in THF (3 ml, 3 mmol). After 10 minutes, the reaction was diluted with ethyl acetate (20 ml) and water (20 ml). The organic solution was collected, dried and concentrated. The crude product was purified on a short silica column eluting with 5% ethyl acetate in DCM. The pure fractions provided the title compound as a pale brown solid (278 mg, 70%). $^1$H-NMR (500 MHz, CDCl$_3$) 2.38 (s, 3H), 3 (s, 1H), 5.29 (s, 2H), 5.9 (s, 1H), 7.61 (s, 1H), 7.63 (s, 1H).

3-((4-(6-Bromo-1-(methylsulfonyl)-1H-pyrrolo[3,2-c]pyridin-2-yl)-1H-pyrazol-1-yl)methyl)-5-methyl-isoxazole (33)

Bis(triphenylphosphine)palladium dichloride (46 mg, 0.066 mmol) was added to a solution of N-(2-bromo-5-iodopyridin-4-yl)methanesulfonamide (8) (0.5 g, 1.32 mmol), 3-((4-ethynyl-1H-pyrazol-1-yl)methyl)-5-methylisoxazole (32) (0.278 g, 1.48 mmol), triethylamine (0.7 g, 7 mmol) and copper iodide (13 mg, 0.065 mmol) in DMF (5 ml). The reaction mixture was heated for 1 h at 60° C. The reaction mixture was cooled to room temperature and diluted with water (20 ml) and dichloromethane (30 ml). The organic solution was dried and concentrated in vacuo. The crude product was purified by flash silica chromatography (10 to 20% ethyl acetate in hexane) to afford the product as a white powder (300 mg, 51.8%). $^1$H-NMR (500 MHz, CDCl$_3$) 2.43 (s, 3H), 2.96 (s, 3H), 5.41 (s, 2H), 6.02 (s, 1H), 6.69 (s, 1H), 7.78 (s, 1H), 7.87 (s, 1H), 8.22 (s, 1H), 8.62 (s, 1H).

tert-Butyl 6-bromo-2-(1-((5-methylisoxazol-3-yl)methyl)-1H-pyrazol-4-yl)-1H-pyrrolo[3,2-c]pyridine-1-carboxylate (34)

3-((4-(6-Bromo-1-(methylsulfonyl)-1H-pyrrolo[3,2-c]pyridin-2-yl)-1H-pyrazol-1-yl)methyl)-5-methylisoxazole (33) (0.3 g, 0.688 mmole) was stirred in THF (10 mL) and DBU (0.51 mL, 0.115 g, 0.75 mmole) was added. The reaction was warmed at 40° C. for 1 hour. The reaction was cooled to room temperature and diluted with ethyl acetate (30 ml) and water (30 ml). The organic solution was dried and concentrated in vacuo. The residue was dissolved in dichloromethane and stirred at room temperature. Di-t-butyl dicarbonate (218 mg, 1 mmole) was added followed by triethylamine (100 mg, 1 mmole) and a crystal of DMAP. The reaction was stirred at room temperature for 18 hours. The reaction was concentrated in vacuo and the residue purified by flash silica chromatography (ethyl acetate:hexane:triethylamine 10:10:1). The pure fractions provided the title compound as a pale white powder (140 mg, 44.4% over 2 steps). 1H-NMR (500 MHz, CDCl$_3$) 1.53 (s, 9H), 2.42 (s, 3H), 5.38 (s, 2H), 6.04 (s, 1H), 6.57 (s, 1H), 7.68 (s, 1H), 7.69 (s, 1H), 8.19 (s, 1H), 8.56 (s, 1H).

tert-Butyl 2-(1-(tert-butoxycarbonyl)-1H-pyrazol-4-yl)-6-(4-methoxyphenylamino)-1H-pyrrolo[3,2-c]pyridine-1-carboxylate (35)

To tert-butyl 6-bromo-2-(1-(tert-butoxycarbonyl)-1H-pyrazol-4-yl)-1H-pyrrolo[3,2-c]pyridine-1-carboxylate (10) (50 mg, 0.108 mmole) was added 4-methoxyaniline (16 mg, 0.129 mmole, 1.2 eq) followed by cesium carbonate (70 mg, 0.216 mmole, 2 eq) and Xantphos (6.2 mg, 0.0108 mmole, 10 mole %). Dioxane (1.2 mL) was added and the flask flushed twice with nitrogen. Pd$_2$(dba)$_3$ complex (5 mg, 0.0054 mmole, 5 mole %) was added and the flask was flushed again with nitrogen (×3) and heated at 80° C. for 2 hours. The reaction was cooled and diluted with ethyl acetate (10 mL).

The solution was washed with water (3 mL) and with brine, dried and evaporated to leave a gum. This was applied in chloroform to a 1 mm, 20×20 cm silica prep plate which was eluted with 9:1 dichloromethane:ethyl acetate. The product band was recovered with acetone. Solution evaporated and residue azeotroped with ethanol to leave the title compound (37 mg, 68%). $^1$H-NMR (d$_6$-DMSO, 500 MHz): δ 1.45 (s, 9H), 1.60 (s, 9H), 3.72 (s, 3H), 6.78 (d, J=0.63 Hz, 1H), 6.87 (d, J=9.14 Hz, 2H), 7.39 (t, J=0.95 Hz, 1H), 7.48 (d, J=9.14 Hz, 2H), 8.02 (d, J=0.63 Hz, 1H), 8.41 (d, J=0.95 Hz, 1H), 8.43 (d, J=0.63 Hz, 1H), 8.73 (br s, 1H).

tert-Butyl 6-(4-((1H-pyrazol-1-yl)methyl)phenylamino)-2-(1-(tert-butoxycarbonyl)-1H-pyrazol-4-yl)-1H-pyrrolo[3,2-c]pyridine-1-carboxylate (36)

The title compound was prepared from tert-butyl 6-bromo-2-(1-(tert-butoxycarbonyl)-1H-pyrazol-4-yl)-1H-pyrrolo[3,2-c]pyridine-1-carboxylate (10) (70 mg, 0.15 mmol) and 4-((1H-pyrazol-1-yl)methyl)aniline (31.3 mg, 0.181 mmol, 1.2 eq), using the method described in Preparation 35 and using silica gel column chromatography eluting with EtOAc:hexane:triethylamine 10:10:1 (12 mg, 14.3%). $^1$H-NMR (500 MHz, CDCl$_3$) 1.49 (s, 9H), 1.69 (s, 9H), 5.2 (s, 2H), 6.32 (s, 1H), 6.58 (s, 1H), 6.66 (d, J=8.3 Hz, 2H), 7 (d, J=8.5 Hz, 1H), 7.06 (d, J=8.3 Hz, 2H), 7.23 (d, J=8.5 Hz, 1H), 7.33 (m, 1H), 7.62 (s, 1H), 7.82 (s, 1H), 8.21 (s, 1H), 8.45 (s, 1H).

tert-Butyl 2-(1-(tert-butoxycarbonyl)-1H-pyrazol-4-yl)-6-(4-(thiomorpholino methyl)phenylamino)-1H-pyrrolo[3,2-c]pyridine-1-carboxylate-S,S-dioxide (37)

The title compound was prepared from tert-butyl 6-bromo-2-(1-(tert-butoxycarbonyl)-1H-pyrazol-4-yl)-1H-pyrrolo[3,2-c]pyridine-1-carboxylate (10) (100 mg, 0.216 mmol) and 4-(4'-aminobenzyl)thiomorpholine 1,1-dioxide (62 mg, 0.26 mmol, 1.2 eq) using the method described in Preparation 35 and using silica gel column chromatography eluting with EtOAc:hexane:triethylamine 10:10:1 (80 mg, 59%). $^1$H-NMR (500 MHz, CDCl$_3$) 1.5 (s, 9H), 1.68 (s, 9H), 2.94 (m, 8H), 3.52 (s, 2H), 3.62 (s, 1H), 6.57 (s, 1H), 6.64 (d, J=8.3 Hz, 2H), 7.06 (d, J=8.3 Hz, 1H), 7.63 (s, 1H), 7.81 (s, 1H), 8.21 (s, 1H), 8.46 (s, 1H).

tert-Butyl 2-(1-(tert-butoxycarbonyl)-1H-pyrazol-4-yl)-6-(4-(2-morpholinoethoxy)phenylamino)-1H-pyrrolo[3,2-c]pyridine-1-carboxylate (38)

The title compound was prepared from tert-butyl 6-bromo-2-(1-(tert-butoxycarbonyl)-1H-pyrazol-4-yl)-1H-pyrrolo[3,2-c]pyridine-1-carboxylate (10) (100 mg, 0.216 mmol) and 4-(2-morpholinoethoxy)aniline (58 mg, 0.26 mmol, 1.2 eq) using the method described in Preparation 35 and using silica gel column chromatography eluting with EtOAc:hexane:triethylamine 10:10:1 (20 mg, 15%). $^1$H-NMR (500 MHz, CDCl$_3$) 1.45 (s, 9H), 1.67 (s, 9H), 2.58 (m, 4H), 2.8 (t, J=5.8 Hz, 2H), 3.73 (m, 4H), 4.11 (t, J=5.8 Hz, 2H), 6.54 (s, 1H), 6.6 (s, 1H), 6.91 (d, J=8.9 Hz, 2H), 7.27 (d, J=8.9 Hz, 2H), 7.37 (s, 1H), 7.8 (s, 1H), 8.19 (s, 1H), 8.39 (s, 1H).

tert-Butyl 2-(1-(tert-butoxycarbonyl)-1H-pyrazol-4-yl)-6-(4-cyanophenylamino)-1H-pyrrolo[3,2-c]pyridine-1-carboxylate (39)

The title compound was prepared from tert-butyl 6-bromo-2-(1-(tert-butoxycarbonyl)-1H-pyrazol-4-yl)-1H-pyrrolo[3,2-c]pyridine-1-carboxylate (10) (50 mg, 0.108 mmol) and 4-aminobenzonitrile (15.3 mg, 0.13 mmol, 1.2 eq) using the method described for Preparation 35 and using silica gel column chromatography eluting with EtOAc:hexane:triethylamine 10:10:1 (9 mg, 17%). $^1$H-NMR (500 MHz, CDCl$_3$) 1.53 (s, 9H), 1.69 (s, 9H), 6.62 (s, 1H), 6.93 (s, 1H), 7.48 (d, J=8.8 Hz, 2H), 7.57 (d, J=8.8 Hz, 1H), 7.74 (s, 1H), 7.83 (s, 1H), 8.23 (s, 1H), 8.54 (s, 1H).

tert-Butyl 2-(1-(tert-butoxycarbonyl)-1H-pyrazol-4-yl)-6-(2-methoxyphenylamino)-1H-pyrrolo[3,2-c]pyridine-1-carboxylate (40)

The title compound was prepared in 48% yield from compound 10 and 2-methoxyphenyl amine using the method described for Preparation 35. $^1$H-NMR (CDCl$_3$, 500 MHz): δ 1.53 (s, 9H), 1.69 (s, 9H), 3.92 (s, 3H), 6.58 (d, J=0.95 Hz, 1H), 6.91-6.99 (m, 3H), 7.08 (br s, 1H), 7.66 (m, 1H), 7.83 (d, J=0.95 Hz, 1H), 7.92-7.95 (m, 1H), 8.33 (d, J=0.63 Hz, 1H), 8.49 (d, J=0.95 Hz, 1H).

tert-Butyl 2-(1-(tert-butoxycarbonyl)-1H-pyrazol-4-yl)-6-(2,4-dimethoxyphenylamino)-1H-pyrrolo[3,2-c]pyridine-1-carboxylate (41)

The title compound was prepared in 53% yield from compound (10) and 2,4-dimethoxyphenylamine using the method described for Preparation 35. $^1$H-NMR (CDCl$_3$, 500 MHz): δ 1.50 (s, 9H), 1.69 (s, 9H), 3.83 (s, 3H), 3.87 (s, 3H), 6.52 (dd, J=2.52, 8.51 Hz, 1H), 6.56 (d, J=0.95 Hz, 1H), 6.57 (d, J=2.52 Hz, 1H), 6.66 (br s, 1H, NH), 7.43 (m, 1H), 7.67 (d, J=8.83 Hz, 1H), 7.82 (m, 1H), 8.20 (d, J=0.95 Hz, 1H), 8.43 (d, J=0.95 Hz, 1H).

tert-Butyl 2-(1-(tert-butoxycarbonyl)-1H-pyrazol-4-yl)-6-(4-(trifluoromethyl)-phenyl amino)-1H-pyrrolo[3,2-c]pyridine-1-carboxylate (42)

The title compound was prepared in 63% yield from compound (10) and 4-trifluoromethyl phenylamine using the method described for Preparation 35. $^1$H-NMR (CDCl$_3$, 500 MHz): δ 1.53 (m, 9H), 1.70 (m, 9H), 6.61 (d, J=0.95 Hz, 1H), 6.81 (br s, 1H), 7.47 (d, J=8.51 Hz, 2H), 7.57 (d, J=8.20 Hz, 2H), 7.73 (m, 1H), 7.83 (d, J=0.63 Hz, 1H), 8.23 (d, J=0.63 Hz, 1H), 8.52 (d, J=0.95 Hz, 1H). $^{19}$F-NMR (CDCl$_3$): δ −61.73.

tert-Butyl 2-(1-(tert-butoxycarbonyl)-1H-pyrazol-4-yl)-6-(3,4-dimethoxyphenylamino)-1H-pyrrolo[3,2-c]pyridine-1-carboxylate (43)

The title compound was prepared in 71% yield from compound (10) and 3,4-dimethoxyphenyl amine using the method described for Preparation 35. $^1$H-NMR (CDCl$_3$, 500 MHz): δ 1.46 (s, 9H), 1.68 (s, 9H), 3.90 (s, 3H), 3.91 (s, 3H), 6.45 (br s, 1H, NH), 6.56 (d, J=0.95 Hz, 1H), 6.89 (m, 2H), 6.96 (m, 1H), 7.45 (m, 1H), 7.81 (d, J=0.63 Hz, 1H), 8.20 (d, J=0.95 Hz, 1H), 8.42 (d, J=0.95 Hz, 1H).

tert-Butyl 2-(1-(tert-butoxycarbonyl)-1H-pyrazol-4-yl)-6-(2-chloro-4-methoxyphenylamino)-1H-pyrrolo[3,2-c]pyridine-1-carboxylate (44)

The title compound was prepared in 72% yield from compound (10) and 2-chloro-4-methoxyphenylamine using the method described for Preparation 35. $^1$H-NMR (CDCl$_3$, 500 MHz): δ 1.49 (s, 9H), 1.69 (s, 9H), 3.82 (s, 3H), 6.58 (d, J=0.95 Hz, 1H over br s, 1H), 6.86 (dd, J=2.84, 8.83 Hz, 1H), 7.03 (d, J=2.84 Hz, 1H), 7.38 (m, 1H), 7.73 (d, J=9.14 Hz, 1H), 7.82 (d, J=0.63 Hz, 1H), 8.21 (d, J=0.63 Hz, 1H), 8.46 (d, J=0.63 Hz, 1H).

tert-Butyl 2-(1-(tert-butoxycarbonyl)-1H-pyrazol-4-yl)-6-(2-(trifluoromethyl)phenylamino)-1H-pyrrolo[3,2-c]pyridine-1-carboxylate (45)

The title compound was prepared in 88% yield from compound (10) and 2-trifluoromethyl phenylamine using the method described for Preparation 35. $^1$H-NMR (CDCl$_3$, 500 MHz): δ 1.49 (s, 9H), 1.69 (s, 9H), 6.61 (d, J=0.95 Hz, 1H), 6.82 (br s, 1H, NH), 7.12 (t, J=7.57 Hz, 1H), 7.51 (t, J=8.20 Hz, 1H), 7.61 (m, 1H), 7.65 (d, J=7.57 Hz, 1H), 7.83 (d, J=0.63 Hz, 1H), 7.89 (d, J=8.20 Hz, 1H), 8.22 (d, J=0.95 Hz, 1H), 8.50 (d, 0.95 Hz, 1H). $^{19}$F-NMR (CDCl$_3$): δ −61.43.

tert-Butyl 2-(1-(tert-butoxycarbonyl)-1H-pyrazol-4-yl)-6-(2-ethoxyphenylamino)-1H-pyrrolo[3,2-c]pyridine-1-carboxylate (46)

The title compound was prepared in 33% yield from compound (10) and 2-ethoxyphenylamine using the method described for Preparation 35. $^1$H-NMR (CDCl$_3$, 500 MHz): δ 1.48 (t, J=6.94 Hz, 3H), 1.54 (s, 9H), 1.69 (s, 9H), 4.14 (q, J=6.94 Hz, 2H), 6.59 (d, J=0.63 Hz, 1H), 6.91-6.98 (m, 3H), 7.11 (br s, 1H), 7.70 (m, 1H), 7.83 (d, J=0.63 Hz, 1H), 7.91 (br d, J=8.20 Hz, 1H), 8.33 (d, J=0.63 Hz, 1H), 8.49 (s, 1H).

tert-Butyl 2-(1-(tert-butoxycarbonyl)-1H-pyrazol-4-yl)-6-(4-(N,N-dimethylsulfamoyl)phenylamino)-1H-pyrrolo[3,2-c]pyridine-1-carboxylate (47)

The title compound was prepared in 86% yield from compound (10) and 4-(N,N-dimethylsulfamoyl)phenylamine using the method described for Preparation 35. $^1$H-NMR (d$_6$-DMSO, 500 MHz): δ 1.48 (s, 9H), 1.60 (s, 9H), 2.58 (s, 9H), 6.87 (d, J=0.63 Hz, 1H), 7.61 (d, J=9.14 Hz, 2H), 7.65 (s, 1H), 7.90 (d, J=8.83 Hz, 2H), 8.05 (d, J=0.63 Hz, 1H), 8.49 (d, J=0.63 Hz, 1H), 8.57 (d, J=0.95 Hz, 1H), 9.67 (s, 1H).

tert-Butyl 2-(1-(tert-butoxycarbonyl)-1H-pyrazol-4-yl)-6-(2-methoxy-4-(1-methyl piperidin-4-yloxy)phenylamino)-1H-pyrrolo[3,2-c]pyridine-1-carboxylate (48)

To tert-butyl 6-bromo-2-(1-(tert-butoxycarbonyl)-1H-pyrazol-4-yl)-1H-pyrrolo[3,2-c]pyridine-1-carboxylate 10 (50 mg, 0.108 mmole) was added cesium carbonate (70 mg, 0.216 mmole, 2 eq) and Xantphos (6.2 mg, 0.0108 mmole, 10 mole %), then a solution of 2-methoxy-4-(1-methylpiperidin-4-yloxy)aniline (30.6 mg, 0.13 mmole, 1.2 eq) in dioxane (0.7 ml). Dioxane (0.5 mL) was added and the flask flushed twice with nitrogen. Pd$_2$(dba)$_3$ complex (5 mg, 0.0054 mmole, 5 mole %) was added and the flask was flushed again with nitrogen (×3) and heated at 80° C. for 4 hours. The reaction was cooled and diluted with ethyl acetate (11 mL). The solution was washed with water (4 mL). The organic layer was washed with brine, dried and evaporated. The residue was applied to two 1 mm 20×20 cm silica prep tlc plates, which were eluted with 10:1 ethyl acetate:2M ammonia in methanol. The product band was recovered with ethanol containing a little 2M ammonia in methanol. This gave a gum, 60 mg, containing (by NMR) ethanol (35%) and residual aniline. This gum was applied to one 1.5 mm alumina prep tlc plate (Merck) which was eluted with 30:1 dichloromethane:2-propanol. The product band was recovered with 30% 2-propanol in dichloromethane to give a gum, 36 mg. The residue was triturated with ether to give (after removal of the ether) the title compound as a solid (22 mg, 33%). $^1$H-NMR (CDCl$_3$, 500 MHz): δ 1.50 (s, 9H), 1.69 (s, 9H), 1.84-1.93 (m, 2H), 2.02-2.09 (m, 2H), 2.29-2.39 (s, 3H over m, 2H), 2.71-2.80 (m, 2H), 3.87 (s, 3H), 4.26-4.32 (m, 1H), 6.53 (dd, J=2.52, 8.83 Hz, 1H), 6.56 (d, J=0.63 Hz, 1H), 6.58 (d, J=2.52 Hz, 1H), 6.67 (s, 1H), 7.45 (s, 1H), 7.70 (d, J=8.51 Hz, 1H), 7.81 (d, J=0.63 Hz, 1H), 8.20 (d, J=0.63 Hz, 1H), 8.44 (d, J=0.95 Hz, 1H).

tert-Butyl 2-(1-(tert-butoxycarbonyl)-1H-pyrazol-4-yl)-6-(4-(dimethylcarbamoyl)phenylamino)-1H-pyrrolo[3,2-c]pyridine-1-carboxylate (49)

Pd$_2$(dba)$_3$ (11.32 mg, 0.012 mmol) was added to a mixture of tert-butyl 2-(1-(tert-butoxycarbonyl)-1H-pyrazol-4-yl)-6-chloro-1H-pyrrolo[3,2-c]pyridine-1-carboxylate (17) (37 mg, 0.088 mmol), potassium phosphate (62.1 mg, 0.29 mmol), 4-amino-N,N-dimethylbenzamide (16.68 mg, 0.10 mmol) and di-tBuX-Phos (15.75 mg, 0.037 mmol) in tert-BuOH containing 3% water (1.0 mL). The reaction mixture was heated at 80° C. for 1 h under microwave irradiation. More palladium catalyst (10.0 mg) and di-tBuX-Phos (8.0 mg) were added and the reaction mixture was heated at 80° C. for an additional 70 min under microwave irradiation. A final portion of palladium catalyst (4.0 mg) was added and the reaction mixture was heated at 80° C. for 70 min under microwave irradiation; it was then diluted with ethyl acetate (40 mL), washed with water (2×10 mL), dried (Na$_2$SO$_4$), and concentrated in vacuo. The residue was absorbed on silica gel (0.7 g), the free-running powder was placed on a 10 g isolute silica column. Elution with 60%, 70%, 80%, 90% ethyl acetate in hexane afforded the title compound (0.017 g) that was contaminated with the aniline starting material (4-amino-N,N-dimethylbenzamide) in a ratio of 1:1. $^1$H-NMR (500 MHz, CDCl$_3$) 1.53 (s, 9H), 1.69 (s, 9H), 3.10 (s, 6H), 6.60 (d, J=0.6 Hz), 6.73 (br s, 1H), 7.39 (d, J=8.6 Hz, 2H), 7.45 (d, J=8.6 Hz, 2H), 7.70 (s, 1H), 7.83 (d, J=0.7 Hz, 1H), 8.23 (d, J=0.6 Hz, 1H), 8.50 (d, J=0.8 Hz, 1H). Also present were the following peaks consistent with the structure of the starting material, 4-amino-N,N-dimethylbenzamide: 3.06 (s, 6H), 3.84 (br s, 2H), 6.66 (d, J=8.6 Hz, 2H), 7.30 (d, J=8.6 Hz, 2H).

tert-Butyl 6-(4-(4-acetylpiperazin-1-yl)phenylamino)-2-(1-(tert-butoxycarbonyl)-1H-pyrazol-4-yl)-1H-pyrrolo[3,2-c]pyridine-1-carboxylate (50)

The title compound was prepared in 27% yield from compound (17) and 4-(4-acetylpiperazin-1-yl)aniline using the method described for compound (49). $^1$H-NMR (500 MHz, CDCl$_3$) 1.47 (s, 9H), 1.69 (s, 9H), 2.17 (s, 3H), 3.13 (t, J=5.0 Hz, 2H), 3.15 (t, J=5.3 Hz, 2H), 3.65 (t, J=5.8 Hz, 2H), 3.81 (t, J=5.2 Hz, 2H), 6.45 (br s, 1H), 6.56 (d, J=0.6 Hz, 1H), 6.96 (d, J=8.9 Hz, 2H), 7.29 (d, J=8.9 Hz, 2H), 7.42 (s, 1H), 7.81 (d, J=0.6 Hz, 1H), 8.20 (d, J=0.4 Hz, 1H), 8.41 (d, J=0.8 Hz, 1H).

tert-Butyl 2-(1-(tert-butoxycarbonyl)-1H-pyrazol-4-yl)-6-(4-(2-methoxyethoxy)phenylamino)-1H-pyrrolo[3,2-c]pyridine-1-carboxylate (51)

The title compound was prepared in 27% yield from compound (17) and 4-(2-methoxyethoxy)aniline using the method described for compound (49). $^1$H-NMR (500 MHz, DMSO-$d_6$) 1.45 (s, 9H), 1.60 (s, 9H), 3.31 (s, 3H), 3.64 (t, J=5.0 Hz, 2H), 4.04 (t, J=5.0 Hz, 2H), 6.79 (s, 1H), 6.88 (d, J=9.0 Hz, 2H), 7.40 (s, 1H), 7.48 (d, J=9.0 Hz, 2H), 8.01 (d, J=0.5 Hz, 1H), 8.41 (d, J=0.9 Hz, 1H), 8.44 (s, 1H), 8.74 (s, 1H).

tert-Butyl 2-(1-(tert-butoxycarbonyl)-1H-pyrazol-4-yl)-6-(4-(morpholinomethyl)phenylamino)-1H-pyrrolo[3,2-c]pyridine-1-carboxylate (52)

The title compound was prepared in 19% yield from compound (17) and 4-(morpholinomethyl)aniline using the method described for compound (49). $^1$H-NMR (500 MHz, CDCl$_3$) 1.51 (s, 9H), 1.69 (s, 9H), 2.47 (br t, J=4.2 Hz, 4H), 3.49 (s, 2H), 3.72 (t, J=4.7 Hz, 4H), 6.58 (d, J=0.5 Hz, 1H), 6.66 (s, 1H), 7.31 (br s, 4H), 7.61 (s, 1H), 7.82 (d, J=0.5 Hz, 1H), 8.22 (d, J=0.5 Hz, 1H), 8.45 (d, J=0.7 Hz, 1H).

tert-Butyl 4-(6-(4-fluorophenylamino)-1-(methylsulfonyl)-1H-pyrrolo[3,2-c]pyridin-2-yl)-1H-pyrazole-1-carboxylate (53)

Pd$_2$(dba)$_3$ (9.2 mg, 0.01 mmol) was added to a mixture of tert-butyl 4-(6-chloro-1-(methylsulfonyl)-1H-pyrrolo[3,2-c]pyridin-2-yl)-1H-pyrazole-1-carboxylate (15) (40 mg, 0.101 mmol), cesium carbonate (131 mg, 0.403 mmol), 4-fluoroaniline (19 μL, 0.202 mmol) and di-tBuX-Phos (17.1 mg, 0.040 mmol) in t-BuOH containing water (3%) (1.1 mL). The reaction mixture was heated at 80° C. for 1.5 hr under microwave irradiation. It was then diluted with EtOAc and washed with water. The organic extracts were dried over MgSO$_4$, filtered and concentrated under vacuum. The residue was then purified by prep TLC (DCM/MeOH, 95/5) to afford 20 mg of title compound mixed with some starting material. This mixture was used in the next step without further purification. $^1$H NMR (500 MHz, CDCl$_3$) 1.69 (s, 9H), 2.90 (s, 3H), 6.69 (d, J=0.9 Hz, 1H), 7.05-7.09 (m, 2H), 7.33-7.37 (m, 2H), 7.46 (br m, 1H), 7.93 (d, J=0.9 Hz, 1H), 8.35 (d, J=0.9 Hz, 1H), 8.48 (m, 1H).

tert-Butyl 4-(6-(5-fluoropyridin-2-ylamino)-1-(methylsulfonyl)-1H-pyrrolo[3,2-c]pyridin-2-yl)-1H-pyrazole-1-carboxylate (54)

Pd$_2$(dba)$_3$ (9.0 mg, 0.01 mmol) was added to a mixture of tert-butyl 4-(6-chloro-1-(methylsulfonyl)-1H-pyrrolo[3,2-c]pyridin-2-yl)-1H-pyrazole-1-carboxylate (15) (39 mg, 0.098 mmol), cesium carbonate (128 mg, 0.393 mmol), 2-amino-5-fluoropyridine (22 mg, 0.197 mmol) and di-tBuX-Phos (16.7 mg, 0.039 mmol) in t-BuOH containing water (3%) (1.1 mL). The reaction mixture was heated at 80° C. for 1.5 hr under microwave irradiation. It was then diluted with EtOAc and washed with water. The organic extracts were dried over MgSO$_4$, filtered and concentrated under vacuum. The residue was then purified by prep TLC (DCM/MeOH, 95/5) to afford 17 mg of title compound mixed with some 2-amino-5-fluoropyridine. This mixture was used in the next step without further purification. $^1$H NMR (500 MHz, CDCl$_3$) 1.70 (s, 9H), 2.97 (s, 3H), 6.72 (d, J=0.9 Hz, 1H), 7.37-7.41 (m, 1H), 7.52-7.56 (m, 1H), 7.62 (br s, 1H), 7.95 (m, 1H), 8.17-8.19 (m, 1H), 8.26 (s, 1H), 8.38 (s, 1H), 8.54 (d, J=0.9 Hz, 1H).

tert-Butyl 4-(6-(3,4-dimethoxyphenylamino)-1-methyl-1H-pyrrolo[3,2-c]pyridin-2-yl)-1H-pyrazole-1-carboxylate (55)

Pd$_2$(dba)$_3$ (9.2 mg, 0.01 mmol) was added to a mixture of tert-butyl 4-(6-bromo-1-methyl-1H-pyrrolo[3,2-c]pyridin-2-yl)-1H-pyrazole-1-carboxylate (28) (38 mg, 0.101 mmol), cesium carbonate (66 mg, 0.201 mmol), 3,4-dimethoxyaniline (18.5 mg, 0.121 mmol) and Xantphos (11.7 mg, 0.020 mmol) in dioxane (1.1 mL). The reaction mixture was heated at 80° C. for 19 hr. The reaction mixture was then filtered and the solution was concentrated under reduced pressure. The residue was purified by prep TLC (DCM/MeOH 95/5) to afford the title compound as a dark red solid (5 mg, 11%). $^1$H NMR (500 MHz, CDCl$_3$) 1.71 (s, 9H), 3.50 (s, 1H), 3.89 (s, 1H), 3.91 (s, 1H), 6.48 (s, 1H), 6.57 (d, J=0.6 Hz, 1H), 6.64 (m, 1H), 6.89 (m, 2H), 6.92 (m, 1H), 7.91 (d, J=0.6 Hz, 1H), 8.26 (d, J=0.6 Hz, 1H), 8.49 (s, 1H).

The following preparations were carried out according to the method described for Preparation 29 using the required benzoic acids and amines. The purification methods used are as described below:

Method A: Biotage silica gel column chromatography eluting with 1 to 10% MeOH/aq NH$_3$ 10/1 in DCM.

Method B: Biotage silica gel column chromatography eluting with DCM/EtOAc 90/10 to 70/30 followed by a second biotage eluting with cyclohexane/EtOAc 70/30 to 50/50.

Method C: Biotage silica gel column chromatography eluting with DCM/EtOAc 90/10 followed by filtration through an SCX-2 column.

Method D: Biotage silica gel column chromatography eluting with 1 to 10% MeOH/aq NH$_3$ 10/1 in DCM.

Method E: Biotage silica gel column chromatography eluting with DCM/EtOAc 80/20 to 60/40.

Method F: Biotage silica gel column chromatography eluting with cyclohexane/EtOAc 50/50 to 0/100 followed by filtration through an SCX-2 column.

Method G: Filtration through an SCX-2 column followed by silica gel column chromatography eluting with 10% (2M ammonia in MeOH) in chloroform.

Method H: Silica gel column chromatography eluting with between 3-20% methanol in EtOAc.

Method I: Silica gel column chromatography eluting with ethyl acetate/dichloromethane (1:1) followed by 1% and 2.5% methanol in ethyl acetate/dichloromethane (1:1).

| Preparation | Name/Structure | Data |
|---|---|---|
| 56 | 4-Amino-3-methoxy-N-(1-methylpiperidin-4-yl)benzamide | $^1$H NMR (500 MHz, CD$_3$OD): δ 1.69 (qd, J = 12.5, 3.8 Hz, 2H), 1.91-1.98 (m, 2H), 2.19 (td, J = 12.1, 2.2 Hz, 2H), 2.32 (s, 3H), 2.89-2.96 (m, 2H), 3.84-3.92 (m, 1H), 3.90 (s, 3H), 6.71 (d, J = 8.2 Hz, 1H), 7.31 (dd, J = 8.2, 1.9 Hz, 1H), 7.35 (d, J = 1.9 Hz, 1H). LC (Method B)-MS (ESI, m/z) t$_R$ 0.44 min, 264 [M + H]$^+$ Using 4-amino-3-methoxybenzoic acid, 1-methylpiperidin-4-amine and purification method A. |
| 57 | 4-Amino-N,N-dimethyl-3-(trifluoromethoxy)benzamide | $^1$H NMR (500 MHz, CDCl$_3$): δ 3.08 (s, 6H), 4.10 (br s, 2H), 6.80 (d, J = 8.2 Hz, 1H), 7.25 (dd, J = 8.2, 1.8 Hz, 1H), 7.30-7.32 (m, 1H). LC (Method C)-MS (ESI, m/z) t$_R$ 2.16 min, 249 [M + H]$^+$ Using 4-amino-3-(trifluoromethoxy)benzoic acid, dimethylamine and purification method B. |
| 58 | 3-Amino-4-methoxy-N,N-dimethylbenzamide | 1H NMR (500 MHz, CD3OD): δ 3.06 (s, 6H), 3.89 (s, 3H), 6.77 (dd, J = 8.2, 2.1 Hz, 1H), 6.82 (d, J = 2.1 Hz, 1H), 6.88 (d, J = 8.2 Hz, 1H). LC (Method C)-MS (ESI, m/z) tR 1.07 min, 195 [M + H]$^+$ Using 3-amino-4-methoxybenzoic acid, dimethylamine and purification method C. |
| 59 | (4-Amino-3-methoxyphenyl)(thiomorpholino)methanone-S,S-dioxide | $^1$H NMR (500 MHz, DMSO d-6): δ 3.19-3.24 (m, 4H), 3.84-3.89 (m, 4H), 3.87 (s, 3H), 5.19 (br s, 2H), 6.62 (d, J = 8.0 Hz, 1H), 6.86 (dd, J = 8.0, 1.7 Hz, 1H), 6.92 (d, J = 1.7 Hz, 1H); LC (Method B)-MS (ESI, m/z) t$_R$ 1.19 min, 285 [M + H]$^+$ Using 4-amino-3-methoxybenzoic acid, thiomorpholine 1,1-dioxide and purification method D. |
| 60 | (4-Amino-3-methoxyphenyl)(morpholino)methanone | 1H NMR (500 MHz, CD3OD): δ 3.63-3.72 (m, 8H), 3.88 (s, 3H), 6.74 (d, J = 8.0 Hz, 1H), 6.88 (dd, J = 8.0, 1.8 Hz, 1H), 6.94 (d, J = 1.8 Hz, 1H) LC (Method C)-MS (ESI, m/z) t$_R$ 1.27 min, 237 [M + H]$^+$ Using 4-amino-3-methoxybenzoic acid, morpholine and purification method E. |

-continued

| Preparation | Name/Structure | Data |
| --- | --- | --- |
| 61 | 4-Amino-3-methoxy-N-(2-methoxyethyl)benzamide 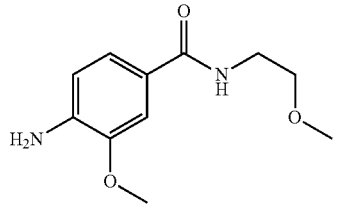 | 1H NMR (500 MHz, CDCl3): δ 3.39 (s, 3H), 3.54-3.57 (m, 2H), 3.61-3.65 (m, 2H), 3.90 (s, 3H), 4.12 (br s, 2H), 6.45 (br s, 1H), 6.66 (d, J = 8.1 Hz, 1H), 7.16 (dd, J = 8.1, 1.8 Hz, 1H), 7.37 (d, J = 1.8 Hz, 1H). LC (Method C)-MS (ESI, m/z) $t_R$ 1.35 min, 225 [M + H]$^+$ Using 4-amino-3-methoxybenzoic acid, 2-methoxyethylamine and purification method B. |
| 62 | (4-Amino-3-methoxyphenyl)(3-methoxyazetidin-1-yl)methanone 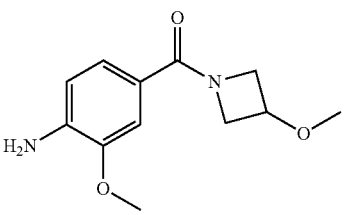 | 1H NMR (500 MHz, CD3OD): δ 3.32 (s, 3H), 3.88 (s, 3H), 3.92-3.99 (m, 1H), 4.18-4.38 (m ,3H), 4.49-4.61 (m, 1H), 3.63-3.72 (m, 8H), 6.71 (d, J = 8.1 Hz, 1H), 7.09 (dd, J = 8.1, 1.8 Hz, 1H), 7.16 (d, J = 1.8 Hz, 1H). LC (Method C)-MS (ESI, m/z) $t_R$ 1.63 min, 237 [M + H]$^+$ Using 4-amino-3-methoxybenzoic acid, 3-methoxyazetidine hydrochloride and purification method F. |
| 63 | 4-Amino-3-methoxy-N-methylbenzamide 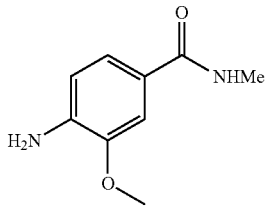 | 1H NMR (500 MHz, CDCl3): δ 2.95 (d, J = 4.9 Hz, 3H), 3.85 (s, 3H), 4.1 (s, br, 2H), 6.38 (s, br, 1H), 6.61 (d, J = 8.1 Hz, 1H), 7.14 (dd, J = 1.9 Hz, 8.1 Hz, 1H), 7.35 (d, J = 1.9 Hz, 1H). Using 4-amino-3-methoxybenzoic acid, methylamine and purification method G. |
| 64 | 4-Amino-3-chloro-N-methylbenzamide 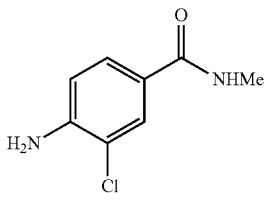 | 1H-NMR (500 MHz, CDCl3): δ 2.93 (d, J = 4.7 Hz, 3H), 4.45 (s, br, 2H), 6.58 (s, br, 1H), 6.69 (d, J = 8.4 Hz, 1H), 7.49 (dd, J = 2 Hz, 8.4 Hz, 1H), 7.72 (d, J = 2 Hz, 1H). Using 4-amino-3-chlorobenzoic acid, methylamine and purification method G. |
| 65 | (4-Amino-3-chlorophenyl)(3-methoxyazetidin-1-yl)methanone 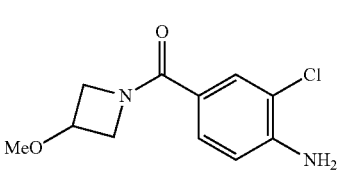 | 1H-NMR (500 MHz, d6-acetone): δ 3.28 (s, 3H), 3.95 (s, br, 2H), 4.28 (s, br, 1H), 4.5 (s, br, 2H), 5.4 (s, br, 2H), 6.86 (d, J = 8.4 Hz, 1H), 7.42 (dd, J = 2 Hz, 8.4 Hz, 1H), 7.58 (d, J = 2 Hz, 1H). Using 4-amino-3-chlorobenzoic acid, 3-methoxyazetidine and chromatography method F. |

-continued

| Preparation | Name/Structure | Data |
|---|---|---|
| 66 | (4-Amino-3-chlorophenyl)(S,S-dioxo-thiomorpholino)methanone 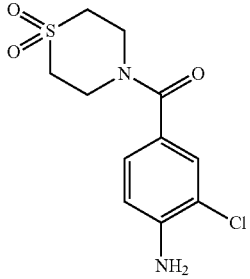 | 1H-NMR (500 MHz, d6-DMSO): δ 3.21 (s, br,, 4H), 3.85 (s, br, 4H), 6.77 (d, J = 8.3 Hz, 1H), 7.18 (dd, J = 1.9 Hz, 8.3 Hz, 1H), 7.37 (d, J = 1.9 Hz, 1H). Using 4-amino-3-chlorobenzoic acid, S,S-dioxo-thiomorpholine and chromatography method F. |
| 67 | 4-Amino-3-chloro-N-ethyl-N-methylbenzamide 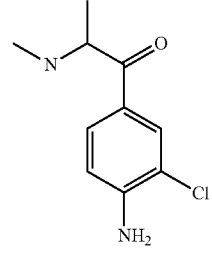 | 1H NMR (500 MHz, CD3OD): δ 1.2 (t, J = 6.8 Hz, 3H), 3.03 (s, 3H), 3.47 (s, br, 2H), 6.83 (d, J = 8.3 Hz, 1H), 7.13 (d, J = 8 Hz, 1H), 7.32 (s, 1H). Using 4-amino-3-chlorobenzoic acid, N-ethylmethylamine and chromatography method F. |
| 68 | (4-Amino-3-chlorophenyl)(pyrrolidin-1-yl)methanone 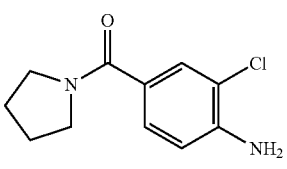 | 1H-NMR (500 MHz, CD3OD): δ 1.95 (m, 4H), 3.55 (m, 4H), 4.85 (s, 2H), 6.82 (d, J = 8.4 Hz, 1H), 7.28 (dd, J = 2 Hz, 8.4 Hz, 1H), 7.46 (d, J = 2 Hz, 1H). Using 4-amino-3-chlorobenzoic acid, pyrrolidine and chromatography method F. |
| 69 | (4-Amino-3-chlorophenyl)(4-methylpiperazin-1-yl)methanone 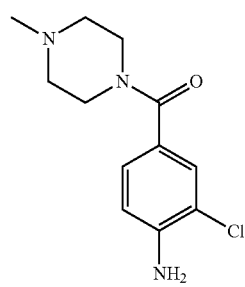 | 1H NMR (500 MHz, DMSO-d6): δ 2.19 (s, 3H), 2.31 (s, br, 4H), 3.47 (s, br, 4H), 6.77 (d, J = 8.4 Hz, 1H), 7.1 (dd, J = 2 Hz, 8.3 Hz, 1H), 7.24 (d, J = 2 Hz, 1H). Using 4-amino-3-chlorobenzoic acid, 1-methylpiperazine and purification method H. |

| Preparation | Name/Structure | Data |
|---|---|---|
| 70 | (4-Amino-3-chlorophenyl)(4-methoxypiperidin-1-yl)methanone 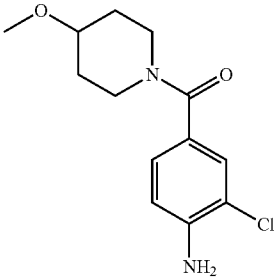 | 1H NMR (500 MHz, DMSO-d6): δ 1.41 (m, 2H), 1.81 (m, 2H), 3.2 (m, 5H), 3.41 (m, 1H), 3.6 (s, br, 2H), 6.76 (d, J = 8.3 Hz, 1H), 7.08 (dd, J = 1.9 Hz, 8.3 Hz, 1H), 7.23 (d, J = 1.9 Hz, 1H). Using 4-amino-3-chlorobenzoic acid, 4-methoxypiperidine and purification method H. |
| 71 | (4-Amino-3-chlorophenyl)(4-(dimethylamino)piperidin-1-yl)methanone 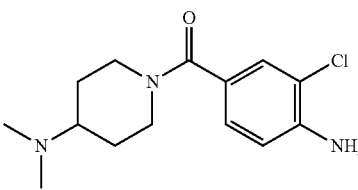 | 1H NMR (500 MHz, DMSO-d6): δ 1.31 (dd, J = 3.8 Hz, 11.7 Hz, 2H), 1.73 (d, J = 10.7 Hz, 2H), 2.19 (s, 6H), 2.4 (t, J = 5.6 Hz, 1H), 2.88 (s, br, 2H), 3.45 (s, br, 2H), 4.05 (s, br, 2H), 6.76 (d, J = 8.3 Hz, 1H), 7.08 (dd, J = 1.9 Hz, 8.3 Hz, 1H), 7.23 (d, J = 1.9 Hz, 1H). Using 4-amino-3-chlorobenzoic acid, N,N-dimethylpiperidin-4-amine and purification method H. |
| 72 | (4-amino-3-chlorophenyl)(3,3-difluoroazetidin-1-yl)methanone 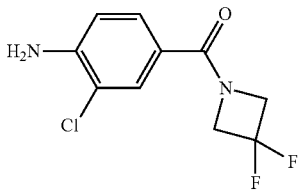 | 1H-NMR (500 MHz, DMSO-d6): δ 4.60 (br s, 4H), 6.07 (s, 2H), 6.79 (d, J = 8.4, 1H), 7.39 (dd, J = 2.1, 8.4 Hz, 1H), 7.54 (d, J = 2.1 Hz, 1H). Using 4-amino-3-chlorobenzoic acid, 3,3-difluoroazetidine hydrochloride and purification method H. |
| 73 | (4-Amino-3-chlorophenyl)(azetidin-1-yl)methanone 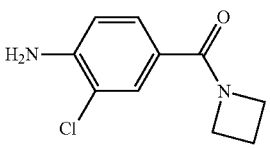 | 1H-NMR (500 MHz, DMSO-d6): δ 2.23 (m, 2H), 3.98 (bs, 2H), 4.30 (br s, 2H), 5.90 (s, 2H), 6.75 (d, J = 8.5, 1H), 7.32 (dd, J = 2.0, 8.5 Hz, 1H), 7.46 (d, J = 1.9 Hz, 1H). Using 4-amino-3-chlorobenzoic acid, azetidine hydrochloride and purification method I. |

Preparation 74:
4-(Bromomethyl)-2-methoxy-1-nitrobenzene

Carbon tetrabromide (0.543 g, 1.638 mmol) and triphenylphosphine (0.430 g, 1.638 mmol) were added to a solution of (3-methoxy-4-nitrophenyl)methanol (0.2 g, 1.092 mmol) in THF (5.46 mL). The reaction mixture was stirred at room temperature overnight before being concentrated under reduced pressure and purified via Biotage silica gel column chromatography eluting with (cyclohexane/EtOAc 99/1 to 80/20) to afford the title product as a yellow solid (220 mg, 82%). $^1$H NMR (500 MHz, CDCl$_3$): δ 4.00 (s, 3H), 4.48 (s, 2H), 7.06 (dd, J=8.3, 1.7 Hz, 1H), 7.12 (d, J=1.7 Hz, 1H), 7.84 (d, J=8.3 Hz, 1H)
LC (Method B) t$_R$ 2.62 min.

Preparation 75: 4-(3-Methoxy-4-nitrobenzyl)thiomorpholine-1,1-dioxide

Thiomorpholine 1,1-dioxide (0.242 g, 1.788 mmol) and triethylamine (0.19 mL, 1.341 mmol) were added to a solution of 4-(bromomethyl)-2-methoxy-1-nitrobenzene (Preparation 74, 0.22 g, 0.894 mmol) in THF (2.2 mL). The reaction mixture was stirred overnight at room temperature before being concentrated under reduced pressure and purified via Biotage silica gel column chromatography eluting with (DCM/EtOAc 99/1 to 90/10) to afford the title product as a white solid (242 mg, 90%). $^1$H NMR (500 MHz, CDCl$_3$): δ 3.00-3.04 (m, 4H), 3.09-3.12 (m, 4H), 3.71 (s, 2H), 3.98 (s, 3H), 7.01 (m, 1H), 7.09 (m, 1H), 7.84 (d, J=8.2 Hz, 1H). LC (Method C)-MS (ESI, m/z) $t_R$ 2.03 min, 301 [(M+H$^+$), 100%].

Preparation 76: 2-Methoxy-4-(thiomorpholinomethyl)aniline-S,S-dioxide

10% Pd on carbon (6 mg, 0.433 mmol) was added to a solution of 4-(3-methoxy-4-nitrobenzyl)thiomorpholine-1,1-dioxide (Preparation 75, 130 mg, 0.433 mmol) in EtOH (1 mL). The reaction mixture was stirred under a hydrogen atmosphere overnight at room temperature before being filtered on a pad of Celite and the filtrate concentrated under reduced pressure. The residue was purified via Biotage silica gel column chromatography eluting with (DCM/EtOH 99/1 to 95/5, 12 g column) to afford the title product as a colourless oil (49 mg, 42%). $^1$H NMR (500 MHz, CDCl$_3$): δ 2.95-2.99 (m, 4H), 3.04-3.07 (m, 4H), 3.55 (s, 2H), 3.81 (br s, 2H), 3.87 (s, 3H), 6.66 (d, J=7.8 Hz, 1H), 6.70 (dd, J=7.8, 1.6 Hz, 1H), 6.75 (d, J=1.6 Hz, 1H).

Preparation 77: 4-Amino-3-chloro-N,N-dimethylbenzenesulfonamide

A suspension of 4-acetamido-3-chlorobenzene-1-sulfonyl chloride (0.96 g, 3.58 mmol) in a dimethylamine solution (2M in MeOH, 5.37 mL, 10.7 mmol) was stirred at room temperature for 2.5 hours. The reaction mixture was concentrated under reduced pressure and the residue was then redissolved in MeOH (17.9 mL). A 1M HCl solution in MeOH (5.37 mL, 5.37 mmol) was added and the reaction mixture was refluxed for 6 hours before being concentrated under reduced pressure. The residue was purified via Biotage silica gel column chromatography eluting with (cyclohexane/EtOAc 80/20 to 60/40) to afford the title product as a white solid (133 mg, 16%). $^1$H NMR (500 MHz, CDCl$_3$) d 2.70 (s, 6H), 4.54 (br s, 2H), 6.83 (d, J=8.5 Hz, 1H), 7.48 (dd, J=8.5, 2.1 Hz, 1H), 7.70 (d, J=2.1 Hz, 1H).

LC (Method B)-MS (ESI, m/z) $t_R$ 2.24 min, 235 [(M+H$^+$), 100%].

Preparation 78: 6-Bromo-1-(cyclopentylmethyl)-2-(1-methyl-1H-pyrazol-4-yl)-1H-pyrrolo[3,2-c]pyridine Sodium hydride (60% in mineral oil, 10.8 mg, 0.271 mmol) was added to a solution of 6-bromo-2-(1-methyl-1H-pyrazol-4-yl)-1H-pyrrolo[3,2-c]pyridine (Preparation 22, 50 mg, 0.180 mmol) in DMF (780 mL). The reaction mixture was then stirred for 15 minutes at room temperature before the addition of (bromomethyl)cyclopentane (44 mg, 0.271 mmol). The reaction mixture was then stirred overnight at room temperature and for 24 hours at 60° C. Sodium hydride (60% in mineral oil, 5 mg, 0.125 mmol) was added and the reaction was stirred for another 7 hours at 60° C. The reaction mixture was then diluted with water and EtOAc. The layers were separated and the aqueous layer was extracted with EtOAc. The combined organic layers were dried (Na$_2$SO$_4$), filtered and concentrated under reduced pressure. The crude was purified via Biotage silica gel column chromatography eluting with (DCM/EtOAc 99/1 to 80/20) to afford the title product as a colourless oil (45 mg, 69%). $^1$H NMR (500 MHz, CDCl$_3$) d 1.10-1.19 (m, 2H), 1.46-1.64 (m, 6H), 2.24-2.33 (m, 1H), 4.03 (s, 3H), 4.09 (d, J=7.6 Hz, 2H), 6.53 (d, J=0.9 Hz, 1H), 7.45 (t, J=0.9 Hz, 1H), 7.59 (s, 1H), 7.68 (s, 1H), 8.60 (d, J=0.9 Hz, 1H). LC (Method B)-MS (ESI, m/z) $t_R$ 3.03 min, 359 [(M+H$^+$), 100%].

Preparation 79: 6-Bromo-3-chloro-2-(1-methyl-1H-pyrazol-4-yl)-1H-pyrrolo[3,2-c]pyridine NCS (48 mg, 0.361 mmol) was added to a solution of 6-bromo-2-(1-methyl-1H-pyrazol-4-yl)-1H-pyrrolo[3,2-c]pyridine (Preparation 22, 100 mg, 0.361 mmol) in DMF (1.1 mL). The reaction mixture was stirred overnight at room temperature before being filtered on an SCX-2 column and concentrated under vacuum. The residue was purified via Biotage silica gel column chromatography eluting with (DCM/EtOH 99/1 to 95/5) to afford the title product as a white solid (86 mg, 76%). $^1$H NMR (500 MHz, CD$_3$OD) δ 4.01 (s, 3H), 7.54 (d, J=0.8 Hz, 1H), 8.05 (s, 1H), 8.28 (s, 1H), 8.47 (d, J=0.8 Hz, 1H). LC (Method B)-MS (ESI, m/z) $t_R$ 2.84 min, 312 [(M+H$^+$), 100%].

Preparation 80: tert-Butyl 6-bromo-3-chloro-2-(1-methyl-1H-pyrazol-4-yl)-1H-pyrrolo[3,2-c]pyridine-1-carboxylate DMAP (1.0 mg, 8.34 μmol) was added to a solution of 6-bromo-3-chloro-2-(1-methyl-1H-pyrazol-4-yl)-1H-pyrrolo[3,2-c]pyridine (Preparation 79, 26 mg, 0.083 mmol), triethylamine (17.5 mL, 0.125 mmol) and di-tert-butyl dicarbonate (27 mg, 0.125 mmol) in EtOAc (673 mL) and DMF (500 mL). The reaction mixture was stirred for overnight at room temperature. Then further di-tert-butyl dicarbonate (27.3 mg, 0.125 mmol) was added. The reaction mixture was stirred for another 5 hours before being diluted with EtOAc and washed with water. The organic layer was dried over Na$_2$SO$_4$, filtered and concentrated under reduced pressure. The crude was purified via Biotage silica gel column chromatography eluting with (DCM/EtOAc 99/1 to 80/20) to afford the title product as a white solid (25 mg, 73%). $^1$H NMR (500 MHz, CDCl$_3$) d 1.51 (s, 9H), 4.02 (s, 3H), 7.63 (s, 1H), 7.66 (s, 1H), 8.26 (d, J=0.8 Hz, 1H), 8.63 (d, J=0.8 Hz, 1H). LC (Method B)-MS (ESI, m/z) $t_R$ 3.31 min, 411 [(M+H$^+$), 100%].

Preparation 81: 6-Bromo-1-(cyclopropylmethyl)-2-(1-methyl-1H-pyrazol-4-yl)-1H-pyrrolo[3,2-c]pyridine NaHMDS (173 mL, 0.173 mmol) was added to a solution of 6-bromo-2-(1-methyl-1H-pyrazol-4-yl)-1H-pyrrolo[3,2-c]pyridine (Preparation 22, 40 mg, 0.144 mmol) in DMF (630 mL). The reaction mixture was stirred for 15 minutes at 60° C. before the addition of (bromomethyl)cyclopropane (21 mL, 0.217 mmol). The reaction was then stirred for 24 hours at 60° C. before being diluted with water and EtOAc. The layers were separated and the aqueous layer was extracted with EtOAc. The combined organic layers were dried (Na$_2$SO$_4$), filtered and concentrated under reduced pressure. The crude was purified via Biotage silica gel column chromatography eluting with DCM/EtOAc (99/1 to 80/20) to afford a colourless oil as the title compound. (29 mg, 61%). $^1$H NMR (500 MHz, CDCl$_3$) d 0.21-0.24 (m, 2H), 0.52-0.56 (m, 2H), 1.08-1.15 (m, 1H), 4.02 (s, 3H), 4.06 (d, J=6.3 Hz, 2H), 6.54 (d, J=0.9 Hz, 1H), 7.45 (t, J=0.9 Hz, 1H), 7.61 (d, J=0.8 Hz, 1H), 7.70 (d, J=0.8 Hz, 1H), 8.60 (d, J=0.9 Hz, 1H). LC (Method B)-MS (ESI, m/z) $t_R$ 2.64 min, 331 [(M+H$^+$), 100%].

Preparation 82: 4-Amino-3,5-dichloro-N,N-dimethylbenzamide

NCS (38 mg, 0.288 mmol) was added to a solution of 4-amino-3-chloro-N,N-dimethylbenzamide (52 mg, 0.262 mmol) in MeCN (520 mL). The reaction mixture was refluxed for 1 hour before being concentrated under vacuum. The residue was purified via Biotage silica gel column chromatography eluting with (cyclohexane/EtOAc 80/20 to 60/40) to afford the title product as a white solid (57 mg, 93%). $^1$H NMR (500 MHz, CDCl$_3$) d 3.06 (s, 6H), 4.68 (br s, 2H), 7.34 (s, 2H). LC (Method D)-MS (ESI, m/z) $t_R$ 1.50 min, 233 [(M+H$^+$), 100%].

Preparation 83: 2-Chloro-4-(1-methyl-1H-pyrazol-4-yl)aniline

Method B

PdCl$_2$(dppf).CH$_2$Cl$_2$ (0.040 g, 0.049 mmol) was added to a solution of 4-bromo-2-chloroaniline (0.102 g, 0.494 mmol), 1-methyl-4-(4,4,5,5-tetramethyl-1,3,2-dioxaborolan-2-yl)-1H-pyrazole (0.134 g, 0.642 mmol) and sodium carbonate (0.115 g, 1.087 mmol) in THF/H$_2$O (3/1, 2.157 mL). The reaction mixture was refluxed overnight. It was then diluted with EtOAc and quenched with water. The layers were separated and the aqueous layer was extracted with EtOAc. The combined organic layers were dried (Na$_2$SO$_4$), filtered and concentrated under reduced pressure. The crude mixture was purified via Biotage silica gel column chromatography eluting with (Cyclohexane/EtOAc 80/20 to 60/40) to give the title product as a white solid (62 mg, 60%). $^1$H NMR (500 MHz, CDCl$_3$): δ 3.92 (s, 3H), 4.05 (br s, 2H), 6.76 (d, J=8.2 Hz, 1H), 7.17 (dd, J=8.2, 2.0 Hz, 1H), 7.36 (d, J=2.0 Hz, 1H), 7.49 (s, 1H), 7.65 (s, 1H); LC (Method B)-MS (ESI, m/z) $t_R$ 2.23 min, 208 [(M+H$^+$), 100%].

Preparation 84: 6-Bromo-1-(cyclohexylmethyl)-2-(1-methyl-1H-pyrazol-4-yl)-1H-pyrrolo[3,2-c]pyridine NaHMDS (1 M solution in THF, 217 mL, 0.217 mmol) was added to a solution of 6-bromo-2-(1-methyl-1H-pyrazol-4-yl)-1H-pyrrolo[3,2-c]pyridine (Preparation 22, 50 mg, 0.180 mmol) in DMF (790 mL). The reaction mixture was then stirred for 10 minutes at room temperature before the addition of (bromomethyl)cyclohexane (38 mL, 0.271 mmol) and was stirred overnight at 60° C. NaH (60% in mineral oil) (14.4 mg, 0.361 mmol) and bromomethylcyclohexane (76 mL, 0.542 mmol) were then added. The reaction mixture was stirred for 1 hour at 60° C. before being diluted with water and EtOAc. The layers were separated and the aqueous layer was extracted with EtOAc. The combined organic layers were dried (Na$_2$SO$_4$), filtered and concentrated under reduced pressure. The crude was purified via Biotage silica gel column chromatography eluting with (DCM/EtOAc 99/1 to 80/20) to afford the title product as a colourless oil (40 mg, 59%). $^1$H NMR (500 MHz, CDCl$_3$) d 0.84-0.94 (m, 2H), 1.06-1.17 (m, 3H), 1.43-1.50 (m, 2H), 1.61-1.69 (m, 3H), 1.70-1.78 (m, 1H), 3.95 (d, J=7.5 Hz, 2H), 4.02 (s, 3H), 6.52 (d, J=0.9 Hz, 1H), 7.41 (t, J=0.9 Hz, 1H), 7.57 (s, 1H), 7.66 (s, 1H), 8.58 (d, J=0.9 Hz, 1H). LC (Method B)-MS (ESI, m/z) $t_R$ 3.14 min, 373 [(M+H$^+$), 100%].

Preparation 85: 2-Chloro-4-(1-methyl-1H-pyrazol-3-yl)aniline

Method C

Tetrakis(triphenylphosphine)palladium (0.046 g, 0.039 mmol) was added to a solution of 2-chloro-4-(4,4,5,5-tetramethyl-1,3,2-dioxaborolan-2-yl)aniline (0.1 g, 0.394 mmol), 3-iodo-1-methyl-1H-pyrazole (0.123 g, 0.592 mmol) and sodium carbonate (0.125 g, 1.183 mmol) in DME/H$_2$O 3/1 (2.00 mL). The reaction mixture was heated for 1 hour at 135° C. under microwave irradiation before being diluted with EtOAc and quenched with water. The layers were separated and the aqueous layer was extracted with EtOAc. The combined organic layers were dried (Na$_2$SO$_4$), filtered and concentrated under reduced pressure. The crude mixture was purified via Biotage silica gel column chromatography eluting with (Cyclohexane/EtOAc 80/20 to 60/40) to afford the title product as a yellow solid (60 mg, 73%). $^1$H NMR (500 MHz, CDCl$_3$): δ 3.93 (s, 3H), 4.09 (br s, 2H), 6.42 (d, J=2.3 Hz, 1H), 6.79 (d, J=8.3 Hz, 1H), 7.34 (d, J=2.3 Hz, 1H), 7.50 (dd, J=8.3, 2.0 Hz, 1H), 7.71 (d, J=2.0 Hz, 1H). LC (Method B)-MS (ESI, m/z) $t_R$ 2.35 min, 208 [(M+H$^+$), 100%].

Preparation 86: 2-Chloro-4-(1-methyl-1H-imidazol-5-yl)aniline

Prepared according to Method C (Preparation 85) using 5-iodo-1-methyl-1H-imidazole. Purified using Biotage silica gel column chromatography eluting with DCM/EtOH 99/1 to 95/5 to afford the title product as a white solid (50 mg, 61%). $^1$H NMR (500 MHz, CDCl$_3$): δ 3.62 (s, 3H), 4.23 (br s, 2H), 6.81 (d, J=8.3 Hz, 1H), 7.01 (d, J=1.2 Hz, 1H), 7.08 (dd, J=8.2, 2.0 Hz, 1H), 7.27 (d, J=2.0 Hz, 1H), 7.47 (s, 1H). LC (Method B)-MS (ESI, m/z) $t_R$ 0.93 min, 208 [(M+H$^+$), 100%].

Preparation 87: 2-Chloro-4-(4-methyl-4H-1,2,4-triazol-3-yl)aniline

NCS (0.077 g, 0.574 mmol) was added to a solution of 4-(4-methyl-4H-1,2,4-triazol-3-yl)aniline (0.1 g, 0.574 mmol) in DMF (1.1 mL). The reaction mixture was heated at 90° C. for 1 hour and was then concentrated under vacuum. The residue was purified via Biotage silica gel column chromatography elutin with (DCM/EtOH 99/1 to 90/10) to afford the title product as a white solid (97 mg, 81%). $^1$H NMR (500 MHz, CD$_3$OD) δ 3.78 (s, 3H), 6.95 (d, J=8.4 Hz, 1H), 7.38 (dd, J=8.4, 2.0 Hz, 1H), 7.58 (d, J=2.0 Hz, 1H), 8.48 (s, 1H). LC (Method B)-MS (ESI, m/z) $t_R$ 1.25 min, 209 [(M+H$^+$), 100%].

Preparation 88: 2-Chloro-4-(pyridin-3-yl)aniline

Prepared according to Method C (Preparation 85) using 4-bromo-2-chloroaniline and pyridin-3-ylboronic acid. Purified using Biotage silica gel column chromatography eluting with DCM/EtOH 99/1 to 97/3 and filtered on SCX-2 column to afford the title product as a yellow oil (93 mg, 94%). $^1$H NMR (500 MHz, CDCl$_3$): δ 3.96 (br s, 2H), 6.87 (d, J=8.2 Hz, 1H), 7.32 (dd, J=8.2, 2.2 Hz, 1H), 7.35 (ddd, J=7.9, 4.8, 1.0 Hz, 1H), 7.51 (d, J=2.2 Hz, 1H), 7.80 (ddd, J=7.9, 2.3, 1.6 Hz, 1H), 8.54 (dd, J=4.8, 1.6 Hz, 1H), 8.79 (dd, J=2.3, 1.0 Hz, 1H).

LC (Method B)-MS (ESI, m/z) $t_R$ 1.41 min, 205 [(M+H$^+$), 100%].

Preparation 89: 2-Chloro-4-(1,5-dimethyl-1H-pyrazol-4-yl)aniline

Prepared according to Method C (Preparation 85) using 4-bromo-1,5-dimethyl-1H-pyrazole in DME/MeOH 2/1 at 150° C. for 10 minutes under microwave irradiation. Purified using Biotage silica gel column chromatography eluting with cyclohexane/EtOAc 80/20 to 70/30 to afford the title product as a white solid (61 mg, 70%). $^1$H NMR (500 MHz, CDCl$_3$): δ 2.35 (s, 3H), 3.85 (s, 3H), 4.07 (br s, 2H), 6.81 (d, J=8.2 Hz, 1H), 7.07 (dd, J=8.2, 2.0 Hz, 1H), 7.26 (d, J=2.0 Hz, 1H), 7.49 (s, 1H). LC (Method B)-MS (ESI, m/z) $t_R$ 2.42 min, 222 [(M+H$^+$), 100%].

Preparation 90:
2-Chloro-4-(1,3-dimethyl-1H-pyrazol-4-yl)

Prepared according to Method C (Preparation 85) using 4-bromo-1,3-dimethyl-1H-pyrazole in DME/MeOH 2/1 at 150° C. for 10 minutes under microwave irradiation. Purified using Biotage silica gel column chromatography eluting with cyclohexane/EtOAc 80/20 to 70/30 to give the title product as a yellow oil (52 mg, 60%). $^1$H NMR (500 MHz, CDCl$_3$): δ 2.37 (s, 3H), 3.87 (s, 3H), 4.07 (br s, 2H), 6.80 (d, J=8.2 Hz, 1H), 7.09 (dd, J=8.2, 2.0 Hz, 1H), 7.28 (d, J=2.0 Hz, 1H), 7.34 (s, 1H). LC (Method B)-MS (ESI, m/z) $t_R$ 2.42 min, 222 [(M+H$^+$), 100%].

Preparation 91:
2-Chloro-4-(1-methyl-1H-imidazol-2-yl)aniline

Prepared according to Method C (Preparation 85) using 2-iodo-1-methyl-1H-imidazole in DME/MeOH 2/1 at 150° C. for 10 minutes under microwave irradiation. Purified using Biotage silica gel column chromatography eluting with DCM/EtOH 99/1 to 97/3 and filtered on SCX-2 column to give the title product as a colourless oil (68 mg, 83%). $^1$H NMR (500 MHz, CDCl$_3$): δ 3.74 (s, 3H), 4.15 (br s, 2H), 6.87 (d, J=8.4 Hz, 1H), 7.00 (d, J=1.3 Hz, 1H), 7.08 (d, J=1.3 Hz, 1H), 7.29 (dd, J=8.4, 2.0 Hz, 1H), 7.48 (d, J=2.0 Hz, 1H). LC (Method B)-MS (ESI, m/z) $t_R$ 0.89 min, 208 [(M+H$^+$), 100%].

Preparation 92:
2-Chloro-4-(5-methylisoxazol-4-yl)aniline

Prepared according to Method B (Preparation 83) using 4-iodo-5-methylisoxazole and 2-chloro-4-(4,4,5,5-tetramethyl-1,3,2-dioxaborolan-2-yl)aniline in DME/H$_2$O 1/1 (1.4 mL). The reaction mixture was stirred at 80° C. for 7 hours before being diluted with EtOAc and quenched with water. The layers were separated and the aqueous layer was extracted with EtOAc. The combined organic layers were dried (Na$_2$SO$_4$), filtered and concentrated under reduced pressure. The crude mixture was purified using Biotage silica gel column chromatography eluting with Cyclohexane/EtOAc 99/1 to 80/20 to give the title product as a colourless oil (36 mg, 44%). $^1$H NMR (500 MHz, CDCl$_3$): δ 2.54 (s, 3H), 4.16 (br s, 2H), 6.83 (d, J=8.2 Hz, 1H), 7.09 (dd, J=8.2, 2.0 Hz, 1H), 7.27 (d, J=2.0 Hz, 1H), 8.28 (s, 1H).
LC (Method B)-MS (ESI, m/z) $t_R$ 2.57 min, 209 [(M+H$^+$), 100%].

Preparation 93: 2-Chloro-4-(thiazol-5-yl)aniline

Prepared according to Method C (Preparation 85) using 5-bromothiazole in DME/MeOH 2/1 at 150° C. for 10 minutes under microwave irradiation. Purified using Biotage silica gel column chromatography eluting with cyclohexane/EtOAc 90/10 to 70/30 to give the title product as a colourless oil (65 mg, 78%). $^1$H NMR (500 MHz, CDCl$_3$): δ 4.22 (br s, 2H), 6.80 (d, J=8.3 Hz, 1H), 7.30 (dd, J=8.3, 2.1 Hz, 1H), 7.49 (d, J=2.1 Hz, 1H), 7.95 (d, J=0.8 Hz, 1H), 8.69 (d, J=0.8 Hz, 1H). LC (Method B)-MS (ESI, m/z) $t_R$ 2.54 min, 211 [(M+H$^+$), 100%].

Preparation 94: 2-Chloro-4-(oxazol-5-yl)aniline

Palladium acetate (5.4 mg, 0.024 mmol) was added to a solution of 4-bromo-2-chloroaniline (0.1 g, 0.484 mmol), oxazole (0.064 mL, 0.969 mmol), di(1-adamantyl)-n-butylphosphine (0.017 g, 0.048 mmol), pivalic acid (0.020 g, 0.194 mmol) and potassium carbonate (0.201 g, 1.453 mmol) in DMA (2.4 mL). The reaction mixture was heated at 110° C. overnight before being diluted with EtOAc and quenched with water. The layers were separated and the aqueous layer was extracted with EtOAc. The combined organic layers were dried (Na$_2$SO$_4$), filtered and concentrated under reduced pressure. The crude mixture was purified via Biotage silica gel column chromatography eluting with (Cyclohexane/EtOAc 80/20 to 60/40) to give the title product as a white solid (35 mg, 37%). $^1$H NMR (500 MHz, CDCl$_3$): δ 4.25 (br s, 2H), 6.82 (d, J=8.3 Hz, 1H), 7.20 (s, 1H), 7.38 (dd, J=8.3, 2.0 Hz, 1H), 7.58 (d, J=2.0 Hz, 1H), 7.87 (s, 1H).
LC (Method B)-MS (ESI, m/z) $t_R$ 2.47 min, 195 [(M+H$^+$), 100%].

Preparation 95:
4-(1,2-Dimethyl-1H-imidazol-5-yl)-2-methoxyaniline

To a microwave vial was added 5-bromo-1,2-dimethyl-1H-imidazole (230 mg, 1.31 mmol), 2-methoxy-4-(4,4,5,5-tetramethyl-1,3,2-dioxaborolan-2-yl)aniline (393 mg, 1.58 mmol), Pd(PPh$_3$)$_4$ (152 mg, 0.13 mmol), CsF (599 mg, 3.94 mmol) and DME/MeOH 3/1 (4 mL). The mixture was heated in a microwave at 150° C. for 1 hour. The reaction mixture was then filtered and concentrated onto silica gel and purified by Biotage silica gel column chromatography eluting with (EtOAc/MeOH 100/0 to 96/4) to give the title product as a light brown oil (120 mg, 42%). $^1$H NMR (500 MHz, CDCl$_3$): δ 2.43 (s, 3H), 3.48 (s, 3H), 3.87 (s, 3H), 6.73-6.78 (m, 3H), 6.87 (s, 1H). LC (Method A)-MS (ESI, m/z) $t_R$ 0.49 min, 218 [(M+H$^+$), 100%].

Preparation 96:
2-Chloro-4-(1H-1,2,4-triazol-1-yl)aniline

2-Chloro-4-iodoaniline (2 g, 7.9 mmol), 1,2,4-triazole (0.62 g, 9 mmol) and copper iodide (0.15 g, 0.79 mmol) in DMF (10 ml) were heated to 140° C. and stirred under dry nitrogen for 72 hours. The reaction was cooled to room temperature and diluted with ethyl acetate (50 ml). The organic layer was washed with water, brine, dried over sodium sulfate and filtered. The solvent was removed under vacuum and the residue purified by silica gel column chromatography eluting with 20% ethyl acetate in dichloromethane to give the title compound as a white powder (1.2 g, 78%). $^1$H-NMR (500 MHz, CDCl$_3$): δ 4.43 (s, 2H), 6.76 (d, J=8.7 Hz, 1H), 7.23 (dd, J=2.5 Hz, 8.6 Hz, 1H), 7.48 (d, J=2.4 Hz, 1H), 7.94 (s, 1H), 8.36 (s, 1H).

Preparation 97: 2-Chloro-4-(difluoromethoxy)aniline

N-Chlorosuccinimide (0.84 g, 6.28 mmol) was added to a solution of 4-(difluoromethoxy)aniline (1 g, 6.28 mmol) in acetonitrile (10 ml). The reaction was refluxed for 3 hours and then cooled to room temperature. The solvent was removed in vacuum and the residue purified by silica gel column chromatography eluting with 20% ethyl acetate in hexane to afford the title compound as a dark pink liquid (0.65 g, 53.4%). $^1$H NMR (500 MHz, CDCl$_3$): δ 4.02 (s, 2H), 6.24 (t, J=74 Hz, 1H), 6.72 (d, J=8.7, 1H), 6.89 (dd, J=2.7 Hz, 8.8 Hz, 1H), 7.11 (d, J=2.6 Hz, 1H).

Preparation 98: 2-Bromo-N,N-dimethylacetamide

2-Bromoacetic acid (1 g, 7.2 mmol) was dissolved in dry dichloromethane (10 ml). To the stirred solution was added oxalyl chloride (1 g, 7.92 mmol) followed by DMF (1 drop) and the reaction was allowed to stir at room temperature for 1 hour. A solution of dimethylamine (5 ml of a 2M solution in THF, 10 mmol) was added. After 1 hour, the reaction was concentrated in vacuo and applied to an SCX-2 column. The column was eluted with 30% methanol in chloroform. The solvents were removed in vacuum and the crude product purified by silica gel column chromatography eluting with neat ethyl acetate to afford the title compound as a white powder (0.82 g, 68.6%). $^1$H-NMR (500 MHz, CDCl$_3$): δ 2.97 (s, 3H), 3.1 (s, 3H), 3.86 (s, 2H).

Preparation 99: 2-(4-Iodo-1H-pyrazol-1-yl)-N,N-dimethylacetamide 4-iodo-1H-pyrazole (0.95 g, 4.94 mmol) and 2-bromo-N,N-dimethylacetamide (Preparation 98, 0.82 g, 4.94 mmol) were dissolved in dry DMF (10 ml). To the stirred solution was added potassium carbonate (1 g, 7.35 mmol) and the reaction mixture was stirred for 24 hours. The solid was filtered and the solution was diluted with dichloromethane (50 ml) and water (30 ml). The organic solution was collected, dried and concentrated in vacuum. The crude was purified by silica gel column chromatography eluting with neat ethyl acetate to afford the title compound as a white crystalline solid (1.1 g, 80%). $^1$H-NMR (500 MHz, CDCl$_3$): δ 3 (s, 3H), 3.09 (s, 3H), 5 (s, 2H), 7.54 (s, 1H), 7.6 (s, 1H).

Preparation 100: N,N-Dimethyl-2-(4-((trimethylsilyl)ethynyl)-1H-pyrazol-1-yl)acetamide 2-(4-Iodo-1H-pyrazol-1-yl)-N,N-dimethylacetamide (Preparation 99, 0.68 g, 2.42 mmol) and trimethylsilylacetylene (0.326 g, 3.32 mmol) were dissolved in dry DMF (5 ml) and placed under argon. Diisopropylamine (0.47 ml, 3.3 mmol), copper (1) iodide (30 mg, 0.16 mmol), triphenylphosphine (126 mg, 0.242 mmol) and palladium acetate (40 mg, 0.16 mmol) were added and the flask was flushed with argon. The reaction was heated to 60° C. for 1 hour. The reaction was cooled to room temperature and diluted with ethyl acetate (30 ml). The organic solution was washed with water, brine, dried over sodium sulphate and filtered. The solvent was removed in vacuum and the crude purified on silica gel column chromatography eluting with neat ethyl acetate to afford the title compound as a pale yellow powder (0.55 g, 91%). $^1$H-NMR (500 MHz, CDCl$_3$): δ 0.21 (s, 9H), 2.96 (s, 3H), 3.04 (s, 3H), 4.92 (s, 2H), 7.59 (s, 1H), 7.65 (s, 1H).

Preparation 101: 2-(4-Ethynyl-1H-pyrazol-1-yl)-N,N-dimethylacetamide

N,N-Dimethyl-2-(4-((trimethylsilyl)ethynyl)-1H-pyrazol-1-yl)acetamide (Preparation 100, 0.55 g, 2.2 mmol) was dissolved in dry THF (10 ml). To the stirred solution was then added a solution of TBAF in THF (2.4 ml of a 1M solution in THF, 2.4 mmol). After 20 minutes the reaction was concentrated in vacuo and the residue taken up in ethyl acetate. The organic solution was washed with water, brine and dried over sodium sulphate. The organic solution was then concentrated in vacuum and the crude product purified by silica gel column chromatography eluting with neat ethyl acetate to afford the title compound as a pale brown powder (0.3 g, 77%). $^1$H-NMR (500 MHz, CDCl$_3$): δ 2.98 (s, 3H), 3.01 (s, 1H), 3.07 (s, 3H), 4.95 (s, 2H), 7.62 (s, 1H), 7.69 (s, 1H).

Preparation 102: 2-(4-(6-Bromo-1-(methylsulfonyl)-1H-pyrrolo[3,2-c]pyridin-2-yl)-1H-pyrazol-1-yl)-N,N-dimethylacetamide Bis(triphenylphosphine)palladiumdichloride (69 mg, 0.099 mmol) was added to a solution of N-(2-bromo-5-iodopyridin-4-yl)methanesulfonamide (Preparation 8, 0.5 g, 1.98 mmol), 2-(4-ethynyl-1H-pyrazol-1-yl)-N,N-dimethylacetamide (Preparation 101, 0.3 g, 1.7 mmol), triethylamine (1.05 g, 1.05 mmol) and copper iodide (19.5 mg, 0.098 mmol) in DMF (5 ml). The reaction mixture was heated for 1 hour at 60° C. The reaction was cooled to room temperature and diluted with ethyl acetate. The organic solution was washed with water, brine and dried over sodium sulphate. The solvent was removed in vacuum and the crude product purified on silica gel column chromatography eluting with a gradient of 10 to 20% methanol in ethyl acetate to afford the title compound as a white powder (0.3 g, 88%). $^1$H-NMR (500 MHz, d$_6$-DMSO): δ 2.86 (s, 3H), 3.04 (s, 1H), 3.42 (s, 3H), 5.2 (s, 2H), 6.96 (s, 1H), 7.76 (s, 1H), 8.05 (s, 2H), 8.72 (s, 1H).

Preparation 103: 1-(4-Amino-3-chlorophenyl)pyrrolidin-2-one 1-(4-Aminophenyl)pyrrolidin-2-one (0.3 g, 1.7 mmol) and N-chlorosuccinimide (0.227 g, 1.7 mmol) were dissolved in acetonitrile (10 ml). The reaction was stirred and heated at reflux for 2 hours. The solvent was removed in vacuum and the residue purified by silica gel column chromatography eluting with 50% ethyl acetate in dichloromethane to afford the title compound as a white powder (0.16 g, 44.6%). $^1$H-NMR (500 MHz, CDCl$_3$): δ 2.14 (m, 2H), 2.57 (t, J=8.3 Hz, 2H), 3.77 (t, J=7.1 Hz, 2H), 6.75 (d, J=8.7 Hz, 1H), 7.31 (dd, J=2.5 Hz, 8.7 Hz, 1H), 7.48 (d, J=2.5 Hz, 1H), 8.8 (s, 2H).

Preparation 104: 4-(Bromomethyl)-2-methoxy-1-nitrobenzene

Carbon tetrabromide (1.63 g, 4.9 mmol) and triphenylphosphine (1.29 g, 4.9 mmol) were added to a solution of (3-methoxy-4-nitrophenyl)methanol (0.6 g, 3.3 mmol) in THF (15 mL). The reaction mixture was stirred at room temperature for 24 hours before being concentrated under reduced pressure and purified on silica gel column chromatography eluting with 20% ethyl acetate in hexane to afford the title compound (0.67 g, 95%). $^1$H-NMR (500 MHz, CDCl$_3$): δ 4.00 (s, 3H), 4.48 (s, 2H), 7.04 (dd, J=8.3 Hz, 1.7 Hz, 1H), 7.12 (d, J=1.7 Hz, 1H), 7.83 (d, J=8.3 Hz, 1H).

Preparation 105: 1-(3-methoxy-4-nitrobenzyl)pyrrolidine

Pyrrolidine (0.2 g, 2.8 mmol) and triethylamine (0.28 g, 2.8 mmol) were added to a solution of 4-(bromomethyl)-2-methoxy-1-nitrobenzene (Preparation 104, 0.22 g, 0.894 mmol) in THF (5 mL). The reaction mixture was stirred for 1 hour at room temperature before being concentrated under reduced pressure and purified by silica gel column chromatography eluting with 10% methanol in ethyl acetate to afford the title compound as a pale yellow powder (0.18 g, 94%). $^1$H-NMR (500 MHz, CDCl$_3$): δ 1.8 (t, J=6.7 Hz, 4H), 2.51 (t, J=6.7 Hz, 4H), 3.65 (s, 2H), 3.96 (s, 3H), 6.96 (dd, J=9.7 Hz, 1.5 Hz 1H), 7.12 (s, 1H), 7.8 (d, J=8.3 Hz, 1H)

Preparation 106: 2-Methoxy-4-(pyrrolidin-1-ylmethyl)aniline

10% Pd on carbon (12 mg, 0.866 mmol) was added to a solution of 1-(3-methoxy-4-nitrobenzyl)pyrrolidine (Preparation 105, 180 mg, 0.76 mmol) in EtOH (3 mL). The reaction mixture was degassed and then stirred for 1 hour at room temperature under an atmosphere of hydrogen. The reaction was filtered on a pad of Celite and the filtrate was concentrated under reduced pressure. The residue was purified on silica gel column chromatography eluting with 5% methanol in dichloromethane to afford the title compound as a colourless oil (0.12 g, 76.3%). $^1$H-NMR (500 MHz, CDCl$_3$): δ 1.79 (t, J=6.7 Hz, 4H), 2.5 (t, J=6.7 Hz, 4H), 3.53 (s, 2H), 3.75 (s, br, 2H), 3.86 (s, 3H), 6.65 (d, J=9.3 Hz, 1H), 6.72 (d, J=9.3 Hz, 1H), 6.81 (d, J=1.5 Hz, 1H).

Preparation 107: tert-Butyl 3-methoxy-4-nitrobenzyl(methyl)carbamate

To a stirred solution of 4-(bromomethyl)-2-methoxy-1-nitrobenzene (Preparation 104, 0.2 g, 0.813 mmol) in dry THF (5 ml), was added triethylamine (0.1 g, 1 mmol) followed by a solution of methylamine in THF (0.5 ml of a 2M solution, 1 mmol). After stirring for 1 hour at room temperature, the solvent was removed in vacuum and the crude product dissolved in dichloromethane (5 ml). To the stirred solution was then added di-tert-butyl dicarbonate (0.22 g, 1 mmol). After 1 hour the solvent was removed under reduced pressure and the crude purified on silica gel column chromatography eluting with 20% ethyl acetate in dichloromethane to afford the title compound as a colourless gum (0.185 g, 77%). $^1$H-NMR (500 MHz, CDCl$_3$) δ 1.48 (s, 9H), 2.83 (s, 3H), 3.93 (s, 3H), 4.45 (s, 2H), 6.85 (d, J=8.1 Hz, 1H), 6.87 (s, br, 1H), 7.81 (d, J=8.2 Hz, 1H).

Preparation 108: tert-Butyl 4-amino-3-methoxybenzyl(methyl)carbamate

10% Pd on carbon (12 mg, 0.866 mmol) was added to a solution of tert-butyl 3-methoxy-4-nitrobenzyl(methyl)carbamate (Preparation 107, 185 mg, 0.62 mmol) in EtOH (3 mL). The reaction mixture was degassed and then stirred for 1 hour at room temperature under an atmosphere of hydrogen. The reaction was filtered on a pad of Celite and the filtrate was concentrated under reduced pressure to afford the title compound (0.16 g, 96%).
$^1$H-NMR (500 MHz, CDCl$_3$): δ 1.5 (s, 9H), 2.8 (s, br, 3H), 3.83 (s, 3H), 3.9 (s, br, 2H), 4.31 (s, br, 2H), 6.68 (m, 3H).

Preparation 109: 1-(3-Methoxy-4-nitrophenyl)-N,N-dimethylmethanamine

To a stirred solution of 4-(bromomethyl)-2-methoxy-1-nitrobenzene (Preparation 104, 0.2 g, 0.813 mmol) in dry THF (5 ml), was added triethylamine (0.1 g, 1 mmol) followed by a solution of dimethylamine in THF (0.5 ml of a 2M solution, 1 mmol). After stirring for 1 hour at room temperature, the solvent was removed in vacuum and the crude product was purified by silica gel column chromatography eluting with 10% methanol in ethyl acetate to afford the title compound as a white powder (0.16 g, 94%).
$^1$H-NMR (500 MHz, CDCl$_3$): δ 2.24 (s, 6H), 3.45 (s, 2H), 3.95 (s, 3H), 6.92 (dd, J=1.5 Hz, 8.3 Hz, 1H), 7.12 (s, 1H), 7.78 (d, J=8.3 Hz, 1H)

Preparation 110: 4-((Dimethylamino)methyl)-2-methoxyaniline

10% Pd on carbon (12 mg, 0.866 mmol) was added to a solution of 1-(3-methoxy-4-nitrophenyl)-N,N-dimethylmethanamine (Preparation 109, 160 mg, 0.76 mmol) in EtOH (3 mL). The reaction mixture was degassed and then stirred for 1 hour at room temperature under an atmosphere of hydrogen before being filtered on a pad of Celite and concentrated under reduced pressure to afford the title compound (0.135 g, 98%).
$^1$H-NMR (500 MHz, CDCl$_3$): δ 2.23 (s, 6H), 3.33 (s, 2H), 3.75 (s, br, 2H), 3.86 (s, 3H), 6.66 (m, 2H), 6.79 (s, 1H).

Preparation 111: di-tert-Butyl 3-methoxy-4-nitrobenzylbiscarbamate 4-(Bromomethyl)-2-methoxy-1-nitrobenzene (Preparation 104, 246 mg, 1 mmol), di-tert-butyl iminodicarbonate (217 mg, 1 mmol) and potassium carbonate (280 mg, 2 mmol) were added to dry DMF (5 ml). The reaction was stirred at room temperature for 24 hours. The solid was filtered and the organic solution was diluted with ethyl acetate, washed with brine, dried over sodium sulphate and concentrated in vacuum. The crude was purified by silica gel column chromatography eluting with 50% hexane in dichloromethane to afford the title compound as a white powder (320 mg, 84%).
$^1$H-NMR (500 MHz, CDCl$_3$): δ 1.47 (s, 6H), 3.93 (s, 3H), 4.8 (s, 2H), 6.95 (d, J=8.1 Hz, 1H), 7.05 (s, 1H), 7.82 (d, J=8.1 Hz, 1H)

Preparation 112: Di-tert-Butyl-4-amino-3-methoxybenzylbiscarbamate

10% Pd on carbon (12 mg, 0.866 mmol) was added to a solution of di-tert-butyl 3-methoxy-4-nitrobenzylbiscarbamate (Preparation 111, 320 mg, 0.76 mmol) in EtOH (3 mL). The reaction mixture was degassed and then stirred for 1 hour at room temperature under an atmosphere of hydrogen. The reaction was filtered on a pad of Celite and concentrated under reduced pressure to afford the title compound (0.29 g, 98%). $^1$H-NMR (500 MHz, CDCl$_3$): δ 1.46 (s, 18H), 3.82 (s, 3H), 4.67 (s, 2H), 5.4 (s, br, 2H), 6.88 (d, J=8.1 Hz, 1H), 6.85 (s, br, 1H), 6.94 (d, J=8.2 Hz, 1H).

Preparation 113: 2-(3-Aminophenoxy)acetonitrile

2-Bromoacetonitrile (0.22 g, 1.83 mmol), 3-aminophenol (0.2 g, 1.83 mmol) and potassium carbonate (0.5 g, 3.67 mmol) were combined in dry DMF (10 ml). The reaction was stirred at room temperature for 24 hours. The reaction was diluted with water and ethyl acetate. The organic solution was washed with brine, dried over sodium sulphate and concentrated under reduced pressure. The crude product was purified by silica gel column chromatography eluting with 50% ethyl acetate in dichloromethane to afford the title compound as a colourless oil (0.16 g, 58.9%). $^1$H-NMR (500 MHz, CDCl$_3$): δ 3.76 (s, br, 2H), 4.69 (s, 2H), 6.29 (d, J=2.3 Hz, 1H), 6.37 (dd, J=2.3 Hz, 8.1 Hz, 1H), 6.41 (dd, J=2.3 Hz, 8.1 Hz, 1H), 7.1 (t, J=8.1 Hz, 1H).

Preparation 114: 6-Bromo-1-(4-fluorobenzyl)-2-(1-methyl-1H-pyrazol-4-yl)-1H-pyrrolo[3,2-c]pyridine Method A
6-bromo-2-(1-methyl-1H-pyrazol-4-yl)-1H-pyrrolo[3,2-c]pyridine (Preparation 22, 50 mg, 0.18 mmol) was dissolved in dry DMF (1 ml). The solution was degassed and a solution of sodium bis(trimethylsilyl)amide (0.27 ml of a 1M solution in THF, 0.27 mmol) was added. After 20 minutes reaction, 1-(bromomethyl)-4-fluorobenzene (51 mg, 0.27 mmol) was added and the reaction heated to 60° C. for 3 hours. The reaction was cooled to room temperature and diluted with ethyl acetate and water. The organic solution was washed with brine, dried over sodium sulphate and concentrated in vacuum. The crude product was purified on silica gel column chromatography eluting with 20% hexane in ethyl acetate to afford the title compound as white foam (50 mg, 71.9%). $^1$H-NMR (500 MHz, CDCl3) 3.92 (s, 3H), 5.31 (s, 2H), 6.62 (s, 1H), 6.93 (m, 2H), 7.02 (m, 2H), 7.27 (s, 1H), 7.39 (s, 1H), 7.51 (s, 1H), 8.63 (s, 1H).

Preparation 115: 6-Bromo-1-(cyclohexylmethyl)-2-(1-methyl-1H-pyrazol-4-yl)-1H-pyrrolo[3,2-c]pyridine Prepared according to Method A (Preparation 114) using (bromomethyl)cyclohexane. Purified using silica gel column chromatography eluting with 20% hexane in ethyl acetate to afford the title compound as white foam (52 mg, 64.3%). $^1$H NMR (500 MHz, CDCl$_3$): δ 0.87 (m, 2H), 1.09 (m, 3H), 1.44 (m, 2H), 1.65 (m, 4H), 3.93 (d, J=7.5 Hz, 2H), 4 (s, 3H), 6.5 (d, J=0.9 Hz, 1H), 7.39 (t, J=0.9 Hz, 1H), 7.56 (s, 1H), 7.65 (s, 1H), 8.56 (d, J=0.9 Hz, 1H).

Preparation 116: Cyclopentyl-6-bromo-2-(1-methyl-1H-pyrazol-4-yl)-1H-pyrrolo[3,2-c]pyridine-1-carboxylate Prepared according to Method A (Preparation 114) using cyclopentylchloroformate. Purified using silica gel column chromatography eluting with 20% hexane in ethyl acetate to afford the title compound as a white powder (56 mg, 80%). $^1$H-NMR (500 MHz, CDCl$_3$) 1.67 (m, 4H), 1.8 (m, 2H), 1.93 (m, 2H), 3.95 (s, 3H), 5.4 (q, J=5.8 Hz, 1H), 6.55 (s, 1H), 7.59 (s, 1H), 7.61 (s, 1H), 8.14 (s. 1H), 8.53 (s, 1H).

Preparation 117: 6-Bromo-1-cyclopentyl-2-(1-methyl-1H-pyrazol-4-yl)-1H-pyrrolo[3,2-c]pyridine Prepared according to Method A (Preparation 114) using cyclopentylbromide and the reaction heated to 80° C. Purified using silica gel column chromatography eluting with 20% hexane in ethyl acetate to afford the title compound as a white powder (18 mg, 28.9%).
$^1$H NMR (500 MHz, CDCl$_3$): δ 1.75 (m, 2H), 2.06 (m, 4H), 2.2 (m, 2H), 4.02 (s, 3H), 4.81 (q, J=8.9 Hz, 1H), 6.45 (s, 1H), 7.49 (s, 1H), 7.53 (s, 1H), 7.6 (s. 1H), 8.59 (s, 1H).

Preparation 118: 6-Bromo-1-isopropyl-2-(1-methyl-1H-pyrazol-4-yl)-1H-pyrrolo[3,2-c]pyridine Prepared according to Method A (Preparation 114) using 2-bromopropane and the reaction heated to 80° C. Purified using silica gel column chromatography eluting with 20% hexane in ethyl acetate to afford the title compound as a white powder (28 mg, 48.6%).
$^1$H-NMR (500 MHz, CDCl$_3$): δ 1.58 (d, J=7.1 Hz, 2H), 4 (s, 3H), 4.73 (q, J=7.1 Hz, 1H), 6.43 (s, 1H), 7.52 (s, 1H), 7.58 (s, 1H), 7.6 (s. 1H), 8.57 (s, 1H).

Preparation 119: 4-Methoxy-2-(1-methyl-1H-pyrazol-4-yl)pyrimidin-5-amine

Tetrakis(triphenylphosphine)palladium (30 mg, 0.026 mmol) was added to a solution of 2-chloro-4-methoxypyrimidin-5-amine (41 mg, 0.257 mmol), 1-methyl-4-(4,4,5,5-tetramethyl-1,3,2-dioxaborolan-2-yl)-1H-pyrazole (107 mg, 0.514 mmol) and cesium fluoride (117 mg, 0.771 mmol) in DME/MeOH (2/1, 1.6 mL). The reaction mixture was heated under microwave irradiation at 150° C. for 10 minutes. The reaction was then diluted with EtOAc and quenched with water. The layers were separated and the aqueous layer was extracted with EtOAc. The combined organic layers were dried (Na$_2$SO$_4$), filtered and concentrated under reduced pressure. The crude mixture was purified via Biotage silica gel column chromatography eluting with DCM/EtOH 99/1 to 90/10 followed by filtration through a SCX-2 column to afford the title product as a white solid (49 mg, 93%). $^1$H NMR (500 MHz, CDCl$_3$): δ 3.68 (br s, 2H), 3.93 (s, 3H), 4.06 (s, 3H), 7.88 (s, 1H), 7.92 (s, 1H), 8.04 (s, 1H). LC (Method B)-MS (ESI, m/z) $t_R$ 1.33 min, 206 [M+H]$^+$ Preparation 120: tert-Butyl-6-bromo-2-(1-(2-(dimethylamino)-2-oxoethyl)-1H-pyrazol-4-yl)-1H-pyrrolo[3,2-c]pyridine-1-carboxylate 2-(4-(6-Bromo-1-(methylsulfonyl)-1H-pyrrolo[3,2-c]pyridin-2-yl)-1H-pyrazol-1-yl)-N,N-dimethylacetamide (Preparation 102, 0.3 g, 0.705 mmol) was dissolved in THF (5 ml) and DMF (1 ml). To the stirred solution was added DBU (0.21 g, 1.4 mmol) and the reaction stirred for 1 hour followed by di-tert-butyldicarbonate (0.3 g, 1.4 mmol) and N,N-dimethylpyridin-4-amine (8.5 mg, 0.07 mmol). The reaction was stirred for 24 hours at room temperature. The solvent was removed in vacuum and the residue purified on silica gel column chromatography eluting with 10% methanol in ethyl acetate to afford the title compound as a white powder (0.2 g, 63%). $^1$H-NMR (500 MHz, CDCl$_3$): δ 1.56 (s, 9H), 3.02 (s, 1H), 3.14 (s, 3H), 5.03 (s, 2H), 6.6 (s, 1H), 7.66 (s, 1H), 7.77 (s, 1H), 8.2 (s, 1H), 8.56 (s, 1H).

Preparation 121: 2-Chloro-4-(1-methyl-1H-pyrazol-5-yl)aniline

Prepared using Method C (Preparation 85) using 1-methyl-5-(4,4,5,5-tetramethyl-1,3,2-dioxaborolan-2-yl)-1H-pyrazole and 4-bromo-2-chloroaniline in DME/MeOH 2/1 for 10 minutes at 150° C. under microwave irradiation. Purified using silica gel column chromatography eluting with 20% hexane in ethyl acetate to afford the title compound as a white powder (77 mg, 74%). $^1$H-NMR (500 MHz, CDCl$_3$): δ 3.86 (s, 3H), 4.26 (s, br, 2H), 6.22 (d, J=2 Hz, 1H), 6.81 (d, J=8.3 Hz, 1H), 7.1 (dd, J=2 Hz, 8.3 Hz. Hz, 1H), 7.31 (d, J=2.0 Hz, 1H), 7.48 (d, J=2 Hz, 1H).

Preparation 122: 2-Chloro-4-(2,4-dimethylthiazol-5-yl)aniline

Prepared using Method C (Preparation 85) using 5-bromo-2,4-dimethylthiazole in DME/MeOH (2/1) for 10 minutes at 150° C. under microwave irradiation. Purified using Biotage silica gel column chromatography eluting with cyclohexane/EtOAc 90/10 to 70/30 to afford the title product as a white solid (88 mg, 93%). $^1$H-NMR (500 MHz, CD$_3$OD): δ 2.35 (s, 3H), 2.63 (s, 3H), 6.86 (d, J=8.3 Hz, 1H), 7.08 (dd, J=8.3, 2.1 Hz, 1H), 7.24 (d, J=2.1 Hz, 1H).

Preparation 123: 2-Chloro-4-(2-methoxypyridin-4-yl)aniline

Prepared using Method C (Preparation 85) using 2-methoxypyridin-4-ylboronic acid in DME/MeOH 2/1 and heated for 10 minutes at 150° C. under microwave irradiation. Purified using Biotage silica gel column chromatography eluting with Cyclohexane/EtOAc 99/1 to 80/20 to afford the title product as a white solid (67 mg, 59%). $^1$H-NMR (500 MHz, CDCl$_3$): δ 3.99 (s, 3H), 4.27 (br s, 2H), 6.84 (d, J=8.3 Hz, 1H), 6.88 (dd, J=1.7, 0.7 Hz, 1H), 7.04 (dd, J=5.4, 1.7 Hz, 1H), 7.37 (dd, J=8.3, 2.1 Hz, 1H), 7.57 (d, J=2.1 Hz, 1H), 8.17 (dd, J=5.4, 0.7 Hz, 1H)

Preparation 124:
2-Chloro-4-(1,2-dimethyl-1H-imidazol-5-yl)aniline

Prepared using Method C (Preparation 85) using 5-bromo-1,2-dimethyl-1H-imidazole in DME/MeOH 2/1 and heated for 10 minutes at 150° C. under microwave irradiation. Purified using Biotage silica gel column chromatography eluting with DCM/EtOH 99/1 to 95/5 to afford the title product as a white solid (82 mg, 94%). $^1$H NMR (500 MHz, CDCl$_3$) 2.43 (s, 3H, CH$_3$), 3.48 (s, 3H, CH$_3$N), 4.21 (br s, 2H, NH$_2$), 6.81 (d, J=8.2 Hz, 1H, phenyl H$_6$), 6.87 (s, 1H, imidazole H$_4$), 7.05 (dd, J=8.2, 2.0 Hz, 1H, phenyl H$_5$), 7.24 (d, J=2.0 Hz, 1H, phenyl H$_3$); LC (Method B)-MS (ESI, m/z) t$_R$ 0.96 min, 222 [(M+H$^+$), 100%].

Preparation 125: Cyclobutyl-6-bromo-2-(1-methyl-1H-pyrazol-4-yl)-1H-pyrrolo[3,2-c]pyridine-1-carboxylate 6-bromo-2-(1-methyl-1H-pyrazol-4-yl)-1H-pyrrolo[3,2-c]pyridine (Preparation 122, 100 mg, 0.36 mmol) was dissolved in dry DMF (1 ml). The solution was degassed and a solution of sodium bis(trimethylsilyl)amide (0.54 ml of a 1M solution in THF, 0.54 mmol) was added. After 20 minutes reaction, a solution of cyclobutylchloroformate [freshly prepared by stirring 40 mg of cyclobutanol with one equivalent of a 20% phosgene solution in toluene (0.275 ml) for 3 h, 0.55 mmol] was added. The reaction was stirred for 2 hours at room temperature then was diluted with ethyl acetate and water. The organic solution was washed with brine, dried over sodium sulphate and concentrated in vacuum. The crude product was purified on silica gel column chromatography eluting with 20% hexane in ethyl acetate to afford the title compound as a white powder (95 mg, 70.2%). $^1$H-NMR (500 MHz, CDCl$_3$): δ 1.69 (m, 1H), 2.12 (m, 1H), 2.15 (m, 2H), 2.4 (m, 2H), 3.94 (s, 3H), 5.17 (quin, J=7.2 Hz, 1H), 6.54 (s, 1H), 7.6 (s, 1H), 7.62 (s, 1H), 8.14 (s. 1H), 8.51 (s, 1H)

Preparation 126:
2-chloro-4-(6-methoxypyridin-3-yl)aniline

Prepared using Method C (Preparation 85) using 5-bromo-2-methoxypyridine in DME/MeOH 2/1 and heated for 10 minutes at 150° C. under microwave irradiation. Purified using silica gel column chromatography eluting with 20% hexane in ethyl acetate to afford the title compound as a white powder (77 mg, 65.6%). $^1$H-NMR (500 MHz, CDCl$_3$): δ 3.97 (s, 3H), 4.15 (br s, 2H), 6.77 (d, J=8.3 Hz, 1H), 6.81 (d, J=8.3 Hz, 1H), 7.21 (dd, J=2.1 Hz, 8.3 Hz, 1H), 7.42 (d, J=2.1 Hz, 1H), 7.68 (dd, J=2.6 Hz, 8.6 Hz, 1H), 8.3 (s, 1H).

Preparation 127:
2-Chloro-4-(6-methylpyridin-3-yl)aniline

Prepared using Method C (Preparation 85) using 5-bromo-2-methylpyridine in DME/MeOH 2/1 and heated for 10 minutes at 150° C. under microwave irradiation. Purified using silica gel column chromatography eluting with 20% hexane in ethyl acetate to afford the title compound as a white powder (82 mg, 75%). $^1$H NMR (500 MHz, CDCl$_3$) 2.56 (s, 3H), 4.22 (br s, 2H), 6.82 (d, J=8.3 Hz, 1H), 7.16 (d, J=8.1 Hz, 1H), 7.26 (d, J=8.3 Hz, 1H), 7.67 (m, 2H), 8.64 (s, 1H).

Preparation 128: Methyl-6-bromo-2-(1-methyl-1H-pyrazol-4-yl)-1H-pyrrolo[3,2-c]pyridine-1-carboxylate 6-Bromo-2-(1-methyl-1H-pyrazol-4-yl)-1H-pyrrolo[3,2-c]pyridine (Preparation 22, 100 mg, 0.36 mmol) was dissolved in dry DMF (1 ml). The solution was degassed and a solution of sodium bis(trimethylsilyl)amide (0.55 ml of a 1M solution in THF, 0.55 mmol) was added. After 20 minutes reaction, methylchloroformate (52 mg, 0.55 mmol) was added and the reaction stirred for 2 hours at room temperature. The reaction was diluted with ethyl acetate and water. The organic solution was washed with brine, dried over sodium sulphate and concentrated in vacuum. The crude product was purified on silica gel column chromatography eluting with 20% hexane in ethyl acetate followed by 2% methanol in ethyl acetate to afford the title compound as a white powder (95 mg, 79%). $^1$H NMR (500 MHz, CDCl$_3$) 3.96 (s, 3H), 4 (s, 3H), 6.57 (s, 1H), 7.63 (s, 1H), 7.64 (s, 1H), 8.1 (s. 1H), 8.53 (s, 1H)

Preparation 129: Ethyl-6-bromo-2-(1-methyl-1H-pyrazol-4-yl)-1H-pyrrolo[3,2-c]pyridine-1-carboxylate Prepared according to Preparation 128 using 6-bromo-2-(1-methyl-1H-pyrazol-4-yl)-1H-pyrrolo[3,2-c]pyridine (Preparation 22) and ethylchloroformate. $^1$H-NMR (500 MHz, CDCl$_3$): δ 1.38 (t, J=7.1 Hz, 3H), 3.95 (s, 3H), 4.45 (q, J=7.1 Hz, 2H), 6.56 (s, 1H), 7.62 (s, 1H), 7.63 (s, 1H), 8.12 (s. 1H), 8.53 (s, 1H).

Preparation 130: Propyl-6-bromo-2-(1-methyl-1H-pyrazol-4-yl)-1H-pyrrolo[3,2-c]pyridine-1-carboxylate Prepared according to Preparation 128 using 6-Bromo-2-(1-methyl-1H-pyrazol-4-yl)-1H-pyrrolo[3,2-c]pyridine (Preparation 22) and propylchloroformate. $^1$H-NMR (500 MHz, CDCl$_3$): δ 0.96 (t, J=7.4 Hz, 3H), 1.38 (m, 2H), 3.97 (s, 3H), 4.36 (t, J=6.7 Hz, 2H), 6.59 (s, 1H), 7.62 (s, 1H), 7.65 (s, 1H), 8.17 (s. 1H), 8.56 (s, 1H)

Preparation 131: tert-Butyl-6-(4-((bis(tert-butoxycarbonyl)amino)methyl)-2-methoxyphenylamino)-2-(1-methyl-1H-pyrazol-4-yl)-1H-pyrrolo[3,2-c]pyridine-1-carboxylate Tris(dibenzylideneacetone)dipalladium(0) (10 mg, 0.011 mmol) was added to a mixture of tert-butyl-6-bromo-2-(1-methyl-1H-pyrazol-4-yl)-1H-pyrrolo[3,2-c]pyridine-1-carboxylate (Preparation 23, 50 mg, 0.133 mmol), cesium carbonate (86 mg, 0.266 mmol), di-tert-butyl-4-amino-3-methoxybenzylbiscarbamate (Preparation 112, 56 mg, 0.158 mmol) and xantphos (12.3 mg, 0.0212 mmol) in dimethylacetamide (1.2 mL). The reaction mixture was heated at 80° C. for 3 hours. The reaction was diluted with dichloromethane (2 ml) and applied to an SCX-2 column. This was washed with 50% methanol in chloroform followed by 10% (7M ammonia in methanol) in ethyl acetate. The solution was concentrated under reduced pressure and the crude product purified by silica gel column chromatography eluting with 40% ethyl acetate in dichloromethane to afford the title product as yellow foam (30 mg, 35%).

$^1$H-NMR (500 MHz, CDCl$_3$): δ 1.5 (s, 27H), 3.88 (s, 3H), 3.95 (s, 3H), 4.75 (s, 2H), 6.47 (s, 1H), 6.95 (m, 2H), 7 (s, 1H), 7 (s, 1H), 7.53 (s, 1H), 7.59 (s, 1H), 7.63 (s, 1H), 7.82 (d, J=8.1 Hz, 1H), 8.44 (s, 1H), ESI-HRMS Found 671.3155, calculated for C$_{34}$H$_{44}$N$_6$O$_7$ (M+H$^+$): 671.3164

Preparation 132:
2-Chloro-5-(1-methyl-1H-pyrazol-4-yl)aniline

To a mixture of 3-amino-4-chlorophenylboronic acid pinacol ester (0.110 g, 0.434 mmol), 4-bromo-1-methylpyrazole (0.087 g, 0.54 mmol), 1,1'-bis(diphenylphosphino)ferrocene)-dichloropalladium(II) DCM complex (24 mg, 0.029 mmol) was added anhydrous DME (2.5 mL) followed by 1M aqueous sodium carbonate (0.99 mL, 0.99 mmol). The microwave vial was heated at 150° C. for 20 minutes under microwave irradiation. Further catalyst (0.005 g) was added and the vial was heated at 130° C. for 10 minutes under microwave irradiation. The reaction mixture was partitioned between ethyl acetate (55 mL) and a saturated aqueous NaHCO$_3$ solution (15 mL). The organic layer was washed with a saturated aqueous NaHCO$_3$ solution (2×13 mL), dried (Na$_2$SO$_4$) and concentrated in vacuo. This residue was purified using preparative TLC eluting with 30% ethyl acetate in CH$_2$Cl$_2$. The product band was recovered and stirred with 2% MeOH in ethyl acetate/CH$_2$Cl$_2$ (v/v; 1:3) (20 mL). The silica was removed by filtration, washed with ethyl acetate/CH$_2$Cl$_2$ (v/v; 1:3) (2×5 mL) and acetone (3×4 mL) to give the title compound as an off-white solid (0.040 g, 44%). $^1$H-NMR (500 MHz, DMSO-d$_6$) 3.84 (s, 3H), 5.29 (s, 2H), 6.72 (dd, J=2.1, 8.2 Hz, 1H), 6.94 (d, J=2.1 Hz, 1H), 7.14 (d, J=8.2 Hz, 1H), 7.68 (d, J=0.7 Hz, 1H), 7.98 (s, 1H).

Preparation 133: 2-Chloro-4-(pyrazin-2-yl)aniline

To a mixture of 4-amino-3-chlorophenylboronic acid pinacol ester (0.110 g, 0.434 mmol), 2-bromopyrazine (0.090 g, 0.56 mmol), 1,1'-bis(diphenylphosphino)ferrocene)-dichloropalladium(II) DCM complex (24 mg, 0.029 mmol) was added anhydrous DME (3.0 mL) followed by 2M aqueous sodium carbonate (0.53 mL, 1.06 mmol). The microwave vial was heated at 75° C. for 40 minutes under microwave irradiation. Further catalyst (0.012 g) was added and the vial was heated at 90° C. for 25 minutes under microwave irradiation. Further 2-bromopyrazine (0.060 g), catalyst (12 mg) and 2M aqueous sodium carbonate (0.25 mL) were added and the reaction mixture was heated at 90° C. for an additional 30 minutes under microwave irradiation. The reaction was partitioned between ethyl acetate (60 mL) and a saturated aqueous NaHCO$_3$ solution (15 mL). The organic layer was washed with a saturated aqueous NaHCO$_3$ solution (2×15 mL), dried (Na$_2$SO$_4$) and concentrated in vacuo. The residue was purified using preparative TLC eluting with 7% ethyl acetate in CH$_2$Cl$_2$. The product band was recovered and stirred with 2% MeOH in ethyl acetate/CH$_2$Cl$_2$ (v/v; 1:10) (20 mL). The silica was removed by filtration, washed with ethyl acetate/CH$_2$Cl$_2$ (v/v; 1:5) (2×5 mL) and acetone (3×4 mL) to give the title compound as an off-white solid (0.039 g, 44%). $^1$H-NMR (500 MHz, DMSO-d$_6$) 5.86 (s, 2H), 6.89 (d, J=8.5, 1H), 7.85 (dd, J=2.1, 8.5 Hz, 1H), 8.02 (d, J=2.1 Hz, 1H), 8.44 (d, J=2.5 Hz, 1H), 8.57 (dd, J=1.6, 2.5 Hz, 1H), 9.12 (d, J=1.5 Hz, 1H).

Preparation 134: 2-Chloro-4-(pyrimidin-5-yl)aniline

To a mixture of 4-amino-3-chlorophenylboronic acid pinacol ester (0.110 g, 0.434 mmol), 5-bromopyrimidine (0.090 g, 0.56 mmol), 1,1'-bis(diphenylphosphino)ferrocene)-dichloropalladium(II) DCM complex (23 mg, 0.028 mmol) was added anhydrous DME (3.0 mL) followed by 2M aqueous sodium carbonate (0.53 mL, 1.06 mmol). The microwave vial was heated at 150° C. for 15 minutes under microwave irradiation. The reaction was partitioned between ethyl acetate (60 mL) and a saturated aqueous NaHCO$_3$ solution (15 mL). The organic layer was washed with a saturated aqueous NaHCO$_3$ solution (15 mL), dried (Na$_2$SO$_4$) and concentrated in vacuo. The residue was purified using preparative TLC eluting with 20% ethyl acetate in CH$_2$Cl$_2$. The product band was recovered and stirred with 2% MeOH in ethyl acetate/CH$_2$Cl$_2$ (v/v; 1:5) (20 mL). The silica was removed by filtration, washed with ethyl acetate/CH$_2$Cl$_2$ (v/v; 1:1) (2×5 mL) and acetone (3×4 mL) to give the title compound as a white solid (0.075 g, 84%). $^1$H-NMR (500 MHz, DMSO-d$_6$) 5.72 (s, 2H), 6.91 (d, J=8.4, 1H), 7.51 (dd, J=2.2, 8.3 Hz, 1H), 7.72 (d, J=2.2 Hz, 1H), 9.04, 9.05 (2×s, 3H).

Preparation 135: 3-((6-Bromo-2-(1-methyl-1H-pyrazol-4-yl)-1H-pyrrolo[3,2-c]pyridin-1-yl)methyl)-5-methylisoxazole To a stirred solution of 6-bromo-2-(1-methyl-1H-pyrazol-4-yl)-1H-pyrrolo[3,2-c]pyridine (Preparation 22, 0.060 g, 0.217) in anhydrous DMF (0.8 mL) was added sodium hydride 60% (0.013 g, 7.8 mg, 0.325 mmol). The reaction mixture was stirred at room temperature for 5 minutes under argon, then a solution of 3-(bromomethyl)-5-methylisoxazole (0.057 g, 0.325 mmol) in anhydrous DMF (0.3 mL) was added. The stirring was continued at room temp for 1 hour and 50 minutes. The reaction mixture was diluted with ethyl acetate (40 mL) and the solution was washed with water (10 mL), brine (2×10 mL), dried (Na$_2$SO$_4$) and concentrated in vacuo. The residue was purified using preparative TLC eluting with 20% ethyl acetate in CH$_2$Cl$_2$. The product band was recovered and stirred with 5% MeOH in ethyl acetate. The silica was removed by filtration, washed with 5% MeOH in EtOAc (2×5 mL), acetone (2×8 mL). The title compound was obtained as an off-white solid (0.065 g, 80%). $^1$H-NMR (500 MHz, DMSO-d$_6$) 2.31 (s, 3H), 3.89 (s, 3H), 5.58 (s, 2H), 5.89 (s, 1H), 6.75 (s, 1H), 7.78 (s, 1H), 7.83 (s, 1H), 8.12 (s, 1H), 8.57 (s, 1H).

Preparation 136: 6-Bromo-2-(diethoxymethyl)-1-(methylsulfonyl)-1H-pyrrolo[3,2-c]pyridine To DMF (3.4 mL) containing triethylamine (0.64 mL, 0.46 g 4.5 mmole) was added propargylaldehyde diethyl acetal (183 uL, 163 mg, 1.27 mmole) and N-(2-bromo-5-iodopyridin-4-yl)methanesulfonamide, (Preparation 8, 400 mg 1.06 mmole) followed by copper(I) iodide (7.1 mg, 0.037 mmole). The reaction was placed under nitrogen. Bis(triphenylphosphine)palladium dichloride (26.1 mg, 0.037 mmole) was added and the reaction was flushed again with nitrogen, then heated at 60° C. for 2 hours. The reaction was cooled and added to water (35 mL) containing a sodium bicarbonate solution (3 mL). The reaction was extracted with ethyl acetate (3×20 mL). The combined organic layers were washed with water containing sodium bicarbonate solution (3×10 mL), brine and concentrated in vacuo. The residue was purified using silica gel column chromatography eluting with 100% dichloromethane to 5% ethyl acetate in dichloromethane to 10% ethyl acetate in dichloromethane to give the title compound (207 mg, 51%). $^1$H-NMR (CDCl$_3$, 500 MHz): δ 1.32 (t, J=6.94 Hz, 6H), 3.38 (s, 3H), 3.75 (m, 2H), 3.84 (m, 2H), 5.86 (d, J=0.95 Hz, 1H), 6.94 (t, J=0.95 Hz, 1H), 8.14 (t, J=0.95 Hz, 1H), 8.67 (d, J=0.95 Hz, 1H).

Preparation 137: 6-Bromo-2-(diethoxymethyl)-1H-pyrrolo[3,2-c]pyridine

6-Bromo-2-(diethoxymethyl)-1-(methylsulfonyl)-1H-pyrrolo[3,2-c]pyridine (Preparation 136, 202 mg, 0.54 mmole) was stirred in methanol (2.4 mL) and 1M sodium hydroxide in water (0.62 mL, 0.62 mmole) was added. The reaction was stirred at 25° C. for 6 hours. The methanol was evaporated and the residue taken up in ethyl acetate (25 mL). The solution was washed with water and brine, the organic layer was concentrated in vacuo to afford the title compound (142 mg, 89%). $^1$H-NMR (CDCl$_3$, 500 MHz): δ 1.27 (t, J=6.94 Hz, 6H), 3.58-3.72 (m, 4H), 5.73 (m, 1H), 6.59 (m, 1H), 7.48 (m, 1H), 8.65 (s, 1H), 8.84 (br s, 1H, NH).

Preparation 138: 6-Bromo-1H-pyrrolo[3,2-c]pyridine-2-carbaldehyde

To a solution of 6-Bromo-2-(diethoxymethyl)-1H-pyrrolo[3,2-c]pyridine (Preparation 137, 142 mg, 0.47 mmole) in THF (1.4 mL) and water (0.28 mL) was added tosic acid hydrate (134 mg, 0.705 mmole) and the reaction was stirred at 25° C. for 55 minutes. The reaction was partitioned between ethyl acetate (20 mL) and sodium bicarbonate (5 mL). The layers were separated and the aqueous layer again extracted with ethyl acetate (7 mL). The combined organic layers were washed with sodium bicarbonate and brine and concentrated in vacuo to afford the title compound (112 mg). $^1$H-NMR (CDCl$_3$, 500 MHz): δ 7.37 (s, 1H), 7.62 (t, J=0.95 Hz, 1H), 8.88 (d, J=0.95 Hz, 1H), 9.32 (br s, 1H), 9.93 (s, 1H).

Preparation 139: 5-(6-Bromo-1H-pyrrolo[3,2-c]pyridin-2-yl)oxazole

6-Bromo-1H-pyrrolo[3,2-c]pyridine-2-carbaldehyde (Preparation 138, 604 mg 2.68 mmole), TOSMIC (1047 mg, 5.37 mmole) and potassium carbonate (759 mg, 5.5 mmole) in methanol (30 mL) was stirred and heated at 65° C. for 110 minutes. The methanol was evaporated and the residue partitioned between ethyl acetate (50 mL) and water (20 mL). The layers were separated and the organic solution was washed with water and brine and concentrated in vacuo. The residue was purified using silica gel column chromatography eluting with ethyl acetate to afford the title compound (561 mg, 79%). $^1$H-NMR (d$_6$-acetone, 500 MHz): δ 7.02 (d, J=0.95 Hz, 1H), 7.60 (t, J=0.95 Hz, 1H), 7.62 (s, 1H), 8.30 (s, 1H), 8.67 (d, J=0.95 Hz, 1H).

Preparation 140: tert-Butyl 6-bromo-2-(oxazol-5-yl)-1H-pyrrolo[3,2-c]pyridine-1-carboxylate 5-(6-Bromo-1H-pyrrolo[3,2-c]pyridin-2-yl)oxazole (Preparation 139, 152 mg, 0.58 mmole) was stirred in ethyl acetate (2 mL). Triethylamine (140 uL, 101 mg 1.0 mmole) was added, followed by a crystal of DMAP and di-t-butyl dicarbonate (190 mg, 0.87 mmole). The reaction was stirred at 25° C. for 60 minutes. Further di-t-butyl dicarbonate (54 mg) was added and the reaction allowed to stir at room temperature overnight. The reaction was concentrated in vacuo and the residue applied in chloroform to a preparative TLC plate. The product was eluted with 1:1 ethyl acetate:cyclohexane (three times) to afford the title compound. $^1$H-NMR (CDCl$_3$, 500 MHz): δ 1.54 (s, 9H), 6.90 (d, J=0.95 Hz, 1H), 7.40 (s, 1H), 8.02 (s, 1H), 8.31 (s, 1H), 8.68 (s, 1H).

Preparation 141: 6-Bromo-2-(1-methyl-1H-pyrazol-4-yl)-1-(5-methylpyridin-2-yl)-1H-pyrrolo[3,2-c]pyridine 6-Bromo-2-(1-methyl-1H-pyrazol-4-yl)-1H-pyrrolo[3,2-c]pyridine (Preparation 22, 84 mg 0.303 mmole) and 2-bromo-5-methylpyridine (78 mg, 0.45 mmole) were dissolved in DMA (2.1 ml) and potassium carbonate (60 mg, 0.42 mmole) and copper(I) iodide (12 mg, 0.066 mmole) were added. The reaction was placed under argon and heated by microwave at 210° C. for 60 minutes. Further 2-bromo-5-methylpyridine (49 mg) and potassium carbonate (40 mg) were added and the reaction again heated at 210° C. under microwave irradiation for 60 minutes. The reaction was taken up in ethyl acetate (30 mL) and the solution washed with water (3×10 mL) and brine. The aqueous was filtered through Celite and backwashed with ethyl acetate (10 mL). The combined organic layers were dried and concentrated in vacuo. The residue was purified using preparative TLC eluting with ethyl acetate to afford the title compound 52 mg (46%). $^1$H-NMR (CDCl$_3$, 500 MHz): 2.48 (s, 3H), 3.88 (s, 3H), 6.70 (d, J=0.95 Hz, 1H), 7.09 (d, J=7.88 Hz, 1H), 7.24 (m, 1H), 7.25 (s, 1H), 7.44 (t, J=0.95 Hz, 1H), 7.66 (m, 1H), 8.53 (m, 1H), 8.65 (d, J=0.95 Hz, 1H).

Preparation 142: 6-Bromo-2-(1-methyl-1H-pyrazol-4-yl)-1-(pyrimidin-2-yl)-1H-pyrrolo[3,2-c]pyridine 6-Bromo-2-(1-methyl-1H-pyrazol-4-yl)-1H-pyrrolo[3,2-c]pyridine (Preparation 22, 27 mg 0.10 mmole) and 2-bromopyrimidine (24 mg, 0.15 mmole) were dissolved in DMA (0.7 ml) and potassium carbonate (20 mg, 0.14 mmole) and copper(I) iodide (4.0 mg, 0.022 mmole) were added. The reaction was placed under argon and heated by microwave at 210° C. for 60 minutes. The reaction was taken up in ethyl acetate (25 mL) and the solution washed with water (3×7 mL) and brine. The combined organic layers were dried and concentrated in vacuo. The residue was purified using preparative TLC eluting with ethyl acetate to afford the title compound (31 mg). $^1$H-NMR (CDCl$_3$, 500 MHz): 3.95 (s, 3H), 6.73 (d, J=0.95 Hz), 7.34 (s, 1H) under 7.34 (t, J=5.04 Hz, 1H), 7.53 (s, 1H), 8.11 (t, J=0.95 Hz, 1H), 8.66 (d, J=0.95 Hz, 1H), 8.85 (d, J=5.04 Hz, 2H), Preparation 143: 6-Bromo-2-(1-methyl-1H-pyrazol-4-yl)-1-(pyridin-2-yl)-1H-pyrrolo[3,2-c]pyridine 6-Bromo-2-(1-methyl-1H-pyrazol-4-yl)-1H-pyrrolo[3,2-c]pyridine (Preparation 22, 27 mg 0.10 mmole) and 2-bromopyridine (24 mg, 15 uL, 0.15 mmole) were dissolved in DMA (0.7 ml) and potassium carbonate (20 mg, 0.14 mmole) and copper(I) iodide (4.0 mg, 0.022 mmole) were added. The reaction was placed under argon and heated by microwave at 180° C. for 60 minutes followed by 210° C. for 45 minutes. The reaction was taken up in ethyl acetate (25 mL) and the solution washed with water (3×7 mL) and brine. The aqueous solutions were backwashed with a single portion of ethyl acetate. The combined organic layers were dried (MgSO$_4$) and concentrated in vacuo. The residue was purified using preparative TLC eluting with ethyl acetate to afford the title compound 17 mg (48%). $^1$H-NMR (CDCl$_3$, 500 MHz): 3.88 (s, 3H), 6.72 (d, J=0.95 Hz, 1H), 7.18 (d of t, J=0.95, 7.88 Hz, 1H), 7.24 (s, 1H), 7.26 (d, J=0.63 Hz, 1H), 7.44 (ddd, J=0.95, 4.73, 7.57 Hz, 1H), 7.51 (t, J=0.95 Hz, 1H), 7.86 (t of d, J=1.89, 7.57 Hz, 1H), 8.66 (d, J=0.95 Hz, 1H), 8.73 (ddd, J=0.95, 1.89, 4.73 Hz, 1H).

Preparation 144: 5-(6-Bromo-3-chloro-1H-pyrrolo[3,2-c]pyridin-2-yl)oxazole 5-(6-Bromo-1H-pyrrolo[3,2-c]pyridin-2-yl)oxazole (Preparation 139, 80 mg 0.303 mmole) was dissolved in DMF (0.8 mL) and N-chlorosuccinimide (40.4 mg 0.303 mmole) was added. The reaction was stirred at room temperature for 48 hours. The reaction was diluted with ethyl acetate (20 mL) and washed with water (3×7 mL) and brine. The combined aqueous layers were back-washed with ethyl acetate. The organic layers were dried (MgSO$_4$) and concentrated in vacuo to afford the title compound (86 mg). $^1$H-NMR (d$_6$-acetone, 500 MHz): 7.66 (d, J=0.95 Hz, 1H), 7.84 (s, 1H), 8.40 (s, 1H), 8.66 (d, J=0.63 Hz, 1H), 11.62 (br s, 1H, NH).

Preparation 145: tert-Butyl 6-bromo-3-chloro-2-(oxazol-5-yl)-1H-pyrrolo[3,2-c]pyridine-1-carboxylate 5-(6-Bromo-3-chloro-1H-pyrrolo[3,2-c]pyridin-2-yl)oxazole (Preparation 144, 86 mg) was stirred in ethyl acetate (1.7 mL) and for 1 hour. The reaction was concentrated and the residue purified using preparative triethylamine (126 uL, 91 mg, 0.9 mmole) and a few crystals of DMAP were added, followed by di-t-butyl dicarbonate (131 mg, 0.6 mmole). The reaction was stirred at room temperature TLC eluting with 1:2 ethyl acetate:cyclohexane to afford the title compound (86 mg). $^1$H-NMR (CDCl$_3$, 500 MHz): 1.48 (s, 9H), 7.45 (s, 1H), 8.09 (s, 1H), 8.38 (d, J=0.95 Hz), 8.72 (d, J=0.95 Hz, 1H).

Preparation 146: 4-Iodo-1-(2,2,2-trifluoroethyl)-1H-pyrazole

A mixture of 4-iodo-pyrazole (582 mg, 3.0 mmole) and cesium carbonate (1.96 g, 6.0 mmole) was stirred with DMF (6 mL) for 5 minutes. Trifluoroethyl triflate (0.52 mL, 870 mg, 3.75 mmole) was added and the reaction was stirred at room temperature for 4.5 hours. The reaction was added to water (60 mL) and extracted with ether (3×25 mL). The combined organic extracts were washed with water (3×20 mL) and with brine; then dried (MgSO$_4$) and evaporated to afford the title compound (857 mg, 89%). $^1$H-NMR (CDCl$_3$, 500 MHz): δ 4.72 (q, J=8.20, 2H), 7.58 (s, 1H), 7.61 (s, 1H). $^{19}$F-NMR (CDCl$_3$, 470.385 MHz): −71.69

Preparation 147: 1-(2,2,2-Trifluoroethyl)-4-((trimethylsilyl)ethynyl)-1H-pyrazole 4-Iodo-1-(2,2,2-trifluoroethyl)-1H-pyrazole (Preparation 146, 970 mg, 3.51 mmol) was dissolved in DMF (4.9 mL) and TMS-acetylene (0.7 ml, 486 mg, 4.96 mmol) was added; followed by di-isopropylamine (0.65 mL), copper(I) iodide (44 mg) and triphenylphosphine (184 mg). The reaction was flushed with nitrogen. Palladium acetate (52.5 mg) was added and the reaction flushed again with nitrogen (×3) before heating at 60° C. for 60 minutes. The reaction was cooled and added to water (50 mL). The product was extracted with ether (3×25 mL). The combined organic layers were washed with water (3×20 mL) and brine, then dried (MgSO$_4$) and concentrated in vacuo. The residue was purified using silica gel column chromatography eluting with 1:2 ethyl acetate:cyclohexane to afford the title compound (844 mg, 97%). $^1$H-NMR (CDCl$_3$, 500 MHz): δ 0.24 (s, 9H), 4.68 (q, J=8.20, 2H), 7.66 (s, 1H), 7.67 (s, 1H).
$^{19}$F-NMR (CDCl$_3$, 470.385 MHz): −71.69.

Preparation 148: 4-Ethynyl-1-(2,2,2-trifluoroethyl)-1H-pyrazole 1-(2,2,2-Trifluoroethyl)-4-((trimethylsilyl)ethynyl)-1H-pyrazole (Preparation 147, 1.19 g) was dissolved in methanol (7 ml) and potassium carbonate (30 mg) was added. The reaction was stirred at room temperature for 3.5 hours. The methanol was evaporated and the residue taken up in dichloromethane (20 ml) and filtered through a plug of silica eluting with DCM to afford the title compound (326 mg, 53%). $^1$H-NMR (CDCl$_3$, 500 MHz): δ 3.06 (s, 1H), 4.70 (q, J=8.20 Hz, 2H), 7.69 (s, 1H), 7.70 (s, 1H). $^{19}$F-NMR (CDCl$_3$, 470.385 MHz): −71.69

Preparation 149: 6-Bromo-1-(methylsulfonyl)-2-(1-(2,2,2-trifluoroethyl)-1H-pyrazol-4-yl)-1H-pyrrolo[3,2-c]pyridine 4-Ethynyl-1-(2,2,2-trifluoroethyl)-1H-pyrazole (Preparation 148, 326 mg 1.87 mmole) was dissolved in DMF (4.9 mL) and N-(2-bromo-5-iodopyridin-4-yl)methanesulfonamide (Preparation 8, 565 mg 1.50 mmole) was added. To the solution was added triethylamine (0.91 mL, 655 mg 6.5 mmole) and copper(I) iodide (10 mg 0.052 mmole). The reaction was sealed and flushed with nitrogen. Bis(triphenylphosphine)palladium dichloride (37 mg 0.052 mmole) was added and the reaction was again flushed with nitrogen, then heated at 60° C. for 110 minutes. The reaction was cooled and added to water (50 ml). The reaction were extracted with ethyl acetate thrice (3×20 ml). The combined organic extracts were washed with water (3×20 mL) and brine, dried and concentrated in vacuo. The residue was purified using column chromatography eluting with 100% dichloromethane, 5% ethyl acetate in dichloromethane to 10% ethyl acetate in dichloromethane to 20% ethyl acetate in dichloromethane to 30% ethyl acetate in dichloromethane to afford the title compound (300 mg, 47%). $^1$H-NMR (CDCl$_3$, 500 MHz): δ 2.98 (s, 3H), 4.80 (q, J=8.20 Hz, 2H), 6.76 (d, J=0.95 Hz, 1H), 7.84 (d, J=0.63 Hz, 1H), 7.94 (s, 1H), 8.25 (t, J=0.95 Hz, 1H), 8.67 (d, J=0.95 Hz, 1H). $^{19}$F-NMR (CDCl$_3$, 470.385 MHz): −71.56.

Preparation 150: tert-Butyl 6-bromo-2-(1-(2,2,2-trifluoroethyl)-1H-pyrazol-4-yl)-1H-pyrrolo[3,2-c]pyridine-1-carboxylate 6-Bromo-1-(methylsulfonyl)-2-(1-(2,2,2-trifluoroethyl)-1H-pyrazol-4-yl)-1H-pyrrolo[3,2-c]pyridine (Preparation 149, 300 mg, 0.71 mmole) was stirred in methanol (3 mL) and 1M sodium hydroxide solution (aqueous, 0.8 mL, 0.8 mmole) was added and the reaction stirred at room temperature for 2 hours 20 minutes. The methanol was evaporated and the residue taken up in ethyl acetate (20 mL), washed with water (4 mL) and with brine; then dried (MgSO$_4$) and evaporated. The residue was dissolved in ethyl acetate (3 mL) and triethylamine (0.15 mL, 017 mg, 1.06 mmole) was added followed by a crystal of DMAP and di-t-butyl dicarbonate (240 mg, 1.1 mmole). The reaction was stirred at room temperature for 2 hours and then evaporated. The residue was purified using preparative TLC eluting with 4:1 dichloromethane:ethyl acetate to afford the title compound (251 mg, 79%). $^1$H-NMR (CDCl$_3$, 500 MHz): δ 1.54 (s, 9H), 4.78 (q, J=8.51 Hz, 2H), 6.61 (d, J=0.63 Hz, 1H), 7.72 (s, 1H), 7.74 (s, 1H), 8.24 (s, 1H), 8.59 (d, J=0.63 Hz, 1H). $^{19}$F-NMR (CDCl$_3$, 470.385 MHz): −71.59.

Preparation 151: 1-(Difluoromethyl)-4-((trimethylsilyl)ethynyl)-1H-pyrazole

4-Iodo-1-difluoromethylpyrazole (521 mg, 1.81 mmole) was dissolved in DMF (3 mL). TMS-acetylene (0.43 ml) was added followed by di-isopropylamine (395 uL), copper(I) iodide (27 mg) and triphenylphosphine (112 mg). The reaction was flushed with nitrogen. Palladium acetate (32 mg) was added and the reaction flushed again with nitrogen (×3) and was heated at 60° C. for 65 minutes. The reaction was cooled and diluted with ethyl acetate (20 mL). The solution was washed with water (3×10 mL) and with brine then dried and concentrated in vacuo. The residue was purified using preparative TLC eluting with 1:1 dichloromethane:cyclohexane to afford the title compound (413 mg 1.92 mmole). $^1$H-NMR (CDCl$_3$, 500 MHz): δ 0.25 (s, 9H), 7.15 (t, J=60.2 Hz, 1H), 7.71 (s, 1H), 7.94 (s, 1H).

Preparation 152: 1-(Difluoromethyl)-4-ethynyl-1H-pyrazole 1-(Difluoromethyl)-4-((trimethylsilyl)ethynyl)-1H-pyrazole (Preparation 151, 413 mg, 1.9 mmole) was stirred with methanol (4 mL). Potassium carbonate (17 mg) was added and stirred at room temperature for 50 minutes. The solvent was evaporated and the residue was filtered in dichloromethane through a short pad of silica to afford the title compound (187 mg 1.31 mmole 72%). $^1$H-NMR (CDCl$_3$, 500 MHz): δ 3.08 (s, 1H), 7.17 (t, J=60.5 Hz, 1H), 7.75 (s, 1H), 7.97 (s, 1H).

Preparation 153: 6-Bromo-2-(1-(difluoromethyl)-1H-pyrazol-4-yl)-1-(methylsulfonyl)-1H-pyrrolo[3,2-c]pyridine 1-(Difluoromethyl)-4-ethynyl-1H-pyrazole (Preparation 152, 187 mg 1.31 mmole) was dissolved in DMF (4.2 mL) and N-(2-bromo-5-iodopyridin-4-yl)methanesulfonamide (Preparation 8, 444 mg 1.17 mmole) was added. To the solution was added triethylamine (0.80 mL, 576 mg 5.7 mmole) and copper(I) iodide (9 mg 0.047 mmole). The reaction was sealed and flushed with nitrogen. Bis(triphenylphosphine)palladium dichloride (37.6 mg 0.046 mmole) was added and the reaction was again flushed with nitrogen, then heated at 60° C. for 140 minutes. The reaction was added to ethyl acetate (45 mL) and washed with water (3×15 mL) and with brine, then dried and concentrated in vacuo. The residue was purified using preparative TLC eluting with 5% ethyl acetate in chloroform to afford the title compound 157 mg. $^1$H-NMR (d$_6$-acetone, 500 MHz): δ 3.37 (s, 3H), 7.06 (d, J=0.63 Hz, 1H), 7.70 (t, J=59.6 Hz, 1H), 8.04 (s, 1H), 8.16 (m, 1H), 8.51 (s, 1H), 8.73 (d, J=0.95 Hz, 1H).

Preparation 154: tert-Butyl 6-bromo-2-(1-(difluoromethyl)-1H-pyrazol-4-yl)-1H-pyrrolo[3,2-c]pyridine-1-carboxylate 6-Bromo-2-(1-(difluoromethyl)-1H-pyrazol-4-yl)-1-(methylsulfonyl)-1H-pyrrolo[3,2-c]pyridine (Preparation 153, 189 mg, 0.48 mmole) was stirred in methanol (2.1 ml) and 1M sodium hydroxide in water (0.53 mL) was added. The reaction was stirred at 25° C. for 85 minutes. The methanol was evaporated and the residue taken up in ethyl acetate (14 mL). The solution was washed with water (3 mL) and with brine; then dried and concentrated in vacuo. The residue was stirred with ethyl acetate (2 mL) and triethylamine (101 uL, 73 mg, 0.72 mmole) was added, along with a small crystal of DMAP. Di-t-butyl dicarbonate (157 mg 0.72 mmole) was added and the reaction stirred at room temperature for 1.5 hours. The solvent was concentrated in vacuo and purified using preparative TLC eluting with 1:2 ethyl acetate:cyclohexane to afford the title compound (131 mg). $^1$H-NMR (CDCl$_3$, 500 MHz): δ 1.53 (s, 9H)<6.65 (d, J=0.63 Hz, 1H), 7.25 (t, J=60.5 Hz, 1H), 7.79 (s, 1H), 8.01 (s, 1H), 8.27 (m, 1H), 8.62 (d, J=0.63 Hz, 1H).
$^{19}$F-NMR (CDCl$_3$, 470.385 MHz): −93.43.

Preparation 155
2-Methoxy-4-(1-methyl-1H-pyrazol-4-yl)aniline

A solution of 2-methoxy-4-(4,4,5,5-tetramethyl-1,3,2-dioxaborolan-2-yl)aniline (5 g, 24.03 mmol), 4-bromo-1-methyl-1H-pyrazole (3.53 g, 17.47 mmol), Pd(dppf)Cl$_2$.DCM (0.38 g, 0.465 mmol) and 2M sodium carbonate (20 ml0 in THF (60 ml) was stirred and heated to 60° C. for 24 hours. The reaction was diluted with ethyl acetate and brine. The organic solution was collected, dried (MgSO$_4$) and concentrated in vacuum. The residue was purified using Biotage silica gel column chromatography eluting with a gradient of 0 to 70% ethyl acetate in cyclohexane to afford the title compound as a white powder (2.5 g, 70%). $^1$H NMR (500 MHz, CDCl$_3$) δ 3.8 (s, br, 2H), 3.9 (s, 3H), 3.94 (s, 3H), 6.71 (d, J=7.9 Hz, 1H), 6.9 (m, 2H), 7.52 (s, 1H), 7.68 (s, 1H).

Preparation 156: 4-(1,3-Dimethyl-1H-pyrazol-4-yl)-2-methoxyaniline

Prepared using method C (Preparation 85) in DME/water 3/1 for 1 hour at 150° C. under microwave irradiation. Purified using silica gel column chromatography eluting with 5% (7M ammonia in methanol) in ethyl acetate to afford the title compound as a purple powder (40 mg, 46%). $^1$H NMR (500 MHz, CDCl$_3$) δ 2.38 (s, 3H), 3.84 (s, br, 2H), 3.87 (s, 3H), 3.88 (s, 3H), 6.74 (d, J=7.9 Hz, 1H), 6.83 (m, 2H), 7.71 (s, 1H).

Preparation 157: 6-Bromo-1-(2-methoxyethyl)-2-(1-methyl-1H-pyrazol-4-yl)-1H-pyrrolo[3,2-c]pyridine 6-Bromo-2-(1-methyl-1H-pyrazol-4-yl)-1H-pyrrolo[3,2-c]pyridine (Preparation 22, 100 mg, 0.36 mmole) was azeotroped with toluene (3 mL) and dissolved in DMF (1 mL). To the solution was added sodium hexamethyldisilazide, 1M in THF (0.4 mL, 0.4 mmole) and the reaction was stirred at room temperature for 20 minutes. Bromoethylmethyl ether (65 uL, 100 mg, 0.8 mmole) was added and the reaction was stirred at room temperature for 18 hours. The reaction was diluted with ethyl acetate (25 mL) and the solution washed with water (3×8 mL) and with brine, dried and evaporated to afford the title compound. $^1$H-NMR (CDCl$_3$, 500 MHz): δ 3.31 (s, 3H), 3.72 (t, J=5.68 Hz, 2H), 4.01 (s, 3H), 4.28 (t, J=5.68 Hz, 2H), 6.54 (d, J=0.95 Hz, 1H), 7.48 (t, J=0.95 Hz, 1H), 7.71 (s, 1H), 7.74 (d, J=0.95 Hz, 1H), 8.60 (d, J=0.95 Hz, 1H).

Preparation 158: 6-Bromo-1-(cyclopropylmethyl)-2-(1-methyl-1H-pyrazol-4-yl)-1H-pyrrolo[3,2-c]pyridine 6-Bromo-2-(1-methyl-1H-pyrazol-4-yl)-1H-pyrrolo[3,2-c]pyridine (Preparation 22, 100 mg, 0.36 mmole) was azeotroped with toluene (3 mL) and dissolved in DMF (1 mL). To the solution was added sodium hexamethyldisilazide, 1M in THF (0.4 mL, 0.4 mmole) and the reaction was stirred at room temperature for 20 minutes. Bromomethylcyclopropane (78 uL, 108 mg, 0.8 mmole) was added and the reaction was stirred at room temperature for 6 hours. Ethyl acetate (25 mL) was added and the solution was washed with water (3×10 mL) and with brine (5 mL), dried and evaporated in vacuo. The crude product was purified using preparative TLC eluting with ethyl acetate to afford the title compound (98 mg, 82%). $^1$H-NMR (CDCl$_3$, 500 MHz): δ 0.23 (m, 2H), 0.55 (m, 2H), 1.12 (m, 1H), 4.03 (s, 3H), 4.07 (d, J=6.31 Hz, 2H), 6.54 (d, J=0.95 Hz, 1H), 7.45 (t, J=0.95 Hz, 1H), 7.61 (s, 1H), 7.71 (d, J=0.95 Hz, 1H), 8.61 (d, J=0.95 Hz, 1H).

Preparation 159:
N-(3-Chloro-4-nitrobenzylidene)methanamine

3-Chloro-4-nitrobenzaldehyde (251 mg 1.35 mmole) was dissolved in dichloromethane (2 mL) and methylamine, 2M in THF (0.88 mL, 1.76 mmole) was added along with 3A Sieves (400 mg). The reaction was stirred at room temperature for 18.5 hours. The sieves were filtered and washed with more dichloromethane. The filtrate was evaporated, however only partial conversion to the imine was observed. The residue was redissolved in dichloromethane (2 mL) and methylamine. 2M in THF (1.0 mL, 2.0 mmole) was added along with powdered 3A Sieves (400 mg). The reaction was stirred at room temperature for a further 16.5 hours. The sieves were filtered and washed and the filtrate evaporated to give the title compound as an oil which quickly crystallised (199 mg). $^1$H-NMR (CDCl$_3$, 500 MHz): δ 3.60 (d, J=1.89 Hz, 3H), 7.73 (dd, J=1.89, 8.51 Hz, 1H), 7.93 (m, 2H), 8.30 (q, J=1.58 Hz, 1H).

Preparation 160: 5-(3-Chloro-4-nitrophenyl)-1,4-dimethyl-1H-imidazole

N-(3-Chloro-4-nitrobenzylidene)methanamine (Preparation 159, 285 mg, 1.43 mmole) and 1-(1-isocyanoethylsulfonyl)-4-methylbenzene (360 mg, 1.72 mmole) were dissolved in THF (6 mL) and 1,5,7-triazabicyclo[4.4.0]dec-5-ene (238 mg 1.72 mmole) was added. The reaction was heated at 60° C. for 7 hours, then allowed to stand at room temperature overnight. The solvent was evaporated and the residue was taken up in ethyl acetate (25 mL). The solution was washed with water (2×10 mL), with brine (5 ml), dried and evaporated to leave a gum. The gum was applied to a
SCX-2 column and the column was washed with methanol followed by 2M ammonia in methanol. The solvent was concentrated in vacuo and purified using preparative TLC eluting with 20:1 ethyl acetate:2M ammonia in methanol to afford the title compound (99 mg, 27%).
$^1$H-NMR (CDCl$_3$, 500 MHz): δ 2.28 (s, 3H), 3.62 (s, 3H), 7.35 (dd, J=1.89, 8.20 Hz, 1H), 7.50 (d, J=1.89 Hz, 1H), 7.50 (s, 1H), 8.02 (d, J=8.20 Hz, 1H).

Preparation 161:
2-Chloro-4-(1,4-dimethyl-1H-imidazol-5-yl)aniline 5-(3-Chloro-4-nitrophenyl)-1,4-dimethyl-1H-imidazole (Preparation 160, 99 mg 0.39 mmole) was stirred in ethanol (3.6 mL) and 1M sodium dithionite in water (1.2 mL, 1.2 mmole) was added. The reaction was heated at 40° C. for 1 hour. 2M Hydrochloric acid (5 mL) was added and the reaction was heated at 50° C. for 1 hour. The solution was cooled and quenched with anhydrous sodium carbonate and the ethanol was evaporated. The solution was saturated with sodium chloride and extracted with ethyl acetate (4×6 mL). The organic layers were dried and evaporated to afford the title compound (62 mg, 71%). $^1$H-NMR (CD$_3$OD, 500 MHz): δ 2.12 (s, 3H), 3.52 (s, 3H), 6.92 (d, J=8.20, 1H), 7.01 (d, J=1.89, 8.20 Hz, 1H), 7.18 (d, J=1.89 Hz, 1H), 7.53 (s, 1H).

Preparation 162: Isopropyl 6-bromo-2-(oxazol-5-yl)-1H-pyrrolo[3,2-c]pyridine-1-carboxylate 5-(6-Bromo-1H-pyrrolo[3,2-c]pyridin-2-yl)oxazole (Preparation 139, 156 mg 0.59 mmole) was azeotroped with benzene (3 mL) and then dissolved in DMF (1.5 mL). The solution was placed under nitrogen and a solution of sodium hexamethyldisilazide (1M in THF, 0.9 mL, 0.9 mmole) was added and stirred at room temperature for 20 minutes. A solution of isopropyl chloroformate (1M in toluene, 0.9 mL, 0.9 mmole) was added and stirred at room temperature for 4 hours. The reaction was diluted with ethyl acetate (25 mL) and the solution was washed with water (3×10 mL), brine, dried and evaporated to a residue. This was purified using preparative TLC eluting with 3:1 ethyl acetate:cyclohexane. The product band was recovered with acetone to afford the title compound (154 mg, 74%). $^1$H-NMR (CDCl$_3$, 500 MHz): δ 1.36 (d, J=6.31 Hz, 6H), 5.23 (sept, J=6.31 Hz, 1H), 6.94 (d, J=0.63 Hz, 1H), 7.41 (s, 1H), 8.02 (s, 1H), 8.32 (t, J=0.95 Hz, 1H), 8.69 (d, J=0.95 Hz, 1H).

Preparation 163:
4-(1,2-dimethyl-1H-imidazol-5-yl)aniline

Tetrakis(triphenylphosphine)palladium (0.053 g, 0.046 mmol) was added to a solution of 4-(4,4,5,5-tetramethyl-1,3,2-dioxaborolan-2-yl)aniline (0.1 g, 0.456 mmol), 5-bromo-1,2-dimethyl-1H-imidazole (0.088 g, 0.502 mmol) and cesium fluoride (0.208 g, 1.369 mmol) in DME/MeOH (2/1, 2.9 mL). The reaction mixture was heated for 10 minutes at 150° C. under microwave irradiation. The reaction was diluted with EtOAc and quenched with water. The layers were separated and the aqueous layer was extracted with EtOAc. The combined organic layers were dried (Na$_2$SO$_4$), filtered and concentrated under reduced pressure. The crude mixture was purified using Biotage silica gel column chromatography eluting with 1 to 5% MeOH/aq. NH$_3$ (10/1) in DCM followed by filtration through a SCX-2 column to afford the title product as a white solid (48 mg, 56%). $^1$H NMR (500 MHz, CDCl$_3$): δ 2.42 (s, 3H), 3.46 (s, 3H), 3.81 (br s, 2H), 6.71-6.74 (m, 1H), 6.85 (s, 1H), 7.12-7.14 (m, 1H).
LC (Method B)-MS (ESI, m/z) t$_R$ 0.24 min, 188 [M+H]$^+$ Preparation 164:
2-Chloro-4-methoxypyrimidin-5-amine Sodium methoxide (0.5M in methanol, 3.7 mL, 1.829 mmol) was added to a solution of 2,4-dichloropyrimidin-5-amine (0.2 g, 1.220 mmol) in MeOH (2.5 mL). The reaction was stirred at room temperature for 1.5 hours. The reaction was then diluted with EtOAc and quenched with water. The layers were separated and the aqueous layer was extracted with EtOAc. The combined organic layers were dried (Na$_2$SO$_4$), filtered and concentrated under reduced pressure to afford the title product as a brown solid (177 mg, 91%). $^1$H NMR (500 MHz, CDCl$_3$): δ 3.93 (s, 3H), 5.31 (br s, 2H), 7.73 (s, 1H). LC (Method B)-MS (ESI, m/z) t$_R$ 1.6 min, 160 [M+H]$^+$

Preparation 165: tert-Butyl 2-(1-(tert-butoxycarbonyl)-1H-pyrazol-4-yl)-6-((2-chloro-4-(methylsulfonyl)phenyl)amino)-1H-pyrrolo[3,2-c]pyridine-1-carboxylate The title compound was prepared from tert-butyl 6-bromo-2-(1-(tert-butoxycarbonyl)-1H-pyrazol-4-yl)-1H-pyrrolo[3,2-c]pyridine-1-carboxylate (Preparation 10) and 2-chloro-4-(methylsulfonyl)aniline using the method described for Example 35. Purified using preparative TLC eluting with 20% ethyl acetate in CH$_2$Cl$_2$. $^1$H-NMR (500 MHz, DMSO-d$_6$) 1.46, 1.60 (2×s, 9H each), 3.21 (s, 3H), 6.90 (s, 1H), 7.74 (dd, J=2.2, 8.9 Hz, 1H), 7.91 (d, J=2.30 Hz, 1H), 7.93 (s, 1H), 8.07 (s, 1H), 8.30 (d, J=8.5 Hz, 1H), 8.52 (s, 1H), 8.57 (s, 1H), 8.98 (s, 1H).

Example 1 tert-Butyl 6-(2-methoxy-4-(1-methylpiperidin-4-ylcarbamoyl)phenylamino)-2-(1-methyl-1H-pyrazol-4-yl)-1H-pyrrolo[3,2-c]pyridine-1-carboxylate

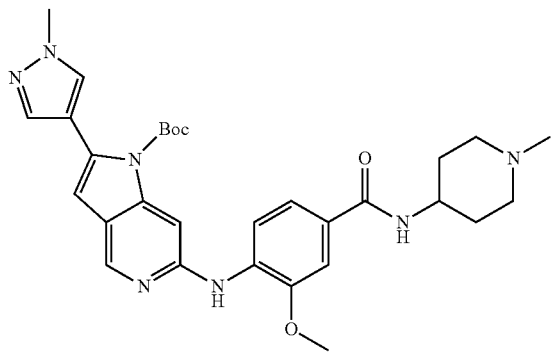 [SMILES: COc1cc(C(=O)NC2CCN(C)CC2)ccc1Nc1cc2c(cn1)cc(-c1cnn(C)c1)n2C(=O)OC(C)(C)C]

Method X

Tris(dibenzylideneacetone)dipalladium(0) (25 mg, 0.027 mmol) was added to a mixture of tert-butyl 6-bromo-2-(1-methyl-1H-pyrazol-4-yl)-1H-pyrrolo[3,2-c]pyridine-1-carboxylate (Preparation 23, 35 mg, 0.091 mmol), caesium carbonate (60 mg, 0.183 mmol), 4-amino-3-methoxy-N-(1-methylpiperidin-4-yl)benzamide (Preparation 56, 29 mg, 0.110 mmol) and xantphos (32 mg, 0.055 mmol) in DMA (1.0 mL) and the reaction heated at 80° C. for 3 hours. The reaction was then filtered through a SCX-2 column and concentrated under vacuum. The residue was purified by preparative TLC (10% MeOH/aq NH$_3$ 10/1 in DCM) to afford the title product as a white solid (15 mg, 29%). $^1$H NMR (500 MHz, CD$_3$OD): δ 1.50 (s, 9H), 1.72 (qd, J=12.6, 3.7 Hz, 2H), 1.95-2.01 (m, 2H), 2.18-2.26 (m, 2H), 2.34 (s, 3H), 2.92-2.99 (m, 2H), 3.89-3.96 (m, 1H), 3.95 (s, 3H), 4.01 (s, 3H), 6.60 (s, 1H), 7.48 (dd, J=8.4, 1.9 Hz, 1H), 7.52 (d, J=1.9 Hz, 1H), 7.61 (s, 1H), 7.80 (s, 1H), 7.81 (s, 1H), 7.91 (d, J=8.4 Hz, 1H), 8.43 (s, 1H). LC (Method B)-MS (ESI, m/z) t$_R$ 2.04 minutes MS m/z 560 [M+H]$^+$ The following Examples were prepared according to Method X (Example 1) above using 6-bromo-2-(1-methyl-1H-pyrazol-4-yl)-1H-pyrrolo[3,2-c]pyridine-1-carboxylate (Preparation 23) or an appropriate preparation as otherwise described, and the appropriate aniline at 80-90° C. for 3 hours. The crude reaction products were purified as above or according to one of the following methods:

Method A: Biotage silica gel column chromatography eluting with DCM/EtOH 99/1 to either 97/3 or 95/5.

Method B: Biotage silica gel column chromatography eluting with DCM/EtOH 99/1 to 90/10.

Method C: Biotage silica gel column chromatography eluting with DCM/EtOH 99/1 to 90/10, followed by preparative TLC (DCM/EtOH 95/5).

Method D: Biotage silica gel column chromatography eluting with DCM/EtOH 99/1 to 97/3, followed by preparative TLC (DCM/EtOH 95/5).

Method E: Biotage silica gel column chromatography eluting with 1 to 5% MeOH/aq. NH$_3$ (10/1) in EtOAc.

Method F: Preparative TLC (DCM/EtOAc from between 70/30 to 55/45).

Method G: Preparative TLC (DCM/EtOAc 80/20).

Method H: Biotage silica gel column chromatography using a Biotage KP-NH column eluting with cyclohexane/EtOAc 70/30 to 40/60.

Method I: The reaction was cooled to room temperature and diluted with ethyl acetate. The organic solution was washed with water, brine, dried over sodium sulphate and filtered. The solvent was removed in vacuum and the residue purified by silica gel column chromatography, eluting with a gradient of 50-20% hexane in ethyl acetate to 100% ethyl acetate.

Method J: The reaction was cooled to room temperature and diluted with ethyl acetate. The organic solution was washed with water, brine, dried over sodium sulphate and filtered. The solvent was removed in vacuum and the residue purified by silica gel column chromatography, eluting with 20% ethyl acetate in dichloromethane.

Method K: Silica gel column chromatography eluting with 100% ethyl acetate or 3-5% MeOH in ethyl acetate.

Method L: Silica gel column chromatography eluting with 5% triethylamine in ethyl acetate.

Method M: Silica gel column chromatography eluting with 50% dichloromethane in ethyl acetate.

Method N: Silica gel column chromatography eluting with 15% MeOH in ethyl acetate.

Method O: Preparative TLC (2% methanol in ethyl acetate/DCM) (v/v; 1;1).

Method P: Preparative TLC (8% ethyl acetate/DCM).

Method Q: The reaction was cooled to room temperature and diluted with ethyl acetate. The organic solution was washed with water, brine, dried over sodium sulphate and filtered. The solvent was removed in vacuum and the residue purified by preparative TLC eluting with 4/1 DCM/EtOAc.

Method R: After heating the solvent was removed in vacuo and partitioned between EtOAc and water. The organic layer was washed with brine, dried (Na$_2$SO$_4$) and concentrated in vacuo before purification using a preparative TLC eluting with 10/1 EtOAc/2M Ammonia in MeOH followed by preparative TLC eluting with 10:1 ethyl acetate: "A"; where "A" is 10:1 methanol: '880' ammonia.

| Example No | Name/Structure | Data | MPS1 IC$_{50}$ (uM) |
|---|---|---|---|
| 2 | tert-Butyl 6-(2-methoxypyridin-3-ylamino)-2-(1-methyl-1H-pyrazol-4-yl)-1H-pyrrolo[3,2-c]pyridine-1-carboxylate | $^1$H NMR (500 MHz, CDCl$_3$): δ 1.51 (s, 9H), 3.97 (s, 3H), 4.06 (s, 3H), 6.49 (d, J = 0.7 Hz, 1H), 6.90 (dd, J = 7.8, 5.0 Hz, 1H), 7.03 (s, 1H), 7.53 (s, 1H), 7.60 (s, 1H), 7.62 (s, 1H), 7.73 (dd, J = 5.0, 1.6 Hz, 1H), 8.41 (dd, J = 7.8, 1.6 Hz, 1H), 8.48 (d, J = 0.7 Hz, 1H). LC (Method B)-MS (ESI, m/z) t$_R$ 2.51 min, 421 [M + H]$^+$ Using 2-methoxypyridin-3-amine and purification method A. | No data |
| 3 | tert-Butyl 6-(4-(dimethylcarbamoyl)-2-(trifluoromethoxy)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.51 (s, 9H), 3.10 (s, 6H), 3.97 (s, 3H), 6.52 (d, J = 0.7 Hz, 1H), 6.91 (s, 1H), 7.38 (dd, J = 8.5, 1.9 Hz, 1H), 7.42-7.44 (m, 1H), 7.55 (s, 1H), 7.60 (s, 1H), 7.71 (s, 1H), 8.22 (d, J = 8.5 Hz, 1H), 8.52 (d, J = 0.7 Hz, 1H); ESI-HRMS Found 545.2115, calculated for C$_{26}$H$_{27}$F$_3$N$_6$O$_4$ [M + H]$^+$: 545.2119. Using 4-amino-N,N-dimethyl-3-(trifluoromethoxy)benzamide (Preparation 57) and purification method A. | 0.006 |
| 4 | tert-Butyl 6-(5-(dimethylcarbamoyl)-2-methoxyphenylamino)-2-(1-methyl-1H-pyrazol-4-yl)-1H-pyrrolo[3,2-c]pyridine-1-carboxylate | $^1$H NMR (500 MHz, CDCl$_3$): δ 1.48 (s, 9H), 3.10 (s, 6H), 3.94 (s, 3H), 3.96 (s, 3H), 6.48 (d, J = 0.7 Hz, 1H), 6.91 (d, J = 8.3 Hz, 1H), 7.07 (dd, J = 8.3, 2.0 Hz, 1H), 7.18 (br s, 1H), 7.53 (s, 1H), 7.58 (s, 1H), 7.64 (s, 1H), 8.17 (d, J = 2.0 Hz, 1H), 8.45 (s, 1H). LC (Method B)-MS (ESI, m/z) t$_R$ 2.30 min 491 [M + H]$^+$ Using 3-amino-4-methoxy-N,N-dimethylbenzamide (Preparation 58) and purification method A. | No data |

| Example No | Name/Structure | Data | MPS1 IC$_{50}$ (uM) |
|---|---|---|---|
| 5 | tert-Butyl 6-(2-methoxy-4-(thiomorpholine-4-carbonyl)phenylamino)-2-(1-methyl-1H-pyrazol-4-yl)-1H-pyrrolo[3,2-c]pyridine-1-carboxylate-S,S-dioxide | $^1$H NMR (500 MHz, CDCl$_3$): δ 1.51 (s, 9H), 3.05-3.13 (m, 4H), 3.95 (s, 6H), 4.14-4.19 (m, 4H), 6.50 (d, J = 0.7 Hz, 1H), 7.04 (dd, J = 8.2, 1.8 Hz, 1H), 7.07 (d, J = 1.8 Hz, 1H), 7.31 (s, 1H), 7.53 (s, 1H), 7.59 (s, 1H), 7.69 (m, 1H), 8.28 (d, J = 8.2 Hz, 1H), 8.51 (d, J = 0.7 Hz, 1H). LC (Method D)-MS (ESI, m/z) t$_R$ 1.52 min, 581 [M + H]$^+$ Using (4-amino-3-methoxyphenyl)(thiomorpholino)methanone-S,S-dioxide (Preparation 59) and purification method A. | No data |
| 6 | tert-Butyl 6-(2-methoxy-4-(thiomorpholinomethyl)phenylamino)-2-(1-methyl-1H-pyrazol-4-yl)-1H-pyrrolo[3,2-c]pyridine-1-carboxylate-S,S-dioxide | $^1$H NMR (500 MHz, CDCl$_3$): δ 1.50 (s, 9H), 2.99-3.03 (m, 4H), 3.06-3.10 (m, 4H), 3.61 (s, 2H), 3.92 (s, 3H), 3.97 (s, 3H), 6.48 (d, J = 0.7 Hz, 1H), 6.86-6.89 (m, 2H), 7.06 (s, 1H), 7.53 (s, 1H), 7.59 (s, 1H), 7.65 (m, 1H), 7.98 (d, J = 8.5 Hz, 1H), 8.46 (d, J = 0.8 Hz, 1H). LC (Method D)-MS (ESI, m/z) t$_R$ 1.46 min, 567 [M + H]$^+$ Using 2-methoxy-4-(thiomorpholinomethyl)aniline-S,S-dioxide (Preparation 76) and purification method A. | No data |
| 7 | tert-Butyl 6-(2-chloro-4-(dimethylcarbamoyl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.52 (s, 9H), 3.10 (s, 6H), 3.98 (s, 3H), 6.53 (s, 1H), 7.08 (s, 1H), 7.34 (dd, J = 8.5, 1.9 Hz, 1H), 7.55 (d, J = 1.9 Hz, 1H), 7.56 (s, 1H), 7.61 (s, 1H), 7.72 (s, 1H), 8.15 (d, J = 8.5 Hz, 1H), 8.53 (s, 1H). ESI-HRMS (Method D) Found 495.1900, calculated for C$_{25}$H$_{28}$ClN$_6$O$_3$ [M + H]$^+$: 495.1906. Using 4-amino-3-chloro-N,N-dimethylbenzamide and purification method B. | 0.006 |

| Example No | Name/Structure | Data | MPS1 IC$_{50}$ (uM) |
|---|---|---|---|
| 8 | tert-Butyl 6-(2-chloro-4-(N,N-dimethylsulfamoyl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.52 (s, 9H), 2.74 (s, 6H), 3.99 (s, 3H), 6.56 (d, J = 0.6 Hz, 1H), 7.28 (s, 1H), 7.57 (s, 1H), 7.62 (s, 1H), 7.63 (dd, J = 8.8, 2.1 Hz, 1H), 7.78 (s, 1H), 7.82 (d, J = 2.1 Hz, 1H), 8.40 (d, J = 8.8 Hz, 1H), 8.57 (s, 1H). ESI-HRMS Found 531.1570, calculated for C$_{24}$H$_{28}$ClN$_6$O$_4$S [M + H]$^+$: 531.1576. Using 4-amino-3-chloro-N,N-dimethylbenzenesulfonamide (Preparation 77) and purification method A. | 0.096 |
| 9 | tert-Butyl 6-(2-acetylphenylamino)-2-(1-methyl-1H-pyrazol-4-yl)-1H-pyrrolo[3,2-c]pyridine-1-carboxylate | $^1$H NMR (500 MHz, CDCl$_3$): δ 1.59 (s, 9H), 2.70 (s, 3H), 3.99 (s, 3H), 6.54 (d, J = 0.9 Hz, 1H), 6.88 (ddd, J = 8.1, 7.0, 1.1 Hz, 1H), 7.49 (ddd, J = 8.6, 7.0, 1.6 Hz, 1H), 7.58 (s, 1H), 7.64 (s, 1H), 7.68 (t, J = 0.9 Hz, 1H), 7.89 (dd, J = 8.1, 1.6 Hz, 1H), 8.52-8.54 (m, 1H), 8.55 (d, J = 0.9 Hz, 1H), 11.46 (s, 1H). ESI-HRMS Found 432.2025, calculated for C$_{24}$H$_{26}$N$_5$O$_3$ [M + H]$^+$: 432.2030. Using 2-aminoacetophenone and purification method A. | 0.077 |
| 10 | tert-Butyl 6-(2-methoxy-4-(morpholine-4-carbonyl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.52 (s, 9H), 3.66-3.76 (m, 8H), 3.96 (s, 3H), 3.97 (s, 3H), 6.50 (s, 1H), 7.02 (dd, J = 8.2, 1.7 Hz, 1H), 7.07 (d, J = 1.7 Hz, 1H), 7.26 (s, 1H), 7.54 (s, 1H), 7.60 (s, 1H), 7.69 (s, 1H), 8.17 (d, J = 8.2 Hz, 1H), 8.50 (s, 1H). ESI-HRMS Found 533.2508, calculated for C$_{28}$H$_{33}$N$_6$O$_5$ [M + H]$^+$: 533.2507. Using (4-amino-3-methoxyphenyl)(morpholino)methanone (Preparation 60) and purification method A. | 0.005 |

-continued

| Example No | Name/Structure | Data | MPS1 IC$_{50}$ (uM) |
|---|---|---|---|
| 11 | tert-Butyl 6-(2-methoxy-4-(2-methoxyethylcarbamoyl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.51 (s, 9H), 3.41 (s, 3H), 3.57-3.60 (m, 2H), 3.65-3.69 (m, 2H), 3.97 (s, 3H), 3.98 (s, 3H), 6.50 (s, 1H), 6.58 (t, J = 5.3 Hz, 1H), 7.30-7.34 (m, 2H), 7.48 (d, J = 1.8 Hz, 1H), 7.54 (s, 1H), 7.60 (s, 1H), 7.72 (s, 1H), 8.15 (d, J = 8.4 Hz, 1H), 8.50 (s, 1H). ESI-HRMS Found 521.2505, calculated for C$_{27}$H$_{33}$N$_6$O$_5$ [M + H]$^+$: 521.2507. Using 4-amino-3-methoxy-N-(2-methoxyethyl)benzamide (Preparation 61) and purification method A. | 0.009 |
| 12 | tert-Butyl 6-(2-methoxy-4-(3-methoxyazetidine-1-carbonyl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.52 (s, 9H), 3.34 (s, 3H), 3.97 (s, 6H), 4.04-4.13 (m, 1H), 4.20-4.29 (m, 2H), 4.36-4.52 (m, 2H), 6.50 (d, J = 0.6 Hz, 1H), 7.20 (dd, J = 8.4, 1.8 Hz, 1H), 7.32 (s, 1H), 7.34 (d, J = 1.8 Hz, 1H), 7.54 (s, 1H), 7.60 (s, 1H), 7.70 (s, 1H), 8.16 (d, J = 8.4 Hz, 1H), 8.51 (s, 1H). ESI-HRMS (Method D) Found 533.2509, calculated for C$_{28}$H$_{33}$N$_6$O$_5$ (M + H$^+$): 533.2507. Using (4-amino-3-methoxyphenyl)(3-methoxyazetidin-1-yl)methanone (Preparation 62) and purification method A. | 0.007 |
| 13 | tert-Butyl 6-(2,6-dichloro-4-(dimethylcarbamoyl)phenyl-amino)-2-(1-methyl-1H-pyrazol-4-yl)-1H-pyrrolo[3,2-c]pyridine-1-carboxylate | $^1$H NMR (500 MHz, CDCl$_3$): δ 1.44 (s, 9H), 3.08 (br s, 3H), 3.11 (br s, 3H), 3.95 (s, 3H), 6.51 (d, J = 0.9 Hz, 1H), 6.75 (s, 1H), 7.03 (t, J = 0.9 Hz, 1 H), 7.50 (s, 2H), 7.55 (d, J = 0.8 Hz, 1 H), 7.59 (d, J = 0.8 Hz, 1H), 8.44 (d, J = 0.9 Hz, 1H). ESI-HRMS (Method D) Found 529.1530, calculated for C$_{25}$H$_{27}$Cl$_2$N$_6$O$_3$ [M + H]$^+$: 529.1516. Using 4-amino-3,5-dichloro-N,N-dimethylbenzamide (Preparation 82) and purification method D. | 0.020 |

| Example No | Name/Structure | Data | MPS1 IC$_{50}$ (uM) |
|---|---|---|---|
| 14 | tert-Butyl 6-(2-chlorophenylamino)-2-(1-methyl-1H-pyrazol-4-yl)-1H-pyrrolo[3,2-c]pyridine-1-carboxylate | $^1$H NMR (500 MHz, CDCl$_3$): δ 1.51 (s, 9H), 3.97 (s, 3H), 6.51 (d, J = 1.0 Hz, 1H), 6.89-6.95 (m, 2H), 7.34 (ddd, J = 8.2, 7.4, 1.5 Hz, 1H), 7.41 (dd, J = 8.0, 1.5 Hz, 1H), 7.55 (s, 1H), 7.61 (s, 1H), 7.65 (t, J = 1.0 Hz, 1H), 7.97 (dd, J = 8.2, 1.5 Hz, 1H), 8.49 (d, J = 1.0 Hz, 1H). ESI-HRMS (Method B) Found 424.1529, calculated for C$_{22}$H$_{23}$ClN$_5$O$_2$ [M + H]$^+$: 421.1535. Using 2-chloroaniline and purification method A. | 0.079 |
| 15 | tert-Butyl 6-(2-chloro-4-(1-methyl-1H-pyrazol-4-yl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.51 (s, 9H), 3.97 (s, 3H), 3.98 (s, 3H), 6.52 (s, 1H), 6.90 (s, 1H), 7.36 (dd, J = 8.5, 2.0 Hz, 1H), 7.54 (d, J = 2.0 Hz, 1H), 7.56 (s, 1H), 7.59 (s, 1H), 7.62 (s, 1H), 7.65 (s, 1H), 7.74 (s, 1H), 7.98 (d, J = 8.5 Hz, 1H), 8.50 (s, 1H). ESI-HRMS (Method B) Found 504.1897, calculated for C$_{26}$H$_{27}$ClN$_7$O$_2$ [M + H]$^+$: 504.1909. Using 2-chloro-4-(1-methyl-1H-pyrazol-4-yl)aniline (Preparation 83) and purification method A. | 0.018 |
| 16 | tert-Butyl 6-(2-chloro-4-(1-methyl-1H-pyrazol-3-yl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.51 (s, 9H), 3.96 (s, 3H), 3.97 (s, 3H), 6.49 (d, J = 2.2 Hz, 1H), 6.51 (d, J = 1.0 Hz, 1H), 6.96 (s, 1H), 7.38 (d, J = 2.2 Hz, 1H), 7.55 (s, 1H), 7.61 (s, 1H), 7.66 (dd, J = 8.5, 2.0 Hz, 1H), 7.69 (t, J = 1.0 Hz, 1H), 7.88 (d, J = 2.0 Hz, 1H), 7.99 (d, J = 8.5 Hz, 1H), 8.50 (d, J = 1.0 Hz, 1H). ESI-HRMS (Method B) Found 504.1898, calculated for C$_{26}$H$_{27}$ClN$_7$O$_2$ [M + H]$^+$: 504.1909. Using 2-chloro-4-(1-methyl-1H-pyrazol-3-yl)aniline (Preparation 85) and purification method A. | 0.019 |

| Example No | Name/Structure | Data | MPS1 IC$_{50}$ (uM) |
|---|---|---|---|
| 17 | tert-Butyl 6-(2-chloro-4-(1-methyl-1H-imidazol-5-yl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.52 (s, 9H), 3.69 (s, 3H), 3.98 (s, 3H), 6.53 (d, J = 0.9 Hz, 1H), 7.04 (s, 1H), 7.09 (br s, 1H), 7.27 (dd, J = 8.5, 2.0 Hz, 1H), 7.45 (d, J = 2.0 Hz, 1H), 7.53 (br s, 1H), 7.56 (s, 1H), 7.61 (s, 1H), 7.72 (t, J = 0.9 Hz, 1H), 8.18 (d, J = 8.5 Hz, 1H), 8.52 (d, J = 0.9 Hz, 1H). ESI-HRMS (Method B) Found 504.1885, calculated for C$_{26}$H$_{27}$ClN$_7$O$_2$ [M + H]$^+$: 504.1909. Using 2-chloro-4-(1-methyl-1H-imidazol-5-yl)aniline (Preparation 86) and purification method A. | 0.004 |
| 18 | tert-Butyl 6-(2-chloro-4-(4-methyl-4H-1,2,4-triazol-3-yl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.51 (s, 9H), 3.79 (s, 3H), 3.97 (s, 3H), 6.53 (d, J = 0.8 Hz, 1H), 7.20 (s, 1H), 7.55 (dd, J = 8.6, 2.1 Hz, 1H), 7.56 (s, 1H), 7.60 (s, 1H), 7.75 (t, J = 0.9 Hz, 1H), 7.77 (d, J = 2.1 Hz, 1H), 8.19 (s, 1H), 8.29 (d, J = 8.6 Hz, 1H), 8.53 (d, J = 0.9 Hz, 1H). ESI-HRMS (Method B) Found 505.1855, calculated for C$_{25}$H$_{26}$ClN$_8$O$_2$ [M + H]$^+$: 505.1862. Using 2-chloro-4-(4-methyl-4H-1,2,4-triazol-3-yl)aniline (Preparation 87) and purification method C. | 0.001 |
| 19 | tert-Butyl 6-(2-chloro-4-(pyridin-3-yl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.52 (s, 9H), 3.97 (s, 3H), 6.52 (d, J = 0.9 Hz, 1H), 7.06 (s, 1H), 7.37 (ddd, J = 7.9, 4.8, 0.9 Hz, 1H), 7.48 (dd, J = 8.5, 2.2 Hz, 1H), 7.55 (d, J = 0.8 Hz, 1H), 7.61 (d, J = 0.8 Hz, 1H), 7.65 (d, J = 2.2 Hz, 1H), 7.72 (t, J = 0.9 Hz, 1H), 7.85 (ddd, J = 7.9, 2.4, 1.6 Hz, 1H), 8.18 (d, J = 8.5 Hz, 1H), 8.52 (d, J = 0.9 Hz, 1H), 8.58 (dd, J = 4.8, 1.6 Hz, 1H), 8.83 (dd, J = 2.4, 0.9 Hz, 1H). ESI-HRMS (Method B) Found 501.1790, calculated for C$_{27}$H$_{26}$ClN$_6$O$_2$ [M + H]$^+$: 501.1800. Using 2-chloro-4-(pyridin-3-yl)aniline (Preparation 88) and purification method D. | 0.007 |

| Example No | Name/Structure | Data | MPS1 IC$_{50}$ (uM) |
|---|---|---|---|
| 20 | tert-Butyl 6-(2-chloro-4-(1,5-dimethyl-1H-pyrazol-4-yl)phenylamino)-2-(1-methyl-1H-pyrazol-4-yl)-1H-pyrrolo[3,2-c]pyridine-1-carboxylate 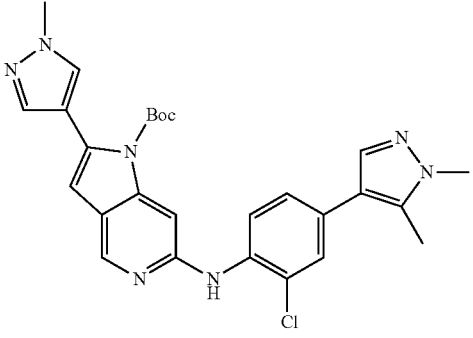 | $^1$H NMR (500 MHz, CDCl$_3$): δ 1.51 (s, 9H), 2.40 (s, 3H), 3.86 (s, 3H), 3.97 (s, 3H), 6.51 (d, J = 0.9 Hz, 1H), 6.94 (s, 1H), 7.23 (dd, J = 8.4, 2.0 Hz, 1H), 7.41 (d, J = 2.0 Hz, 1H), 7.53 (s, 1H), 7.55 (d, J = 0.8 Hz, 1H), 7.61 (d, J = 0.8 Hz, 1H), 7.64 (t, J = 0.9 Hz, 1H), 8.00 (d, J = 8.4 Hz, 1H), 8.49 (d, J = 0.9 Hz, 1H). ESI-HRMS (Method B) Found 518.2059, calculated for C$_{27}$H$_{29}$ClN$_7$O$_2$ [M + H]$^+$: 518.2066. Using 2-chloro-4-(1,5-dimethyl-1H-pyrazol-4-yl)aniline (Preparation 89) and purification method D. | 0.007 |
| 21 | tert-Butyl 6-(2-chloro-4-(1,3-dimethyl-1H-pyrazol-4-yl)phenylamino)-2-(1-methyl-1H-pyrazol-4-yl)-1H-pyrrolo[3,2-c]pyridine-1-carboxylate 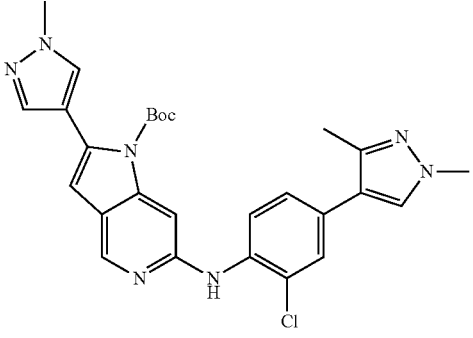 | $^1$H NMR (500 MHz, CDCl$_3$): δ 1.51 (s, 9H), 2.40 (s, 3H), 3.89 (s, 3H), 3.97 (s, 3H), 6.51 (d, J = 0.9 Hz, 1H), 6.93 (s, 1H), 7.26 (dd, J = 8.4, 2.0 Hz, 1H), 7.41 (s, 1H), 7.43 (d, J = 2.0 Hz, 1H), 7.55 (d, J = 0.8 Hz, 1H), 7.61 (d, J = 0.8 Hz, 1H), 7.64 (t, J = 0.9 Hz, 1H), 7.99 (d, J = 8.4 Hz, 1H), 8.49 (d, J = 0.9 Hz, 1H). ESI-HRMS (Method B) Found 518.2068, calculated for C$_{27}$H$_{29}$ClN$_7$O$_2$ [M + H]$^+$: 518.2066. Using 2-chloro-4-(1,3-dimethyl-1H-pyrazol-4-yl)aniline (Preparation 90) and purification method D. | 0.007 |
| 22 | tert-Butyl 6-(2-chloro-4-(1-methyl-1H-imidazol-2-yl)phenylamino)-2-(1-methyl-1H-pyrazol-4-yl)-1H-pyrrolo[3,2-c]pyridine-1-carboxylate 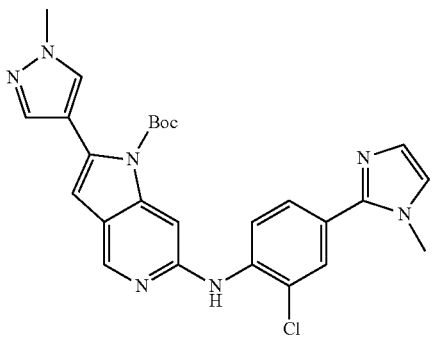 | $^1$H NMR (500 MHz, CDCl$_3$): δ 1.52 (s, 9H), 3.77 (s, 3H), 3.97 (s, 3H), 6.52 (d, J = 0.8 Hz, 1H), 6.96 (d, J = 1.3 Hz, 1H), 7.08 (s, 1H), 7.11 (d, J = 1.3 Hz, 1H), 7.50 (dd, J = 8.5, 2.1 Hz, 1H), 7.55 (d, J = 0.8 Hz, 1H), 7.61 (d, J = 0.8 Hz, 1H), 7.72-7.74 (m, 2H), 8.18 (d, J = 8.5 Hz, 1H), 8.52 (d, J = 0.9 Hz, 1H). ESI-HRMS (Method B) Found 504.1900, calculated for C$_{26}$H$_{27}$ClN$_7$O$_2$ [M + H]$^+$: 504.1909. Using 2-chloro-4-(1-methyl-1H-imidazol-2-yl)aniline (Preparation 91) and purification method E. | 0.003 |

| Example No | Name/Structure | Data | MPS1 IC$_{50}$ (uM) |
|---|---|---|---|
| 23 | tert-Butyl 6-(2-chloro-4-(5-methylisoxazol-4-yl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.52 (s, 9H), 2.60 (d, J = 0.7 Hz, 3H), 3.99 (s, 3H), 6.53 (d, J = 0.9 Hz, 1H), 7.03 (s, 1H), 7.26 (dd, J = 8.5, 2.0 Hz, 1H), 7.43 (d, J = 2.0 Hz, 1H), 7.56 (d, J = 0.8 Hz, 1H), 7.62 (d, J = 0.8 Hz, 1H), 7.71 (t, J = 0.9 Hz, 1H), 8.17 (d, J = 8.5 Hz, 1H), 8.35 (d, J = 0.7 Hz, 1H), 8.52 (d, J = 0.9 Hz, 1H). ESI-HRMS (Method B) Found 505.1742, calculated for C$_{26}$H$_{26}$ClN$_6$O$_3$ [M + H]$^+$: 505.1749. Using 2-chloro-4-(5-methylisoxazol-4-yl)aniline (Preparation 92) and purification method F. | 0.011 |
| 24 | tert-Butyl 6-(2-chloro-4-(thiazol-5-yl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.52 (s, 9H), 3.99 (s, 3H), 6.53 (d, J = 0.9 Hz, 1H), 7.07 (s, 1H), 7.46 (dd, J = 8.6, 2.1 Hz, 1H), 7.56 (s, 1H), 7.62 (s, 1H), 7.64 (d, J = 2.1 Hz, 1H), 7.72 (t, J = 0.9 Hz, 1H), 8.03 (d, J = 0.7 Hz, 1H), 8.16 (d, J = 8.6 Hz, 1H), 8.53 (d, J = 0.9 Hz, 1H), 8.74 (d, J = 0.7 Hz, 1H). ESI-HRMS (Method B) Found 507.1350, calculated for C$_{25}$H$_{24}$ClN$_6$O$_2$S [M + H]$^+$: 507.1364. Using 2-chloro-4-(thiazol-5-yl)aniline (Preparation 93) and purification method G. | 0.009 |
| 25 | tert-Butyl 6-(2-chloro-4-(oxazol-5-yl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.53 (s, 9H), 3.99 (s, 3H), 6.54 (d, J = 0.8 Hz, 1H), 7.08 (s, 1H), 7.29 (s, 1H), 7.54 (dd, J = 8.6, 2.1 Hz, 1H), 7.57 (s, 1H), 7.62 (s, 1H), 7.72-7.74 (m, 2H), 7.91 (s, 1H), 8.19 (d, J = 8.6 Hz, 1H), 8.54 (d, J = 0.9 Hz, 1H). ESI-HRMS (Method B) Found 491.1583, calculated for C$_{25}$H$_{24}$ClN$_6$O$_3$ [M + H]$^+$: 491.1593. Using 2-chloro-4-(oxazol-5-yl)aniline (Preparation 94) and purification method H. | 0.008 |

| Example No | Name/Structure | Data | MPS1 IC$_{50}$ (uM) |
|---|---|---|---|
| 26 | tert-Butyl 6-(2-chloro-4-(1H-1,2,4-triazol-1-yl)phenylamino)-2-(1-methyl-1H-pyrazol-4-yl)-1H-pyrrolo[3,2-c]pyridine-1-carboxylate 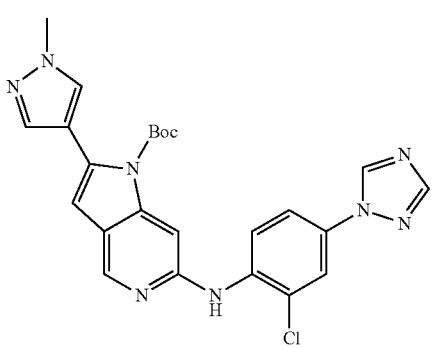 | $^1$H-NMR (500 MHz, d$_6$-DMSO): δ 1.52 (s, 9H)), 3.9 (s, 3H), 6.65 (s, 1H), 6.82 (s, 1H), 7.4 (s, 1H), 7.62 (s, 1H), 7.65 (s, 1H), 7.7 (s, 1H), 7.93 (s, 1H), 8.22 (s, 1H), 8.55 (s, 1H), 9.17 (s, 1H), 9.23 (s, 1H). Using 2-chloro-4-(1H-1,2,4-triazol-1-yl)aniline (Preparation 96) in dioxane and purification method I. | No data |
| 27 | tert-Butyl-6-(2-chloro-4-fluorophenylamino)-2-(1-methyl-1H-pyrazol-4-yl)-1H-pyrrolo[3,2-c]pyridine-1-carboxylate 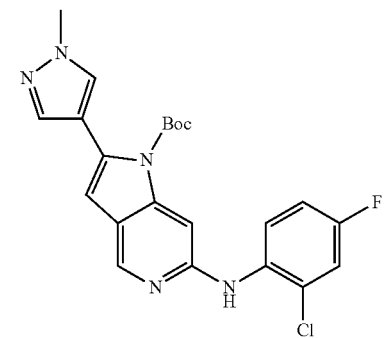 | $^1$H NMR (500 MHz, CDCl$_3$): δ 1.56 (s, 9H)), 3.96 (s, 3H), 6.49 (s, 1H), 6.71 (s, 1H), 7 (m, 1H), 7.2 (m, 1H), 7.55 (s, 1H), 7.59 (s, 1H), 7.95 (m, 1H), 8.18 (s, 1H), 8.46 (s, 1H). Using 2-chloro-4-fluoroaniline in dioxane and purification method I. | No data |
| 28 | tert-Butyl-6-(2-chloro-4-(methylsulfonyl)phenyl-amino)-2-(1-methyl-1H-pyrazol-4-yl)-1H-pyrrolo[3,2-c]pyridine-1-carboxylate 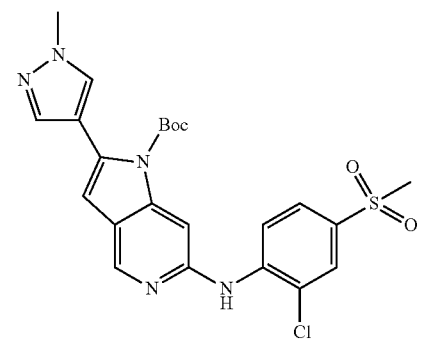 | $^1$H-NMR (500 MHz, CDCl$_3$): δ 1.57 (s, 9H)), 3.06 (s, 3H), 3.98 (s, 3H), 6.55 (s, 1H), 7.31 (s, 1H), 7.56 (s, 1H), 7.61 (s, 1H), 7.78 (m, 2H), 7.96 (s, 1H), 8.4 (d, J = 8.8, 1H), 8.57 (s, 1H). Using 2-chloro-4-(methylsulfonyl)aniline in dioxane and purification method J. | No data |

| Example No | Name/Structure | Data | MPS1 IC$_{50}$ (uM) |
|---|---|---|---|
| 29 | tert-Butyl-6-(2-chloro-4-(difluoromethoxy)phenyl-amino)-2-(1-methyl-1H-pyrazol-4-yl)-1H-pyrrolo[3,2-c]pyridine-1-carboxylate | $^1$H NMR (500 MHz, CDCl$_3$): δ 1.57 (s, 9H)), 3.98 (s, 3H), 6.3 (t, J = 80 Hz, 1H), 6.51 (s, 1H), 6.82 (s, 1H), 7.08 (m, 1H), 7.55 (s, 1H), 7.6 (d, J = 3.4 Hz, 2H), 8.03 (d, J = 9, 1H), 8.48 (s, 1H), 8.57 (s, 1H). Using 2-chloro-4-(difluoromethoxy)aniline (Preparation 97) and purification method J. | No data |
| 30 | tert-Butyl-6-(2-methoxy-4-(methylcarbamoyl)phenyl-amino)-2-(1-methyl-1H-pyrazol-4-yl)-1H-pyrrolo[3,2-c]pyridine-1-carboxylate | $^1$H NMR (500 MHz, CDCl$_3$): δ 1.51 (s, 9H), 3.02 (d, J = 4.8 Hz, 3H), 3.96 (s, 3H), 4.02 (s, 3H), 6.2 (s, br, 1H), 6.49 (s, 1H), 7.27 (m, 2H), 7.47 (s, 1H), 7.53 (s, 1H), 7.59 (s, 1H), 7.7 (s, 1H), 8.14 (d, J = 8.4 Hz, 1H), 8.49 (s, 1H). Using 4-amino-3-methoxy-N-methylbenzamide (Preparation 63) and purification method K. | No data |
| 31 | tert-Butyl-6-(2-chloro-4-(methylcarbamoyl)phenyl-amino)-2-(1-methyl-1H-pyrazol-4-yl)-1H-pyrrolo[3,2-c]pyridine-1-carboxylate | $^1$H-NMR (500 MHz, CDCl$_3$): δ 1.48 (s, 9H), 2.97 (d, J = 4.8 Hz, 3H), 3.94 (s, 3H), 6.2 (s, br, 1H), 6.5 (s, 1H), 6.65 (q, J = 4.6 Hz, 1H), 7.13 (s, 1H), 7.53 (s, 1H), 7.57 (s, 1H), 7.64 (dd, J = 2 Hz, 8.7 Hz, 1H), 7.72 (s, 1H), 7.88 (d, J = 2.1 Hz, 1H), 8.1 (d, J = 8.7 Hz, 1H), 8.49 (s, 1H). Using 4-amino-3-chloro-N-methylbenzamide (Preparation 64) and purification method K. | No data |

| Example No | Name/Structure | Data | MPS1 IC$_{50}$ (uM) |
|---|---|---|---|
| 32 | tert-Butyl-6-(2-chloro-4-(2-oxopyrrolidin-1-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.5 (s, 9H), 2.17 (m, 2H), 2.62 (t, J = 8.3 Hz, 2H), 3.85 (t, J = 7.1 Hz, 2H), 3.96 (s, 3H), 6.5 (s, 1H), 6.85 (s, 1H), 7.54 (s, 1H), 7.6 (s, 1H), 7.62 (d, J = 6 Hz, 2H), 7.76 (s, 1H), 7.97 (s, 1H), 8.47 (s, 1H). Using 1-(4-amino-3-chlorophenyl)pyrrolidin-2-one (Preparation 103) and purification method K. | No data. |
| 33 | tert-Butyl 6-(2-methoxy-4-(pyrrolidin-1-ylmethyl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.51 (s, 9H), 1.8 (t, J = 6.6 Hz, 4H), 2.52 (t, J = 6.6 Hz, 4H), 3.59 (s, 2H), 3.91 (s, 3H), 3.95 (s, 3H), 6.47 (s, 1H), 6.9 (d, J = 8 Hz, 1H), 6.94 (s, 1H), 6.98 (s, 1H), 7.53 (s, 1H), 7.59 (s, 1H), 7.63 (s, 1H), 7.81 (d, J = 8 Hz, 1H), 8.4 (s, 1H). ESI-HRMS Found 503.277 calculated for C$_{28}$H$_{34}$N$_6$O$_3$ [M + H]$^+$: 503.2765 Using 1-(4-amino-3-chlorophenyl)pyrrolidin-2-one (Preparation 106) and purification method L. | 0.016 |
| 34 | tert-Butyl 6-(4-((tert-butoxycarbonyl(methyl)amino)methyl)-2-methoxyphenylamino)-2-(1-methyl-1H-pyrazol-4-yl)-1H-pyrrolo[3,2-c]pyridine-1-carboxylate | $^1$H-NMR (500 MHz, CDCl$_3$): δ 1.5 (s, 9H), 1.51 (s, 9H), 2.94 (s, br, 3H), 3.89 (s, 3H), 3.95 (s, 3H), 4.38 (s, 2H), 6.47 (s, 1H), 6.85 (s, br, , 2H), 7 (s, 1H), 7.53 (s, 1H), 7.59 (s, 1H), 7.62 (s, 1H), 7.92 (s, br, 1H), 8.44 (s, 1H). ESI-HRMS Found 563.298, calculated for C$_{30}$H$_{38}$N$_6$O$_5$[M + H]$^+$: 563.2976 Using tert-butyl-4-amino-3-methoxybenzyl(methyl) carbamate (Preparation 108) and purification method M. | 0.111 |

-continued

| Example No | Name/Structure | Data | MPS1 IC$_{50}$ (uM) |
|---|---|---|---|
| 35 | tert-butyl 6-(4-((dimethylamino)methyl)-2-methoxyphenylamino)-2-(1-methyl-1H-pyrazol-4-yl)-1H-pyrrolo[3,2-c]pyridine-1-carboxylate 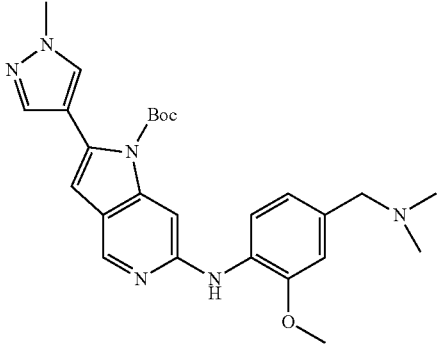 | $^1$H-NMR (500 MHz, CDCl$_3$): δ 1.5 (s, 9H), 2.26 (s, 6H), 3.4 (s, 2H), 3.92 (s, 3H), 3.95 (s, 3H), 6.47 (s, 1H), 6.85 (d, J = 8 Hz, 1H), 6.92 (s, 1H), 7 (s, 1H), 7.53 (s, 1H), 7.59 (s, 1H), 7.64 (s, 1H), 7.84 (d, J = 8 Hz, 1H), 8.44 (s, 1H). ESI-HRMS Found 477.2617, calculated for C$_{26}$H$_{32}$N$_6$O$_3$ [M + H]$^+$: 477.2609 Using 4-((dimethylamino)methyl)-2-methoxyaniline (Preparation 110) and purification method L. | 0.008 |
| 36 | tert-Butyl 6-(3-(cyanomethoxy)phenyl-amino)-2-(1-methyl-1H-pyrazol-4-yl)-1H-pyrrolo[3,2-c]pyridine-1-carboxylate 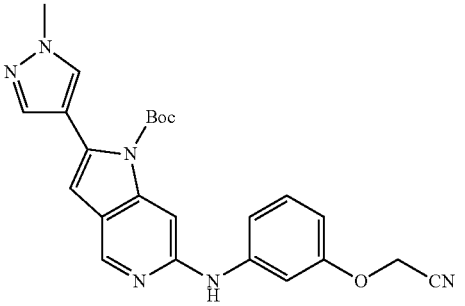 | $^1$H-NMR (500 MHz, CDCl$_3$): δ 1.49 (s, 9H), 3.95 (s, 3H), 4.77 (s, 2H), 6.48 (s, 1H), 6.62 (d, J = 8.1 Hz, 1H), 7.05 (d, J = 8.1 Hz, 1H), 7.12 (s, 1H), 7.25 (s, 1H), 7.55 (s, br 2H), 7.6 (s, 1H), 7.67 (s, 1H), 8.4 (s, 1H). ESI-HRMS Found 445.2132, calculated for C$_{24}$H$_{24}$N$_6$O$_3$ [M + H]$^+$: 445.2103 Using 2-(3-aminophenoxy)acetonitrile (Preparation 113) and purification method H. | 0.156 |
| 37 | tert-Butyl 6-(2-chloro-4-(3-methoxyazetidine-1-carbonyl)phenylamino)-2-(1-methyl-1H-pyrazol-4-yl)-1H-pyrrolo[3,2-c]pyridine-1-carboxylate 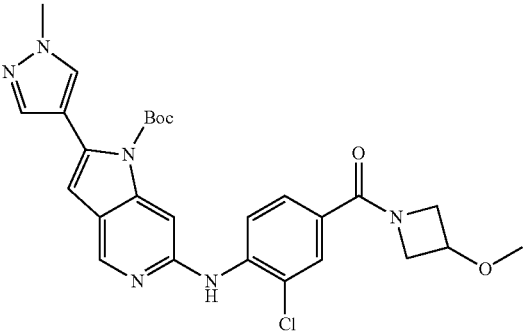 | $^1$H NMR (500 MHz, CDCl$_3$): δ 1.51 (s, 9H), 3.32 (s, 3H), 3.96 (s, 3H), 4.05 (m, 1H), 4.25 (m, 1H), 4.36 (m, 2H), 6.52 (s, 1H), 7.17 (s, 1H), 7.52 (d, J = 8.6 Hz, 1H), 7.55 (s, 1H), 7.60 (s, 1H), 7.74 (m, 2H), 8.15 (d, J = 8.6 Hz, 1H), 8.52 (s, 1H). ESI-HRMS Found 537.4879, calculated for C$_{27}$H$_{29}$ClN$_6$O$_4$ [M + H]$^+$: 537.4872 Using (4-amino-3-chlorophenyl)(3-methoxyazetidin-1-yl)methanone (Preparation 65) and purification method K. | 0.008 |

-continued

| Example No | Name/Structure | Data | MPS1 IC$_{50}$ (uM) |
|---|---|---|---|
| 38 | tert-Butyl 6-(2-chloro-4-(S,S-dioxo-thiomorpholine-4-carbonyl)phenylamino)-2-(1-methyl-1H-pyrazol-4-yl)-1H-pyrrolo[3,2-c]pyridine-1-carboxylate 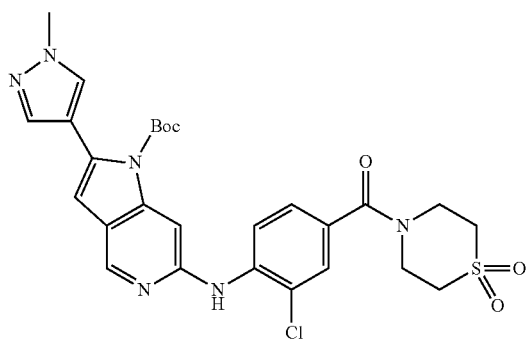 | $^1$H-NMR (500 MHz, CDCl$_3$): δ 1.50 (s, 9H), 3.09 (s, br, 4H), 3.97 (s, 3H), 4.14 (s, br, 4H), 6.53 (s, 1H), 7.17 (s, 1H), 7.32 (d, J = 8.6 Hz, 1H), 7.55 (m, 2H), 7.6 (s, 1H), 7.74 (s, 1H), 8.27 (d, J = 8.6 Hz, 1H), 8.53 (s, 1H). ESI-HRMS Found 585.2117, calculated for C$_{27}$H$_{29}$ClN$_6$O$_5$S [M + H]$^+$: 585.2112 Using (4-amino-3-chlorophenyl)(S,S-dioxo-thiomorpholino)methanone (Preparation 66) and purification method K. | 0.006 |
| 39 | tert-Butyl 6-(2-chloro-4-(ethyl(methyl)carbamoyl)phenylamino)-2-(1-methyl-1H-pyrazol-4-yl)-1H-pyrrolo[3,2-c]pyridine-1-carboxylate 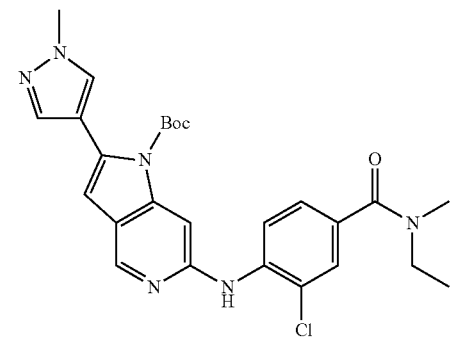 | $^1$H-NMR (500 MHz, CDCl$_3$): δ 1.25 (s, br, 3H), 1.51 (s, 9H), 3.04 (s, 3H), 3.45 (s, br, 2H), 3.96 (s, 3H), 6.51 (s, 1H), 7.07 (s, 1H), 7.51 (d, J = 1.7 Hz, 1H), 7.55 (s, 1H), 7.6 (s, 1H), 7.7 (s, 1H), 8.12 (d, J = 8.5 Hz, 1H), 8.51 (s, 1H). ESI-HRMS Found 509.2298 calculated for C$_{26}$H$_{29}$ClN$_6$O$_3$ [M + H]$^+$: 509.2291 Using 4-amino-3-chloro-N-ethyl-N-methylbenzamide (Preparation 67) and purification method K. | 0.004 |
| 40 | tert-Butyl 6-(2-chloro-4-(pyrrolidine-1-carbonyl)phenylamino)-2-(1-methyl-1H-pyrazol-4-yl)-1H-pyrrolo[3,2-c]pyridine-1-carboxylate 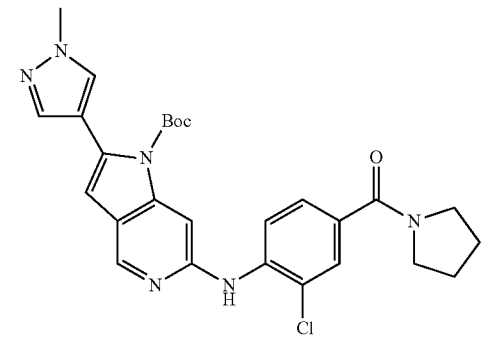 | $^1$H-NMR (500 MHz, CDCl$_3$): δ 1.5 (s, 9H), 1.95 (m, 4H), 3.6 (m, 4H), 3.96 (s, 3H), 6.51 (s, 1H), 7.11 (s, 1H), 7.45 (d, J = 8.6 Hz, 1H), 7.54 (s, 1H), 7.59 (s, 1H), 7.64 (s, 1H), 7.71 (s, 1H), 8.11 (d, J = 8.6 Hz, 1H), 8.5 (s, 1H). ESI-HRMS Found 521.4943 calculated for C$_{27}$H$_{29}$ClN$_6$O$_3$ [M + H]$^+$: 521.4939 Using (4-amino-3-chlorophenyl)(pyrrolidin-1-yl)methanone (Preparation 68) and purification method K. | 0.004 |

| Example No | Name/Structure | Data | MPS1 IC$_{50}$ (uM) |
|---|---|---|---|
| 41 | tert-Butyl 6-(2-chloro-4-(4-methylpiperazine-1-carbonyl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.5 (s, 9H), 2.31 (s, 3H), 2.42 (s, br, 4H), 3.65 (s, br, , 4H), 3.96 (s, 3H), 6.51 (s, 1H), 7.29 (m, 2H), 7.51 (s, 1H), 7.54 (s, 1H), 7.59 (s, 1H), 7.7 (s, 1H), 8.14 (d, J = 8.5 Hz, 1H), 8.5 (s, 1H). ESI-HRMS (Method D) Found 550.2416 calculated for C$_{28}$H$_{32}$ClN$_7$O$_3$ [M + H]$^+$: 550.2414 Using (4-amino-3-chlorophenyl)(4-methylpiperazin-1-yl)methanone (Preparation 69) and purification method J. | 0.008 |
| 42 | tert-Butyl 6-(2-chloro-4-(4-methoxypiperidine-1-carbonyl)phenylamino)-2-(1-methyl-1H-pyrazol-4-yl)-1H-pyrrolo[3,2-c]pyridine-1-carboxylate | $^1$H-NMR (500 MHz, CDCl$_3$) 1.29 (s, br, 2H), 1.39 (s, 9H), 1.7 (m, 2H), 1.95 (m, 2H), 3.3 (s, br, 1H), 3.39 (s, 3H), 3.5 (m, 1H), 3.6 (s, br, 1H), 3.96 (s, 3H), 6.55 (s, 1H), 7.3 (s, 1H), 7.3 (s, 1H), 7.35 (dd, J = 1.9 Hz, 8.2 Hz, 1H), 7.56 (m, 4H), 8.18 (s, 1H). ESI-HRMS Found 565.2233 calculated for C$_{29}$H$_{33}$ClN$_6$O$_4$ [M + H]$^+$: 565.2235 Using), (4-amino-3-chlorophenyl)(4-methoxypiperidin-1-yl)methanone (Preparation 70) and purification method K. | 0.008 |
| 43 | tert-Butyl-6-(2-chloro-4-(4-(dimethylamino)piperidine-1-carbonyl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.42 (s, br, 2H), 1.5 (s, 9H), 1.9 (s, br, 2H), 2.29 (s, 6H), 2.4 (m, 1H), 2.9 (s, br, 2H), 3.96 (s, 3H), 4.3 (s, br, 2H), 6.51 (s, 1H), 7.08 (s, 1H), 7.29 (d, J = 8.5 Hz, 1H), 7.5 (d, J = 1.9 Hz, 1H), 7.54 (s, 1H), 7.59 (s, 1H), 7.7 (s, 1H), 8.13 (d, J = 8.5 Hz, 1H), 8.51 (s, 1H). ESI-HRMS Found 578.2623, calculated for C$_{30}$H$_{36}$ClN$_7$O$_3$ [M + H]$^+$: 578.2641 Using (4-amino-3-chlorophenyl)(4-(dimethylamino)piperidin-1-yl)methanone (Preparation 71) and purification method N. | 0.005 |

-continued

| Example No | Name/Structure | Data | MPS1 IC$_{50}$ (uM) |
|---|---|---|---|
| 44 | tert-Butyl 6-(2-chloro-4-(1-methyl-1H-pyrazol-5-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.5 (s, 9H), 3.91 (s, 3H), 3.96 (s, 3H), 6.28 (d, J = 1.9 Hz, 1H), 6.51 (s, 1H), 7.06 (s, 1H), 7.3 (d, J = 8.5 Hz, 1H), 7.45 (d, J = 2 Hz, 1H), 7.5 (s, 1H), 7.54 (s, 1H), 7.6 (s, 1H), 7.72 (s, 1H), 8.19 (d, J = 8.5 Hz, 1H), 8.51 (s, 1H). ESI-HRMS Found 504.2129 calculated for C$_{26}$H$_{26}$ClN$_7$O$_2$ [M + H]$^+$: 504.2122 Using 2-chloro-4-(1-methyl-1H-pyrazol-5-yl)aniline (Preparation 121) and purification method K. | 0.019 |
| 45 | tert-Butyl 6-(2-chloro-4-(2,4-dimethylthiazol-5-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.51 (s, 9H), 2.46 (s, 3H), 2.68 (s, 3H), 3.96 (s, 3H), 6.5 (s, 1H), 7.02 (s, 1H), 7.26 (d, J = 6.4 Hz, 1H), 7.44 (s, 1H), 7.54 (s, 1H), 7.6 (s, 1H), 7.68 (s, 1H), 8.08 (d, J = 8.6 Hz, 1H), 8.49 (s, 1H). ESI-HRMS Found 535.1668 calculated for C$_{27}$H$_{27}$ClN$_6$O$_2$S [M + H]$^+$: 535.1677. Using 2-Chloro-4-(2,4-dimethylthiazol-5-yl)aniline (Preparation 122) and purification method K. | 0.052 |
| 46 | tert-Butyl 6-(2-chloro-4-(2-methoxypyridin-4-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.52 (s, 9H), 3.96 (s, 3H), 3.97 (s, 3H) 6.52 (s, 1H), 6.92 (s, 1H), 7.08 (m, 2H), 7.55 (s, 1H), 7.61 (s, 1H), 7.69 (s, 1H), 7.72 (s, 1H), 8.2 (m, 2H), 8.52 (s, 1H). ESI-HRMS Found 531.171 calculated for C$_{28}$H$_{27}$ClN$_6$O$_3$ [M + H]$^+$: 531.1725 Using 2-Chloro-4-(2-methoxypyridin-4-yl)aniline (Preparation 123) and purification method K. | 0.075 |

-continued

| Example No | Name/Structure | Data | MPS1 IC$_{50}$ (uM) |
|---|---|---|---|
| 47 | tert-Butyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.5 (s, 9H), 2.44 (s, 3H), 3.52 (s, 3H), 3.96 (s, 3H), 6.5 (s, 1H), 6.92 (s, 1H), 7.05 (s, br, 1H), 7.2 (d, J = 8.5 Hz, 1H), 7.38 (d, J = 2.1 Hz, 1H), 7.54 (s, 1H), 7.59 (s, 1H), 7.68 (s, 1H), 8.1 (d, J = 8.5 Hz, 1H), 8.49 (s, 1H). ESI-HRMS Found 518.2072 calculated for C$_{27}$H$_{28}$ClN$_7$O$_2$ [M + H]$^+$: 518.2066 Using 2-chloro-4-(1,2-dimethyl-1H-imidazol-5-yl)aniline (Preparation 124) and purification method E. | 0.005 |
| 48 | tert-Butyl-6-(2-chloro-4-(6-methoxypyridin-3-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.51 (s, 9H), 3.96 (s, 3H), 3.98 (s, 3H), 6.51 (s, 1H), 6.8 (d, J = 8.6 Hz, 1H), 6.98 (s, 1H), 7.41 (s, 1H), 7.55 (s, 1H), 7.57 (d, J = 2.2 Hz, 1H), 7.6 (s, 1H), 7.68 (s, 1H), 7.74 (dd, J = 2.5 Hz, 8.5 Hz, 1H), 8.09 (d, J = 8.5 Hz, 1H), 8.35 (d, J = 2.5 Hz, 1H), 8.5 (s, 1H). ESI-HRMS Found 531.1892 calculated for C$_{28}$H$_{27}$ClN$_6$O$_3$ [M + H]$^+$: 531.1906 Using 2-chloro-4-(6-methoxypyridin-3-yl)aniline (Preparation 126) and the chromatography purification method I. | 0.016 |
| 49 | tert-Butyl 6-(2-chloro-4-(6-methylpyridin-3-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.51 (s, 9H), 2.61 (s, 3H), 3.97 (s, 3H), 6.51 (s, 1H), 7.02 (s, 1H), 7.21 (d, J = 8.1 Hz, 1H), 7.46 (s, 1H), 7.55 (s, 1H), 7.61 (s, 1H), 7.62 (d, J = 2.2 Hz, 1H), 7.7 (s, 1H), 7.73 (d, J = 8.6 Hz, 1H), 8.14 (d, J = 8.6 Hz, 1H), 8.51 (s, 1H), 8.7 (d, J = 2.1 Hz, 1H). ESI-HRMS Found 515.1983 calculated for C$_{28}$H$_{27}$ClN$_6$O$_2$ [M + H]$^+$: 515.1978 Using 2-chloro-4-(6-methylpyridin-3-yl)aniline (Preparation 127) and purification method K. | 0.009 |

| Example No | Name/Structure | Data | MPS1 IC$_{50}$ (uM) |
|---|---|---|---|
| 50 | tert-Butyl 6-((2-chloro-4-(3,3-difluoroazetidine-1-carbonyl)phenyl)amino)-2-(1-methyl-1H-pyrazol-4-yl)-1H-pyrrolo[3,2-c]pyridine-1-carboxylate 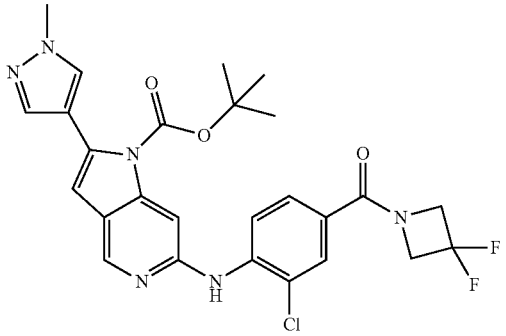 | $^1$H-NMR (500 MHz, DMSO-d$_6$): δ 1.45 (s, 9H), 3.88 (s, 3H), 4.60 (br s, 4H), 6.66 (s, 1H), 7.57 (dd, J = 2.1, 8.6 Hz, 1H), 7.62 (s, 1H), 7.74 (d, J = 2.0 Hz, 1H), 7.82 (s, 1H), 7.94 (s, 1H), 8.17 (d, J = 8.5 Hz, 1H), 8.49 (s, 1H), 8.70 (s, 1H). ESI-HRMS: Found 543.1711; calculated for C$_{26}$H$_{26}$ClF$_2$N$_6$O$_3$ [M + H]$^+$: 543.1717. Using (4-amino-3-chlorophenyl)(3,3-difluoroazetidin-1-yl)methanone (Preparation 72), work up method I followed by purification method F. | 0.006 |
| 51 | tert-Butyl 6-((2-chloro-4-(pyrazin-2-yl)phenyl)amino)-2-(1-methyl-1H-pyrazol-4-yl)-1H-pyrrolo[3,2-c]pyridine-1-carboxylate 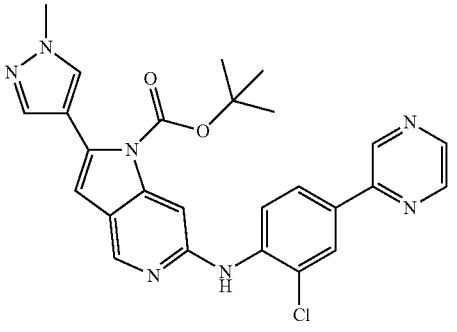 | $^1$H-NMR (500 MHz, DMSO-d$_6$): δ 1.45 (s, 9H), 3.88 (s, 3H), 6.65 (s, 1H), 7.62 (s, 1H), 7.75 (s, 1 H), 7.94 (s, 1H), 8.07 (dd, J = 2.1, 8.8 Hz, 1H), 8.19 (d, J = 8.8 Hz, 1H), 8.24 (d, J = 2.1 Hz, 1H), 8.49 (s, 1H), 8.56 (d, J = 2.4 Hz, 1H), 8.64 (s, 1H), 8.68 (dd, J = 1.6, 2.5 Hz, 1H), 9.27 (d, J = 1.3 Hz, 1H). ESI-HRMS: Found 502.1766; calculated for C$_{26}$H$_{25}$ClN$_7$O$_2$ [M + H]$^+$: 502.1753. Using 2-chloro-4-(pyrazin-2-yl)aniline (Preparation 133), work up method I followed by purification method F and semipreparative HPLC. | 0.028 |
| 52 | tert-Butyl 6-((2-chloro-4-(pyrimidin-5-yl)phenyl)amino)-2-(1-methyl-1H-pyrazol-4-yl)-1H-pyrrolo[3,2-c]pyridine-1-carboxylate 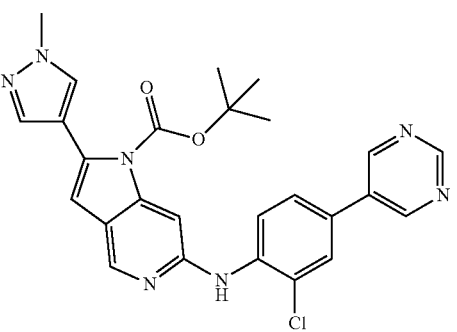 | $^1$H-NMR (500 MHz, DMSO-d$_6$): δ 1.45 (s, 9H), 3.88 (s, 3H), 6.64 (s, 1H), 7.61 (d, J = 0.6 Hz, 1H), 7.70 (s, 1H), 7.75 (dd, J = 2.2, 8.6 Hz, 1H), 7.93 (s, 1H), 7.98 (d, J = 2.3 Hz, 1H), 8.16 (d, J = 8.8 Hz, 1H), 8.46 (d, J = 0.6 Hz, 1H), 8.61 (s, 1H), 9.15 and 9.17 (2 × s, 3H). ESI-HRMS: Found 502.1768; calculated for C$_{26}$H$_{25}$ClN$_7$O$_2$ [M + H]$^+$: 502.1753. Using 2-chloro-4-(pyrimidin-5-yl)aniline (Preparation 134), work up method I followed by purification method F. | 0.004 |

| Example No | Name/Structure | Data | MPS1 IC$_{50}$ (uM) |
|---|---|---|---|
| 53 | tert-Butyl 6-((4-(azetidine-1-carbonyl)-2-chlorophenyl)amino)-2-(1-methyl-1H-pyrazol-4-yl)-1H-pyrrolo[3,2-c]pyridine-1-carboxylate | $^1$H-NMR (500 MHz, DMSO-d$_6$): δ 1.45 (s, 9H), 2.26 (m, 2H), 3.88 (s, 3H), 4.04 (br s, 2H), 4.38 (br s, 2H), 6.66 (s, 1H), 7.52 (dd, J = 2.0, 8.6 Hz, 1H), 7.61 (d, J = 0.9 Hz, 1H), 7.66 (d, J = 2.0 Hz, 1H), 7.76 (s, 1H), 7.94 (s, 1H), 8.12 (d, J = 8.6 Hz, 1H), 8.48 (d, J = 0.9 Hz, 1H), 8.63 (s, 1H). ESI-HRMS: Found 507.1911; calculated for C$_{26}$H$_{28}$ClN$_6$O$_3$ [M + H]$^+$: 507.1906. Using (4-amino-3-chlorophenyl)(azetidin-1-yl)methanone (Preparation 73), work up method I followed by purification method O. | 0.007 |
| 54 | tert-Butyl 6-((2-cyanophenyl)amino)-2-(1-methyl-1H-pyrazol-4-yl)-1H-pyrrolo[3,2-c]pyridine-1-carboxylate | $^1$H-NMR (500 MHz, DMSO-d$_6$): δ 1.45 (s, 9H), 3.88 (s, 3H), 6.63 (d, J = 0.5 Hz, 1H), 7.10 (td, J = 1.0, 7.6 Hz, 1H), 7.58 (s, 1H), 7.59 (td obscured, 1H), 7.60 (d, J = 0.5 Hz, 1H), 7.70 (dd, J = 1.4, 7.9 Hz, 1H), 7.72 (d, J = 8.4 Hz, 1H), 7.93 (s, 1H), 8.41 (d, J = 0.8 Hz, 1H), 9.12 (s, 1H). ESI-HRMS: Found 415.1872; calculated for C$_{23}$H$_{23}$N$_6$O$_2$ [M + H]$^+$: 415.1877. Using 2-cyanoaniline, work up method I followed by purification method F. | 0.032 |
| 55 | tert-Butyl 6-((2-chloro-4-(methylsulfonyl)phenyl)amino)-2-(1-methyl-1H-pyrazol-4-yl)-1H-pyrrolo[3,2-c]pyridine-1-carboxylate | $^1$H-NMR (500 MHz, DMSO-d$_6$): δ 1.45 (s, 9H), 3.21 (s, 3H), 3.88 (s, 3H), 6.68 (s, 1H), 7.62 (s, 1H), 7.73 (dd, J = 2.2, 8.9 Hz, 1H), 7.88 (s, 1H), 7.90 (d, J = 2.3 Hz, 1H), 7.95 (s, 1H), 8.28 (d, J = 8.6 Hz, 1H), 8.52 (s, 1H), 8.90 (s, 1H). ESI-HRMS: Found 502.1305; calculated for C$_{23}$H$_{25}$ClN$_5$O$_4$S (M + H)$^+$: 502.1310. Using 2-chloro-4-(methylsulfonyl)aniline, work up method I followed by purification method F. | 0.024 |

| Example No | Name/Structure | Data | MPS1 IC$_{50}$ (uM) |
|---|---|---|---|
| 56 | tert-Butyl 6-((2-fluoro-4-methoxyphenyl)amino)-2-(1-methyl-1H-pyrazol-4-yl)-1H-pyrrolo[3,2-c]pyridine-1-carboxylate | $^1$H-NMR (500 MHz, DMSO-d$_6$): δ 1.41 (s, 9H), 3.76 (s, 3H), 3.86 (s, 3H), 6.56 (s, 1H), 6.75 (dd, J = 2.2, 8.6 Hz, 1H), 6.90 (dd, J = 2.7, 12.6 Hz, 1H), 7.20 (s, 1H), 7.57 (s, 1H), 7.59 (t obscured, J = 9.0 Hz, 1H), 7.88 (s, 1H), 8.31 (s, 2H). Using 2-fluoro-4-methoxyaniline, work up method I followed by purification method F. | No data |
| 57 | tert-Butyl 6-((2-methoxy-4-(trifluoromethyl)phenyl)amino)-2-(1-methyl-1H-pyrazol-4-yl)-1H-pyrrolo[3,2-c]pyridine-1-carboxylate | $^1$H-NMR (500 MHz, DMSO-d$_6$): δ 1.45 (s, 9H), 3.87 (s, 3H), 3.94 (s, 3H), 6.63 (s, 1H), 7.22 (s, 1H), 7.24 (d, J = 9.0 Hz, 1H), 7.60 (s, 1H), 7.76 (s, 1H), 7.92 (s, 1H), 8.45 (d, J = 8.7 Hz, 1H), 8.48 (s, 1H), 8.54 (s, 1H). Using 2-methoxy-4-trifluoromethylaniline, work up method I followed by method P. | No data |
| 58 | tert-Butyl 6-((4-fluoro-2-methoxyphenyl)amino)-2-(1-methyl-1H-pyrazol-4-yl)-1H-pyrrolo[3,2-c]pyridine-1-carboxylate | $^1$H-NMR (500 MHz, DMSO-d$_6$): δ 1.42 (s, 9H), 3.82 (s, 3H), 3.86 (s, 3H), 6.57 (s, 1H), 6.74 (td, J = 2.9, 8.7 Hz, 1H), 6.96 (dd, J = 2.8, 10.8 Hz, 1H), 7.35 (s, 1H), 7.57 (s, 1H), 7.86 (dd, J = 6.7, 8.9 Hz, 1H), 7.89 (s, 1H), 7.99 (s, 1H), 8.34 (s, 1H). Using 4-fluoro-2-methoxyaniline, work up method I followed by purification method F. | No data |

| Example No | Name/Structure | Data | MPS1 IC$_{50}$ (uM) |
|---|---|---|---|
| 59 | tert-Butyl 6-(2-methoxyphenylamino)-2-(1-methyl-1H-pyrazol-4-yl)-1H-pyrrolo[3,2-c]pyridine-1-carboxylate | $^1$H-NMR (CDCl$_3$, 500 MHz): δ 1.52 (s, 9H), 3.92 (s, 3H), 3.96 (s, 3H), 6.49 (d, J = 0.63 Hz, 1H), 6.91-6.99 (m, 3H), 7.04 (br s, 1H), 7.54 (s, 1H), 7.60 (s, 1H), 7.66 (s, 1H), 7.93 (m, 1H), 8.46 (d, J = 0.95 Hz, 1H). Using 2-methoxyaniline and purification method Q. | No data |
| 60 | tert-Butyl 6-(2-chloro-4-(dimethylcarbamoyl)phenyl-amino)-2-(1-methyl-1H-pyrazol-4-yl)-1H-pyrrolo[3,2-c]pyridine-1-carboxylate | $^1$H NMR (500 MHz, CDCl$_3$): δ 1.52 (s, 9H), 3.10 (s, 6H), 3.98 (s, 3H), 6.53 (s, 1H), 7.08 (s, 1H), 7.34 (dd, J = 8.5, 1.9 Hz, 1H), 7.54-7.56 (m, 2H), 7.61 (s, 1H), 7.72 (s, 1H), 8.15 (d, J = 8.5 Hz, 1H), 8.53 (s, 1H). Using 4-amino-3-chloro-N,N-dimethylbenzamide and purification method B. | No data |
| 61 | tert-Butyl 6-(4-(dimethylcarbamoyl)-2-methoxyphenylamino)-2-(1-methyl-1H-pyrazol-4-yl)-1H-pyrrolo[3,2-c]pyridine-1-carboxylate | $^1$H NMR (500 MHz, CDCl$_3$): δ 1.52 (s, 9H), 3.11 (s, 6H), 3.95 (s, 3H), 3.97 (s, 3H), 6.50 (s, 1H), 7.05 (dd, J = 8.2, 1.7 Hz, 1H), 7.08 (d, J = 1.7 Hz, 1H), 7.22 (s, 1H), 7.54 (s, 1H), 7.60 (s, 1H), 7.69 (s, 1H), 8.10 (d, J = 8.2 Hz, 1H), 8.49 (s, 1H). Using 4-amino-3-methoxy-N,N-dimethylbenzamide and purification method B. | No data |

| Example No | Name/Structure | Data | MPS1 IC$_{50}$ (uM) |
|---|---|---|---|
| 62 | tert-Butyl 6-((2-chloro-5-(1-methyl-1H-pyrazol-4-yl)phenyl)amino)-2-(1-methyl-1H-pyrazol-4-yl)-1H-pyrrolo[3,2-c]pyridine-1-carboxylate | $^1$H-NMR (500 MHz, DMSO-d$_6$): δ 1.40 (s, 9H), 3.84 (s, 3H), 3.87 (s, 3H), 6.62 (d, J = 0.6 Hz, 1H), 7.23 (dd, J = 2.2, 8.4 Hz, 1H), 7.43 (d, J = 8.3 Hz, 1H), 7.48 (s, 1H), 7.59 (d, J = 0.7 Hz, 1H), 7.81 (d, J = 0.8 Hz, 1H), 7.91 (s, 1H), 7.96 (d, J = 2.3 Hz, 1H), 8.11 (s, 1H), 8.33 (s, 1H), 8.42 (d, J = 0.8 Hz, 1H). ESI-HRMS: Found 504.1899; calculated for C$_{26}$H$_{27}$ClN$_7$O$_2$ (M + H)$^+$: 504.1909. Using 2-chloro-5-(1-methyl-1H-pyrazol-4-yl)aniline (Preparation 132) and purification method Q. | 0.537 |
| 63 | tert-Butyl 6-(2-chloro-4-(1,4-dimethyl-1H-imidazol-5-yl)phenylamino)-2-(1-methyl-1H-pyrazol-4-yl)-1H-pyrrolo[3,2-c]pyridine-1-carboxylate | $^1$H-NMR (CDCl$_3$, 500 MHz): δ 1.52 (s, 9H), 2.23 (s, 3H), 3.55 (s, 3H), 3.97 (s, 3H), 6.53 (d, J = 0.63 Hz, 1H), 7.04 (s, 1H), 7.17 (dd, J = 1.89, 8.51 Hz, 1H), 7.34 (d, J = 1.89 Hz, 1H), 7.43 (s, 1H), 7.56 (s, 1H), 7.61 (s, 1H), 7.72 (s, 1H), 8.17 (d, J = 8.51 Hz, 1H), 8.52 (d, J = 0.95 Hz, 1H). HRMS calcd for C$_{27}$H$_{27}$$^{35}$ClN$_7$O$_2$ (M + H)$^+$ 518.2069, found 518.2053 Using 2-Chloro-4-(1,4-dimethyl-1H-imidazol-5-yl)aniline (Preparation 161) and purification method R. | 0.005 |

Example 64

3-Chloro-4-(1-(cyclopentylmethyl)-2-(1-methyl-1H-pyrazol-4-yl)-1H-pyrrolo[3,2-c]pyridin-6-ylamino)-N,N-dimethylbenzamide

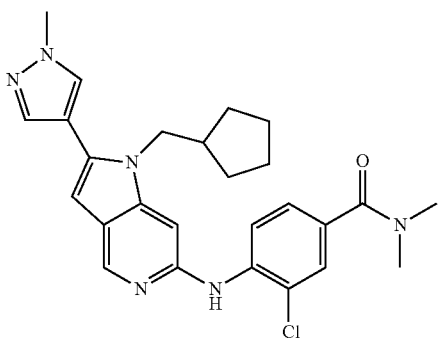 [SMILES: CN(C)C(=O)c1ccc(Nc2cc3c(cn2)cc(-c2cnn(C)c2)n3CC2CCCC2)c(Cl)c1]

Method W

Tris(dibenzylideneacetone)dipalladium(0) (5.5 mg, 5.98 mmol) was added to a mixture of 6-bromo-1-(cyclopentylmethyl)-2-(1-methyl-1H-pyrazol-4-yl)-1H-pyrrolo[3,2-c]pyridine (Preparation 78, 43 mg, 0.120 mmol), cesium carbonate (78 mg, 0.239 mmol), 4-amino-3-chloro-N,N-dimethylbenzamide (32 mg, 0.144 mmol) and Xantphos (6.9 mg, 0.012 mmol) in DMA (1.3 mL). The reaction mixture was heated at 80 to 90° C. for 5 hours. The reaction was filtered on SCX-2 column and concentrated under vacuum. The residue was purified using Biotage silica gel column chromatography eluting with DCM/EtOH 99/1 to 97/3 to afford the title product as a white solid (39 mg, 68%). $^1$H NMR (500 MHz, CDCl$_3$): δ 1.12-1.21 (m, 2H), 1.46-1.54 (m, 2H), 1.54-1.64 (m, 4H), 2.23-2.33 (m, 1H), 3.09 (s, 6H), 4.01 (s, 3H), 4.05 (d, J=7.5 Hz, 2H), 6.49 (d, J=0.8 Hz, 1H), 6.92-6.97 (m, 2H), 7.31 (dd, J=8.5, 2.0 Hz, 1H), 7.52 (d, J=2.0 Hz, 1H), 7.56 (s, 1H), 7.67 (s, 1H), 7.90 (d, J=8.5 Hz, 1H), 8.59 (s, 1H).

ESI-HRMS (Method B) Found 477.2157, calculated for C$_{26}$H$_{30}$ClN$_6$O (M+H$^+$): 477.2164. MPS1 IC$_{50}$ (uM): 0.047

The following examples were prepared according to Method W (Example 64) above using the appropriate 6-bromo-1H-pyrrolo[3,2-c]pyridine and the appropriate aniline at a temperature from 80-90° C. for between 1.5-3 hours. The crude reaction products were purified as above or according to one of the following methods:

Method A: Preparative TLC eluting with (DCM/EtOH 97/3).

Method B: Biotage KP-NH column eluting with (DCM/EtOAc 99/1 to 90/10).

Method C: Silica gel column chromatography eluting from 0-5-10% methanol in ethyl acetate.

Method D: Silica gel column chromatography eluting with hexane:dichloromethane:7M $NH_3$ in MeOH (5:15:1).

Method E: Silica gel column chromatography eluting with ethyl acetate:hexane:7M $NH_3$ in methanol (25:5:0.5).

Method F: Biotage silica gel column chromatography eluting with 1 to 5% [MeOH/aq. $NH_3$ (10:1)] in ethyl acetate.

Method G: After heating the solvent was removed in vacuo and partitioned between EtOAc and water. The organic layer was washed with brine, dried ($Na_2SO_4$) and concentrated in vacuo before purification using a preparative TLC eluting with 35% EtOAc in DCM.

Method H: After heating the solvent was removed in vacuo and partitioned between EtOAc and water. The organic layer was washed with brine, dried (Na2SO4) and concentrated in vacuo before purification using a preparative TLC eluting with between 0-5% MeOH in EtOAc.

Method I: After heating the solvent was removed in vacuo and partitioned between EtOAc and water. The organic layer was washed with brine, dried (Na2SO4) and concentrated in vacuo before purification using a preparative TLC eluting with 40/1 EtOAc/2M Ammonia in MeOH followed by preparative HPLC (See General Experimental)

Method J: Crystallisation with ethyl acetate.

Method K: After heating the solvent was removed in vacuo and partitioned between EtOAc and water. The organic layer was washed with brine, dried (Na2SO4) and concentrated in vacuo before purification using a preparative TLC eluting with 20/1 EtOAc/EtOH. Followed by SCX-2 column eluting with MeOH.

Method L: SCX-2 column followed by preparative TLC eluting with EtOAc twice followed by preparative HPLC (See General Experimental)

Method M: Preparative TLC eluting twice with EtOAc followed by preparative TLC eluting twice with EtOAc/DCM 1/1.

Method N: After heating the solvent was removed in vacuo and partitioned between EtOAc and water. The organic layer was washed with brine, dried ($Na_2SO_4$) and concentrated in vacuo before purification using silica gel column chromatography eluting with EtOAc/hexane/triethylamine 10/10/1.

Method O: After heating the solvent was removed in vacuo and partitioned between EtOAc and water. The organic layer was washed with brine, dried ($Na_2SO_4$) and concentrated in vacuo before purification using a preparative TLC eluting with 10/1 EtOAc/2M Ammonia in MeOH.

Method P: Preparative TLC eluting with 10/1 ethyl acetate: "A"; where "A" is 10/1 methanol: '880' ammonia.

Method Q: After heating the reaction was partitioned between EtOAc and water. The organic layer was washed with brine, dried ($Na_2SO_4$) and concentrated in vacuo before applying to an SCX-2 column. The residue was dissolved in EtOAc and filtered through celite before further purification using preparative HPLC (See General Experimental)

Method R: Preparative HPLC (See General Experimental) eluting with water/MeOH 75/25 to 40/60.

Method S: Biotage silica gel column chromatography eluting with DCM/EtOH 99/1 to 97/3 followed by preparative HPLC eluting with water/MeOH 60/40 to 0/100.

| Example No | Name/Structure | Data | MPS1 $IC_{50}$ (uM) |
|---|---|---|---|
| 65 | tert-Butyl 3-chloro-6-(2-chloro-4-(dimethylcarbamoyl)phenylamino)-2-(1-methyl-1H-pyrazol-4-yl)-1H-pyrrolo[3,2-c]pyridine-1-carboxylate 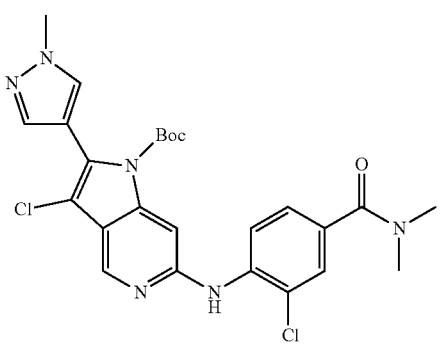 | $^1$H NMR (500 MHz, CDCl$_3$): δ 1.46 (s, 9H), 3.10 (s, 6H), 4.01 (s, 3H), 7.15 (s, 1H), 7.36 (dd, J =8.5, 1.9 Hz, 1H), 7.55 (d, J = 1.9 Hz, 1H), 7.60 (s, 1H), 7.62 (s, 1H), 7.72 (d, J = 0.9 Hz, 1H), 8.21 (d, J = 8.5 Hz, 1H), 8.56 (d, J = 0.9 Hz, 1H). ESI-HRMS (Method B) Found 529.1510, calculated for $C_{25}H_{27}Cl_2N_6O_3$ [M + H]$^+$: 529.1516. Using Preparation 80 and 4-amino-3-chloro-N,N-dimethylbenzamide. | 0.127 |

-continued

| Example No | Name/Structure | Data | MPS1 IC$_{50}$ (uM) |
|---|---|---|---|
| 66 | 3-Chloro-4-(1-(cyclopropylmethyl)-2-(1-methyl-1H-pyrazol-4-yl)-1H-pyrrolo[3,2-c]pyridin-6-ylamino)-N,N-dimethylbenzamide | $^1$H NMR (500 MHz, CD$_3$OD): δ 0.24-0.27 (m, 2H), 0.47-0.51 (m, 2H), 1.08-1.16 (m, 1H), 3.10 (s, 6H), 4.00 (s, 3H), 4.16 (d, J = 6.3 Hz, 2H), 6.62 (d, J = 0.8 Hz, 1H), 7.20 (t, J = 0.8 Hz, 1H), 7.30 (dd, J = 8.5, 2.0 Hz, 1H), 7.53 (d, J = 2.0 Hz, 1H), 7.69 (d, J = 8.5 Hz, 1H), 7.77 (d, J = 0.8 Hz, 1H), 7.97 (d, J = 0.8 Hz, 1H), 8.49 (d, J = 0.9 Hz, 1H). ESI-HRMS (Method B) Found 449.1850, calculated for C$_{24}$H$_{26}$ClN$_6$O [M + H]$^+$: 449.1851. Using Preparation 81 and 4-amino-3-chloro-N,N-dimethylbenzamide. | 0.030 |
| 67 | N-(2-Chlorophenyl)-1-(cyclohexylmethyl)-2-(1-methyl-1H-pyrazol-4-yl)-1H-pyrrolo[3,2-c]pyridin-6-amine | $^1$H NMR (500 MHz, CD$_3$OD): δ 0.87-0.97 (m, 2H), 1.06-1.17 (m, 3H), 1.43-1.49 (m, 2H), 1.58-1.67 (m, 3H), 1.68-1.76 (m, 1H), 3.98 (s, 3H), 4.01 (d, J = 7.3 Hz, 2H), 6.56 (s, 1H), 6.91 (ddd, J = 8.0, 7.3, 1.5 Hz, 1H), 7.01 (s, 1H), 7.20 (ddd, J = 8.2, 7.3, 1.5 Hz, 1H), 7.40 (dd, J = 8.0, 1.5 Hz, 1H), 7.58 (dd, J = 8.2, 1.5 Hz, 1H), 7.72 (s, 1H), 7.90 (s, 1H), 8.41 (s, 1H). ESI-HRMS (Method B) Found 420.1960, calculated for C$_{24}$H$_{27}$ClN$_5$ [M + H]$^+$: 420.1950. Using Preparation 84, 2-chloroaniline and purification method A. | 4.879 |
| 68 | Isopropyl 6-(4-(1,2-dimethyl-1H-imidazol-5-yl)-2-methoxyphenylamino)-2-(1-methyl-1H-pyrazol-4-yl)-1H-pyrrolo[3,2-c]pyridine-1-carboxylate | $^1$H NMR (500 MHz, CDCl$_3$): δ 1.35 (d, J = 6.3 Hz, 6H), 2.48 (s, 3H), 3.56 (s, 3H), 3.96 (s, 3H), 3.98 (s, 3H), 5.20 (sept, J = 6.3 Hz, 1H), 6.54 (d, J = 0.9 Hz, 1H), 6.90 (d, J = 1.8 Hz, 1H), 6.95 (dd, J = 8.2, 1.8 Hz, 1H), 6.96 (s, 1H), 7.21 (s, 1H), 7.58 (d, J = 0.8 Hz, 1H), 7.64 (d, J = 0.8 Hz, 1H), 7.74 (t, J = 0.9 Hz, 1H), 8.07 (d, J = 8.2 Hz, 1H), 8.50 (d, J = 0.9 Hz, 1H). ESI-HRMS (Method B) Found 500.2408, calculated for C$_{27}$H$_{30}$N$_7$O$_3$ [M + H]$^+$: 500.2405. Using Preparation 26, Preparation 95 and purification method B. | 0.002 |

| Example No | Name/Structure | Data | MPS1 IC$_{50}$ (uM) |
|---|---|---|---|
| 69 | tert-Butyl-6-(2,4-dimethoxyphenylamino)-2-(1-(2-(dimethylamino)-2-oxoethyl)-1H-pyrazol-4-yl)-1H-pyrrolo[3,2-c]pyridine-1-carboxylate | $^1$H-NMR (500 MHz, CDCl$_3$): δ 1.47 (s, 9H), 3.0 (s, 3H), 3.11 (s, 3H), 3.81 (s, 3H), 3.85 (s, 3H), 5 (s, 2H), 6.5 (m, 2H), 6.55 (s, 1H), 6.63 (s, 1H), 7.42 (s, 1H), 7.62 (s, 1H), 7.66 (d, J = 8.7 Hz, 1H), 7.7 (s, 1H), 8.39 (s, 1H). Using Preparation 120, 2,4-dimethoxyaniline and purification method C. | No data |
| 70 | 3-Chloro-4-(1-(4-fluorobenzyl)-2-(1-methyl-1H-pyrazol-4-yl)-1H-pyrrolo[3,2-c]pyridin-6-ylamino)-N,N-dimethylbenzamide | $^1$H-NMR (500 MHz, d$_6$-DMSO): δ 2.97 (s, 6H), 3.86 (s, 3H), 5.42 (s, 2H), 6.66 (s, 1H), 7 (m, 2H), 7.16 (m, 3H), 7.44 (s, 1H), 7.64 (s, 1H), 7.97 (s, 1H), 8.08 (d, J = 8.4, 2H), 8.52 (s, 1H), ESI-HRMS Found 503.175, calculated for C$_{27}$H$_{24}$ClFN$_6$O (M + H$^+$): 503.1757 Using Preparation 114, 4-amino-3-chloro-N,N-dimethylbenzamide and purification method C. | 0.038 |
| 71 | 3-Chloro-4-(1-(cyclohexylmethyl)-2-(1-methyl-1H-pyrazol-4-yl)-1H-pyrrolo[3,2-c]pyridine-6-ylamino)-N,N-dimethylbenzamide | $^1$H-NMR (500 MHz, d$_6$-DMSO): δ 0.95 (m, 2H), 1.11 (m, 4H), 1.4 (m, 2H), 1.6 (m, 2H), 1.7 (m, 1H), 2.98 (s, 6H), 3.92 (s, 3H), 4.02 (d, J = 7.4 Hz, 2H), 6.55 (d, J = 0.8 Hz, 1H), 7.29 (m, 2H), 7.46 (d, J = 2.0 Hz, 1H), 7.78 (s, 1H), 8.09 (s, 1H), 8.11 (d, J = 8.6 Hz, 1H), 8.18 (d, J = 8.6 Hz, 1H), 8.46 (s, 1H). ESI-HRMS Found 491.2315, calculated for C$_{27}$H$_{31}$ClN$_6$O (M + H$^+$): 491.2321 Using Preparation 115, 4-amino-3-chloro-N,N-dimethylbenzamide and purification method C. | 0.067 |

| Example No | Name/Structure | Data | MPS1 IC$_{50}$ (uM) |
|---|---|---|---|
| 72 | Cyclopentyl 6-(2-chloro-4-(dimethylcarbamoyl)phenyl-amino)-2-(1-methyl-1H-pyrazol-4-yl)-1H-pyrrolo[3,2-c]pyridine-1-carboxylate | $^1$H-NMR (500 MHz, CDCl$_3$): δ 1.61 (m, 4H), 1.77 (m, 4H), 3.09 (s, 6H), 3.96 (s, 3H), 5.38 (quin, J = 5.6 Hz, 1H), 6.54 (s, 1H), 7.1 (s, 1H), 7.34 (dd, J = 1.8 Hz, 8.5 Hz, 1H), 7.55 (m, 2H), 7.62 (s, 1H), 7.73 (s, 1H), 8.11 (d, J = 8.5 Hz, 1H), 8.52 (s, 1H). ESI-HRMS Found 507.1933, calculated for C$_{26}$H$_{27}$ClN$_6$O$_3$ (M + H$^+$): 507.1906 Using Preparation 116, 4-amino-3-chloro-N,N-dimethylbenzamide and purification method C. | 0.003 |
| 73 | 3-Chloro-4-(1-cyclopentyl-2-(1-methyl-1H-pyrazol-4-yl)-1H-pyrrolo[3,2-c]pyridin-6-ylamino)-N,N-dimethylbenzamide | $^1$H-NMR (500 MHz, d$_6$-DMSO): 1.7 (m, 2H), 1.75 (m, 4H), 2.18 (m, 2H), 2.98 (s, 6H), 3.92 (s, 3H), 4.86 (quin, J = 5.6 Hz, 1H), 6.45 (s, 1H), 7.25 (s, 1H), 7.32 (d, J = 8.3 Hz, 1H), 7.5 (s, 1H), 7.69 (s, 1H), 8.03 (s, 1H), 8.1 (m, 1H), 8.33 (s, br, 1H), 8.49 (s, 1H). ESI-HRMS (Method B) Found 463.2024, calculated for C$_{25}$H$_{27}$ClN$_6$O (M + H$^+$): 463.2008 Using Preparation 117, 4-amino-3-chloro-N,N-dimethylbenzamide and purification method C. | 0.007 |
| 74 | 3-Chloro-4-(1-isopropyl-2-(1-methyl-1H-pyrazol-4-yl)-1H-pyrrolo[3,2-c]pyridin-6-ylamino)-N,N-dimethylbenzamide | $^1$H-NMR (500 MHz, d$_6$-DMSO): δ 1.55 (d, J = 7 Hz, 6H), 2.98 (s, 6H), 3.92 (s, 3H), 4.7 (sep, J = 7 Hz, 1H), 6.42 (s, 1H), 7.3 (d, J = 8.6 Hz, 1H), 7.46 (d, J = 2 Hz, 1H), 7.53 (s, 1H), 7.66 (s, 1H), 8 (s, 1H), 8.2 (s, 1H), 8.27 (d, J = 8.6 Hz, 1H), 8.48 (s, 1H). ESI-HRMS Found 437.2252, calculated for C$_{23}$H$_{25}$ClN$_6$O (M + H$^+$): 437.2248 Using Preparation 118, 4-amino-3-chloro-N,N-dimethylbenzamide and purification method C. | 0.050 |

| Example No | Name/Structure | Data | MPS1 IC$_{50}$ (uM) |
|---|---|---|---|
| 75 | Cyclopentyl 6-(2-chloro-4-(1-methyl-1H-pyrazol-4-yl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.56 (m, 4H), 1.73 (m, 2H), 1.87 (m, 2H), 3.94 (s, 3H), 3.95 (s, 3H), 5.35 (quin, J = 3.2 Hz, 1H), 6.5 (s, 1H), 6.91 (s, 1H), 7.33 (dd, J = 2.1 Hz, 8.5 Hz, 1H), 7.52 (s, 1H), 7.56 (s, 1H), 7.61 (d, J = 6.6 Hz, 1 H), 7.71 (s, 1H), 7.91 (d, J = 8.5 Hz, 1H), 8.47 (s, 1H). ESI-HRMS Found 516.1897, calculated for C$_{27}$H$_{26}$ClN$_7$O$_2$ (M + H$^+$): 516.1909 Using Preparation 116, Preparation 83 and purification method C. | 0.012 |
| 76 | Isopropyl 6-(2-chloro-4-(1-methyl-1H-pyrazol-4-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.3 (d, J = 6.7 Hz, 6H), 3.94 (s, 3H), 3.95 (s, 3H), 5.16 (sep, J = 6.3 Hz, 1H), 6.51 (s, 1H), 6.93 (s, 1H), 7.34 (d, J = 8.5 Hz, 1H), 7.51 (s, 1H), 7.56 (s, 2H), 7.62 (s, 1H), 7.66 (s, 1H), 7.71 (s, 1H), 7.91 (d, J = 8.5 Hz, 1H), 8.47 (s, 1H). ESI-HRMS Found 490.1767, calculated for C$_{25}$H$_{24}$ClN$_7$O$_2$ (M + H$^+$): 490.175 Using Preparation 26, Preparation 83 and purification method C. | 0.017 |
| 77 | Isopropyl 6-(2-chloro-4-(dimethylcarbamoyl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.35 (d, J = 6.3 Hz, 6H), 3.09 (s, 6H), 3.98 (s, 3H), 5.2 (sep, J = 6.2 Hz, 1H), 6.55 (s, 1H), 7.11 (s, 1H), 7.34 (dd, J = 2 Hz, 8.5 Hz, 1H), 7.55 (s, 1H), 7.58 (s, 1H), 7.63 (s, 1H), 7.74 (s, 1H), 8.09 (d, J = 8.5 Hz, 1H), 8.52 (s, 1H). ESI-HRMS Found 481.1737, calculated for C$_{24}$H$_{25}$ClN$_6$O$_3$ (M + H$^+$): 481.1749 Using Preparation 26, 4-amino-3-chloro-N,N-dimethylbenzamide and purification method D. | 0.006 |

| Example No | Name/Structure | Data | MPS1 IC$_{50}$ (uM) |
|---|---|---|---|
| 78 | Cyclopentyl 6-((2-chloro-4-(1-methyl-1H-imidazol-5-yl)phenyl)amino)-2-(1-methyl-1H-pyrazol-4-yl)-1H-pyrrolo[3,2-c]pyridine-1-carboxylate | $^1$H-NMR (500 MHz, CDCl$_3$): δ 1.58 (m, 4H), 1.76 (m, 2H), 1.91 (m, 2H), 3.65 (s, 3H), 3.95 (s, 3H), 5.35 (quin, J = 3 Hz, 1H), 6.51 (s, 1H), 7.04 (s, 1H), 7.06 (s, 1H), 7.24 (dd, J = 2.1 Hz, 8.5 Hz, 1H), 7.42 (s, 1H), 7.5 (s, 1H), 7.54 (s, 1H), 7.6 (s, 1H), 7.7 (s, 1H), 8.1 (d, J = 8.5 Hz, 1H), 8.49 (s, 1H); ESI-HRMS (Method B) Found 516.1895, calculated for C$_{27}$H$_{26}$ClN$_7$O$_2$ (M + H$^+$): 516.1909 Using Preparation 116, Preparation 86 and purification method E. | 0.011 |
| 79 | Isopropyl 6-(2-chloro-4-(1-methyl-1H-imidazol-5-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.33 (d, J = 6.3 Hz, 6H), 3.69 (s, 3H), 3.96 (s, 3H), 5.19 (sep, J = 6.3 Hz, 1H), 6.55 (s, 1H), 7.04 (s, 1H), 7.09 (s, 1H), 7.26 (dd, J = 2 Hz, 8.5 Hz, 2H), 7.45 (s, 1H), 7.52 (s, 1H), 7.63 (s, 1H), 7.74 (s, 1H), 8.12 (d, J = 8.5 Hz, 1H), 8.52 (s, 1H); ESI-HRMS Found 490.1736, calculated for C$_{25}$H$_{24}$ClN$_7$O$_2$ (M + H$^+$): 490.1753 Using Preparation 26, Preparation 86 and purification method E. | 0.003 |
| 80 | N-(2-chloro-4-(1-methyl-1H-imidazol-5-yl)phenyl)-1-cyclopentyl-2-(1-methyl-1H-pyrazol-4-yl)-1H-pyrrolo[3,2-c]pyridin-6-amine | $^1$H-NMR (500 MHz, CDCl$_3$): δ 1.73 (m, 2H), 2.02 (m, 4H), 2.34 (m, 2H), 3.68 (s, 3H), 4.02 (s, 3H), 4.84 (quin, J = 3 Hz, 1H), 6.42 (s, 1H), 6.92 (s, 1H), 7.02 (s, 1H), 7.08 (s, 1H), 7.21 (dd, J = 2 Hz, 8.5 Hz, 1H), 7.43 (s, 1H), 7.51 (s, 1H), 7.52 (s, 1H), 7.61 (s, 1H), 7.91 (d, J = 8.5 Hz, 1H), 8.61 (s, 1H); ESI-HRMS (Method B) Found 472.2002, calculated for C$_{26}$H$_{26}$ClN$_7$ (M + H$^+$): 472.2011 Using Preparation 117, Preparation 86 and purification method F. | 0.003 |

| Example No | Name/Structure | Data | MPS1 IC$_{50}$ (uM) |
|---|---|---|---|
| 81 | Cyclobutyl-6-(2-chloro-4-(dimethylcarbamoyl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.71 (m, 1H), 1.88 (m, 1H), 2.13 (m, 2H), 2.44 (m, 2H), 3.1 (s, 6H), 3.98 (s, 3H), 5.19 (quin, J = 5.6 Hz, 1H), 6.56 (s, 1H), 7.12 (s, 1H), 7.34 (dd, J = 2 Hz, 8.5 Hz, 1H), 7.55 (d, J = 2 Hz, 1H), 7.59 (s, 1H), 7.65 (s, 1H), 7.76 (s, 1H), 8.13 (d, J = 8.5 Hz, 1H), 8.53 (s, 1H); ESI-HRMS Found 493.1734, calculated for C$_{25}$H$_{25}$ClN$_6$O$_3$ (M + H$^+$): 493.1749 Using Preparation 125, 4-amino-3-chloro-N,N-dimethylbenzamide and purification method F. | 0.003 |
| 82 | Cyclobutyl-6-(2-chloro-4-(1-methyl-1H-imidazol-5-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.68 (m, 1H), 1.86 (m, 1H), 2.12 (m, 2H), 2.44 (m, 2H), 3.68 (s, 3H), 3.97 (s, 3H), 5.18 (quin, J = 7.3 Hz, 1H), 6.55 (s, 1H), 7.06 (s, 1H), 7.08 (s, 1H), 7.26 (d, J = 8.5 Hz, 1H), 7.44 (d, J = 2.1 Hz, 1H), 7.52 (s, 1H), 7.58 (s, 1H), 7.64 (s, 1H), 7.75 (s, 1H), 8.14 (d, J = 8.5 Hz, 1H), 8.51 (s, 1H); ESI-HRMS (Method B) Found 502.1744, calculated for C$_{26}$H$_{24}$ClN$_7$O$_2$ (M + H$^+$): 502.1753 Using Preparation 125, Preparation 86 and purification method F. | 0.005 |
| 83 | Isopropyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.32 (d, J = 6.3 Hz, 6H), 2.44 (s, 3H), 3.53 (s, 3H), 3.96 (s, 3H), 5.19 (sep, J = 6.3 Hz, 1H), 6.53 (s, 1H), 6.93 (s, 1H), 7.04 (s, 1H), 7.21 (dd, J = 2 Hz, 8.5 Hz, 1H), 7.4 (d, J = 2 Hz, 1H), 7.57 (s, 1H), 7.62 (s, 1H), 7.72 (s, 1H), 8.08 (d, J = 8.5 Hz, 1H), 8.5 (s, 1H); ESI-HRMS Found 504.1903, calculated for C$_{26}$H$_{26}$ClN$_7$O$_2$ (M + H$^+$): 504.1909 Using Preparation 26, Preparation 124 and purification method F. | 0.002 |

| Example No | Name/Structure | Data | MPS1 IC$_{50}$ (uM) |
|---|---|---|---|
| 84 | Cyclopentyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.59 (m, 4H), 1.75 (m, 2H), 1.89 (m, 2H), 2.45 (s, 3H), 3.53 (s, 3H), 3.96 (s, 3H), 5.36 (quin, J = 3 Hz, 1H), 6.52 (s, 1H), 6.93 (s, 1H), 7.01 (s, 1H), 7.21 (dd, J = 2 Hz, 8.5 Hz, 1H), 7.4 (d, J = 2 Hz, 1H), 7.55 (s, 1H), 7.61 (s, 1H), 7.7 (s, 1H), 8.08 (d, J = 8.5 Hz, 1H), 8.5 (s, 1H); ESI-HRMS Found 530.206, calculated for C$_{28}$H$_{28}$ClN$_7$O$_2$ (M + H$^+$): 530.2066 Using Preparation 116, Preparation 124 and purification method F. | 0.002 |
| 85 | Cyclobutyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.67 (m, 1H), 2.09 (m, 1H), 2.11 (m, 2H), 2.39 (m, 2H), 2.44 (s, 3H), 3.6 (s, 3H), 3.96 (s, 3H), 5.17 (q, J = 7.4 Hz, 1H), 6.54 (s, 1H), 6.93 (s, 1H), 7.04 (s, 1H), 7.21 (dd, J = 2 Hz, 8.5 Hz, 1H), 7.4 (d, J = 2 Hz, 1H), 7.58 (s, 1H), 7.64 (s, 1H), 7.73 (s, 1H), 8.11 (d, J = 8.5 Hz, 1H), 8.5 (s, 1H); ESI-HRMS Found 516.2109 calculated for C$_{27}$H$_{26}$ClN$_7$O$_2$ (M + H$^+$): 516.2067 Using Preparation 125, Preparation 124 and purification method F. | 0.004 |
| 86 | Methyl-6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 2.45 (s, 3H), 3.49 (s, 3H), 3.94 (s, 3H), 3.97 (s, 3H), 6.55 (s, 1H), 6.94 (s, 1H), 7.04 (s, 1H), 7.22 (dd, J = 2 Hz, 8.5 Hz, 1H), 7.4 (d, J = 2 Hz, 1H), 7.59 (s, 1H), 7.63 (s, 1H), 7.67 (s, 1H), 8.21 (d, J = 8.5 Hz, 1H), 8.51 (s, 1H); ESI-HRMS (Method B) Found 476.1584 calculated for C$_{24}$H$_{22}$ClN$_7$O$_2$ (M + H$^+$): 476.1596 Using Preparation 128, Preparation 124 and purification method F. | 0.007 |

| Example No | Name/Structure | Data | MPS1 IC$_{50}$ (uM) |
|---|---|---|---|
| 87 | Ethyl-6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.34 (t, J = 7.2 Hz, 3H), 2.45 (s, 3H), 3.53 (s, 3H), 3.96 (s, 3H), 4.42 (q, J = 7.2 Hz, 2H), 6.54 (s, 1H), 6.93 (s, 1H), 7.04 (s, 1H), 7.22 (dd, J = 2.1 Hz, 8.5 Hz, 1H), 7.4 (d, J = 2 Hz, 1H), 7.58 (s, 1H), 7.63 (s, 1H), 7.7 (s, 1H), 8.13 (d, J = 8.5 Hz, 1H), 8.5 (s, 1H); ESI-HRMS Found 490.1741 calculated for C$_{25}$H$_{24}$ClN$_7$O$_2$ (M + H$^+$): 490.1753 Using Preparation 129, Preparation 124 and purification method F. | 0.002 |
| 88 | Propyl-6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 0.89 (t, J = 7.4 Hz, 3H), 1.69 (m, 2H), 2.45 (s, 3H), 3.53 (s, 3H), 3.95 (s, 3H), 4.3 (t, J = 6.7 Hz, 2H), 6.53 (s, 1H), 6.93 (s, 1H), 7.03 (s, 1H), 7.21 (dd, J = 2 Hz, 8.5 Hz, 1H), 7.39 (d, J = 2 Hz, 1H), 7.57 (s, 1H), 7.62 (s, 1H), 7.7 (s, 1H), 8.12 (d, J = 8.5 Hz, 1H), 8.5 (s, 1H); ESI-HRMS Found 504.1899 calculated for C$_{26}$H$_{26}$ClN$_7$O$_2$ (M + H$^+$): 504.1909 Using Preparation 130, Preparation 124 and purification method F. | 0.002 |
| 89 | Isopropyl 6-((2-chloro-5-(1-methyl-1H-pyrazol-4-yl)phenyl)amino)-2-(1-methyl-1H-pyrazol-4-yl)-1H-pyrrolo[3,2-c]pyridine-1-carboxylate | $^1$H-NMR (500 MHz, DMSO-d$_6$): δ 1.20 (d, J = 6.5 Hz, 6H), 3.84 (s, 3H), 3.87 (s, 3H), 5.05 (septet, J = 6.1 Hz, 1H), 6.66 (s, 1H), 7.24 (dd, J = 2.2, 8.2 Hz, 1H), 7.44 (d, J = 8.4 Hz, 1H), 7.48 (s, 1H), 7.63 (s, 1H), 7.81 (d, J = 0.6 Hz, 1H), 7.94 (s, 1H), 7.94 (d obscured, 1H), 8.11 (s, 1H), 8.36 (s, 1H), 8.42 (d, J = 0.6 Hz, 1H); ESI-HRMS: Found 490.1746; calculated for C$_{25}$H$_{25}$ClN$_7$O$_2$ (M + H)$^+$: 490.1753 Using Preparation 26, Preparation 132 and purification method G. | 0.287 |

| Example No | Name/Structure | Data | MPS1 IC$_{50}$ (uM) |
|---|---|---|---|
| 90 | 3-Chloro-N,N-dimethyl-4-((2-(1-methyl-1H-pyrazol-4-yl)-1-((5-methylisoxazol-3-yl)methyl)-1H-pyrrolo[3,2-c]pyridin-6-yl)amino)benzamide | $^1$H-NMR (500 MHz, DMSO-d$_6$): δ 2.32 (s, 3H), 2.97 (s, 6H), 3.90 (s, 3H), 5.39 (s, 2H), 5.94 (s, 1H), 6.62 (s, 1H), 7.24 (s, 1H), 7.29 (dd, J = 2.1, 8.7 Hz, 1H), 7.45 (d, J = 2.1 Hz, 1H), 7.76 (s, 1H), 8.08 (s, 1H), 8.12 (d, J = 8.7 Hz, 1H), 8.20 (s, 1H), 8.49 (s, 1H). ESI-HRMS: Found 490.1752; calculated for C$_{25}$H$_{25}$ClN$_7$O$_2$ (M + H)$^+$: 490.1753. Using Preparation 135, 4-amino-3-chloro-N,N-dimethylbenzamide and purification method H. | 0.343 |
| 91 | tert-Butyl 6-(2-chloro-4-(1-methyl-1H-imidazol-5-yl)phenylamino)-2-(oxazol-5-yl)-1H-pyrrolo[3,2-c]pyridine-1-carboxylate | $^1$H-NMR (CDCl$_3$, 500 MHz): δ 1.50 (s, 9H), 3.70 (s, 3H), 6.84 (d, J = 0.95 Hz, 1H), 7.11 (br s, 2H), 7.30 (dd, J = 2.21, 8.51 Hz, 1H), 7.32 (s, 1H), 7.46 (d, J = 2.21 Hz, 1H), 7.55 (br s, 1H), 7.77 (m, 1H), 8.01 (s, 1H), 8.24 (d, J = 8.51 Hz, 1H), 8.61 (d, J = 0.95 Hz, 1H). HRMS calcd for C$_{25}$H$_{24}$$^{35}$ClN$_6$O$_3$ (M + H)$^+$ 491.1593, found 491.1580 Using Preparation 140, Preparation 86 and purification method I. | 0.006 |
| 92 | 3-Chloro-N,N-dimethyl-4-(2-(1-methyl-1H-pyrazol-4-yl)-1-(5-methylpyridin-2-yl)-1H-pyrrolo[3,2-c]pyridin-6-ylamino)benzamide | $^1$H-NMR (CDCl$_3$, 500 MHz): δ 2.46 (s, 3H), 3.08 (s, 6H,), 3.88 (s, 3H), 6.68 (d, J = 0.95 Hz, 1H), 6.93 (br s, 1H, NH), 6.97 (t, J = 0.95 Hz, 1H), 7.06 (d, J = 8.51 Hz, 1H), 7.22 (s, 1H), 7.25 (d, J = 0.63 Hz, 1H), 7.29 (dd, J = 1.58, 8.51 Hz, 1H), 7.49 (d, J = 1.89 Hz, 1H), 7.63 (ddd, J = 0.63, 2.21, 8.20 Hz, 1H), 7.97 (d, J = 8.51 Hz, 1H), 8.52 (m, 1H), 8.64 (d, J = 0.95 Hz, 1H). HRMS calcd for C$_{26}$H$_{25}$$^{35}$ClN$_7$O (M + H)$^+$ 486.1804, found 486.1787 Using Preparation 141, 4-amino-3-chloro-N,N-dimethylbenzamide and work up method H followed by method J. | 0.043 |

| Example No | Name/Structure | Data | MPS1 IC$_{50}$ (uM) |
|---|---|---|---|
| 93 | 3-Chloro-N,N-dimethyl-4-(2-(1-methyl-1H-pyrazol-4-yl)-1-(pyrimidin-2-yl)-1H-pyrrolo[3,2-c]pyridin-6-ylamino)benzamide | $^1$H-NMR (CDCl$_3$, 500 MHz): δ 3.09 (s, 6H), 3.93 (s, 3H), 6.70 (d, J = 0.63 Hz, 1H), 7.03 (s, 1H, NH), 7.27 (t, J = 4.73 Hz, 1H), 7.32 (dd, J = 1.89, 8.51 Hz, 1H), 7.33 (d, J = 0.63 Hz, 1H), 7.50 (s, 1H), 7.52 (d, J = 1.89 Hz, 1H), 7.64 (m, 1H), 8.11 (d, J = 8.51 Hz, 1H), 8.63 (d, J = 0.95 Hz, 1H), 8.81 (d, J = 4.73 Hz, 2H). HRMS calcd for C$_{24}$H$_{22}$$^{35}$ClN$_8$O (M + H)$^+$ 473.1600, found 473.1584. Using Preparation 142, 4-amino-3-chloro-N,N-dimethylbenzamide and purification method J. | 0.094 |
| 94 | 3-Chloro-N,N-dimethyl-4-(2-(1-methyl-1H-pyrazol-4-yl)-1-(pyridin-2-yl)-1H-pyrrolo[3,2-c]pyridin-6-ylamino)benzamide | $^1$H-NMR (CDCl$_3$, 500 MHz): δ 3.08 (s, 6H), 3.88 (s, 3H), 6.70 (d, J = 0.63 Hz, 1H), 6.94 (s, 1H), 7.05 (t, J = 0.95 Hz, 1H), 7.15 (d of t, J = 0.95, 7.88 Hz, 1H), 7.21 (s, 1H), 7.27 (d, J = 0.63 Hz, 1H), 7.29 (dd, J = 1.57, 8.51 Hz, 1H), 7.40 (m, 1H), 7.50 (d, J = 1.89 Hz, 1H), 7.82 (t of d, J = 1.89, 7.56 Hz), 8.01 (d, J = 8.51 Hz, 1H), 8.65 (d, J = 0.95 Hz, 1H), 8.71 (ddd, J = 0.95, 1.89, 4.73 Hz, 1H). HRMS calcd for C$_{25}$H$_{23}$$^{35}$ClN$_7$O (M + H)$^+$ 472.1647, found 472.1634. Using Preparation 143, 4-amino-3-chloro-N,N-dimethylbenzamide and purification method J. | 0.078 |
| 95 | tert-Butyl 3-chloro-6-(2-chloro-4-(dimethylcarbamoyl)phenyl-amino)-2-(oxazol-5-yl)-1H-pyrrolo[3,2-c]pyridine-1-carboxylate | HRMS calcd for C$_{24}$H$_{24}$$^{35}$Cl$_2$N$_5$O$_4$ (M + H)$^+$ requires 516.1200, found 516.1198 (ret time = 3.22 min). Product contaminated with 3-Chloro-4-(3-chloro-2-(oxazol-5-yl)-1H-pyrrolo[3,2-c]pyridin-6-ylamino)-N,N-dimethylbenzamide. HRMS calcd for C$_{19}$H$_{16}$$^{35}$Cl$_2$N$_5$O$_4$ (M + H)$^+$ requires 416.0676, found 416.0676 (ret time = 2.48 min). Using Preparation 145 and taken on crude. | No data |

| Example No | Name/Structure | Data | MPS1 IC$_{50}$ (uM) |
|---|---|---|---|
| 96 | tert-Butyl 6-(2-methoxyphenylamino)-2-(oxazol-5-yl)-1H-pyrrolo[3,2-c]pyridine-1-carboxylate | $^1$H-NMR (CDCl$_3$, 500 MHz): δ 1.50 (s, 9H), 3.92 (s, 3H), 6.80 (d, J = 0.63 Hz, 1H), 6.92-7.02 (m, 3H), 7.14 (br s, 1H), 7.30 (s, 1H), 7.70 (t, J = 0.95 Hz, 1H), 7.99 (m, 2H), 8.55 (d, J = 0.95 Hz, 1H). HRMS calcd for C$_{22}$H$_{23}$N$_4$O$_4$ (M + H)$^+$ 407.1714, found 407.1707 Using Preparation 140, 2-methoxyaniline and purification method H. | 0.254 |
| 97 | tert-Butyl 6-(2-methoxy-4-(3-methoxyazetidine-1-carbonyl)phenyl amino)-2-(oxazol-5-yl)-1H-pyrrolo[3,2-c]pyridine-1-carboxylate | $^1$H-NMR (CDCl$_3$, 500 MHz): δ 1.50 (s, 9H), 3.34 (s, 3H), 3.98 (s, 3H), 4.15 (s, v br, 2H), 4.27 (m, 1H), 4.45 (s, v br, 2H), 6.82 (d, J = 0.95 Hz), 7.22 (dd, J = 1.89, 8.51 Hz, 1H), 7.30 (s, 1H), 7.35 (d, J = 1.89 Hz, 1H), 7.40 (br s, 1H, NH), 7.75 (m, 1H), 8.00 (s, 1H), 8.23 (d, J = 8.51 Hz, 1H), 8.60 (d, J = 0.63 Hz, 1H). HRMS calcd for C$_{27}$H$_{30}$N$_5$O$_6$ (M + H)$^+$ 520.2191, found 520.2186 Using Preparation 140, Preparation 62 and purification method L. | 0.010 |
| 98 | tert-Butyl 6-(2-chloro-4-(dimethylcarbamoyl)phenyl-amino)-2-(oxazol-5-yl)-1H-pyrrolo[3,2-c]pyridine-1-carboxylate | $^1$H-NMR (CDCl$_3$, 500 MHz): δ 1.50 (s, 9H), 3.10 (s, 6H), 6.84 (d, J = 0.63 Hz, 1H), 7.17 (br s, 1H, NH), 7.37 (dd, J = 1.89, 8.51 Hz, 1H), 7.56 (d, J = 1.89 Hz, 1H), 7.77 (s, 1H), 8.01 (s, 1H), 8.21 (d, J = 8.51 Hz, 1H), 8.61 (d, J = 0.95 Hz, 1H). HRMS calcd for C$_{24}$H$_{25}$ClN$_5$O$_4$ (M + H)$^+$ 482.1590, found 482.1586 Using Preparation 140, 4-amino-3-chloro-N,N-dimethylbenzamide and purification method M. | 0.023 |

| Example No | Name/Structure | Data | MPS1 IC$_{50}$ (uM) |
|---|---|---|---|
| 99 | tert-Butyl 6-(2-methoxyphenylamino)-2-(1-(2,2,2-trifluoroethyl)-1H-pyrazol-4-yl)-1H-pyrrolo[3,2-c]pyridine-1-carboxylate | $^1$H-NMR (CDCl$_3$, 500 MHz): δ 1.50 (s, 9H), 3.92 (s, 3H), 4.76 (q, J = 8.51 Hz, 2H), 6.53 (d, J = 0.63 Hz, 1H), 6.91-7.01 (m, 3H), 7.07 (br s, 1H), 7.68 (s, 1H), 7.69 (s, 1H), 7.70 (d, J = 0.63 Hz, 1H), 7.96 (dd, J = 1.89, 7.25 Hz, 1H), 8.48 (s, 1H). $^{19}$F-NMR (CDCl$_3$, 470.385 MHz): -71.61<br>Using Preparation 150, 2-methoxyaniline and purification method G. | No data |
| 100 | tert-Butyl 2-(1-(difluoromethyl)-1H-pyrazol-4-yl)-6-(2-methoxyphenylamino)-1H-pyrrolo[3,2-c]pyridine-1-carboxylate | $^1$H-NMR (CDCl$_3$, 500 MHz): δ 1.50 (s, 9H), 3.92 (s, 3H), 6.57 (d, J = 0.63 Hz, 1H), 6.91-7.01 (m, 3H), 7.09 (s, 1H, NH), 7.24 (t, J = 60.5 Hz, 1H), 7.69 (s, 1H), 7.77 (s, 1H), 7.95-8.01 (m, 2H), 8.49 (s, 1H). $^{19}$F-NMR (CDCl$_3$, 470.385 MHz): δ -93.22<br>Using Preparation 154, 2-methoxyaniline and purification method G. | No data |
| 101 | tert-Butyl 6-(2,4-dimethoxyphenylamino)-2-(1-((5-methylisoxazol-3-yl)methyl)-1H-pyrazol-4-yl)-1H-pyrrolo[3,2-c]pyridine-1-carboxylate | $^1$H-NMR (500 MHz, CDCl$_3$) 1.45 (s, 9H), 2.41 (s, 3H), 3.82 (s, 3H), 3.85 (s, 3H), 5.36 (s, 2H), 6.01 (s, 1H), 6.46 (s, 1H), 6.50 (m, 2H), 6.55 (s, 1H), 6.62 (s, 1H), 7.41 (s, 1H), 7.62 (s, 1H), 7.69 (s, 1 H), 8.39 (s, 1H).<br>Using Preparation 34 and purification method N. | No data |

-continued

| Example No | Name/Structure | Data | MPS1 IC$_{50}$ (uM) |
|---|---|---|---|
| 102 | Isopropyl 6-(2-methoxy-4-(1-methyl-1H-pyrazol-4-yl)phenylamino)-2-(1-methyl-1H-pyrazol-4-yl)-1H-pyrrolo[3,2-c]pyridine-1-carboxylate | $^1$H-NMR (500 MHz, CDCl$_3$): δ 1.33 (d, J = 6.3 Hz, 6H), 3.95 (s, 3H), 3.96 (s, 3H), 5.18 (sep, J = 6.3 Hz, 1H), 6.51 (s, 1H), 7.01 (d, J = 1.9 Hz, 1H), 7.05 (s, 1H), 7.07 (dd, J = 1.9 Hz, 8.2 Hz, 1H), 7.56 (s, 1H), 7.58 (s, 1H), 7.62 (s, 1H), 7.69 (s, 1H), 7.74 (s, 1H), 7.87 (d, J = 8.2 Hz, 1H), 8.46 (s, 1H). ESI-HRMS Found 486.226, calculated for C$_{26}$H$_{28}$N$_7$O$_3$ (M + H$^+$): 486.2248 Using Preparation 155, Preparation 26 and purification method F. | 0.007 |
| 103 | Isopropyl 6-(4-(1,3-dimethyl-1H-pyrazol-4-yl)-2-methoxyphenylamino)-2-(1-methyl-1H-pyrazol-4-yl)-1H-pyrrolo[3,2-c]pyridine-1-carboxylate | $^1$H-NMR (500 MHz, CDCl$_3$): δ 1.34 (d, J = 6.3 Hz, 6H), 2.42 (s, 3H), 3.89 (s, 3H), 3.94 (s, 3H), 3.96 (s, 3H), 5.18 (sep, J = 6.3 Hz, 1H), 6.51 (s, 1H), 6.93 (d, J = 1.8 Hz, 1H), 6.98 (dd, J = 1.9 Hz, 8.2 Hz, 1H), 7.05 (s, 1H), 7.42 (s, 1H), 7.57 (s, 1H), 7.63 (s, 1H), 7.71 (s, 1H), 7.9 (d, J = 8.2 Hz, 1H), 8.46 (s, 1H). ESI-HRMS Found 500.2389, calculated for C$_{27}$H$_{30}$N$_7$O$_3$ (M + H$^+$): 500.2405 Using Preparation 156, Preparation 26 and purification method F. | 0.002 |
| 104 | N-(2-Chloro-4-(1,2-dimethyl-1H-imidazol-5-yl)phenyl)-1-(2-methoxyethyl)-2-(1-methyl-1H-pyrazol-4-yl)-1H-pyrrolo[3,2-c]pyridin-6-amine | $^1$H-NMR (CDCl$_3$, 500 MHz): δ 2.46 (s, 3H), 3.32 (s, 3H), 3.54 (s, 3H), 3.71 (t, J = 5.68 Hz, 2H), 4.02 (s, 3H), 4.27 (t, J = 5.68 Hz, 2H), 6.52 (d, J = 0.63 Hz, 1H), 6.94 (s, 1H), 6.98 (s, 1H), 6.99 (br s, 1H, NH), 7.20 (dd, J = 2.21, 8.51 Hz, 1H), 7.39 (d, J = 2.21 Hz, 1H), 7.68 (s, 1H), 7.73 (d, J = 0.95 Hz, 1H), 7.97 (d, J = 8.51 Hz, 1H), 8.59 (d, J = 0.95 Hz, 1H). HRMS calcd for C$_{25}$H$_{27}$$^{35}$ClN$_7$O (M + H)$^+$ 476.1960, found 476.1949 Using Preparation 157, Preparation 124 and purification method O. | 0.083 |

| Example No | Name/Structure | Data | MPS1 IC$_{50}$ (uM) |
|---|---|---|---|
| 105 | N-(2-Chloro-4-(1,2-dimethyl-1H-imidazol-5-yl)phenyl)-1-(cyclopropylmethyl)-2-(1-methyl-1H-pyrazol-4-yl)-1H-pyrrolo[3,2-c]pyridin-6-amine 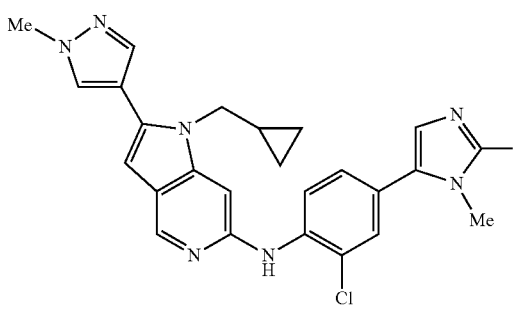 | $^1$H-NMR (d$_6$-DMSO, 500 MHz): δ 0.29 (m, 2H), 0.43 (m, 2H), 1.10 (m, 1H), 2.34 (s, 3H), 3.52 (s, 3H), 3.93 (s, 3H), 4.08 (d, J = 6.62 Hz, 2H), 6.54 (s, 1H), 6.84 (s, 1H), 7.24 (s, 1H), 7.27 (dd, J = 1.89, 8.51 Hz, 1H), 7.44 (d, J = 1.89 Hz, 1H), 7.79 (s, 1H), 8.04 (s, 1H), 8.12 (s, 1H), 8.20 (d, J = 8.51 Hz, 1H), 8.46 (s, 1H). HRMS calcd for C$_{26}$H$_{27}$$^{35}$ClN$_7$ (M + H)$^+$ 472.2011, found 472.2001 Using Preparation 158, Preparation 124 and purification method O followed by method P. | 0.029 |
| 106 | Isopropyl 6-(2-chloro-4-(1,2-dimethyl-1H-imidazol-5-yl)phenylamino)-2-(oxazol-5-yl)-1H-pyrrolo[3,2-c]pyridine-1-carboxylate 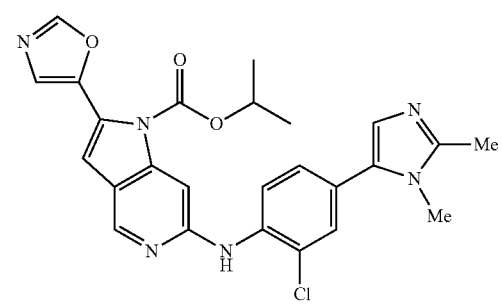 | $^1$H-NMR (CDCl$_3$, 500 MHz): δ 1.30 (d, J = 6.31 Hz, 6H), 2.47 (s, 3H), 3.56 (s, 3H), 5.19 (sept, J = 6.31 Hz, 1H), 6.88 (d, J = 0.63 Hz, 1H), 6.96 (s, 1H), 7.12 (s, 1H), 7.26 (dd, J = 1.89, 8.51 Hz, 1H), 7.34 (s, 1H), 7.43 (d, J = 2.21 Hz, 1H), 7.79 (s, 1H), 8.01 (s, 1H), 8.16 (d, J = 8.51 Hz, 1H), 8.61 (d, J = 0.95 Hz, 1H). HRMS calcd for C$_{25}$H$_{24}$$^{35}$ClN$_6$O$_3$ (M + H)$^+$ 491.1593, found 491.1587 Using Preparation 162, Preparation 124 and purification method Q. | 0.002 |
| 107 | tert-Butyl 6-(2-chloro-4-(1,2-dimethyl-1H-imidazol-5-yl)phenylamino)-2-(oxazol-5-yl)-1H-pyrrolo[3,2-c]pyridine-1-carboxylate 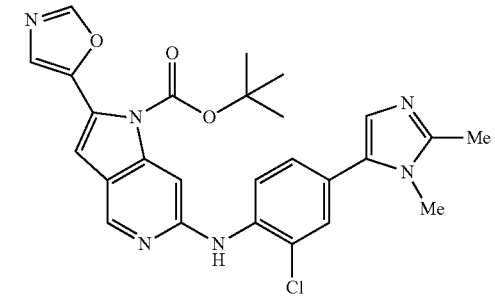 | $^1$H-NMR (CDCl$_3$, 500 MHz): δ 1.50 (s, 9H), 2.47 (s, 3H), 3.56 (s, 3H), 6.84 (d, J = 0.63 Hz, 1H), 6.96 (s, 1H), 7.11 (s, 1H), 7.26 (dd, J = 1.89, 8.20 Hz, 1H), 7.32 (s, 1H), 7.42 (d, J = 1.89 Hz, 1H), 7.75 (s, 1H), 8.01 (s, 1H), 8.20 (d, J = 8.83 Hz, 1H), 8.60 (d, J = 0.95 Hz, 1H). HRMS calcd for C$_{26}$H$_{26}$$^{35}$ClN$_6$O$_3$ (M + H)$^+$ 505.1750, found 505.1739 Using Preparation 140, Preparation 124 and purification method Q. | 0.002 |

| Example No | Name/Structure | Data | MPS1 IC$_{50}$ (uM) |
|---|---|---|---|
| 108 | Isopropyl 6-(4-(1,2-dimethyl-1H-imidazol-5-yl)phenylamino)-2-(1-methyl-1H-pyrazol-4-yl)-1H-pyrrolo[3,2-c]pyridine-1-carboxylate | $^1$H NMR (500 MHz, CDCl$_3$): δ 1.32 (d, J = 6.3 Hz, 6H), 2.46 (s, 3H), 3.54 (s, 3H), 3.97 (s, 3H), 5.18 (sept, J = 6.3 Hz, 1H), 6.53 (d, J = 0.9 Hz, 1H), 6.90 (s, 1H), 6.93 (s, 1H), 7.30-7.34 (m, 2H), 7.41-7.45 (m, 2H), 7.58 (d, J = 0.8 Hz, 1H), 7.63 (d, J = 0.8 Hz, 1H), 7.72 (t, J = 0.9 Hz, 1H), 8.46 (d, J = 0.9 Hz, 1H); ESI-HRMS (Method B) Found 470.2294, calculated for C$_{26}$H$_{28}$N$_7$O$_2$ (M + H$^+$): 470.2299. Using Preparation 26, Preparation 163 and purification method F followed by method R. | 0.002 |
| 109 | Isopropyl 6-(4-methoxy-2-(1-methyl-1H-pyrazol-4-yl)pyrimidin-5-ylamino)-2-(1-methyl-1H-pyrazol-4-yl)-1H-pyrrolo[3,2-c]pyridine-1-carboxylate | $^1$H NMR (500 MHz, CDCl$_3$) d 1.33 (d, J = 6.3 Hz, 6H), 3.97 (s, 3H), 3.97 (s, 3H), 4.14 (s, 3H), 5.17 (sept, J = 6.3 Hz, 1H), 6.51 (d, J = 0.8 Hz, 1H), 6.73 (s, 1H), 7.55 (d, J = 0.8 Hz, 1H), 7.59 (t, J = 0.8 Hz, 1H), 7.61 (d, J = 0.8 Hz, 1H), 8.01 (s, 1H), 8.12 (s, 1H), 8.47 (d, J = 0.9 Hz, 1H), 9.34 (s, 1H); ESI-HRMS (Method B) Found 488.2165, calculated for C$_{24}$H$_{26}$N$_9$O$_3$ (M + H$^+$): 488.2153. Using Preparation 26, Preparation 119 and purification method S. | 0.014 |

Example 110

3-Chloro-4-(1-(cyclopentylsulfonyl)-2-(1-methyl-1H-pyrazol-4-yl)-1H-pyrrolo[3,2-c]pyridin-6-ylamino)-N,N-dimethylbenzamide

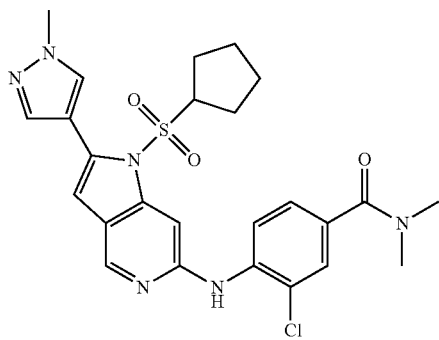 [SMILES: CN(C)C(=O)c1ccc(Nc2cc3c(cn2)cc(-c2cnn(C)c2)n3S(=O)(=O)C2CCCC2)c(Cl)c1]

3-Chloro-N,N-dimethyl-4-(2-(1-methyl-1H-pyrazol-4-yl)-1H-pyrrolo[3,2-c]pyridin-6-ylamino)benzamide (Example 127, 25 mg, 0.063 mmol) was dissolved in dry DMF. The solution was degassed and a solution of sodium bis(trimethylsilyl)amide (0.1 ml of a 1M solution in THF, 1 mmol) was added. After 20 minutes reaction, cyclopentyl sulfonyl chloride (17 mg, 0.1 mmol) was added and the reaction heated to 60° C. for 3 hours. The reaction was cooled to room temperature and diluted with ethyl acetate and water. The organic solution was washed with brine, dried over sodium sulphate and concentrated in vacuum. The crude product was purified by silica gel column chromatography eluting with 5% methanol in ethyl acetate to afford the title compound as white foam (6 mg, 18%). $^1$H-NMR (500 MHz, d$_6$-DMSO): δ 1.5 (m, 2H), 1.6 (m, 2H), 1.75 (m, 4H), 2.97 (s, 6H), 3.11 (m, 1H), 3.89 (s, 3H), 6.77 (s, 1H), 7.33 (dd, J=2 Hz, 8.6 Hz, 1H), 7.48 (d, J=2 Hz, 1H), 7.68 (s, 1H), 7.76 (s, 1H), 8.01 (s, 1H), 8.12 (d, J=8.6 Hz, 1H), 8.51 (s, 1H), 8.7 (s, 1H).

ESI-HRMS Found 527.1621, calculated for $C_{25}H_{27}ClN_6O_3S$ (M+H$^+$): 527.1627. MPS1 IC$_{50}$ (uM): 0.092

Example 111

3-Methoxy-4-((2-(1-methyl-1H-pyrazol-4-yl)-1H-pyrrolo[3,2-c]pyridin-6-yl)amino)-N-(1-methylpiperidin-4-yl)benzamide

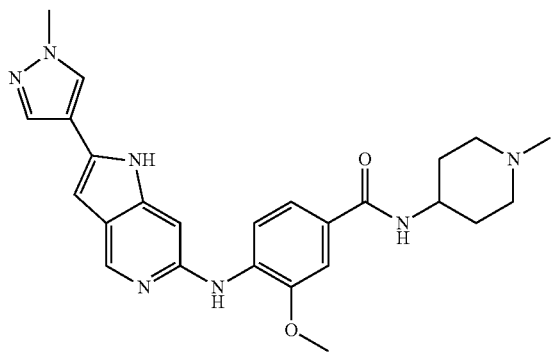 [SMILES: COc1cc(C(=O)NC2CCN(C)CC2)ccc1Nc1cc2[nH]c(-c3cnn(C)c3)cc2cn1]

Method Y tert-Butyl 6-(2-methoxy-4-(1-methylpiperidin-4-ylcarbamoyl)phenylamino)-2-(1-methyl-1H-pyrazol-4-yl)-1H-pyrrolo[3,2-c]pyridine-1-carboxylate (Example 1, 15 mg, 0.027 mmol) in TFA (268 μL) was stirred for 30 minutes at room temperature. The reaction mixture was then concentrated and the residue dissolved in MeOH and filtered through an Isolute Flash NH$_2$ SPE column. The solution was then concentrated under reduced pressure and the residue purified via Biotage silica gel column chromatography eluting with 10% MeOH/aq NH$_3$ 10/1 in DCM to afford the title product as a white solid (12 mg, 97%). $^1$H NMR (500 MHz, CD$_3$OD): δ 1.71 (qd, J=12.6, 3.7 Hz, 2H), 1.94-2.00 (m, 2H), 2.14-2.21 (m, 2H), 2.32 (s, 3H), 2.90-2.96 (m, 2H), 3.87-3.95 (m, 1H), 3.96 (s, 3H), 4.00 (s, 3H), 6.60 (d, J=0.7 Hz, 1H), 7.11 (s, 1H), 7.45 (dd, J=8.4, 1.9 Hz, 1H), 7.50 (d, J=1.9 Hz, 1H), 7.67 (d, J=8.4 Hz, 1H), 7.87 (s, 1H), 7.97 (s, 1H), 8.43 (d, J=0.7 Hz, 1H). ESI-HRMS Found 460.2463, calculated for $C_{25}H_{30}N_7O_2$ (M+H$^+$): 460.2455. MPS1 IC$_{50}$ (uM): 0.042

The following Examples were prepared according to Method Y (Example 111) above using the appropriate precursor at room temperature for between 30 minutes to 3 hours. The crude reaction residues were purified as above and/or according to one of the following methods:

Method A: Biotage silica gel column chromatography eluting with 1-10% MeOH/aq NH$_3$ 10/1 in DCM.

| Example No | Name/Structure | Data | MPS1 IC$_{50}$ (uM) |
|---|---|---|---|
| 112 | N-(2-Methoxypyridin-3-yl)-2-(1-methyl-1H-pyrazol-4-yl)-1H-pyrrolo[3,2-c]pyridin-6-amine | 1H NMR (500 MHz, CD$_3$OD): δ 3.94 (s, 3H), 4.03 (s, 3H), 6.56 (d, J = 0.8 Hz, 1H), 6.88 (dd, J = 7.8, 5.0 Hz, 1H), 6.99 (s, 1H), 7.62 (dd, J = 5.0, 1.6 Hz, 1H), 7.85 (s, 1H), 7.93 (s, 1H), 7.97 (dd, J = 7.8, 1.6 Hz, 1H), 8.39 (d, J = 0.8 Hz, 1H). ESI-HRMS Found 321.1452, calculated for $C_{17}H_{17}N_6O$ [M + H]$^+$: 321.1458. Using Example 2. | 0.021 |
| 113 | N,N-Dimethyl-4-(2-(1-methyl-1H-pyrazol-4-yl)-1H-pyrrolo[3,2-c]pyridin-6-ylamino)-3-(trifluoromethoxy)benzamide | 1H NMR (500 MHz, CD$_3$OD): δ 3.09 (s, 6H), 3.94 (s, 3H), 6.61 (d, J = 0.9 Hz, 1H), 7.10 (t, J = 0.9 Hz, 1H), 7.32 (dd, J = 8.6, 2.0 Hz, 1H), 7.40-7.42 (m, 1H), 7.74 (d, J = 8.6 Hz, 1H), 7.87 (s, 1H), 7.97 (s, 1H), 8.44 (d, J = 0.9 Hz, 1H). ESI-HRMS Found 445.1604, calculated for $C_{21}H_{20}F_3N_6O_2$ [M + H]$^+$: 445.1594. Using Example 3. | 0.068 |

| Example No | Name/Structure | Data | MPS1 IC$_{50}$ (uM) |
|---|---|---|---|
| 114 | 4-Methoxy-N,N-dimethyl-3-(2-(1-methyl-1H-pyrazol-4-yl)-1H-pyrrolo[3,2-c]pyridin-6-ylamino)benzamide 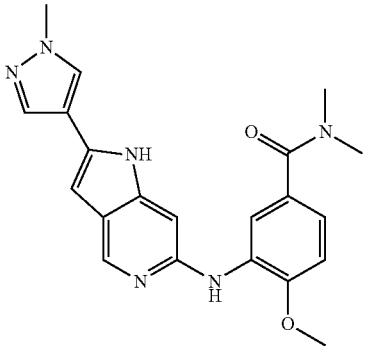 [SMILES: COc1ccc(C(=O)N(C)C)cc1Nc1cc2[nH]c(-c3cnn(C)c3)cc2cn1] | 1H NMR (500 MHz, CD$_3$OD): δ 3.06 (s, 6H), 3.92 (s, 3H), 3.94 (s, 3H), 6.54 (d, J = 0.9 Hz, 1H), 6.96 (dd, J = 8.3, 2.0 Hz, 1H), 7.00 (d, J = 8.3 Hz, 1H), 7.02 (d, J = 0.9 Hz, 1H), 7.72 (d, J = 2.0 Hz, 1H), 7.83 (s, 1H), 7.91 (s, 1H), 8.36 (d, J = 0.9 Hz, 1H). ESI-HRMS Found 391.1884, calculated for C$_{21}$H$_{23}$N$_6$O$_2$ [M + H]$^+$: 391.1877. Using Example 4. | 0.497 |
| 115 | (3-Methoxy-4-(2-(1-methyl-1H-pyrazol-4-yl)-1H-pyrrolo[3,2-c]pyridin-6-ylamino)phenyl)(thiomorpholino)methanone-S,S-dioxide 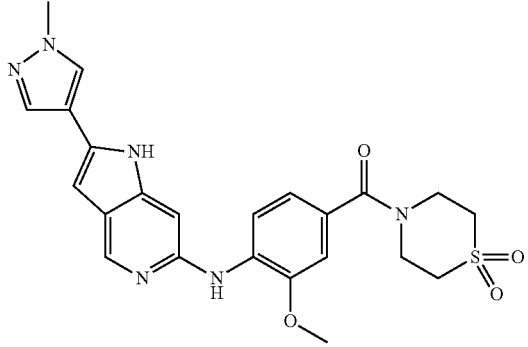 [SMILES: COc1cc(C(=O)N2CCS(=O)(=O)CC2)ccc1Nc1cc2[nH]c(-c3cnn(C)c3)cc2cn1] | 1H NMR (500 MHz, CD$_3$OD): δ 3.21-3.26 (m, 4H), 3.96 (s, 3H), 3.99 (s, 3H), 4.09-4.15 (m, 4H), 6.61 (d, J = 0.9 Hz, 1H), 7.08 (dd, J = 8.2, 1.9 Hz, 1H), 7.10 (m, 1H), 7.16 (d, J = 1.9 Hz, 1H), 7.71 (d, J = 8.2 Hz, 1H), 7.87 (s, 1H), 7.99 (s, 1H), 8.42 (d, J = 0.9 Hz, 1H). ESI-HRMS Found 481.01639, calculated for C$_{23}$H$_{25}$N$_6$O$_4$S [M + H]$^+$: 481.1653. Using Example 5 and purification method A. | 0.007 |
| 116 | N-(2-Methoxy-4-(thiomorpholinomethyl)phenyl)-2-(1-methyl-1H-pyrazol-4-yl)-1H-pyrrolo[3,2-c]pyridin-6-amine-S,S-dioxide 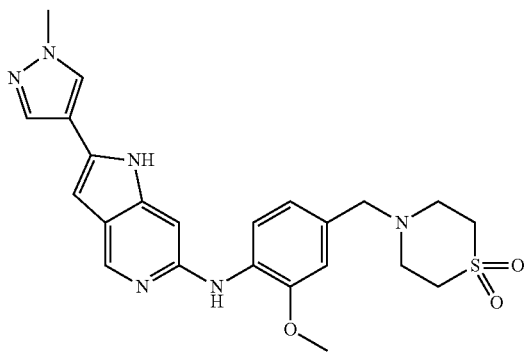 [SMILES: COc1cc(CN2CCS(=O)(=O)CC2)ccc1Nc1cc2[nH]c(-c3cnn(C)c3)cc2cn1] | 1H NMR (500 MHz, CD$_3$OD): δ 2.98-3.02 (m, 4H), 3.11-3.15 (m, 4H), 3.66 (s, 2H), 3.93 (s, 3H), 3.95 (s, 3H), 6.57 (d, J = 0.9 Hz, 1H), 6.89 (dd, J = 8.1, 1.8 Hz, 1H), 7.00 (m, 1H), 7.03 (d, J = 1.8 Hz, 1H), 7.50 (d, J = 8.1 Hz, 1H), 7.84 (s, 1H), 7.96 (s, 1H), 8.34 (d, J = 0.9 Hz, 1H). ESI-HRMS Found 467.1852, calculated for C$_{23}$H$_{27}$N$_6$O$_3$S [M + H]$^+$: 467.1860. Using Example 6 and purification method A. | 0.010 |

| Example No | Name/Structure | Data | MPS1 IC$_{50}$ (uM) |
|---|---|---|---|
| 117 | 3-Chloro-N,N-dimethyl-4-(2-(1-methyl-1H-pyrazol-4-yl)-1H-pyrrolo[3,2-c]pyridin-6-ylamino)benzenesulfonamide 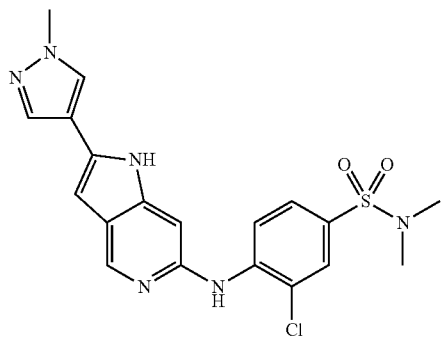 [SMILES: CN(C)S(=O)(=O)c1ccc(Nc2cc3[nH]c(-c4cnn(C)c4)cc3cn2)c(Cl)c1] | 1H NMR (500 MHz, CD$_3$OD): δ 2.68 (s, 6H), 3.96 (s, 3H), 6.67 (d, J = 0.9 Hz, 1H), 7.19 (t, J = 0.9 Hz, 1H), 7.53 (dd, J = 8.8, 2.2 Hz, 1H), 7.68 (d, J = 8.8 Hz, 1H), 7.75 (d, J = 2.2 Hz, 1H), 7.88 (s, 1H), 8.01 (s, 1H), 8.50 (d, J = 0.9 Hz, 1H). ESI-HRMS Found 431.1042, calculated for C$_{19}$H$_{20}$ClN$_6$O$_2$S [M + H]$^+$: 431.1051. Using Example 8. | 0.026 |
| 118 | (3-Methoxy-4-(2-(1-methyl-1H-pyrazol-4-yl)-1H-pyrrolo[3,2-c]pyridin-6-ylamino)phenyl)(morpholino)methanone 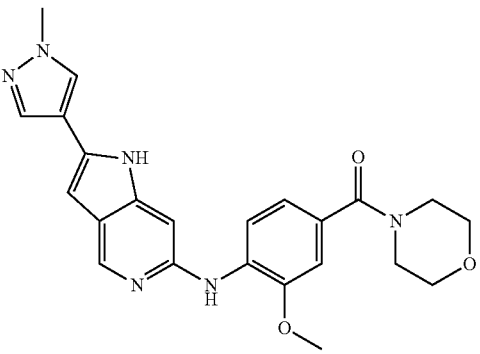 [SMILES: COc1cc(C(=O)N2CCOCC2)ccc1Nc1cc2[nH]c(-c3cnn(C)c3)cc2cn1] | 1H NMR (500 MHz, CD$_3$OD): δ 3.66-3.76 (m, 8H), 3.94 (s, 3H), 3.95 (s, 3H), 6.58 (d, J = 0.8 Hz, 1H), 6.99 (dd, J = 8.2, 1.8 Hz, 1H), 7.06 (s, 1H), 7.07 (d, J = 1.8 Hz, 1H), 7.67 (d, J = 8.2 Hz, 1H), 7.86 (s, 1H), 7.95 (s, 1H), 8.40 (d, J = 0.8 Hz, 1H). ESI-HRMS Found 433.1975, calculated for C$_{23}$H$_{25}$N$_6$O$_3$ [M + H]$^+$: 433.1983. Using Example 10. | 0.012 |
| 119 | 3-Methoxy-N-(2-methoxyethyl)-4-(2-(1-methyl-1H-pyrazol-4-yl)-1H-pyrrolo[3,2-c]pyridin-6-ylamino)benzamide 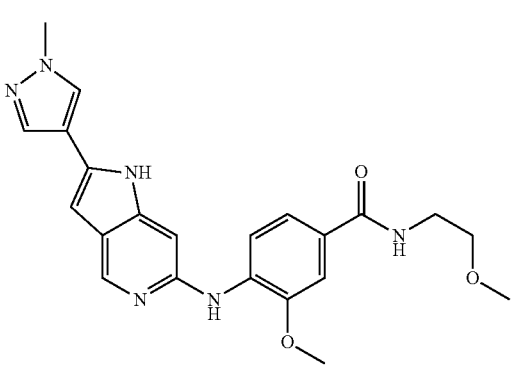 [SMILES: COCCNC(=O)c1ccc(Nc2cc3[nH]c(-c4cnn(C)c4)cc3cn2)c(OC)c1] | 1H NMR (500 MHz, CD$_3$OD): δ 3.40 (s, 3H), 3.57-3.59 (m, 4H), 3.94 (s, 3H), 3.98 (s, 3H), 6.58 (d, J = 0.8 Hz, 1H), 7.06 (t, J = 0.8 Hz, 1H), 7.43 (dd, J = 8.4, 1.9 Hz, 1H), 7.48 (d, J = 1.9 Hz, 1H), 7.66 (d, J = 8.4 Hz, 1H), 7.85 (s, 1H), 7.94 (s, 1H), 8.41 (d, J = 0.9 Hz, 1H). ESI-HRMS Found 421.1985, calculated for C$_{22}$H$_{25}$N$_6$O$_3$ [M + H]$^+$: 421.1983. Using Example 11. | 0.019 |

| Example No | Name/Structure | Data | MPS1 IC$_{50}$ (uM) |
|---|---|---|---|
| 120 | (3-Methoxy-4-(2-(1-methyl-1H-pyrazol-4-yl)-1H-pyrrolo[3,2-c]pyridin-6-ylamino)phenyl)(3-methoxyazetidin-1-yl)methanone | 1H NMR (500 MHz, CD$_3$OD): δ 3.35 (s, 3H), 3.97 (s, 3H), 4.00 (s, 3H), 3.95-4.03 (m, 1H), 4.25-4.40 (m, 3H), 4.58-4.65 (m, 1H), 6.63 (s, 1H), 7.12 (s, 1H), 7.24 (dd, J = 8.4, 1.8 Hz, 1H), 7.31 (d, J = 1.8 Hz, 1H), 7.68 (d, J = 8.4 Hz, 1H), 7.88 (s, 1H), 8.00 (s, 1H), 8.44 (s, 1H). ESI-HRMS Found 433.1980, calculated for C$_{23}$H$_{25}$N$_6$O$_3$ [M + H]$^+$: 433.1983. Using Example 12. | 0.007 |
| 121 | 3,5-Dichloro-N,N-dimethyl-4-(2-(1-methyl-1H-pyrazol-4-yl)-1H-pyrrolo[3,2-c]pyridin-6-ylamino)benzamide | 1H NMR (500 MHz, CD$_3$OD): δ 3.10 (br s, 3H), 3.12 (br s, 3H), 3.95 (s, 3H), 6.57 (d, J = 0.9 Hz, 1H), 6.60 (t, J = 0.9 Hz, 1H), 7.54 (s, 2H), 7.85 (d, J = 0.8 Hz, 1H), 7.96 (d, J = 0.8 Hz, 1H), 8.27 (d, J = 0.9 Hz, 1H). ESI-HRMS Found 429.0986, calculated for C$_{20}$H$_{19}$Cl$_2$N$_6$O [M + H]$^+$: 429.0992. Using Example 13. | 0.091 |
| 122 | N-(2-Chlorophenyl)-2-(1-methyl-1H-pyrazol-4-yl)-1H-pyrrolo[3,2-c]pyridin-6-amine | $^1$H NMR (500 MHz, CD$_3$OD): δ 3.95 (s, 3H), 6.60 (d, J = 0.9 Hz, 1H), 6.90 (ddd, J = 8.0, 7.4, 1.5 Hz, 1H), 7.00 (t, J = 0.9 Hz, 1H), 7.18-7.23 (m, 1H), 7.40 (dd, J = 8.0, 1.5 Hz, 1H), 7.54 (dd, J = 8.2, 1.5 Hz, 1H), 7.85 (s, 1H), 7.96 (s, 1H), 8.39 (d, J = 0.9 Hz, 1H). ESI-HRMS (Method B) Found 324.1007, calculated for C$_{17}$H$_{15}$ClN$_5$ [M + H]$^+$: 324.1010. Using Example 14. | 0.078 |

-continued

| Example No | Name/Structure | Data | MPS1 IC$_{50}$ (uM) |
|---|---|---|---|
| 123 | N-(2-Chlorophenyl)-2-(1-methyl-1H-pyrazol-4-yl)-1H-pyrrolo[3,2-c]pyridin-6-amine | 1H NMR (500 MHz, CD$_3$OD): δ 3.90 (s, 3H), 3.93 (s, 3H), 6.57 (s, 1H), 6.97 (s, 1H), 7.35 (dd, J = 8.5, 1.9 Hz, 1H), 7.53 (d, J = 8.5 Hz, 1H), 7.58 (d, J = 1.9 Hz, 1H), 7.75 (s, 1H), 7.84 (s, 1H), 7.86 (s, 1H), 7.93 (s, 1H), 8.37 (s, 1H). ESI-HRMS (Method B) Found 404.1377, calculated for C$_{21}$H$_{19}$ClN$_7$ [M + H]$^+$: 404.1385. Using Example 15. | 0.018 |
| 124 | N-(2-Chloro-4-(1-methyl-1H-pyrazol-3-yl)phenyl)-2-(1-methyl-1H-pyrazol-4-yl)-1H-pyrrolo[3,2-c]pyridin-6-amine | 1H NMR (500 MHz, CD$_3$OD): δ 3.93 (s, 3H), 3.96 (s, 3H), 6.57 (d, J = 2.3 Hz, 1H), 6.61 (d, J = 0.9 Hz, 1H), 7.05 (t, J = 0.9 Hz, 1H), 7.59 (d, J = 2.3 Hz, 1H), 7.59-7.60 (m, 2H), 7.83 (dd, J = 1.5, 0.9 Hz, 1H), 7.87 (s, 1H), 7.97 (s, 1H), 8.42 (d, J = 0.9 Hz, 1H). ESI-HRMS (Method B) Found 404.1376, calculated for C21H19ClN7 [M + H]$^+$: 404.1385. Using Example 16. | 0.052 |
| 125 | N-(2-Chloro-4-(1-methyl-1H-imidazol-5-yl)phenyl)-2-(1-methyl-1H-pyrazol-4-yl)-1H-pyrrolo[3,2-c]pyridin-6-amine | 1H NMR (500 MHz, CD$_3$OD): δ 3.71 (s, 3H), 3.96 (s, 3H), 6.62 (d, J = 0.9 Hz, 1H), 7.01 (br s, 1H), 7.09 (t, J = 0.9 Hz, 1H), 7.27 (dd, J = 8.5, 2.0 Hz, 1H), 7.49 (d, J = 2.0 Hz, 1H), 7.66 (d, J = 8.5 Hz, 1H), 7.68 (br s, 1H), 7.87 (s, 1H), 7.98 (s, 1H), 8.43 (d, J = 0.9 Hz, 1H). ESI-HRMS (Method B) Found 404.1373, calculated for C$_{21}$H$_{19}$ClN$_7$ [M + H]$^+$: 404.1385. Using Example 17. | 0.004 |

| Example No | Name/Structure | Data | MPS1 IC$_{50}$ (uM) |
|---|---|---|---|
| 126 | N-(3,4-dimethoxyphenyl)-1-methyl-2-(1H-pyrazol-4-yl)-1H-pyrrolo[3,2-c]pyridin-6-amine | 1H NMR (500 MHz, CD$_3$OD): δ 3.68 (s, 3H), 3.83 (s, 3H), 3.84 (s, 3H), 6.54 (d, J = 0.9 Hz, 1H), 6.79 (s, 1H), 6.88 (dd, J = 8.6, 2.4 Hz, 1H), 6.92 (d, J = 8.6 Hz, 1H), 7.02 (d, J = 2.4 Hz, 1H), 7.92 (br s, 2H), 8.34 (d, J = 0.9 Hz, 1H). ESI-HRMS Found 350.1620, calculated for C$_{19}$H$_{20}$N$_5$O$_2$ [M + H]$^+$: 350.1612. Using Preparation 55. | 0.026 |
| 127 | 3-chloro-N,N-dimethyl-4-(2-(1-methyl-1H-pyrazol-4-yl)-1H-pyrrolo[3,2-c]pyridin-6-ylamino)benzamide | $^1$H NMR (500 MHz, CD$_3$OD): δ 3.08 (s, 6H), 3.95 (s, 3H), 6.62 (s, 1H), 7.10 (s, 1H) 7.27 (dd, J = 8.5, 2.0 Hz, 1H), 7.51 (d, J = 2.0 Hz, 1H), 7.61 (d, J = 8.5 Hz, 1H), 7.86 (s, 1H), 7.97 (s, 1H), 8.44 (s, 1H). ESI-HRMS Found 395.1370, calculated for C$_{20}$H$_{20}$ClN$_6$O [M + H]$^+$: 395.1382. Using Example 7. | 0.014 |
| 128 | 3-methoxy-N,N-dimethyl-4-(2-(1-methyl-1H-pyrazol-4-yl)-1H-pyrrolo[3,2-c]pyridin-6-ylamino)benzamide | 1H NMR (500 MHz, CD$_3$OD): δ 3.11 (s, 6H), 3.95 (s, 3H), 3.96 (s, 3H), 6.59 (d, J = 0.8 Hz, 1H), 7.01 (dd, J = 8.2, 1.8 Hz, 1H), 7.06-7.09 (m, 2H), 7.65 (d, J = 8.2 Hz, 1H), 7.85 (s, 1H), 7.95 (s, 1H), 8.40 (d, J = 0.8 Hz, 1H). ESI-HRMS Found 391.1873, calculated for C$_{21}$H$_{23}$N$_6$O$_2$ [M + H]$^+$: 391.1877. Using Example 61. | 0.024 |

Example 129

N-(2-Chloro-4-(1H-1,2,4-triazol-1-yl)phenyl)-2-(1-methyl-1H-pyrazol-4-yl)-1H-pyrrolo[3,2-c]pyridin-6-amine

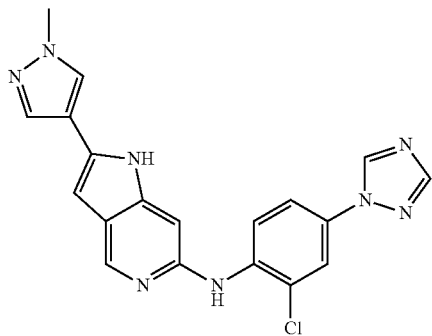 [SMILES: Cn1cc(-c2cc3cnc(Nc4ccc(-n5cncn5)cc4Cl)cc3[nH]2)cn1]

Method Z tert-Butyl 6-(2-chloro-4-(1H-1,2,4-triazol-1-yl)phenylamino)-2-(1-methyl-1H-pyrazol-4-yl)-1H-pyrrolo[3,2-c]pyridine-1-carboxylate (Example 26, 16 mg, 0.033 mmol) was stirred in 2 mL of 50% TFA in dichloromethane for 2 hours. The solvent was removed in vacuo and the residue taken up in dichloromethane (10 mL) and saturated bicarbonate solution (5 mL). The dichloromethane solution was collected, dried over sodium sulphate and filtered. The solvent was removed in vacuo and the residue purified using silica gel column chromatography eluting with dichloromethane:ethylacetate:triethylamine (20:5:1) to afford the title compound as a pale brown solid (4.5 mg, 35.3%). $^1$H-NMR (500 MHz, DMSO-d6): δ 3.9 (s, 3H), 6.56 (s, 1H), 7.08 (s, 1H), 7.38 (s, br, 1H), 7.68 (dd, J=2.3 Hz, 9.1 Hz, 1H), 7.89 (s, 1H), 7.93 (d, J=5 Hz, 1H), 8.11 (s, 1H), 8.12 (s, 1H), 8.19 (s, 1H), 8.41 (s, 1H), 9.21 (s, 1H), 11.43 (s, 1H). ESI-HRMS Found 391.1203, calculated for $C_{19}H_{15}ClN_8$ [M+H]$^+$: 391.1208

MPS1 IC$_{50}$ (uM): 0.055

The following Examples were prepared according to Method Z (Example 129) above using the appropriate precursor at room temperature for between 30 minutes to 3 hours.

The crude reaction residues were purified as above and/or according to one of the following methods:

Method A: Trituration with ether.

Method B: Silica gel column chromatography eluting with ethylacetate:methanol:triethylamine (10:1:1) followed by trituration with ether.

Method C: Isolute Flash NH$_2$ SPE column eluting with 50% methanol in dichloromethane followed by trituration with ether or ether/hexane.

Method D: Isolute Flash NH$_2$ SPE column eluting with 50% methanol in dichloromethane followed by silica gel column chromatography eluting with ethylacetate:methanol:triethylamine (10:1:0.5).

Method E: Isolute Si-carbonate column eluting with methanol followed by preparative TLC eluting with 95% EtOAc/DCM.

Method F: Si-carbonate column—eluting with methanol followed by trituration with ether.

Method G: Isolute Si-carbonate column eluting with methanol followed by preparative TLC eluting with EtOAc/Hexane 80/20.

Method H: Isolute Si-carbonate column eluting with methanol.

Method I: Work-up using EtOAc instead of DCM followed by trituration with ether.

Method J: After removal of solvent from the reaction, the residue was purified using a SCX column eluting with 0.1-0.5-1M ammonia in MeOH followed by trituration with DCM.

Method K: Work-up using EtOAc instead of DCM followed by silica gel column chromatography eluting with ethylacetate/hexane/triethylamine (10/10/2).

Method L: Preparative HPLC eluting with 1/1 acetone/cyclohexane

Method M: Work-up using EtOAc instead of DCM followed by trituration with EtOAc.

Method N: Isolute Si-carbonate column eluting with methanol followed by preparative TLC eluting with 7% MeOH in EtOAc.

Method O: Work up using EtOAc followed by preparative TLC eluting with 10/1 EtOAc/2M ammonia in MeOH to 20/1 EtOH/2M ammonia in MeOH.

Method P: Isolute Flash NH$_2$ SPE column eluting with MeOH.

| Example No | Name/Structure | Data | MPS1 IC$_{50}$ (uM) |
|---|---|---|---|
| 130 | N-(2-Chloro-4-fluorophenyl)-2-(1-methyl-1H-pyrazol-4-yl)-1H-pyrrolo[3,2-c]pyridin-6-amine 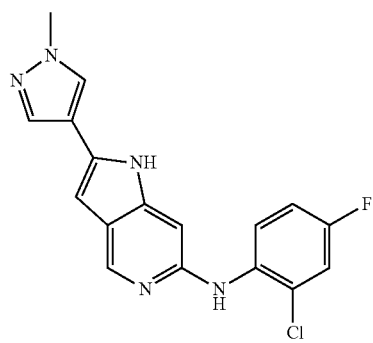 [SMILES: Cn1cc(-c2cc3cnc(Nc4ccc(F)cc4Cl)cc3[nH]2)cn1] | $^1$H NMR (500 MHz, d$^6$-DMSO): δ 3.88 (s, 3H), 6.5 (s, 1H), 6.97 (s, 1H), 7.16 (m, 1H), 7.42 (m, 1H), 7.86 (m, 2H), 7.95 (m, 1H), 8.07 (s, 1H), 8.36 (s, 1H), 11.3 (s, 1H). ESI-HRMS Found 342.0958 calculated for $C_{19}H_{15}ClN_8$ [M + H]$^+$: 342.0916 Using Example 27 and purification method A. | 0.51 |

-continued

| Example No | Name/Structure | Data | MPS1 IC$_{50}$ (uM) |
|---|---|---|---|
| 131 | N-(2-Chloro-4-(methylsulfonyl)phenyl)-2-(1-methyl-1H-pyrazol-4-yl)-1H-pyrrolo[3,2-c]pyridin-6-amine | $^1$H-NMR (500 MHz, d$^6$-DMSO): δ 3.18 (s, 3H), 3.9 (s, 3H), 6.6 (s, 1H), 7.23 (s, 1H), 7.67 (d, J = 8.9 Hz, 1H), 7.86 (s, 1H), 7.91 (s, 1H), 8.13 (s, 1H), 8.22 (d, J = 8.9 Hz, 1H), 8.48 (s, 1H), 8.51 (s, 1H), 11.58 (s, 1H); ESI-HRMS Found 402.0729, calculated for C$_{18}$H$_{16}$ClN$_5$O$_2$S [M + H]$^+$: 342.0786 Using Example 28 and purification method A. | 0.024 |
| 132 | N-(2-Chloro-4-(difluoromethoxy)phenyl)-2-(1-methyl-1H-pyrazol-4-yl)-1H-pyrrolo[3,2-c]pyridin-6-amine | $^1$H NMR (500 MHz, CDCl$_3$): δ 3.94 (s, 3H), 6.44 (t, J = 74 Hz, 1H), 6.52 (s, 1H), 6.58 (s, 1H), 6.9 (s, 1H), 6.95 (dd, J = 2.7 Hz, 9 Hz, 1H), 7.2 (d, J = 2.7 Hz, 1H), 7.78 (m, 3H), 8.53 (s, 1H), 9.49 (s, 1H). ESI-HRMS Found 390.0935, calculated for C$_{18}$H$_{15}$ClF$_2$N$_5$O [M + H]$^+$: 390.0928 Using Example 29 and purification method A. | 0.288 |
| 133 | 3-Methoxy-N-methyl-4-(2-(1-methyl-1H-pyrazol-4-yl)-1H-pyrrolo[3,2-c]pyridin-6-ylamino)benzamide | $^1$H NMR (500 MHz, d$^6$-DMSO): δ 2.78 (d, J = 4.5 Hz, 3H), 3.89 (s, 3H), 3.98 (s, 3H), 6.54 (s, 1H), 7.09 (s, 1H), 7.39 (s, 1H), 7.41 (s, 1H), 7.45 (m, 1H), 7.89 (s, 1H), 8.1 (s, 1H), 8.15 (s, br, 1H), 8.26 (s, br, 1H), 8.42 (s, 1H), 11.4 (s, 1H). ESI-HRMS Found 377.1232 calculated for C$_{20}$H$_{20}$N$_6$O$_2$ [M + H]$^+$: 377.1235 Using Example 30 and purification method B. | 0.027 |

| Example No | Name/Structure | Data | MPS1 IC$_{50}$ (uM) |
|---|---|---|---|
| 134 | 3-Chloro-N-methyl-4-(2-(1-methyl-1H-pyrazol-4-yl)-1H-pyrrolo[3,2-c]pyridin-6-ylamino)benzamide | $^1$H-NMR (500 MHz, d$^6$-DMSO): δ 3.16 (d, J = 5 Hz, 3H), 3.89 (s, 3H), 4.1 (q, br, 1H), 6.57 (s, 1H), 7.14 (s, 1H), 7.7 (dd, J = 2 Hz, 8.1 Hz, 1H), 7.88 (m, 2H), 8.08 (m, 1H), 8.15 (s, 1H), 8.3 (s, br, 1H), 8.44 (s, 1H), 11.5 (s, 1H). ESI-HRMS Found 381.0713 calculated for C$_{19}$H$_{17}$ClN$_6$O [M + H]$^+$: 381.0711. Using Example 31 and purification method C. | 0.020 |
| 135 | 2-(4-(6-(2,4-Dimethoxyphenylamino)-1H-pyrrolo[3,2-c]pyridin-2-yl)-1H-pyrazol-1-yl)-N,N-dimethylacetamide | $^1$H-NMR (500 MHz, d$^6$-DMSO): δ 2.86 (s, 1H), 2.94 (s, 3H), 3.74 (s, 3H), 3.81 (s, 3H), 5.15 (s, 2H), 6.48 (s, 1H), 6.5 (s, 1H), 6.62 (d, J = 2.7 Hz, 1H), 6.66 (s, 1H), 7.22 (s, 1H), 7.72 (d, J = 8.7 Hz, 1H), 7.84 (s, 1H), 8 (s, 1H), 8.28 (s, 1H), 11.2 (s, 1H). ESI-HRMS Found 421.1959 calculated for C$_{22}$H$_{24}$N$_6$O$_3$ [M + H]$^+$: 421.1983 Using Example 69 and purification method C. | 0.821 |
| 136 | 1-(3-chloro-4-((2-(1-methyl-1H-pyrazol-4-yl)-1H-pyrrolo[3,2-c]pyridin-6-yl)amino)phenyl)pyrrolidin-2-one | $^1$H-NMR (500 MHz, d$^6$-DMSO): δ 2.04 (m, 2H), 2.47 (t, J = 8.3 Hz, 2H), 3.82 (t, J = 7 Hz, 2H), 3.88 (s, 3H), 6.52 (s, 1H), 6.89 (s, 1H), 7.1 (m, 1H), 7.42 (d, J = 9 Hz, 1H), 7.86 (m, 2H), 7.9 (d, J = 9 Hz, 1H), 8.08 (s, 1H), 8.35 (s, 1H), 11.35 (s, 1H). ESI-HRMS Found 407.1371 calculated for C$_{21}$H$_{19}$ClN$_6$O [M + H]$^+$: 407.1382 Using Example 32 and purification method C. | 0.018 |

| Example No | Name/Structure | Data | MPS1 IC$_{50}$ (uM) |
|---|---|---|---|
| 137 | N-(2-methoxy-4-(pyrrolidin-1-ylmethyl)phenyl)-2-(1-methyl-1H-pyrazol-4-yl)-1H-pyrrolo[3,2-c]pyridin-6-amine | $^1$H-NMR (500 MHz, d$^6$-DMSO): δ 1.68 (t, J = 3.3 Hz, 4H), 2.43 (s, br, 4H), 3.5 (s, 2H), 3.84 (s, 3H), 3.88 (s, 3H), 6.48 (s, 1H), 6.8 (d, J = 8.1 Hz, 1H), 6.9 (m, 2H), 7.46 (s, 1H), 7.85 (s, 1H), 7.94 (d, J = 8.1 Hz, 1H), 8.06 (s, 1H), 8.34 (s, 1H), 11.25 (s, 1H). ESI-HRMS Found 403.2236 calculated for C$_{28}$H$_{34}$N$_6$O$_3$ [M + H]$^+$: 403.2241 Using Example 33 and purification method C | 0.025 |
| 138 | N-(2-methoxy-4-((methylamino)methyl)phenyl)-2-(1-methyl-1H-pyrazol-4-yl)-1H-pyrrolo[3,2-c]pyridin-6-amine | $^1$H NMR (500 MHz, d$^6$-DMSO): δ 2.15 (s, br, 1H), 2.27 (s, 3H), 3.57 (s, 2H), 3.84 (s, 3H), 3.88 (s, 3H), 6.48 (s, 1H), 6.8 (d, J = 8 Hz, 1H), 6.88 (s, 1H), 6.95 (d, J = 1.4 Hz, 1H), 7.43 (s, 1H), 7.85 (s, 1H), 7.92 (d, J = 8 Hz, 1H), 8.06 (s, 1H), 8.33 (s, 1H), 11.2 (s, 1H). ESI-HRMS Found 363.1924, calculated for C$_{20}$H$_{22}$N$_6$O [M + H]$^+$: 363.1928. Using Example 34 and purification method C. | 0.031 |
| 139 | N-(4-((dimethylamino)methyl)-2-methoxyphenyl)-2-(1-methyl-1H-pyrazol-4-yl)-1H-pyrrolo[3,2-c]pyridin-6-amine | $^1$H-NMR (500 MHz, d$^6$-DMSO): δ 2.35 (s, br, 6H), 3.6 (s, br, 2H), 3.86 (s, 3H), 3.88 (s, 3H), 6.47 (s, 1H), 6.55 (s, 1H), 6.82 (s, 1H), 6.95 (m, 2H), 7.64 (s, 1H), 7.85 (s, 1H), 8.1 (m, 2H), 8.36 (s, 1H), 11.25 (s, 1H). ESI-HRMS Found 377.2078, calculated for C$_{21}$H$_{24}$N$_6$O [M + H]$^+$: 377.2084 Using Example 35 and purification method D. | 0.055 |

-continued

| Example No | Name/Structure | Data | MPS1 IC$_{50}$ (uM) |
|---|---|---|---|
| 140 | N-(4-(Aminomethyl)-2-methoxyphenyl)-2-(1-methyl-1H-pyrazol-4-yl)-1H-pyrrolo[3,2-c]pyridin-6-amine | $^1$H-NMR (500 MHz, d$^6$-DMSO): δ 3.66 (s, 2H), 3.85 (s, 3H), 3.88 (s, 3H), 6.48 (s, 1H), 6.8 (d, J = 8.2 Hz, 1H), 6.87 (s, 1H), 7 (s, 1H), 7.41 (s, 1H), 7.85 (s, 1H), 7.9 (d, J = 8.1 Hz, 1H), 8.06 (s, 1H), 8.33 (s, 1H), 11.25 (s, 1H). ESI-HRMS Found 371.1594, calculated for C$_{19}$H$_{20}$N$_6$O [M + H]$^+$: 371.1591 Using Preparation 131 and purification method C. | 0.043 |
| 141 | 2-(3-(2-(1-Methyl-1H-pyrazol-4-yl)-1H-pyrrolo[3,2-c]pyridin-6-ylamino)phenoxy)acetonitrile | $^1$H-NMR (500 MHz, d6-DMSO): δ 3.89 (s, 3H), 5.1 (s, 2H), 6.51 (m, 2H), 6.8 (s, 1H), 7.17 (m, 2H), 7.48 (s, 1H), 7.86 (s, 1H), 8.07 (s, 1H), 8.39 (s, 1H), 8.73 (s, 1H), 11.3 (s, 1H). ESI-HRMS Found 345.1984, calculated for C$_{19}$H$_{16}$N$_6$O [M + H]$^+$: 345.1983 Using Example 36 and purification method C. | 0.132 |
| 142 | (3-Chloro-4-(2-(1-methyl-1H-pyrazol-4-yl)-1H-pyrrolo[3,2-c]pyridin-6-ylamino)phenyl)(3-methoxyazetidin-1-yl)methanone | $^1$H-NMR (500 MHz, d$^6$-DMSO): δ 3.22 (s, 3H), 3.89 (s, 3H), 4.23 (m, 4H), 4.5 (s, br., 1H), 6.57 (s, 1H), 7.16 (s, 1H), 7.49 (dd, J = 2.1 Hz, 8.4 Hz, 1H), 7.65 (d, J = 2.1 Hz, 1H), 7.9 (s, 1H), 8.11 (s, 1H), 8.13 (d, J = 2.1 Hz, 1H), 8.21 (s, 1H), 8.44 (s, 1H), 11.55 (s, 1H). ESI-HRMS Found 437.1757, calculated for C$_{22}$H$_{21}$ClN$_6$O$_2$ [M + H]$^+$: 437.1772 Using Example 37 and purification method C. | 0.010 |

-continued

| Example No | Name/Structure | Data | MPS1 IC$_{50}$ (uM) |
|---|---|---|---|
| 143 | (3-Chloro-4-(2-(1-methyl-1H-pyrazol-4-yl)-1H-pyrrolo[3,2-c]pyridin-6-ylamino)phenyl)(S,S-dioxo-thiomorpholino)methanone | $^1$H-NMR (500 MHz, d$^6$-DMSO): δ 3.22 (s, 3H), 3.89 (s, 3H), 4.23 (m, 4H), 4.5 (s, br., 1H), 6.57 (s, 1H), 7.16 (s, 1H), 7.49 (dd, J = 2.1 Hz, 8.4 Hz, 1H), 7.65 (d, J = 2.1 Hz, 1H), 7.9 (s, 1H), 8.11 (s, 1H), 8.13 (d, J = 2.1 Hz, 1H), 8.21 (s, 1H), 8.44 (s, 1H), 11.55 (s, 1H). ESI-HRMS Found 437.1757, calculated for C$_{22}$H$_{21}$ClN$_6$O$_2$ [M + H]$^+$: 437.1772 Using Example 38 and purification method C. | 0.006 |
| 144 | 3-Chloro-N-ethyl-N-methyl-4-(2-(1-methyl-1H-pyrazol-4-yl)-1H-pyrrolo[3,2-c]pyridin-6-ylamino)benzamide | $^1$H-NMR (500 MHz, d$^6$-DMSO): δ 1.1 (t, J = 7.1 Hz, 3H), 2.94 (s, 3H), 3.37 (q, J = 7.1 Hz, 2H), 3.89 (s, 3H), 6.56 (s, 1H), 7.1 (s, 1H), 7.24 (d, J = 8.3 Hz, 1H), 7.42 (s, 1H), 7.89 (s, 1H), 8.08 (m, 3H), 8.42 (s, 1H), 11.45 (s, 1H). ESI-HRMS Found 409.1537 calculated for C$_{21}$H$_{21}$ClN$_6$O [M + H]$^+$: 409.1538 Using Example 39 and purification method C. | 0.011 |
| 145 | (3-Chloro-4-(2-(1-methyl-1H-pyrazol-4-yl)-1H-pyrrolo[3,2-c]pyridin-6-ylamino)phenyl)(pyrrolidin-1-yl)methanone | $^1$H-NMR (500 MHz, d$^6$-DMSO): δ 1.83 (s, br, 4H), 3.45 (s, br, 4H), 3.89 (s, 3H), 6.56 (s, 1H), 7.12 (s, 1H), 7.42 (d, J = 8.1 Hz, 1H), 7.56 (s, 1H), 7.89 (s, 1H), 8.1 (m, 3H), 8.43 (s, 1H), 11.5 (s, 1H). ESI-HRMS Found 421.1535 calculated for C$_{22}$H$_{21}$ClN$_6$O [M + H]$^+$: 421.1538 Using Example 40 and purification method C. | 0.012 |

| Example No | Name/Structure | Data | MPS1 IC$_{50}$ (uM) |
|---|---|---|---|
| 146 | (3-Chloro-4-(2-(1-methyl-1H-pyrazol-4-yl)-1H-pyrrolo[3,2-c]pyridin-6-ylamino)phenyl)(4-methylpiperazin-1-yl)methanone | $^1$H NMR (500 MHz, d$^6$-DMSO): δ 2.16 (s, 3H), 2.31 (s, br, 4H), 3.5 (s, br,, 4H), 3.89 (s, 3H), 6.56 (s, 1H), 7.11 (s, 1H), 7.23 (m, 2H), 7.43 (s, 1H), 7.89 (s, 1H), 8.09 (m, 2H), 8.42 (s, 1H), 8.5 (s, 1H), 11.5 (s, 1H); ESI-HRMS Found 450.1888 calculated for C$_{23}$H$_{24}$ClN$_7$O [M + H]$^+$: 450.1881<br>Using Example 41 and purification method C. | 0.020 |
| 147 | (3-Chloro-4-(2-(1-methyl-1H-pyrazol-4-yl)-1H-pyrrolo[3,2-c]pyridin-6-ylamino)phenyl)(4-methoxypiperidin-1-yl)methanone | $^1$H NMR (500 MHz, d$^6$-DMSO): δ 1.46 (s, br, 2H), 1.85 (s, br,, 2H), 3.26 (s, br, 4H), 3.29 (s, 3H), 3.46 (s, br, 1H), 3.9 (s, 3H), 6.57 (s, 1H), 7.11 (s, 1H), 7.43 (d, J = 1.9 Hz, 1H), 7.89 (s, 1H), 8.1 (m, 3H), 8.42 (s, 1H), 11.5 (s, 1H). ESI-HRMS (Method D) Found 465.1789 calculated for C$_{24}$H$_{25}$ClN$_6$O$_2$ [M + H]$^+$: 465.18<br>Using Example 42 and purification method C. | 0.012 |
| 148 | (3-Chloro-4-(2-(1-methyl-1H-pyrazol-4-yl)-1H-pyrrolo[3,2-c]pyridin-6-ylamino)phenyl)(4-(dimethylamino)piperidin-1-yl)methanone | $^1$H-NMR (500 MHz, d$^6$-DMSO): δ 1.35 (m, 2H), 1.75 (s, br, 2H), 2.16 (s, 6H), 2.32 (t, J = 7 Hz, 1H), 2.9 (s, br, 2H), 3.9 (s, 3H), 4.05 (s, br, 2H), 6.57 (s, 1H), 7.11 (s, 1H), 7.28 (d, J = 8.2 Hz, 1H), 7.43 (d, J = 2 Hz, 1H), 7.89 (s, 1H), 8.09 (m, 3H), 8.42 (s, 1H), 11.45 (s, 1H). ESI-HRMS Found 478.2099, calculated for C$_{25}$H$_{28}$ClN$_7$O [M + H]$^+$: 478.2117<br>Using Example 43 and purification method C. | 0.020 |

-continued

| Example No | Name/Structure | Data | MPS1 IC$_{50}$ (uM) |
|---|---|---|---|
| 149 | N-(2-Chloro-4-(1-methyl-1H-pyrazol-5-yl)phenyl)-2-(1-methyl-1H-pyrazol-4-yl)-1H-pyrrolo[3,2-c]pyridin-6-amine | $^1$H-NMR (500 MHz, d$^6$-DMSO): δ 3.87 (s, 3H), 3.9 (s, 3H), 6.39 (d, J = 1.8 Hz, 1H), 6.56 (s, 1H), 7.44 (d, J = 1.9 Hz, 1H), 7.56 (s, 1H), 7.89 (s, 1H), 8.09 (s, 1H), 8.11 (s, 1H), 8.16 (d, J = 8.6 Hz, 1H), 8.42 (s, 1H), 11.45 (s, 1H). ESI-HRMS Found 404.1375 calculated for C$_{21}$H$_{18}$ClN$_7$ [M + H]$^+$: 404.1385 Using Example 44 and purification method C. | 0.022 |
| 150 | N-(2-Chloro-4-(2,4-dimethylthiazol-5-yl)phenyl)-2-(1-methyl-1H-pyrazol-4-yl)-1H-pyrrolo[3,2-c]pyridin-6-amine | $^1$H-NMR (500 MHz, d$^6$-DMSO): δ 2.38 (s, 3H), 2.61 (s, 3H), 3.89 (s, 3H), 6.55 (s, 1H), 7.08 (s, 1H), 7.32 (d, J = 8.5 Hz, 1H), 7.44 (d, J = 2.2 Hz, 1H), 7.89 (s, 1H), 8.06 (s, 1H), 8.11 (s, 1H), 8.12 (s, 1H), 8.41 (s, 1H), 11.45 (s, 1H). ESI-HRMS Found 435.1159 calculated for C$_{22}$H$_{19}$ClN$_6$S [M + H]$^+$: 435.1153 Using Example 45 and purification method C. | 0.114 |
| 151 | N-(2-Chloro-4-(2-methoxypyridin-4-yl)phenyl)-2-(1-methyl-1H-pyrazol-4-yl)-1H-pyrrolo[3,2-c]pyridin-6-amine | $^1$H-NMR (500 MHz, d$^6$-DMSO): δ 3.89 (s, 3H), 3.9 (s, 3H), 6.57 (s, 1H), 7.11 (s, 1H), 7.13 (s, 1H), 7.32 (d, J = 2.2 Hz, 1H), 7.7 (d, J = 2.2 Hz 1H), 7.9 (s, 1H), 8.12 (d, J = 10 Hz, 1H), 8.17 (s, 1H), 8.2 (s, 1H), 8.44 (s, 1H), 11.46 (s, 1H). ESI-HRMS Found 431.1315 calculated for C$_{23}$H$_{19}$ClN$_6$O [M + H]$^+$: 431.1312 Using Example 46 and purification method C. | 0.182 |

| Example No | Name/Structure | Data | MPS1 IC$_{50}$ (uM) |
|---|---|---|---|
| 152 | N-(2-Chloro-4-(1,2-dimethyl-1H-imidazol-5-yl)phenyl)-2-(1-methyl-1H-pyrazol-4-yl)-1H-pyrrolo[3,2-c]pyridin-6-amine | $^1$H-NMR (500 MHz, d$^6$-DMSO): δ 2.34 (s, 3H), 3.53 (s, 3H), 3.89 (s, 3H), 6.55 (s, 1H), 6.85 (s, 1H), 7.05 (s, 1H), 7.26 (d, J = 8.6 Hz, 1H), 7.44 (s, 1H), 7.88 (s, 1H), 8 (s, 1H), 8.09 (d, J = 8.6 Hz, 1H), 8.1 (s, 1H), 8.4 (s, 1H), 11.4 (s, 1H). ESI-HRMS Found 418.1531 calculated for C$_{22}$H$_{20}$ClN$_7$ [M + H]$^+$: 418.1541 Using Example 47 and purification method C. | 0.005 |
| 153 | (3-Chloro-4-((2-(1-methyl-1H-pyrazol-4-yl)-1H-pyrrolo[3,2-c]pyridin-6-yl)amino)phenyl)(3,3-difluoroazetidin-1-yl)methanone | $^1$H-NMR (500 MHz, DMSO-d$_6$): δ 3.90 (s, 3H), 4.60 (br s, 4H), 6.59 (s, 1H), 7.19 (s, 1H), 7.54 (dd, J = 2.2, 8.8 Hz, 1H), 7.71 (d, J = 2.0 Hz, 1H), 7.90 (s, 1H), 8.12 (s, 1H), 8.16 (d, J = 8.5 Hz, 1H), 8.28 (s, 1H), 8.46 (s, 1H), 11.52 (s, 1H). ESI-HRMS: Found 465.1006; calculated for C$_{21}$H$_{17}$ClF$_2$N$_6$ONa [M + Na]$^+$: 465.1013. Using Example 50 and purification method E. | 0.021 |
| 154 | N-(2-chloro-4-(methylsulfonyl)phenyl)-2-(1H-pyrazol-4-yl)-1H-pyrrolo[3,2-c]pyridin-6-amine | $^1$H-NMR (500 MHz, DMSO-d$^6$): δ 3.18 (s, 3H), 6.63 (s, 1H), 7.22 (s, 1H), 7.67 (dd, J = 2.2, 8.9 Hz, 1H), 7.85 (d, J = 2.2 Hz, 1H), 8.09 (br s, 2H), 8.22 (d, J = 9.0 Hz, 1H), 8.47 (s, 1H), 8.50 (br s, 1H). ESI-HRMS: Found 388.0620, calculated for C$_{17}$H$_{15}$ClN$_5$O$_2$S [M + H]$^+$: 388.0629. Using Preparation 165 and purification method F. | 0.002 |

-continued

| Example No | Name/Structure | Data | MPS1 IC$_{50}$ (uM) |
|---|---|---|---|
| 155 | N-(2-Fluoro-4-methoxyphenyl)-2-(1-methyl-1H-pyrazol-4-yl)-1H-pyrrolo[3,2-c]pyridin-6-amine | $^1$H-NMR (500 MHz, DMSO-d$^6$): δ 3.74 (s, 3H), 3.87 (s, 3H), 6.46 (d, J = 1.0 Hz, 1H), 6.62 (s, 1H), 6.73 (dd, J = 2.5, 8.9 Hz, 1H), 6.86 (dd, J = 2.8, 10.1 Hz, 1H), 7.76 (t, J = 9.4 Hz, 1H), 7.83 (s, 1H), 7.87 (s, 1H), 8.04 (s, 1H), 8.28 (s, 1H), 11.14 (s, 1H). ESI-HRMS: Found 338.1407, calculated for C$_{18}$H$_{17}$FN$_5$O [M + H]$^+$: 338.1412. Using Example 56 and purification method C. | 0.053 |
| 156 | N-(2-Methoxy-4-(trifluoromethyl)phenyl)-2-(1-methyl-1H-pyrazol-4-yl)-1H-pyrrolo[3,2-c]pyridin-6-amine | $^1$H-NMR (500 MHz, DMSO-d$^6$): δ 3.88 (s, 3H), 3.96 (s, 3H), 6.54 (s, 1H), 7.13 (s, 1H), 7.18 (s, 1H), 7.20 (d, J = 9.2 Hz, 1H), 7.89 (s, 1H), 8.10 (s, 1H), 8.11 (s, 1H), 8.43 (s, 1H), 8.47 (d, J = 8.6 Hz, 1H), 11.41 (s, 1H). ESI-HRMS: Found 388.1387, calculated for C$_{19}$H$_{17}$F$_3$N$_5$O [M + H]$^+$: 388.1380. Using Example 57 and purification method G. | 0.164 |
| 157 | N-(4-Fluoro-2-methoxyphenyl)-2-(1-methyl-1H-pyrazol-4-yl)-1H-pyrrolo[3,2-c]pyridin-6-amine | $^1$H-NMR (500 MHz, DMSO-d$^6$): δ 3.86 (s, 3H), 3.88 (s, 3H), 6.48 (s, 1H), 6.70 (td, J = 2.6, 8.6 Hz, 1H), 6.84 (s, 1H), 6.92 (dd, J = 3.2, 11.2 Hz, 1H), 7.51 (s, 1H), 7.85 (d, J = 0.6 Hz, 1H), 8.04 (dd, J = 6.5, 8.6 Hz, 1H), 8.06 (s, 1H), 8.32 (s, 1H), 11.22 (s, 1H). ESI-HRMS: Found 338.1408. calculated for C$_{18}$H$_{17}$FN$_5$O [M + H]$^+$: 338.1412. Using Example 58 and purification method H. | 0.119 |

| Example No | Name/Structure | Data | MPS1 IC$_{50}$ (uM) |
|---|---|---|---|
| 158 | N-(4-Methoxyphenyl)-2-(1H-pyrazol-4-yl)-1H-pyrrolo[3,2-c]pyridin-6-amine | $^{1}$H-NMR (d$^{4}$-MeOH, 500 MHz): δ 3.80 (s, 3H), 6.57 (d, J = 0.95 Hz, 1H), 6.75 (m, 1H), 6.91 (d, J = 8.83 Hz, 1H), 7.22 (d, J = 8.83 Hz, 2H), 7.97 (br s, 2H), 8.28 (d, J = 0.95 Hz, 1H). ESI-HRMS Found 306.1375, calculated for C$_{17}$H$_{16}$N$_{5}$O [M + H]$^{+}$: 306.1349. Using Preparation 35 and purification method I. | 0.035 |
| 159 | N-(2-Methoxyphenyl)-2-(1H-pyrazol-4-yl)-1H-pyrrolo[3,2-c]pyridin-6-amine | $^{1}$H-NMR (d$^{4}$-MeOH, 500 MHz): δ 3.92 (s, 3H), 6.61 (d, J = 0.95 Hz, 1H), 6.91-6.97 (m, 2H), 7.00-7.03 (m, 2H), 7.51 (dd, J = 1.89, 7.57 Hz, 1H), 8.00 (br s, 2H), 8.35 (d, J = 0.95 Hz, 1H). ESI-HRMS Found 307.1384, calculated for C$_{17}$H$_{17}$N$_{5}$O [M + 2H]$^{2+}$: 307.1422 Using Preparation 40 and purification method I. | 0.017 |
| 160 | N-(2,4-Dimethoxyphenyl)-2-(1H-pyrazol-4-yl)-1H-pyrrolo[3,2-c]pyridin-6-amine | $^{1}$H-NMR (d$^{6}$-DMSO, 500 MHz): δ 3.75 (s, 3H), 3.81 (s, 3H), 6.47-6.51 (m, 2H), 6.62 (d, J = 2.52 Hz, 1H), 6.66 (s, 1H), 7.18 (s, 1H), 7.72 (d, J = 8.83 Hz, 1H), 7.90 (br s, 1H), 8.10 (br s, 1H), 8.28 (s, 1H), 11.08 (br s, 1H, NH), 12.95 (br s, 1H, NH). ESI-HRMS Found 336.1456, calculated for C$_{18}$H$_{18}$N$_{5}$O$_{2}$ [M + H]$^{+}$: 336.1455 Using Preparation 41 and purification method I. | 0.019 |
| 161 | 2-(1H-Pyrazol-4-yl)-N-(4-(trifluoromethyl)phenyl)-1H-pyrrolo[3,2-c]pyridin-6-amine | $^{1}$H-NMR (d$^{6}$-DMSO, 500 MHz): δ 6.57 (d, J = 0.95 Hz, 1H), 6.87 (s, 1H), 7.52 (d, J = 8.51 Hz, 2H), 7.76 (d, J = 8.51 Hz, 2H), 7.95 (br s, 1H), 8.16 (br s, 1H). 8.44 (s, 1H), 9.10 (s, 1H), 11.32 (br s, 1H, NH), 13.00 (br s, 1H, NH). 19F-NMR (CDCl3): δ −59.34. ESI-HRMS Found 344.1112, calculated for C$_{17}$H$_{13}$F$_{3}$N$_{5}$ [M + H]$^{+}$: 344.1118 Using Preparation 42 and purification method I. | 1.065 |

-continued

| Example No | Name/Structure | Data | MPS1 IC$_{50}$ (uM) |
|---|---|---|---|
| 162 | N-(3,4-Dimethoxyphenyl)-2-(1H-pyrazol-4-yl)-1H-pyrrolo[3,2-c]pyridin-6-amine | $^1$H-NMR (d$^6$-DMSO, 500 MHz): δ 3.74 (s, 3H), 3.74 (s, 3H), 6.50 (s, 1H), 6.72 (s, 1H), 6.84 (d, J = 8.83 Hz, 1H), 7.06 (dd, J = 2.21, 8.51 Hz, 1H), 7.21 (d, J = 2.52 Hz, 1H), 8.01 (s, 1H), 8.25 (s, 1H), 8.33 (s, 1H), 11.11 (br s, 1H, NH), 12.96 (br s, 1H, NH). ESI-HRMS Found 336.1468, calculated for C$_{18}$H$_{18}$N$_5$O$_2$ [M + H]$^+$: 336.1455 Using Preparation 43 and purification method I. | 0.024 |
| 163 | N-(2-Chloro-4-methoxyphenyl)-2-(1H-pyrazol-4-yl)-1H-pyrrolo[3,2-c]pyridin-6-amine | $^1$H-NMR (d$^6$-DMSO, 500 MHz): δ 3.76 (s, 3H), 6.51 (m, 1H), 6.65 (m, 1H), 6.89 (dd, J = 2.84, 8.83 Hz, 1H), 7.05 (d, J = 2.84 Hz, 1H), 7.60 (s, 1H), 7.69 (d, J = 8.83 Hz, 1H), 7.91 (br s, 1H), 8.12 (br s, 1H), 8.29 (s, 1H), 11.15 (br s, 1H, NH), 12.96 (br s, 1H, NH). ESI-HRMS Found 340.0971, calculated for C$_{17}$H$_{15}$ClN$_5$O [M + H]$^+$: 340.0960. Using Preparation 44 and purification method I. | 0.012 |
| 164 | 2-(1H-Pyrazol-4-yl)-N-(2-(trifluoromethyl)phenyl)-1H-pyrrolo[3,2-c]pyridin-6-amine | $^1$H-NMR (d$^6$-DMSO, 500 MHz): δ 6.56 (m, 1H), 6.92 (s, 1H), 7.09 (t, J = 7.88 Hz, 1H), 7.51 (t, J = 7.57 Hz, 1H), 7.55 (s, 1H), 7.62 (dd, J = 1.58, 7.88 Hz, 1H), 7.70 (d, J = 8.20 Hz, 1H), 7.94 (br s, 1H), 8.15 (br s, 1H), 8.35 (s, 1H), 11.32 (br s, 1H, NH), 12.99 (br s, 1H, NH). 19F-NMR (d6-DMSO): δ −59.50. ESI-HRMS Found 344.1124, calculated for C$_{17}$H$_{13}$F$_3$N$_5$ [M + H]$^+$: 344.1118 Using Preparation 45 and purification method I. | 0.512 |
| 165 | N-(2-Ethoxyphenyl)-2-(1H-pyrazol-4-yl)-1H-pyrrolo[3,2-c]pyridin-6-amine | $^1$H-NMR (d$^6$-DMSO, 500 MHz): δ 1.40 (t, J = 6.94 Hz, 3H), 4.11 (q, J = 6.94 Hz, 2H), 6.54 (m, 1H), 6.79-6.89 (m, 2H), 6.94 (m, 1H), 6.97 (dd, J = 1.58, 7.88 Hz, 1H), 7.35 (s, 1H), 7.95 (dd, J = 1.89, 7.88 Hz, 1H) over 7.93 (br s, 1H), 8.14 (br s, 1H), 8.36 (s, 1H), 11.23 (br s, 1H, NH), 12.98 (br s, 1H, NH). ESI-HRMS Found 321.1541, calculated for C$_{18}$H$_{18}$N$_5$O [M + H]$^+$: 321.1579 Using Preparation 46 and purification method I. | 0.017 |

-continued

| Example No | Name/Structure | Data | MPS1 IC$_{50}$ (uM) |
|---|---|---|---|
| 166 | N-(2-Methoxy-4-(1-methylpiperidin-4-yloxy)phenyl)-2-(1H-pyrazol-4-yl)-1H-pyrrolo[3,2-c]pyridin-6-amine | $^1$H-NMR (d$^6$-DMSO, 500 MHz): δ 1.64 (m, 2H), 1.93 (m, 2H), 2.20 (s, 3H over m, 2H), 2.64 (m, 2H), 3.80 (s, 3H), 4.29 (m, 1H), 6.48 (s, 1H), 6.51 (dd, J = 2.52, 8.83 Hz, 1H), 6.62 (d, J = 2.52 Hz, 1H), 6.68 (s, 1H), 7.19 (s, 1H), 7.72 (d, J = 8.51 Hz, 1H), 7.90 (br s, 1H), 8.10 (br s, 1H), 8.28 (s, 1H), 11.08 (br s, 1H, NH), 12.95 (br s, 1H, NH). ESI-HRMS Found 419.2194, calculated for C$_{23}$H$_{27}$N$_6$O [M + H]$^+$: 419.2190<br>Using Preparation 48 and purification method I. | 0.007 |
| 167 | 4-(2-(1H-Pyrazol-4-yl)-1H-pyrrolo[3,2-c]pyridin-6-ylamino)-N,N-dimethylbenzenesulfonamide | $^1$H-NMR (d$^6$-DMSO, 500 MHz): δ 2.57 (s, 6H), 6.59 (d, J = 0.95 Hz, 1H), 6.90 (s, 1H), 7.56 (d, J = 8.83 Hz, 2H), 7.79 (d, J = 8.83 Hz, 2H), 7.95 (br s, 1H), 8.16 (br s, 1H), 8.45 (s, 1H), 9.27 (s, 1H), 11.37 (s, 1H, NH), 13.01 (br s, 1H, NH). ESI-HRMS Found 383.1293, calculated for C$_{18}$H$_{19}$N$_6$O$_2$S [M + H]$^+$: 383.1285<br>Using Preparation 47 and purification method I. | 0.017 |
| 168 | 4-(2-(1H-Pyrazol-4-yl)-1H-pyrrolo[3,2-c]pyridin-6-ylamino)-N,N-dimethylbenzamide | $_1$H-NMR (500 MHz, CD$_3$OD): δ 3.11 (s, 6H), 6.63 (d, J = 0.8 Hz, 1H), 7.00 (s, 1H), 7.36 (m, 4H), 7.96 (br s, 1H), 8.06 (br s, 1H), 8.42 (d, J = 0.6 Hz, 1H). ESI-HRMS: Found 347.1631, calculated for C$_{19}$H$_{19}$N$_6$O [M + H]$^+$: 347.1615.<br>Using Preparation 49 and purification method J. | 0.011 |
| 169 | 1-(4-(4-(2-(1H-Pyrazol-4-yl)-1H-pyrrolo[3,2-c]pyridin-6-ylamino)phenyl)piperazin-1-yl)ethanone | $^1$H-NMR (500 MHz, CD$_3$OD): δ 2.16 (s, 3H), 3.10 (t, J = 5.5 Hz, 2H), 3.15 (t, J = 5.2 Hz, 2H), 3.71 (t, J = 5.1 Hz, 2H), 3.76 (t, J = 5.1 Hz, 2H), 6.56 (d, J = 0.9 Hz, 1H), 6.80 (s, 1H), 7.00 (d, J = 8.9 Hz, 2H), 7.23 (d, J = 8.8 Hz, 2H), 7.97 (br s, 2H), 8.29 (d, J = 0.9 Hz, 1H). ESI-HRMS: Found 402.2026; calculated for C$_{22}$H$_{24}$N$_7$O [M + H]$^+$: 402.2037.<br>Using Preparation 50 and purification method J. | 0.080 |

| Example No | Name/Structure | Data | MPS1 IC$_{50}$ (uM) |
|---|---|---|---|
| 170 | N-(4-(2-Methoxyethoxy)phenyl)-2-(1H-pyrazol-4-yl)-1H-pyrrolo[3,2-c]pyridin-6-amine | $^1$H-NMR (500 MHz, DMSO-d$_6$): δ 3.31 (s, 3H), 3.65 (t, J = 4.6 Hz, 2H), 4.03 (t, J = 4.6 Hz, 2H), 6.49 (s, 1H), 6.68 (s, 1H), 6.84 (d, J = 9.0 Hz, 2H), 7.43 (d, J = 9.0 Hz, 2H), 7.90 (br s, 1H), 8.10 (br s, 1H), 8.24 (s, 1H), 8.31 (s, 1H), 11.08 (s, 1H), 12.97 (s, 1H). ESI-HRMS: Found 350.1615; calculated for C$_{19}$H$_{20}$N$_5$O$^2$ [M + H]$^+$: 350.1612. Using Preparation 51 and purification method J. | 0.009 |
| 171 | N-(4-(Morpholinomethyl)phenyl)-2-(1H-pyrazol-4-yl)-1H-pyrrolo[3,2-c]pyridin-6-amine | $^1$H-NMR (500 MHz, DMSO-d6): δ 2.34 (m, 4H), 3.36 (s, 2H), 3.57 (t, J = 4.7 Hz, 4H), 6.52 (m, 1H), 6.78 (s, 1H), 7.12 (d, J = 8.4 Hz, 2H), 7.48 (d, J = 8.3 Hz, 2H), 7.92 (s, 1H), 8.12 (s, 1H), 8.35 (s, 1H), 8.49 (s, 1H), 11.16 (s, 1H), 12.97 (s, 1H). ESI-HRMS: Found 375.1942; calculated for C$_{21}$H$_{23}$N$_6$O [M + H]$^+$: 375.1928. Using Preparation 52 and purification method J. | 0.009 |
| 172 | N-(2-Methoxyphenyl)-2-(1-methyl-1H-pyrazol-4-yl)-1H-pyrrolo[3,2-c]pyridin-6-amine | $^1$H-NMR (d$_6$-DMSO, 500 MHz): δ 3.86 (s, 3H), 3.89 (s, 3H), 6.49 (d, J = 0.95 Hz, 1H), 6.81-6.89 (m, 2H), 6.93 (dd, J = 7.88, 1.58 Hz, 1H), 7.50 (s, 1H), 7.86 (s, 1H), 8.04-8.08 (s over dd, 2H), 8.36 (s, 1H), 11.23 (br s, 1H). ESI-HRMS Found 320.1522, calculated for C$_{18}$H$_{18}$N$_5$O [M + H]$^+$: 320.1506 Using Example 59 and purification method I. | 0.085 |

| Example No | Name/Structure | Data | MPS1 IC$_{50}$ (uM) |
|---|---|---|---|
| 173 | N-(2,4-Dimethoxyphenyl)-2-(1-((5-methylisoxazol-3-yl)methyl)-1H-pyrazol-4-yl)-1H-pyrrolo[3,2-c]pyridin-6-amine | $^1$H-NMR (500 MHz, CDCl$_3$): δ 2.36 (s, 3H), 3.76 (s, 6H), 5.3 (s, 2H), 5.92 (s, 1H), 6.41 (m, 1H), 6.46 (s, 2H), 6.50 (s, 1H), 6.70 (s, 1H), 7.47 (d, J = 8.7 Hz, 1H), 7.66 (s, 1H), 7.79 (s, 1 H), 8.46 (s, 1H), 9.01 (s, 1H). ESI-HRMS: Found 430.1769, calculated for C$_{23}$H$_{23}$N$_6$O$_3$ [M + H]$^+$: 430.1754 Using Example 101 and purification method K. | 0.207 |
| 174 | N-(4-((1H-Pyrazol-1-yl)methyl)phenyl)-2-(1H-pyrazol-4-yl)-1H-pyrrolo[3,2-c]pyridin-6-amine | $^1$H-NMR (500 MHz, CDCl$_3$): δ 5.22 (s, 2H), 6.25 (d, J = 2 Hz, 1H), 6.57 (s, 1H), 6.82 (s, 1H), 7.14 (d, J = 8.5 Hz, 2H), 7.44 (s, 1H), 7.46 (d, J = 8.5 Hz, 2H), 7.75 (d, J = 2 Hz, 1H), 8.38 (s, 1H), 8.69 (s, 1H), 11.3 (s, 1H), 13 (s, 1H). ESI-HRMS: Found 355.1548, calculated for C$_{20}$H$_{18}$N$_7$ [M + H]$^+$: 355.1545 Using Preparation 36 and purification method J. | 0.012 |
| 175 | 2-(1H-Pyrazol-4-yl)-N-(4-(thiomorpholinomethyl)phenyl)-1H-pyrrolo[3,2-c]pyridin-6-amine-S,S-dioxide | $^1$H-NMR (500 MHz, DMSO-d$_6$): δ 2.81 (m, br, 4H), 3.04 (m, br, 4H), 3.57 (s, 2H), 6.51 (s, 1H), 6.57 (s, 1H), 6.83 (s, 1H), 7.18 (d, J = 8.3 Hz, 2H), 7.46 (d, J = 8.3 Hz, 1H), 7.95 (br, s, 1H), 8.15 (br, s, 1H), 8.39 (s, 1H), 8.68 (s, 1H), 11.3 (s, 1H), 13 (s, 1H). ESI-HRMS: Found 422.1535, calculated for C$_{21}$H$_{23}$N$_6$O$_2$S [M + H]$^+$: 422.1525 Using Preparation 37 and purification method J. | 0.004 |

| Example No | Name/Structure | Data | MPS1 IC$_{50}$ (uM) |
|---|---|---|---|
| 176 | N-(4-(2-Morpholinoethoxy)phenyl)-2-(1H-pyrazol-4-yl)-1H-pyrrolo[3,2-c]pyridin-6-amine 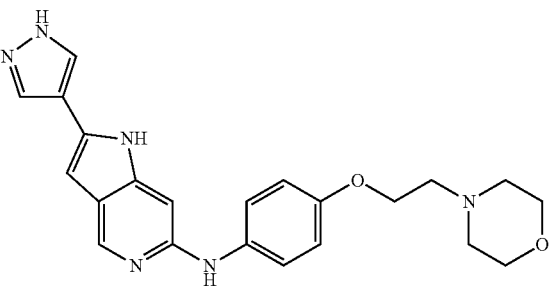 [SMILES: c1cc(OCCN2CCOCC2)ccc1Nc1cc2[nH]c(-c3cn[nH]c3)cc2cn1] | $^1$H-NMR (500 MHz, DMSO-d$_6$): δ 2.49 (br, s, 4H), 2.68 (t, J = 5.7 Hz, 2H), 3.58 (m, 4H), 4.02 (t, J = 5.7 Hz, 2H), 6.5 (s, 1H), 6.69 (s, 1H), 6.84 (d, J = 9 Hz, 2H), 7.42 (d, J = 9 Hz, 2H), 8.1 (br s, 1H), 8.15 (br s, 1H), 8.25 (s, 1H), 8.32 (s, 1H), 11.1 (s, 1H), 12.96 (s, 1H). ESI-HRMS: Found 404.1976, calculated for C$_{22}$H$_{25}$N$_6$O$_2$ [M + H]$^+$: 404.1961 Using Preparation 38 and purification method J. | 0.030 |
| 177 | 4-(2-(1H-pyrazol-4-yl)-1H-pyrrolo[3,2-c]pyridin-6-ylamino)benzonitrile 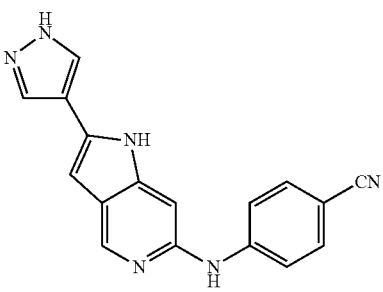 [SMILES: N#Cc1ccc(Nc2cc3[nH]c(-c4cn[nH]c4)cc3cn2)cc1] | $^1$H-NMR (500 MHz, DMSO-d$_6$): δ 6.6 (s, 1H), 6.9 (s, 1H), 7.59 (d, J = 8.9 Hz, 2H), 7.73 (d, J = 8.9 Hz, 2H), 7.95 (s, 1H), 8.69 (s, 1H), 11.3 (br s, 1H), 8.15 (brs , 1H), 8.46 (s, 1H), 9.31(s, 1H), 11.4 (s, 1H), 13 (s, 1H). ESI-HRMS: Found 300.1121, calculated for C$_{17}$H$_{12}$N$_6$ [M + H]$^+$: 300.1123 Using Preparation 39 and purification method J. | '0.150 |
| 178 | 3-Chloro-4-(3-chloro-2-(oxazol-5-yl)-1H-pyrrolo[3,2-c]pyridin-6-ylamino)-N,N-dimethylbenzamide 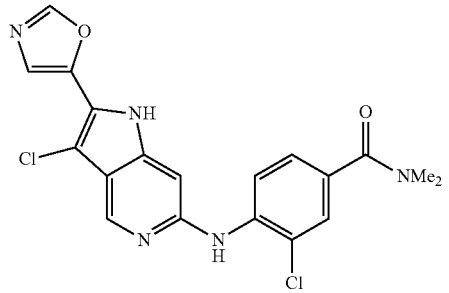 [SMILES: CN(C)C(=O)c1ccc(Nc2cc3[nH]c(-c4cnco4)c(Cl)c3cn2)c(Cl)c1] | $^1$H-NMR (d$_6$-DMSO, 500 MHz): δ 2.97 (s, 6H), 7.14 (d, J = 0.95 Hz, 1H), 7.31 (dd, J = 1.89, 8.51 Hz, 1H), 7.49 (d, J = 1.89 Hz, 1H), 7.75 (s, 1H), 8.07 (d, J = 8.51 Hz, 1H), 8.52 (s, 1 H), 8.64 (s, 1H), 12.16 (br s, 1H, NH). HRMS calcd for C$_{19}$H$_{16}$Cl$_2$N$_5$O$_4$ (M + H)$^+$ 416.0676, found 416.0668 Using Example 95 and purification method L. | 0.003 |
| 179 | (3-Methoxy-4-(2-(oxazol-5-yl)-1H-pyrrolo[3,2-c]pyridin-6-ylamino)phenyl)(3-methoxyazetidin-1-yl)methanone 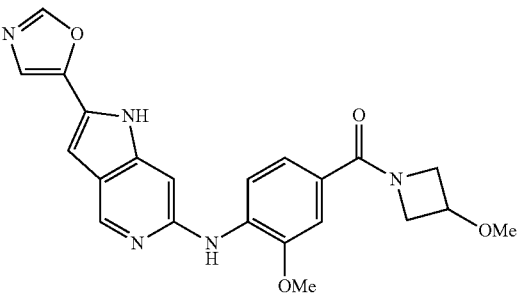 [SMILES: COc1cc(C(=O)N2CC(OC)C2)ccc1Nc1cc2[nH]c(-c3cnco3)cc2cn1] | $^1$H-NMR (d$_6$-DMSO, 500 MHz): δ 3.22 (s, 3H), 3.83 (s, v br, 1H), 3.92 (s, 3H), 4.19 (s, v br, 2H), 4.23 (m, 1H), 4.50 (s, v br, 2H), 6.82 d, J = 0.95 Hz, 1H), 7.16 (t, J = 0.95 Hz, 1H), 7.20 (dd, J = 1.89, 8.51 Hz, 1H), 7.22 (d, J = 1.89 Hz, 1H), 7.57 (s, 1H), 8.16 (s, 1H, NH), 8.33 (d, J = 8.51 Hz, 1H), 8.49 (s, 1H), 8.56 (s, 1H), 11.80 (s, 1H, NH). HRMS calcd for C$_{22}$H$_{22}$N$_5$O$_4$ (M + H)$^+$ 420.1666, found 420.1663 Using Example 97 and purification method I. | 0.003 |

| Example No | Name/Structure | Data | MPS1 IC$_{50}$ (uM) |
|---|---|---|---|
| 180 | 3-Chloro-N,N-dimethyl-4-(2-(oxazol-5-yl)-1H-pyrrolo[3,2-c]pyridin-6-ylamino)benzamide | $^1$H-NMR (d$_6$-DMSO, 500 MHz): δ 2.98 (s, 6H), 6.84 (s, 1H), 7.14 (s, 1H), 7.30 (dd, J = 1.89, 8.51 Hz, 1H), 7.47 (d, J = 1.89 Hz, 1H), 7.58 (s, 1H), 8.09 (d, J = 8.51 Hz, 1H), 8.25 (s, 1H), 8.50 (s, 1H), 8.55 (s, 1H), 11.86 (br s, 1H, NH). HRMS calcd for C$_{19}$H$_{17}$ClN$_5$O$_2$ (M + H)$^+$ 382.1065, found 382.1063 Using Example 98 and purification method M. | 0.005 |
| 181 | N-(2-Methoxyphenyl)-2-(oxazol-5-yl)-1H-pyrrolo[3,2-c]pyridin-6-amine | $^1$H-NMR (d$_6$-DMSO, 500 MHz): δ 3.86 (s, 3H), 6.78 (d, J = 0.95 Hz, 1H), 6.84-6.91 (m, 2H), 6.96 (t, J = 0.95 Hz, 1H), 6.98-7.01 (m, 1H), 7.53 (s, 1H), 7.70 (br s, 1H, NH), 8.04-8.07 (m, 1H), 8.47 (s, 1H), 8.49 (s, 1H), 11.65 (br s, 1H, NH). HRMS calcd for C$_{17}$H$_{15}$N$_4$O$_2$ (M + H)$^+$ 307.1190, found 307.1186 Using Example 96 and purification method A. | 0.025 |
| 182 | N-(2-Methoxyphenyl)-2-(1-(2,2,2-trifluoroethyl)-1H-pyrazol-4-yl)-1H-pyrrolo[3,2-c]pyridin-6-amine | $^1$H-NMR (d$_6$-acetone, 500 MHz): δ 3.90 (s, 3H), 5.11 (q, J = 8.83 Hz, 2H), 6.67 (m, 1H), 6.81-6.93 (m, 2H), 6.96-7.00 (m, 2H), 7.21 (br s, 0.4H, NH), 8.02 (d, J = 0.63 Hz, 1H), 8.14 (t of d, J = 1.89, 7.88 Hz, 1H), 8.25 (s, 1H), 8.47 (s, 1H), 10.53 (br s, 0.4H, NH). The partial NH signals are due to exchange with the d$_6$-acetone $^{19}$F-NMR (d6-acetone, 470.385 MHz): −72.25. ESI-HRMS Found 388.1369, calculated for C$_{19}$H$_{16}$F$_3$N$_5$O (M + H$^+$): 388.1380. Using Example 99 and purification method A. | 0.049 |

-continued

| Example No | Name/Structure | Data | MPS1 IC$_{50}$ (uM) |
|---|---|---|---|
| 183 | 2-(1-(Difluoromethyl)-1H-pyrazol-4-yl)-N-(2-methoxyphenyl)-1H-pyrrolo[3,2-c]pyridin-6-amine | $^1$H-NMR (d$_6$-acetone, 500 MHz): δ 3-90 (s, 3H), 6.79 (s, 1H), 6.83-6.93 (m, 2H), 6.98 (d, J = 7.88 Hz, 1H), 7.01 (s, 1H), 7.25 (br s, 0.5H, NH), 7.68 (t, J = 59.9 Hz, 1H), 8.15, (t of d, J = 1.58, 7.88 Hz, 1H), 8.20 (s, 1H), 8.50 (s, 1H), 8.54 (s, 1H), 10.58 (br s, 0.5H, NH).The partial NH signals arise from exchange with the d$_6$-acetone. $^{19}$F-NMR (d$_6$-acetone, 470.385 MHz): −95.39. ESI-HRMS Found 356.1322, calculated for C$_{18}$H$_{16}$F$_2$N$_5$O (M + H$^+$): 356.1318. Using Example 100 and purification method A. | 0.482 |
| 184 | N-(2-Chloro-5-(1-methyl-1H-pyrazol-4-yl)phenyl)-2-(1-methyl-1H-pyrazol-4-yl)-1H-pyrrolo[3,2-c]pyridin-6-amine | $^1$H-NMR (500 MHz, DMSO-d$_6$): δ 3.84 (s, 3H), 3.89 (s, 3H), 6.55 (s, 1H), 6.97 (s, 1H), 7.10 (dd, J = 1.6, 8.0 Hz, 1H), 7.38 (d, J = 8.2 Hz, 1H), 7.76 (s, 1H), 7.83 (s, 1H), 7.88 (s, 1H), 8.06 (s, 1H), 8.08 (d, J = 1.9 Hz, 1H), 8.09 (s, 1H), 8.41 (s, 1H), 11.35 (s, 1H). ESI-HRMS: Found 404.1375; calculated for C$_{21}$H$_{19}$ClN$_7$ (M + H)$^+$: 404.1385. Using Example 62 and purification method N. | 0.548 |
| 185 | N-(2-Chloro-4-(1-methyl-1H-imidazol-5-yl)phenyl)-2-(oxazol-5-yl)-1H-pyrrolo[3,2-c]pyridin-6-amine | $^1$H-NMR (CD$_3$OD, 500 MHz): δ 3.74 (s, 3H), 6.92 (d, J = 0.95 Hz, 1H), 7.04 (br s, 1H), 7.11 (s, 1H), 7.33 (dd, J = 1.89, 8.51 Hz, 1H), 7.49 (s, 1H), 7.53 (d, J = 1.89 Hz, 1H)), 7.71 (br s, 1H), 7.77 (d, J = 8.51 Hz, 1H), 8.30 (s, 1H), 8.55 (s, 1H). ESI-HRMS calcd for C$_{20}$H$_{16}$$^{35}$ClN$_6$O (M + H)$^+$ 391.1069, found 391.1060 Using Example 91 and purification method O. | 0.005 |

| Example No | Name/Structure | Data | MPS1 IC$_{50}$ (uM) |
|---|---|---|---|
| 186 | N-(2-Chloro-4-(1,2-dimethyl-1H-imidazol-5-yl)phenyl)-2-(oxazol-5-yl)-1H-pyrrolo[3,2-c]pyridin-6-amine | $^1$H-NMR (d$_6$-DMSO, 500 MHz): δ 2.34 (s, 3H), 3.53 (s, 3H), 6.81 (d J = 0.95 Hz, 1H), 6.85 (s, 1H), 7.07 (t, J = 0.95 Hz, 1H), 7.28 (dd, J = 2.21, 8.51 Hz, 1H), 7.45 (d, J = 1.89 Hz, 1H), 7.55 (s, 1H), 8.07 (d, J = 8.51 Hz, 1H), 8.13 (br s, 1H, NH), 8.48 (s, 1H), 8.53 (d, J = 0.95 Hz, 1H), 11.9 (v br s, 1H, NH). HRMS calcd for C$_{21}$H$_{18}$$^{35}$ClN$_6$O (M + H)$^+$ 405.1225, found 405.1214 Using Example 107 and purification method P. | 0.001 |

Example 187

N-(4-fluorophenyl)-1-(methylsulfonyl)-2-(1H-pyrazol-4-yl)-1H-pyrrolo[3,2-c]pyridin-6-amine

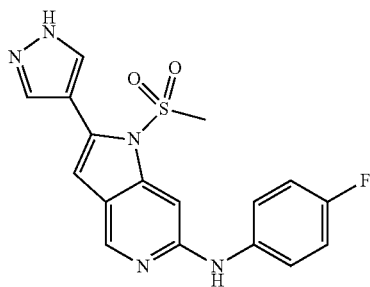 [SMILES: CS(=O)(=O)n1c(-c2cn[nH]c2)cc2cnc(Nc3ccc(F)cc3)cc21]

Aqueous sodium hydroxide (127 μL, 1 M, 0.127 mmol) was added to a solution of tert-butyl 4-(6-(4-fluorophenylamino)-1-(methylsulfonyl)-1H-pyrrolo[3,2-c]pyridin-2-yl)-1H-pyrazole-1-carboxylate (Preparation 53, 20 mg, 0.042 mmol) (mixed with some tert-butyl 4-(6-chloro-1-(methylsulfonyl)-1H-pyrrolo[3,2-c]pyridin-2-yl)-1H-pyrazole-1-carboxylate) in EtOH (339 μL). The reaction mixture was stirred for 4 hours at 40° C. The reaction mixture was filtered on SCX-2 column and was then purified using preparative TLC eluting with DCM/MeOH, 95/5 to afford the title compound as a white solid (7 mg, 20%). $^1$H NMR (500 MHz, CD$_3$OD): δ 3.02 (s, 3H), 6.73 (d, J=0.8 Hz, 1H), 7.00-7.07 (m, 2H), 7.45-7.49 (m, 2H), 7.51 (t, J=0.8 Hz, 1H), 7.90 (br s, 2H), 8.40 (d, J=0.8 Hz, 1H). ESI-HRMS Found 372.0936, calculated for C$_{17}$H$_{15}$FN$_5$O$_2$S [M+H]$^+$: 372.0925. MPS1 IC$_{50}$ (uM): 6.43

Example 188

N-(4-fluorophenyl)-2-(1H-pyrazol-4-yl)-1H-pyrrolo[3,2-c]pyridin-6-amine

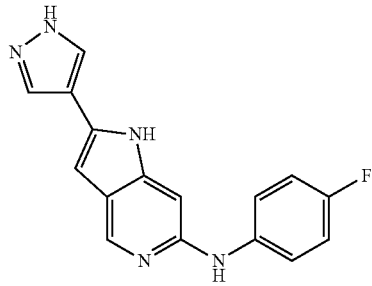 [SMILES: Fc1ccc(Nc2cc3[nH]c(-c4cn[nH]c4)cc3cn2)cc1]

DBU (2 μL, 0.016 mmol) was added to a solution of N-(4-fluorophenyl)-1-(methylsulfonyl)-2-(1H-pyrazol-4-yl)-1H-pyrrolo[3,2-c]pyridin-6-amine (Example 187, 3 mg, 8.08 μmol) in DMF (54 μL). The reaction mixture was stirred for 1 hour at 50° C. and for 1 hour at 100° C. The reaction mixture was diluted with water and the aqueous layer was extracted with EtOAc. The combined organic layers were dried over MgSO$_4$, filtered and concentrated under reduced pressure. The residue was then purified using preparative TLC eluting with DCM/MeOH, 90/10 to afford the title compound as a brown solid (2 mg, 84%). $^1$H NMR (500 MHz, CD$_3$OD): δ 6.60 (d, J=0.9 Hz), 6.85 (s, 1H), 6.99-7.06 (m, 2H), 7.26-7.32 (m, 2H), 8.00 (br s, 2H), 8.34 (s, 1H). ESI-HRMS Found 294.1158, calculated for C$_{16}$H$_{13}$FN$_5$ [M+H]$^+$: 294.1150. MPS1 IC$_{50}$ (uM): 0.140

Example 189

N-(5-fluoropyridin-2-yl)-2-(1H-pyrazol-4-yl)-1H-pyrrolo[3,2-c]pyridin-6-amine

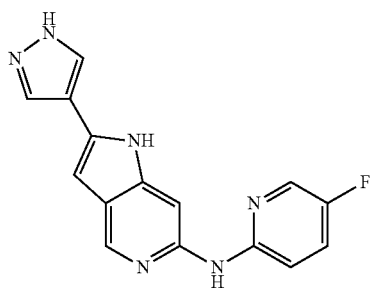 [SMILES: Fc1ccc(Nc2cc3[nH]c(-c4cn[nH]c4)cc3cn2)nc1]

DBU (10.8 µL, 0.072 mmol) was added to a solution of tert-butyl 4-(6-(5-fluoropyridin-2-ylamino)-1-(methylsulfonyl)-1H-pyrrolo[3,2-c]pyridin-2-yl)-1H-pyrazole-1-carboxylate (Preparation 54, 17 mg, 0.036 mmol) in DMF (240 µL). The reaction mixture was stirred for 1 hour at 50° C. and for 1 hour at 100° C. The reaction mixture was diluted with water and the aqueous layer was extracted with EtOAc. The combined organic layers were dried over MgSO$_4$, filtered and concentrated under reduced pressure. The residue was then purified using preparative TLC eluting with 5% MeOH/aq NH$_3$ 10/1 in DCM to afford the title compound as a white solid (7 mg, 24%). $^1$H NMR (500 MHz, CD$_3$OD): δ 6.66 (d, J=0.9 Hz, 1H), 7.18-7.21 (m, 1H), 7.46-7.50 (m, 1H), 7.71 (s, 1H), 8.03 (br s, 2H), 8.07-8.09 (m, 1H), 8.42 (d, J=0.9 Hz, 1H). ESI-HRMS Found 295.1103, calculated for C$_{15}$H$_{12}$FN$_6$ [M+H]$^+$: 295.1102. MPS1 IC$_{50}$ (uM): 0.1586

Example 190

3-Chloro-4-(3-chloro-2-(1-methyl-1H-pyrazol-4-yl)-1H-pyrrolo[3,2-c]pyridin-6-ylamino)-N,N-dimethyl-benzamide

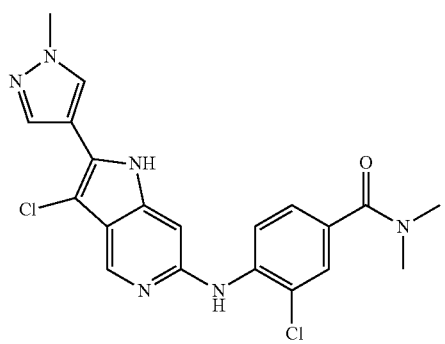 [SMILES: CN(C)C(=O)c1ccc(Nc2cc3[nH]c(-c4cnn(C)c4)c(Cl)c3cn2)c(Cl)c1]

Method NCS

NCS (8.6 mg, 0.065 mmol) was added to a solution of 3-chloro-N,N-dimethyl-4-(2-(1-methyl-1H-pyrazol-4-yl)-1H-pyrrolo[3,2-c]pyridin-6-ylamino)benzamide (Example 127, 14 mg, 0.043 mmol) in DMF (130 µL). The reaction mixture was then stirred overnight at room temperature. The reaction was filtered on SCX-2 column and concentrated under vacuum. The residue was purified using Biotage silica gel column chromatography eluting with DCM/EtOH 99/1 to 90/10 to afford the title product as a brown solid (8 mg, 54%). $^1$H NMR (500 MHz, CD$_3$OD): δ 3.10 (s, 6H), 4.00 (s, 3H), 7.08 (s, 1H), 7.32 (dd, J=8.5, 1.9 Hz, 1H), 7.54 (d, J=1.9 Hz, 1H), 7.77 (d, J=8.5 Hz, 1H), 8.03 (s, 1H), 8.23 (s, 1H), 8.43 (s, 1H). ESI-HRMS Found 429.0995, calculated for C$_{20}$H$_{19}$Cl$_2$N$_6$O [M+H]$^+$: 429.0992. MPS1 IC$_{50}$ (uM): 0.0084

The following Examples were prepared according to Method NCS (Example 190) above using the appropriate precursor at room temperature. The crude reaction residues were purified as above or according to one of the following methods:

Method A: Silica gel column chromatography eluting with 3% methanol in ethyl acetate.

Method B: The residue was dissolved in methanol and passed through an Isolute Si-carbonate column washing with MeOH. The product obtained was dissolved in MeOH and loaded on a preparative TLC plate eluting with 2% MeOH in ethyl acetate/DCM (85/15).

| Example No | Name/Structure | Data | MPS1 IC$_{50}$ (uM) |
|---|---|---|---|
| 191 | 3-Chloro-4-(3-chloro-1-(cyclopentylmethyl)-2-(1-methyl-1H-pyrazol-4-yl)-1H-pyrrolo[3,2-c]pyridin-6-ylamino)-N,N-dimethylbenzamide | $^1$H NMR (500 MHz, CDCl$_3$): δ 1.08-1.18 (m, 2H), 1.45-1.63 (m, 6H), 2.18-2.28 (m, 1H), 3.11 (s, 6H), 4.04 (d, J = 7.6 Hz, 2H), 4.06 (s, 3H), 6.92 (d, J = 0.9 Hz, 1H), 7.00 (s, 1H), 7.34 (dd, J = 8.5, 2.0 Hz, 1H), 7.55 (d, J = 2.0 Hz, 1H), 7.72 (s, 1H), 7.73 (s, 1H), 7.95 (d, J = 8.5 Hz, 1H), 8.62 (d, J = 0.9 Hz, 1H); ESI-HRMS (Method B) Found 511.1770, calculated for C$_{26}$H$_{29}$Cl$_2$N$_6$O (M + H$^+$): 511.1774. Using Example 64. | 0.097 |
| 192 | 3-Chloro-4-(3-chloro-1-(cyclopropylmethyl)-2-(1-methyl-1H-pyrazol-4-yl)-1H-pyrrolo[3,2-c]pyridin-6-ylamino)-N,N-dimethylbenzamide | $^1$H NMR (500 MHz, CDCl$_3$): δ 0.18-0.22 (m, 2H), 0.52-0.56 (m, 2H), 1.03-1.11 (m, 1H), 3.11 (s, 6H), 4.01 (d, J = 6.3 Hz, 2H), 4.06 (s, 3H), 6.90 (s, 1H), 7.36 (dd, J = 8.5, 2.0 Hz, 1H), 7.56 (d, J = 2.0 Hz, 1H), 7.75 (s, 1H), 7.76 (s, 1H), 7.92 (d, J = 8.5 Hz, 1H), 8.61 (s, 1H); ESI-HRMS (Method B) Found 483.1459, calculated for C$_{24}$H$_{25}$Cl$_2$N$_6$O (M + H$^+$): 483.1461. Using Example 66. | 0.053 |
| 193 | 3-Chloro-N-(2-chlorophenyl)-2-(1-methyl-1H-pyrazol-4-yl)-1H-pyrrolo[3,2-c]pyridin-6-amine | $^1$H NMR (500 MHz, CD$_3$OD): δ 4.01 (s, 3H), 6.96 (s, 1H), 6.95-7.00 (m, 1H), 7.26 (m, 1H), 7.44 (dd, J = 8.0, 1.5 Hz, 1H), 7.64 (dd, J = 8.2, 1.5 Hz, 1H), 8.02 (s, 1H), 8.24 (s, 1H), 8.38 (br s, 1H); ESI-HRMS (Method B) Found 358.0615, calculated for C$_{17}$H$_{14}$Cl$_2$N$_5$ (M + H$^+$): 358.0621. Using Example 122. | 0.421 |

-continued

| Example No | Name/Structure | Data | MPS1 IC$_{50}$ (uM) |
|---|---|---|---|
| 194 | 3-Chloro-N-(2-chloro-4-(1-methyl-1H-pyrazol-4-yl)phenyl)-2-(1-methyl-1H-pyrazol-4-yl)-1H-pyrrolo[3,2-c]pyridin-6-amine | $^1$H NMR (500 MHz, CD$_3$OD): δ 3.93 (s, 3H), 3.99 (s, 3H), 6.91 (s, 1H), 7.41 (dd, J = 8.5, 2.1 Hz, 1H), 7.62 (d, J = 2.1 Hz, 1H), 7.62 (d, J = 8.5 Hz, 1H), 7.78 (s, 1H), 7.91 (s, 1H), 8.00 (s, 1H), 8.19 (s, 1H), 8.35 (s, 1H); ESI-HRMS (Method B) Found 438.0986, calculated for C$_{21}$H$_{18}$Cl$_2$N$_7$ (M + H$^+$): 438.0995. Using Example 123. | 0.128 |
| 195 | (3-chloro-4-(3-chloro-2-(1-methyl-1H-pyrazol-4-yl)-1H-pyrrolo[3,2-c]pyridin-6-ylamino)phenyl)(3-methoxyazetidin-1-yl)methanone | $^1$H NMR (500 MHz, CD$_3$OD): δ 3.32 (m, 5H), 3.99 (s, 3H), 4.31 (s, 3H), 7.2 (s, 1H), 7.61 (m, 2H), 7.84 (d, J = 1.9 Hz, 1H), 8.08 (s, 1H), 8.33 (s, 1H), 8.51 (s, 1H); ESI-HRMS (Method D) Found 471.1092, calculated for C$_{22}$H$_{20}$Cl$_2$N$_6$O$_2$ (M + H$^+$): 471.1098 Using Example 142 and purification method A. | 0.021 |
| 196 | (3-Chloro-4-(3-chloro-2-(1-methyl-1H-pyrazol-4-yl)-1H-pyrrolo[3,2-c]pyridin-6-ylamino)phenyl)(S,S-dioxo-thiomorpholino)methanone | $^1$H-NMR (500 MHz, CD$_3$OD): δ 3.24 (s, br, 4H), 4.01 (s, 3H), 4.1 (s, br, 4H), 7.13 (s, 1H), 7.41 (dd, J = 2.1 Hz, 8.5 Hz, 1H), 7.67 (s, 1H), 7.73 (d, J = 8.5 Hz, 1H), 8.05 (s, 1H), 8.27 (s, 1H), 8.45 (s, 1H); ESI-HRMS Found 519.0761, calculated for C$_{22}$H$_{20}$Cl$_2$N$_6$O$_3$S (M + H$^+$): 519.0767 Using Example 143 and purification method A. | 0.009 |

| Example No | Name/Structure | Data | MPS1 IC$_{50}$ (uM) |
|---|---|---|---|
| 197 | 3-Chloro-N-(2-chloro-4-(methylsulfonyl)phenyl)-2-(1-methyl-1H-pyrazol-4-yl)-1H-pyrrolo[3,2-c]pyridin-6-amine 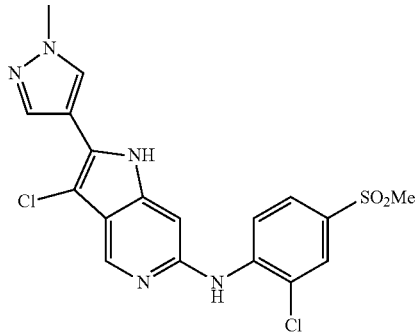 [SMILES: Cn1cc(-c2[nH]c3cc(Nc4ccc(S(C)(=O)=O)cc4Cl)ncc3c2Cl)cn1] | $^1$H-NMR (500 MHz, DMSO-d$_6$): δ 3.20 (s, 3H), 3.95 (s, 3H), 7.25 (s, 1H), 7.70 (dd, J = 1.8, 8.8 Hz, 1H), 7.87 (d, J = 2.2 Hz,. 1H), 8.03 (s, 1H), 8.24 (d, J = 9.4 Hz, 1H), 8.34 (s, 1H), 8.45 (s, 1H), 8.66 (s, 1H), 11.86 (s, 1H). ESI-HRMS: Found 436.0395; calculated for C$_{18}$H$_{16}$Cl$_2$N$_5$O$_2$S (M + H)$^+$: 436.0396. Using Example 131 and purification method B. | 0.069 |

The invention claimed is:

1. A compound of formula I

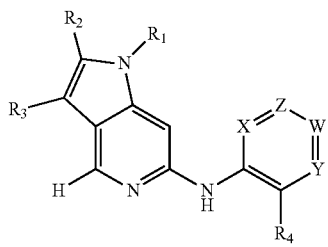

Formula I wherein:

R$_1$ is hydrogen, (1-5C)alkyl, (1-5C)fluoroalkyl, (3-8C)cycloalkyl, (3-8C)cycloalkyl-(1-4C)alkyl, aryl, aryl-(1-4C)alkyl, heteroaryl, heteroaryl-(1-4C)alkyl, —S(O)$_2$—R$^a$, —C(O)—R$^a$, or —C(O)—O—R$^a$, wherein R$^a$ is (1-5C)alkyl, (3-8C)cycloalkyl, (3-8C)cycloalkyl-(1-4C)alkyl, aryl, aryl-(1-4C)alkyl, heteroaryl or heteroaryl-(1-4C)alkyl, and wherein any (1-5C)alkyl, (3-8C)cycloalkyl, (3-8C)cycloalkyl-(1-4C)alkyl, aryl, aryl-(1-4C)alkyl, heteroaryl, heteroaryl-(1-4C)alkyl group present in a R$_1$ substituent group is optionally substituted by methyl, trifluoromethyl, methoxy, trifluoromethoxy, halo, cyano, nitro, hydroxy, mercapto, amino, carboxy, carbamoyl, or sulphamoyl;

R$_2$ is an aryl, aryl(1-2C)alkyl, 5- or 6-membered heteroaryl or a 5- or 6-membered heteroaryl(1 -2C)alkyl, wherein R$_2$ is optionally substituted by one or more substituents selected from halogeno, trifluoromethyl, trifluoromethoxy, cyano, nitro, hydroxy, mercapto, amino, carboxy, carbamoyl, sulphamoyl, or a group of the formula:

-L-L$^0$-R$^b$ wherein

L is absent or a linker group of the formula —[CR$_g$R$_h$]$_n$— in which n is an integer selected from 1, 2, 3 or 4, and R$_g$ and R$_h$ are each independently selected from hydrogen or (1-2C)alkyl;

L$^0$ is absent or is selected from O, S, SO, SO$_2$, N(R$^c$), C(O), C(O)O, OC(O), CH(OR$^c$),)C(O)N(R$^c$), N(R$^c$)C(O), N(R$^c$)C(O)N(R$^d$), SO$_2$N(R$^c$), or N(R$^c$) SO$_2$, wherein R$^c$ and R$^d$ are each independently selected from hydrogen or (1-2C)alkyl; and R$^b$ is (1-4C)alkyl, aryl, aryl-(1-4C)alkyl, (3-6C)cycloalkyl, (3-6C)cycloalkyl-(1-4C)alkyl, heteroaryl, heteroaryl-(1 -4C)alkyl, heterocyclyl, or heterocyclyl-(1-4C)alkyl;

and wherein R$^b$ is optionally further substituted by one or more substituents independently selected from oxo, halogeno, cyano, nitro, hydroxy, NR$^e$R$^f$, (1-5C)alkyl, (1-5C)alkoxy, (1-5C)alkanoyl, (1-5C) sulphonyl or aryl; and wherein R$^e$ and R$^f$ are each independently selected from hydrogen or (1-4C) alkyl or (3-6C)cycloalkyl-(1-4C)alkyl; or R$^e$ and R$^f$ can be linked such that, together with the nitrogen atom to which they are attached, they form a 4-7 membered heterocyclic, heteroaryl or carbocyclic ring;

R$_3$ is H, (1-3C)alkyl, halogeno or CF$_3$;

R$_4$ is cyano, (1-3C)alkyl, (1-3C)fluoroalkyl, (1-3C)alkoxy, (1-3C)perfluoroalkoxy, halo, (1-3C)alkanoyl, C(O)NR$^i$R$^j$, or S(O)$_2$NR$^i$R$^j$; wherein R$^i$ and R$^j$ are each independently selected from H or (1-3C)alkyl;

X is CH or CR$_5$;

W, Y and Z are each independently selected from N, CH, or CR$_5$;

R$_5$ is halogeno, trifluoromethyl, trifluoromethoxy, cyano, nitro, hydroxy, mercapto, amino, carboxy, carbamoyl, sulphamoyl, ureido, (1-6C)alkyl, (2-6C)alkenyl, (2-6C) alkynyl, or R$_5$ is a group of the formula:

-L$^1$-L$^2$-R$_7$ wherein

L$^1$ is absent or a linker group of the formula —[CR$_8$R$_9$]$_n$— in which n is an integer selected from 1, 2, 3 or 4, and R$_8$ and R$_9$ are each independently selected from hydrogen or (1-2C)alkyl;

L$^2$ is absent or is selected from O, S, SO, SO$_2$, N(R$_{10}$), C(O), C(O)O, OC(O), CH(OR$_{10}$), C(O)N(R$_{10}$), N(R$_{10}$)C(O), N(R$_{10}$)C(O)N(R$_{11}$), S(O)$_2$N(R$_{10}$), or N(R$_{13}$)SO$_2$, wherein R$_{10}$ and R$_{11}$ are each independently selected from hydrogen or (1-2C)alkyl; and R$_7$ is (1-6C)alkyl, aryl, aryl-(1-6C)alkyl, (3-6C)cycloalkyl, (3-6C)cycloalkyl-(1-6C)alkyl, heteroaryl, heteroaryl-(1-6C)alkyl, heterocyclyl, heterocyclyl-(1-6C)alkyl, and wherein R$_7$ is optionally further substituted by one or more substituents independently selected from hydrogen, oxo, halogeno, cyano, nitro, hydroxy, NR$_{12}$R$_{13}$, (1-4C)alkoxy, (1-5C)alkyl, (3-8C)cycloalkyl, (3-8C)cycloalkyl-(1-5C)alkyl, aryl, aryl-(1-5C)alkyl, (1-5C)alkanoyl, (1-5C)alkylsulphonyl, heterocyclyl, heterocyclyl-(1-5C)alkyl, heteroaryl, heteroaryl-(1-5C)alkyl, CONR$_{12}$R$_{13}$ and SO$_2$NR$_{12}$R$_{13}$;

R$_{12}$ and R$_{13}$ are each independently selected from hydrogen or (1-2C)alkyl; or R$_{12}$ and R$_{13}$ can be linked such that, together with the nitrogen atom to which they are attached, they form a 4-7 membered heterocyclic or heteroaryl ring;

or either W and Z, W and Y or Z and X are both CR$_5$ and the R$_5$ groups on the adjacent carbon atoms are linked such that, together with the carbon atoms to which they are attached, they form a fused 4-7 membered heterocyclic, heteroaryl or carbocyclic ring;

or a pharmaceutically acceptable salt or solvate thereof.

2. A compound according to claim 1, wherein R$_1$ is hydrogen, (1-5C)alkyl, (1-5C)fluoroalkyl, (3-8C)cycloalkyl, (3-8C)cycloalkyl-(1-4C)alkyl, aryl, aryl-(1-4C)alkyl, heteroaryl, heteroaryl-(1-4C)alkyl, —S(O)$_2$—R$^a$, —C(O)—R$^a$, or —C(O)—O—R$^a$, wherein R$^a$ is (1-5C)alkyl, (3-8C)cycloalkyl, (3-8C)cycloalkyl-(1-2C)alkyl, aryl, aryl-(1-2C)alkyl, heteroaryl or heteroaryl-(1-2C)alkyl, and wherein any (1-5C)alkyl, (3-8C)cycloalkyl, (3-8C)cycloalkyl-(12C)alkyl, aryl, aryl-(1-2C)alkyl, heteroaryl, heteroaryl-(1-2C)alkyl group present in a R$_1$ substituent group is optionally substituted by methyl, trifluoromethyl, methoxy, trifluoromethoxy, halo, cyano, hydroxy or amino.

3. A compound according to claim 1, wherein R$_1$ is hydrogen or —C(O)—O—R$^a$, wherein R$^a$ is (1-5C)alkyl, (3-6C)cycloalkyl, (3-6C)cycloalkyl-(1-2C)alkyl, and wherein any (1-5C)alkyl, (3-8C)cycloalkyl, (3-8C)cycloalkyl-(1-2C) alkyl group is optionally substituted by methyl, trifluoromethyl, methoxy, trifluoromethoxy, halo, cyano, hydroxy or amino.

4. A compound according to claim 1, wherein R$_1$ is hydrogen or —C(O)—O—R$^a$, wherein R$^a$ is (1-5C)alkyl, (3-6C)cycloalkyl, (3-6C)cycloalkyl-(1-2C)alkyl.

5. A compound according to claim 1, wherein R$_2$ is an aryl or a 5- or 6-membered heteroaryl, wherein R$_2$ is optionally substituted by one or more substituents selected from trifluoromethyl, cyano, amino, or a group of the formula:

L-L$^0$-R$^b$ wherein

L is absent or a linker group of the formula —[CR$_g$R$_h$]$_n$— in which n is 1 or 2, and R$_g$ and R$_h$ are hydrogen;

L$^0$ is absent or is selected from O, SO$_2$, N(R$^c$), C(O)O, C(O)N(R$^c$), or SO$_2$N(R$^c$), wherein R$^c$ is selected from hydrogen or (1-2C)alkyl; and R$^b$ is (1-4C)alkyl, heteroaryl, or heterocyclyl-(1-4C)alkyl; and wherein R$^b$ is optionally further substituted by one or more substituents independently selected from oxo, and NR$^e$R$^f$; and wherein R$^e$ and R$^f$ can be linked such that, together with the nitrogen atom to which they are attached, they form a 4-7 membered heterocyclic ring.

6. A compound according to claim 5, wherein R$_2$ is a 5-membered heteroaryl having one of the following structures:

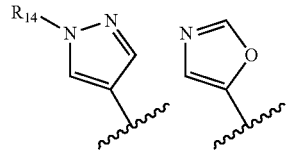

wherein R$_{14}$ is H, methyl or trifluoromethyl.

7. A compound according to claim 1, wherein R$_3$ is H or chloro.

8. A compound according to claim 7, wherein R$_3$ is H.

9. A compound according to claim 1, wherein R$_4$ is cyano, (1-3C)alkyl, (1-3C)perfluoroalkyl, (1-3C)alkoxy, (1-3C)perfluoroalkoxy or halo.

10. A compound according to claim 9, wherein R$_4$ is chloro of methoxy.

11. A compound according to claim 1, wherein X is CH, and W, Y or Z are selected from N, CH or CR$_5$, with the proviso that one of W, Y and Z is CR$^5$.

12. A compound according to claim 1, wherein R$_5$ is halogeno, trifluoromethyl, cyano, hydroxy, or R$_5$ is a group of formula:

-L$^1$-L$^2$-R$_7$ wherein

L$^1$ is absent or a linker group of the formula —[CR$_8$R$_9$]$_n$— in which n is 1, and R$_8$ and R$_9$ are each independently selected from hydrogen or (1-2C)alkyl;

L$^2$ is absent or is selected from O, SO$_2$, N(R$_{10}$), C(O), C(O)N(R$_{10}$), N(R$_{10}$)C(O), or S(O)$_2$N(R$_{10}$), or N(R$_{13}$)SO$_2$, wherein R$_{10}$ is selected from hydrogen or (1-2C)alkyl; and R$_7$ is (1-6C)alkyl, aryl, heteroaryl, heteroaryl-(1-6C)alkyl, heterocyclyl, or heterocyclyl-(1-6C)alkyl, wherein R$_7$ is optionally further substituted by one or more substituents independently selected from oxo, halogeno, cyano, NR$_{12}$R$_{13}$, (1-4C)alkoxy, (1-5C)alkyl, or (1-5C)alkanoyl; and wherein R$_{12}$, and R$_{13}$ are each independently selected from hydrogen or (1-2C)alkyl; or R$_{12}$ and R$_{13}$ can be linked such that, together with the nitrogen atom to which they are attached, they form a 4-7 membered heterocyclic ring.

13. A compound according to claim 12, wherein R$_5$ is selected from one of the following structures:

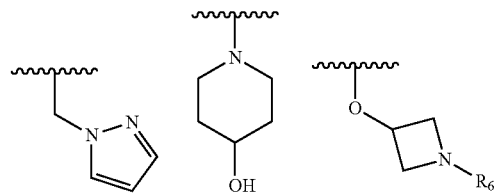

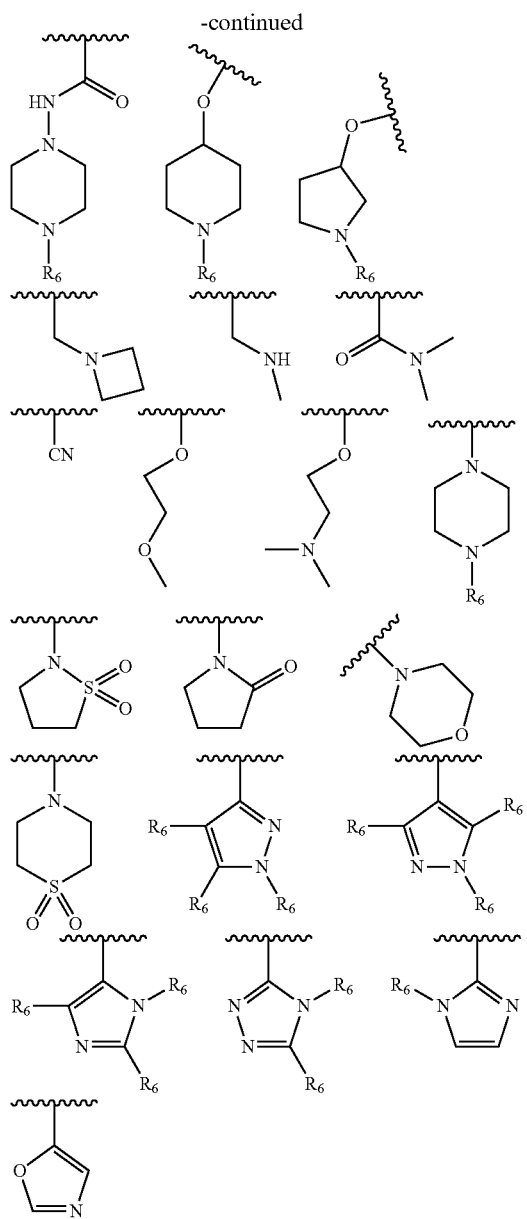

wherein R₆ is independently selected from the group including hydrogen, (1-5C)alkyl, (3-8C)cycloalkyl, (3-8C)cycloalkyl-(1-5C)alkyl, aryl, aryl-(1-5C)alkyl, (1-5C)alkanoyl, (1-5C)sulphonyl.

14. A compound selected from any one of the following:
- isopropyl 6-((4-methoxy-2-(1-methyl-1H-pyrazol-4-yl)pyrimidin-5-yl)amino)-2-(1-methyl-1H-pyrazol-4-yl)-1H-pyrrolo[3,2-c]pyridine-1-carboxylate;
- isopropyl 6-((4-(1,2-dimethyl-1H-imidazol-5-yl)phenyl)amino)-2-(1-methyl-1H-pyrazol-4-yl)-1H-pyrrolo[3,2-c]pyridine-1-carboxylate;
- isopropyl 6-(4-(1,3-dimethyl-1H-pyrazol-4-yl)-2-methoxyphenylamino)-2-(1-methyl-1H-pyrazol-4-yl)-1H-pyrrolo[3,2-c]pyridine-1-carboxylate;
- N-(2-chloro-5-(1-methyl-1H-pyrazol-4-yl)phenyl)-2-(1-methyl-1H-pyrazol-4-yl)-1H-pyrrolo [3,2-c]pyridin-6-amine;
- tert-butyl 6-((2-chloro-5-(1-methyl-1H-pyrazol-4-yl)phenyl)amino)-2-(1-methyl-1H-pyrazol-4-yl)-1H-pyrrolo[3,2-c]pyridine-1-carboxylate;
- N-(2-chloro-4-(1,2-dimethyl-1H-imidazol-5-yl)phenyl)-2-(oxazol-5-yl)-1H-pyrrolo[3,2-c]pyridin-6-amine;
- tert-butyl 6-(2-chloro-4-(1,2-dimethyl-1H-imidazol-5-yl)phenylamino)-2-(oxazol-5-yl)-1H-pyrrolo[3,2-c]pyridine-1-carboxylate;
- isopropyl 6-(2-chloro-4-(1,2-dimethyl-1H-imidazol-5-yl)phenylamino)-2-(oxazol-5-yl)-1H-pyrrolo[3,2-c]pyridine-1-carboxylate;
- isopropyl 6-(2-methoxy-4-(1-methyl-1H-pyrazol-4-yl)phenylamino)-2-(1-methyl-1H-pyrazol-4-yl)-1H-pyrrolo[3,2-c]pyridine-1-carboxylate;
- isopropyl 6-((2-chloro-5-(1-methyl-1H-pyrazol-4-yl)phenyl)amino)-2-(1-methyl-1H-pyrazol-4-yl)-1H-pyrrolo[3,2-c]pyridine-1-carboxylate;
- N-(2-chloro-4-(1,2-dimethyl-1H-imidazol-5-yl)phenyl)-1-(2-methoxyethyl)-2-(1-methyl-1H-pyrazol-4-yl)-1H-pyrrolo[3,2-c]pyridin-6-amine;
- tert-butyl 6-(2-chloro-4-(1,4-dimethyl-1H-imidazol-5-yl)phenylamino)-2-(1-methyl-1H-pyrazol-4-yl)-1H-pyrrolo[3,2-c]pyridine-1-carboxylate;
- N-(2-chloro-4-(1,2-dimethyl-1H-imidazol-5-yl)phenyl)-1-(cyclopropylmethyl)-2-(1-methyl-1H-pyrazol-4-yl)-1H-pyrrolo[3,2-c]pyridin-6-amine;
- N-(2-chloro-4-(1-methyl-1H-imidazol-5-yl)phenyl)-2-(oxazol-5-yl)-1H-pyrrolo[3,2-c]pyridin-6-amine;
- tert-butyl 6-((2-chloro-4-(3,3-difluoroazetidine-1-carbonyl)phenyl)amino)-2-(1-methyl-1H-pyrazol-4-yl)-1H-pyrrolo[3,2-c]pyridine-1-carboxylate;
- (3-chloro-4-((2-(1-methyl-1H-pyrazol-4-yl)-1H-pyrrolo[3,2-c]pyridin-6-yl)amino)phenyl)(3,3-difluoroazetidin-1-yl)methanone;
- propyl-6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
- ethyl-6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
- methyl-6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
- isopropyl 6-(4-(1,2-dimethyl-1H-imidazol-5-yl)-2-methoxyphenylamino)-2-(1-methyl-1H-pyrazol-4-yl)-1H-pyrrolo[3,2-c]pyridine-1-carboxylate;
- tert-butyl 6-(2-chloro-4-(oxazol-5-yl)phenylamino)-2-(1-methyl-1H-pyrazol-4-yl)-1H-pyrrolo [3,2-c]pyridine-1-carboxylate;
- tert-butyl 6-(2-chloro-4-(thiazol-5-yl)phenylamino)-2-(1-methyl-1H-pyrazol-4-yl)-1H-pyrrolo [3,2-c]pyridine-1-carboxylate;
- tert-butyl 6-(2-chloro-4-(5-methylisoxazol-4-yl)phenylamino)-2-(1-methyl-1H-pyrazol-4-yl)-1H-pyrrolo[3,2-c]pyridine-1-carboxylate;
- tert-butyl 6-((2-chloro-4-(pyrazin-2-yl)phenyl)amino)-2-(1-methyl-1H-pyrazol-4-yl)-1H-pyrrolo [3,2-c]pyridine-1-carboxylate;
- cyclobutyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
- cyclopentyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
- isopropyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
- tert-butyl 6-(2-chloro-4-(6-methylpyridin-3-yl)phenylamino)-2-(1-methyl-1H-pyrazol-4-yl)-1H-pyrrolo[3,2-c]pyridine-1-carboxylate;

tert-butyl 6-(2-chloro-4-(1-methyl-1H-imidazol-2-yl)phenylamino)-2-(1-methyl-1H-pyrazol-4-yl)-1H-pyrrolo[3,2-c]pyridine-1-carboxylate;
tert-butyl 6-(2-chloro-4-(1,3-dimethyl-1H-pyrazol-4-yl)phenylamino)-2-(1-methyl-1H-pyrazol-4-yl)-1H-pyrrolo[3,2-c]pyridine-1-carboxylate;
tert-butyl 6-(2-chloro-4-(1,5-dimethyl-1H-pyrazol-4-yl)phenylamino)-2-(1-methyl-1H-pyrazol-4-yl)-1H-pyrrolo[3,2-c]pyridine-1-carboxylate;
tert-butyl 6-(2-chloro-4-(pyridin-3-yl)phenylamino)-2-(1-methyl-1H-pyrazol-4-yl)-1H-pyrrolo [3,2-c]pyridine-1-carboxylate;
tert-butyl 6-(2-chloro-4-(4-methyl-4H-1,2,4-triazol-3-yl)phenylamino)-2-(1-methyl-1H-pyrazol-4-yl)-1H-pyrrolo[3,2-c]pyridine-1-carboxylate;
tert-butyl 6-((2-chloro-4-(pyrimidin-5-yl)phenyl)amino)-2-(1-methyl-1H-pyrazol-4-yl)-1H-pyrrolo[3,2-c]pyridine-1-carboxylate;
tert-butyl-6-(2-chloro-4-(6-methoxypyridin-3-yl)phenylamino)-2-(1-methyl-1H-pyrazol-4-yl)-1H-pyrrolo[3,2-c]pyridine-1-carboxylate;
cyclobutyl-6-(2-chloro-4-(1-methyl-1H-imidazol-5-yl)phenylamino)-2-(1-methyl-1H-pyrazol-4-yl)-1H-pyrrolo[3,2-c]pyridine-1-carboxylate;
cyclobutyl-6-(2-chloro-4-(dimethylcarbamoyl)phenylamino)-2-(1-methyl-1H-pyrazol-4-yl)-1H-pyrrolo[3,2-c]pyridine-1-carboxylate;
N-(2-chloro-4-(1-methyl-1H-imidazol-5-yl)phenyl)-1-cyclopentyl-2-(1-methyl-1H-pyrazol-4-yl)-1H-pyrrolo[3,2-c]pyridin-6-amine;
isopropyl 6-(2-chloro-4-(1-methyl-1H-imidazol-5-yl)phenylamino)-2-(1-methyl-1H-pyrazol-4-yl)-1H-pyrrolo[3,2-c]pyridine-1-carboxylate;
tert-butyl 6-(2-chloro-4-(1-methyl-1H-imidazol-5-yl)phenylamino)-2-(oxazol-5-yl)-1H-pyrrolo [3,2-c]pyridine-1-carboxylate;
cyclopentyl 6-((2-chloro-4-(1-methyl-1H-imidazol-5-yl)phenyl)amino)-2-(1-methyl-1H-pyrazol-4-yl)-1H-pyrrolo[3,2-c]pyridine-1-carboxylate;
tert-butyl 6-((4-(azetidine-1-carbonyl)-2-chlorophenyl)amino)-2-(1-methyl-1H-pyrazol-4-yl)-1H-pyrrolo[3,2-c]pyridine-1-carboxylate;
N-(2-chloro-4-(1,2-dimethyl-1H-imidazol-5-yl)phenyl)-2-(1-methyl-1H-pyrazol-4-yl)-1H-pyrrolo[3,2-c]pyridin-6-amine;
tert-butyl 6-(2-chloro-4-(1,2-dimethyl-1H-imidazol-5-yl)phenylamino)-2-(1-methyl-1H-pyrazol-4-yl)-1H-pyrrolo[3,2-c]pyridine-1-carboxylate;
3-chloro-N,N-dimethyl-4-(2-(1-methyl-1H-pyrazol-4-yl)-1-(5-methylpyridin-2-yl)-1H-pyrrolo [3,2-c]pyridin-6-ylamino)benzamide;
3-chloro-N,N-dimethyl-4-(2-(1-methyl-1H-pyrazol-4-yl)-1-(pyrimidin-2-yl)-1H-pyrrolo [3,2-c]pyridin-6-ylamino)benzamide;
3-chloro-N,N-dimethyl-4-(2-(1-methyl-1H-pyrazol-4-yl)-1-(pyridin-2-yl)-1H-pyrrolo [3,2-c]pyridin-6-ylamino)benzamide;
N-(2-chloro-4-(2-methoxypyridin-4-yl)phenyl)-2-(1-methyl-1H-pyrazol-4-yl)-1H-pyrrolo [3,2-c]pyridin-6-amine;
tert-butyl 6-(2-chloro-4-(2-methoxypyridin-4-yl)phenylamino)-2-(1-methyl-1H-pyrazol-4-yl)-1H-pyrrolo[3,2-c]pyridine-1-carboxylate;
N-(2-chloro-4-(2,4-dimethylthiazol-5-yl)phenyl)-2-(1-methyl-1H-pyrazol-4-yl)-1H-pyrrolo [3,2-c]pyridin-6-amine;
tert-butyl 6-(2-chloro-4-(2,4-dimethylthiazol-5-yl)phenylamino)-2-(1-methyl-1H-pyrazol-4-yl)-1H-pyrrolo[3,2-c]pyridine-1-carboxylate;
N-(2-chloro-4-(1-methyl-1H-pyrazol-5-yl)phenyl)-2-(1-methyl-1H-pyrazol-4-yl)-1H-pyrrolo [3,2-c]pyridin-6-amine;
tert-butyl 6-(2-chloro-4-(1-methyl-1H-pyrazol-5-yl)phenylamino)-2-(1-methyl-1H-pyrazol-4-yl)-1H-pyrrolo[3,2-c]pyridine-1-carboxylate;
isopropyl 6-(2-chloro-4-(dimethylcarbamoyl)phenylamino)-2-(1-methyl-1H-pyrazol-4-yl)-1H-pyrrolo[3,2-c]pyridine-1-carboxylate;
isopropyl 6-(2-chloro-4-(1-methyl-1H-pyrazol-4-yl)phenylamino)-2-(1-methyl-1H-pyrazol-4-yl)-1H-pyrrolo[3,2-c]pyridine-1-carboxylate;
N-(2-chloro-4-(1-methyl-1H-imidazol-5-yl)phenyl)-2-(1-methyl-1H-pyrazol-4-yl)-1H-pyrrolo [3,2-c]pyridin-6-amine;
N-(2-chloro-4-(1-methyl-1H-pyrazol-3-yl)phenyl)-2-(1-methyl-1H-pyrazol-4-yl)-1H-pyrrolo [3,2-c]pyridin-6-amine;
(3-chloro-4-(2-(1-methyl-1H-pyrazol-4-yl)-1H-pyrrolo[3,2-c]pyridin-6-ylamino)phenyl)(4-(dimethylamino)piperidin-1-yl)methanone;
tert-butyl-6-(2-chloro-4-(4-(dimethylamino)piperidine-1-carbonyl)phenylamino)-2-(1-methyl-1H-pyrazol-4-yl)-1H-pyrrolo[3,2-c]pyridine-1-carboxylate;
cyclopentyl 6-(2-chloro-4-(1-methyl-1H-pyrazol-4-yl)phenylamino)-2-(1-methyl-1H-pyrazol-4-yl)-1H-pyrrolo[3,2-c]pyridine-1-carboxylate;
(3-chloro-4-(2-(1-methyl-1H-pyrazol-4-yl)-1H-pyrrolo[3,2-c]pyridin-6-ylamino)phenyl)(4-methoxypiperidin-1-yl)methanone;
tert-butyl 6-(2-chloro-4-(4-methoxypiperidine-1-carbonyl)phenylamino)-2-(1-methyl-1H-pyrazol-4-yl)-1H-pyrrolo[3,2-c]pyridine-1-carboxylate;
tert-butyl 6-(2-chloro-4-(1-methyl-1H-imidazol-5-yl)phenylamino)-2-(1-methyl-1H-pyrazol-4-yl)-1H-pyrrolo [3,2-c]pyridine-1-carboxylate;
tert-butyl 6-(2-chloro-4-(1-methyl-1H-pyrazol-3-yl)phenylamino)-2-(1-methyl-1H-pyrazol-4-yl)-1H-pyrrolo [3,2-c]pyridine-1-carboxylate;
(3-chloro-4-(2-(1-methyl-1H-pyrazol-4-yl)-1H-pyrrolo[3,2-c]pyridin-6-ylamino)phenyl)(4-methylpiperazin-1-yl)methanone;
tert-butyl 6-(2-chloro-4-(4-methylpiperazine-1-carbonyl)phenylamino)-2-(1-methyl-1H-pyrazol-4-yl)-1H-pyrrolo[3,2-c]pyridine-1-carboxylate;
(3-chloro-4-(3-chloro-2-(1-methyl-1H-pyrazol-4-yl)-1H-pyrrolo[3,2-c]pyridin-6-ylamino)phenyl)(S,S-dioxothiomorpholino)methanone;
(3-chloro-4-(3-chloro-2-(1-methyl-1H-pyrazol-4-yl)-1H-pyrrolo[3,2-c]pyridin-6-ylamino)phenyl)(3-methoxyazetidin-1-yl)methanone;
(3-chloro-4-(2-(1-methyl-1H-pyrazol-4-yl)-1H-pyrrolo[3,2-c]pyridin-6-ylamino)phenyl)(pyrrolidin-1-yl)methanone;
tert-butyl 6-(2-chloro-4-(pyrrolidine-1-carbonyl)phenylamino)-2-(1-methyl-1H-pyrazol-4-yl)-1H-pyrrolo[3,2-c]pyridine-1-carboxylate;
3-chloro-N-ethyl-N-methyl-4-(2-(1-methyl-1H-pyrazol-4-yl)-1H-pyrrolo[3,2-c]pyridin-6-ylamino)benzamide;
tert-butyl 6-(2-chloro-4-(ethyl(methyl)carbamoyl)phenylamino)-2-(1-methyl-1H-pyrazol-4-yl)-1H-pyrrolo[3,2-c]pyridine-1-carboxylate;

(3-chloro-4-(2-(1-methyl-1H-pyrazol-4-yl)-1H-pyrrolo[3,2-c]pyridin-6-ylamino)phenyl)(S,S-dioxo-thiomorpholino)methanone;
tert-butyl 6-(2-chloro-4-(S,S-dioxo-thiomorpholine-4-carbonyl)phenylamino)-2-(1-methyl-1H-pyrazol-4-yl)-1H-pyrrolo[3,2-c]pyridine-1-carboxylate;
N-(2-chlorophenyl)-1-(cyclohexylmethyl)-2-(1-methyl-1H-pyrazol-4-yl)-1H-pyrrolo [3,2-c]pyridin-6-amine;
3-chloro-N-(2-chloro-4-(1-methyl-1H-pyrazol-4-yl)phenyl)-2-(1-methyl-1H-pyrazol-4-yl)-1H-pyrrolo[3,2-c]pyridin-6-amine;
3-chloro-N-(2-chlorophenyl)-2-(1-methyl-1H-pyrazol-4-yl)-1H-pyrrolo[3,2-c]pyridin-6-amine;
N-(2-chlorophenyl)-2-(1-methyl-1H-pyrazol-4-yl)-1H-pyrrolo[3,2-c]pyridin-6-amine;
N-(2-chlorophenyl)-2-(1-methyl-1H-pyrazol-4-yl)-1H-pyrrolo[3,2-c]pyridin-6-amine;
(3-chloro-4-(2-(1-methyl-1H-pyrazol-4-yl)-1H-pyrrolo[3,2-c]pyridin-6-ylamino)phenyl)(3-methoxyazetidin-1-yl)methanone;
tert-butyl 6-(2-chloro-4-(3-methoxyazetidine-1-carbonyl)phenylamino)-2-(1-methyl-1H-pyrazol-4-yl)-1H-pyrrolo[3,2-c]pyridine-1-carboxylate;
tert-butyl 6-(2-chloro-4-(1-methyl-1H-pyrazol-4-yl)phenylamino)-2-(1-methyl-1H-pyrazol-4-yl)-1H-pyrrolo[3,2-c]pyridine-1-carboxylate;
tert-butyl 6-(2-chlorophenylamino)-2-(1-methyl-1H-pyrazol-4-yl)-1H-pyrrolo[3,2-c]pyridine-1-carboxylate;
3-chloro-4-(1-isopropyl-2-(1-methyl-1H-pyrazol-4-yl)-1H-pyrrolo[3,2-c]pyridin-6-ylamino)-N,N-dimethylbenzamide;
3-chloro-4-(1-cyclopentyl-2-(1-methyl-1H-pyrazol-4-yl)-1H-pyrrolo[3,2-c]pyridin-6-ylamino)-N,N-dimethylbenzamide;
3-chloro-4-(3-chloro-1-(cyclopentylmethyl)-2-(1-methyl-1H-pyrazol-4-yl)-1H-pyrrolo [3,2-c]pyridin-6-ylamino)-N,N-dimethylbenzamide;
3-chloro-4-(3-chloro-1-(cyclopropylmethyl)-2-(1-methyl-1H-pyrazol-4-yl)-1H-pyrrolo [3,2-c]pyridin-6-ylamino)-N,N-dimethylbenzamide;
3,5-dichloro-N,N-dimethyl-4-(2-(1-methyl-1H-pyrazol-4-yl)-1H-pyrrolo[3,2-c]pyridin-6-ylamino)benzamide;
tert-butyl 6-(4-(dimethylcarbamoyl)-2-(trifluoromethoxy)phenylamino)-2-(1-methyl-1H-pyrazol-4-yl)-1H-pyrrolo[3,2-c]pyridine-1-carboxylate;
tert-butyl 6-(2,6-dichloro-4-(dimethylcarbamoyl)phenylamino)-2-(1-methyl-1H-pyrazol-4-yl)-1H-pyrrolo[3,2-c]pyridine-1-carboxylate;
3-chloro-4-(1-(cyclopropylmethyl)-2-(1-methyl-1H-pyrazol-4-yl)-1H-pyrrolo[3,2-c]pyridin-6-ylamino)-N,N-dimethylbenzamide;
cyclopentyl 6-(2-chloro-4-(dimethylcarbamoyl)phenylamino)-2-(1-methyl-1H-pyrazol-4-yl)-1H-pyrrolo[3,2-c]pyridine-1-carboxylate;
3-chloro-4-(1-(cyclohexylmethyl)-2-(1-methyl-1H-pyrazol-4-yl)-1H-pyrrolo[3,2-c]pyridin-6-ylamino)-N,N-dimethylbenzamide;
3-chloro-4-(1-(4-fluorobenzyl)-2-(1-methyl-1H-pyrazol-4-yl)-1H-pyrrolo[3,2-c]pyridin-6-ylamino)-N,N-dimethylbenzamide;
3-chloro-4-(1-(cyclopentylsulfonyl)-2-(1-methyl-1H-pyrazol-4-yl)-1H-pyrrolo[3,2-c]pyridin-6-ylamino)-N,N-dimethylbenzamide;
3-chloro-4-(3-chloro-2-(oxazol-5-yl)-1H-pyrrolo[3,2-c]pyridin-6-ylamino)-N,N-dimethylbenzamide;
tert-butyl 6-(2-methoxyphenylamino)-2-(oxazol-5-yl)-1H-pyrrolo[3,2-c]pyridine-1-carboxylate;
3-chloro-N,N-dimethyl-4-((2-(1-methyl-1H-pyrazol-4-yl)-1((5-methylisoxazol-3-yl)methyl)-1H-pyrrolo[3,2-c]pyridin-6-yl)amino)benzamide;
(3-methoxy-4-(2-(oxazol-5-yl)-1H-pyrrolo[3,2-c]pyridin-6-ylamino)phenyl)(3-methoxyazetidin-1-yl)methanone;
tert-butyl 6-(2-methoxy-4-(3-methoxyazetidine-1-carbonyl)phenylamino)-2-(oxazol-5-yl)-1H-pyrrolo[3,2-c]pyridine-1-carboxylate;
3-chloro-N,N-dimethyl-4-(2-(oxazol-5-yl)-1H-pyrrolo[3,2-c]pyridin-6-ylamino)benzamide;
tert-butyl 6-(2-chloro-4-(dimethylcarbamoyl)phenylamino)-2-(oxazol-5-yl)-1H-pyrrolo [3,2-c]pyridine-1-carboxylate;
3-chloro-N-(2-chloro-4-(methylsulfonyl)phenyl)-2-(1-methyl-1H-pyrazol-4-yl)-1H-pyrrolo [3,2-c]pyridin-6-amine;
2-(3-(2-(1-methyl-1H-pyrazol-4-yl)-1H-pyrrolo[3,2-c]pyridin-6-ylamino)phenoxy)acetonitrile;
tert-butyl 6-(3-(cyanomethoxy)phenylamino)-2-(1-methyl-1H-pyrazol-4-yl)-1H-pyrrolo [3,2-c]pyridine-1-carboxylate;
tert-butyl 3-chloro-6-(2-chloro-4-(dimethylcarbamoyl)phenylamino)-2-(1-methyl-1H-pyrazol-4-yl)-1H-pyrrolo[3,2-c]pyridine-1-carboxylate;
3-chloro-4-(1-(cyclopentylmethyl)-2-(1-methyl-1H-pyrazol-4-yl)-1H-pyrrolo[3,2-c]pyridin-6-ylamino)-N,N-dimethylbenzamide;
N-(4-(aminomethyl)-2-methoxyphenyl)-2-(1-methyl-1H-pyrazol-4-yl)-1H-pyrrolo[3,2-c]pyridin-6-amine;
N-(4-((dimethylamino)methyl)-2-methoxyphenyl)-2-(1-methyl-1H-pyrazol-4-yl)-1H-pyrrolo [3,2-c]pyridin-6-amine;
tert-butyl 6-(4-((dimethylamino)methyl)-2-methoxyphenylamino)-2-(1-methyl-1H-pyrazol-4-yl)-1H-pyrrolo [3,2-c]pyridine-1-carboxylate;
N-(2-methoxy-4-((methylamino)methyl)phenyl)-2-(1-methyl-1H-pyrazol-4-yl)-1H-pyrrolo [3,2-c]pyridin-6-amine;
tert-butyl 6-(4-((tert-butoxycarbonyl(methyl)amino)methyl)-2-methoxyphenylamino)-2-(1-methyl-1H-pyrazol-4-yl)-1H-pyrrolo[3,2-c]pyridine-1-carboxylate;
N-(2-methoxy-4-(pyrrolidin-1-ylmethyl)phenyl)-2-(1-methyl-1H-pyrazol-4-yl)-1H-pyrrolo [3,2-c]pyridin-6-amine;
tert-butyl 6-(2-methoxy-4-(pyrrolidin-1-ylmethyl)phenylamino)-2-(1-methyl-1H-pyrazol-4-yl)-1H-pyrrolo[3,2-c]pyridine-1-carboxylate;
tert-butyl 6-((2-cyanophenyl)amino)-2-(1-methyl-1H-pyrazol-4-yl)-1H-pyrrolo[3,2-c]pyridine-1-carboxylate;
tert-butyl 6-((2-chloro-4-(methylsulfonyl)phenyl)amino)-2-(1-methyl-1H-pyrazol-4-yl)-1H-pyrrolo[3,2-c]pyridine-1-carboxylate;
(3-methoxy-4-(2-(1-methyl-1H-pyrazol-4-yl)-1H-pyrrolo[3,2-c]pyridin-6-ylamino)phenyl)(3-methoxyazetidin-1-yl)methanone;
3-methoxy-N-(2-methoxyethyl)-4-(2-(1-methyl-1H-pyrazol-4-yl)-1H-pyrrolo[3,2-c]pyridin-6-ylamino)benzamide;
(3-methoxy-4-(2-(1-methyl-1H-pyrazol-4-yl)-1H-pyrrolo[3,2-c]pyridin-6-ylamino)phenyl)(morpholino)methanone;

tert-butyl 6-(2-methoxy-4-(3-methoxyazetidine-1-carbonyl)phenylamino)-2-(1-methyl-1H-pyrazol-4-yl)-1H-pyrrolo[3,2-c]pyridine-1-carboxylate;
tert-butyl 6-(2-methoxy-4-(2-methoxyethylcarbamoyl)phenylamino)-2-(1-methyl-1H-pyrazol-4-yl)-1H-pyrrolo[3,2-c]pyridine-1-carboxylate;
tert-butyl 6-(2-methoxy-4-(morpholine-4-carbonyl)phenylamino)-2-(1-methyl-1H-pyrazol-4-yl)-1H-pyrrolo[3,2-c]pyridine-1-carboxylate;
N-(2-methoxyphenyl)-2-(oxazol-5-yl)-1H-pyrrolo[3,2-c]pyridin-6-amine;
tert-butyl 6-(2-chloro-4-(dimethylcarbamoyl)phenylamino)-2-(1-methyl-1H-pyrazol-4-yl)-1H-pyrrolo[3,2-c]pyridine-1-carboxylate;
tert-butyl 6-(2-acetylphenylamino)-2-(1-methyl-1H-pyrazol-4-yl)-1H-pyrrolo[3,2-c]pyridine-1-carboxylate;
3-chloro-N,N-dimethyl-4-(2-(1-methyl-1H-pyrazol-4-yl)-1H-pyrrolo[3,2-c]pyridin-6-ylamino)benzenesulfonamide;
tert-butyl 6-(2-chloro-4-(N,N-dimethylsulfamoyl)phenylamino)-2-(1-methyl-1H-pyrazol-4-yl)-1H-pyrrolo[3,2-c]pyridine-1-carboxylate;
tert-butyl 6-(2-chloro-4-(2-oxopyrrolidin-1-yl)phenylamino)-2-(1-methyl-1H-pyrazol-4-yl)-1H-pyrrolo[3,2-c]pyridine-1-carboxylate;
2-(4-(6-(2,4-dimethoxyphenylamino)-1H-pyrrolo[3,2-c]pyridin-2-yl)-1H-pyrazol-1-yl)-N,N-dimethylacetamide;
3-chloro-4-(3-chloro-2-(1-methyl-1H-pyrazol-4-yl)-1H-pyrrolo[3,2-c]pyridin-6-ylamino)-N,N-dimethylbenzamide;
N-(2-methoxy-4-(thiomorpholinomethyl)phenyl)-2-(1-methyl-1H-pyrazol-4-yl)-1H-pyrrolo[3,2-c]pyridin-6-amine-S,S-dioxide;
(3-methoxy-4-(2-(1-methyl-1H-pyrazol-4-yl)-1H-pyrrolo[3,2-c]pyridin-6-ylamino)phenyl)(thiomorpholino)methanone-S,S-dioxide;
N-(2-chloro-4-(methylsulfonyl)phenyl)-2-(1H-pyrazol-4-yl)-1H-pyrrolo[3,2-c]pyridin-6-amine;
4-methoxy-N,N-dimethyl-3-(2-(1-methyl-1H-pyrazol-4-yl)-1H-pyrrolo[3,2-c]pyridin-6-ylamino)benzamide;
N,N-dimethyl-4-(2-(1-methyl-1H-pyrazol-4-yl)-1H-pyrrolo[3,2-c]pyridin-6-ylamino)-3-(trifluoromethoxy)benzamide
3-chloro-N-methyl-4-(2-(1-methyl-1H-pyrazol-4-yl)-1H-pyrrolo[3,2-c]pyridin-6-ylamino)benzamide;
3-methoxy-N-methyl-4-(2-(1-methyl-1H-pyrazol-4-yl)-1H-pyrrolo[3,2-c]pyridin-6-ylamino)benzamide;
N-(2-fluoro-4-methoxyphenyl)-2-(1-methyl-1H-pyrazol-4-yl)-1H-pyrrolo[3,2-c]pyridin-6-amine;
N-(2-methoxy-4-(trifluoromethyl)phenyl)-2-(1-methyl-1H-pyrazol-4-yl)-1H-pyrrolo[3,2-c]pyridin-6-amine;
N-(2-chloro-4-(difluoromethoxy)phenyl)-2-(1-methyl-1H-pyrazol-4-yl)-1H-pyrrolo[3,2-c]pyridin-6-amine;
N-(2-methoxypyridin-3-yl)-2-(1-methyl-1H-pyrazol-4-yl)-1H-pyrrolo[3,2-c]pyridin-6-amine;
N-(4-fluoro-2-methoxyphenyl)-2-(1-methyl-1H-pyrazol-4-yl)-1H-pyrrolo[3,2-c]pyridin-6-amine;
N-(2-methoxyphenyl)-2-(1-(2,2,2-trifluoroethyl)-1H-pyrazol-4-yl)-1H-pyrrolo[3,2-c]pyridin-6-amine;
N-(2-chloro-4-(methylsulfonyl)phenyl)-2-(1-methyl-1H-pyrazol-4-yl)-1H-pyrrolo[3,2-c]pyridin-6-amine;
3-methoxy-4-((2-(1-methyl-1H-pyrazol-4-yl)-1H-pyrrolo[3,2-c]pyridin-6-yl)amino)-N-(1-methylpiperidin-4-yl)benzamide;
N-(2-chloro-4-fluorophenyl)-2-(1-methyl-1H-pyrazol-4-yl)-1H-pyrrolo[3,2-c]pyridin-6-amine;
N-(2-chloro-4-(1H-1,2,4-triazol-1-yl)phenyl)-2-(1-methyl-1H-pyrazol-4-yl)-1H-pyrrolo[3,2-c]pyridin-6-amine;
2-(1-(difluoromethyl)-1H-pyrazol-4-yl)-N-(2-methoxyphenyl)-1H-pyrrolo[3,2-c]pyridin-6-amine;
3-methoxy-N,N-dimethyl-4-(2-(1-methyl-1H-pyrazol-4-yl)-1H-pyrrolo[3,2-c]pyridin-6-ylamino)benzamide;
3-chloro-N,N-dimethyl-4-(2-(1-methyl-1H-pyrazol-4-yl)-1H-pyrrolo[3,2-c]pyridin-6-ylamino)benzamide;
N-(2,4-dimethoxyphenyl)-2-(1((5-methylisoxazol-3-yl)methyl)-1H-pyrazol-4-yl)-1H-pyrrolo[3,2-c]pyridin-6-amine;
1-(4-(4-(2-(1H-pyrazol-4-yl)-1H-pyrrolo[3,2-c]pyridin-6-ylamino)phenyl)piperazin-1-yl)ethanone;
N-(4-(morpholinomethyl)phenyl)-2-(1H-pyrazol-4-yl)-1H-pyrrolo[3,2-c]pyridin-6-amine;
N-(4-(2-methoxyethoxy)phenyl)-2-(1H-pyrazol-4-yl)-1H-pyrrolo[3,2-c]pyridin-6-amine;
N-(4-((1H-pyrazol-1-yl)methyl)phenyl)-2-(1H-pyrazol-4-yl)-1H-pyrrolo[3,2-c]pyridin-6-amine;
N-(4-(2-morpholinoethoxy)phenyl)-2-(1H-pyrazol-4-yl)-1H-pyrrolo[3,2-c]pyridin-6-amine;
2-(1H-pyrazol-4-yl)-N-(4-(thiomorpholinomethyl)phenyl)-1H-pyrrolo[3,2-c]pyridin-6-amine-S,S-dioxide;
4-(2-(1H-pyrazol-4-yl)-1H-pyrrolo[3,2-c]pyridin-6-ylamino)benzonitrile;
N-(3,4-dimethoxyphenyl)-1-methyl-2-(1H-pyrazol-4-yl)-1H-pyrrolo[3,2-c]pyridin-6-amine;
N-(2-methoxyphenyl)-2-(1-methyl-1H-pyrazol-4-yl)-1H-pyrrolo[3,2-c]pyridin-6-amine;
4-(2-(1H-pyrazol-4-yl)-1H-pyrrolo[3,2-c]pyridin-6-ylamino)-N,N-dimethylbenzenesulfonamide;
N-(2-ethoxyphenyl)-2-(1H-pyrazol-4-yl)-1H-pyrrolo[3,2-c]pyridin-6-amine;
4-(2-(1H-pyrazol-4-yl)-1H-pyrrolo[3,2-c]pyridin-6-ylamino)-N,N-dimethylbenzamide;
2-(1H-pyrazol-4-yl)-N-(2-(trifluoromethyl)phenyl)-1H-pyrrolo[3,2-c]pyridin-6-amine;
N-(2-chloro-4-methoxyphenyl)-2-(1H-pyrazol-4-yl)-1H-pyrrolo[3,2-c]pyridin-6-amine;
N-(2,4-dimethoxyphenyl)-2-(1H-pyrazol-4-yl)-1H-pyrrolo[3,2-c]pyridin-6-amine;
N-(2-methoxyphenyl)-2-(1H-pyrazol-4-yl)-1H-pyrrolo[3,2-c]pyridin-6-amine;
N-(2-methoxy-4-(1-methylpiperidin-4-yloxy)phenyl)-2-(1H-pyrazol-4-yl)-1H-pyrrolo[3,2-c]pyridin-6-amine;
N-(4-methoxyphenyl)-2-(1H-pyrazol-4-yl)-1H-pyrrolo[3,2-c]pyridin-6-amine;
N-(5-fluoropyridin-2-yl)-2-(1H-pyrazol-4-yl)-1H-pyrrolo[3,2-c]pyridin-6-amine;
N-(4-fluorophenyl)-1-(methylsulfonyl)-2-(1H-pyrazol-4-yl)-1H-pyrrolo[3,2-c]pyridin-6-amine;
tert-butyl 2-(1-(tert-butoxycarbonyl)-1H-pyrazol-4-yl)-6-(p-tolylamino)-1H-pyrrolo[3,2-c]pyridine-1-carboxylate;
2-(1H-pyrazol-4-yl)-N-(4-(trifluoromethyl)phenyl)-1H-pyrrolo[3,2-c]pyridin-6-amine;
N-(4-fluorophenyl)-2-(1H-pyrazol-4-yl)-1H-pyrrolo[3,2-c]pyridin-6-amine;
N-(3,4-dimethoxyphenyl)-2-(1H-pyrazol-4-yl)-1H-pyrrolo[3,2-c]pyridin-6-amine;
tert-butyl 6-(2-chloro-4-(2-oxopyrrolidin-1-yl)phenylamino)-2-(1-methyl-1H-pyrazol-4-yl)-1H-pyrrolo[3,2-c]pyridine-1-carboxylate;
tert-butyl 6-(2-methoxy-4-(thiomorpholinomethyl)phenylamino)-2-(1-methyl-1H-pyrazol-4-yl)-1H-pyrrolo[3,2-c]pyridine-1-carboxylate-S,S-dioxide;

tert-butyl 6-(2-methoxy-4-(thiomorpholine-4-carbonyl) phenylamino)-2-(1-methyl-1H-pyrazol-4-yl)-1H-pyrrolo[3,2-c]pyridine-1-carboxylate-S,S-dioxide;
tert-butyl-6-(2-chloro-4-(methylcarbamoyl)phenylamino)-2-(1-methyl-1H-pyrazol-4-yl)-1H-pyrrolo[3,2-c]pyridine-1-carboxylate;
tert-butyl-6-(2-methoxy-4-(methylcarbamoyl)phenylamino)-2-(1-methyl-1H-pyrazol-4-yl)-1H-pyrrolo[3,2-c]pyridine-1-carboxylate;
tert-butyl 6-((2-fluoro-4-methoxyphenyl)amino)-2-(1-methyl-1H-pyrazol-4-yl)-1H-pyrrolo [3,2-c]pyridine-1-carboxylate;
tert-butyl 6-((2-methoxy-4-(trifluoromethyl)phenyl)amino)-2-(1-methyl-1H-pyrazol-4-yl)-1H-pyrrolo[3,2-c]pyridine-1-carboxylate;
tert-butyl-6-(2-chloro-4-(difluoromethoxy)phenylamino)-2-(1-methyl-1H-pyrazol-4-yl)-1H-pyrrolo[3,2-c]pyridine-1-carboxylate;
tert-butyl 6-(2-methoxypyridin-3-ylamino)-2-(1-methyl-1H-pyrazol-4-yl)-1H-pyrrolo [3,2-c]pyridine-1-carboxylate;
tert-butyl 6-((4-fluoro-2-methoxyphenyl)amino)-2-(1-methyl-1H-pyrazol-4-yl)-1H-pyrrolo [3,2-c]pyridine-1-carboxylate;
tert-butyl 6-(2-methoxyphenylamino)-2-(1-(2,2,2-trifluoroethyl)-1H-pyrazol-4-yl)-1H-pyrrolo [3,2-c]pyridine-1-carboxylate;
tert-butyl-6-(2-chloro-4-(methylsulfonyl)phenylamino)-2-(1-methyl-1H-pyrazol-4-yl)-1H-pyrrolo[3,2-c]pyridine-1-carboxylate;
tert-butyl 6-(2-methoxy-4-(1-methylpiperidin-4-ylcarbamoyl)phenylamino)-2-(1-methyl-1H-pyrazol-4-yl)-1H-pyrrolo[3,2-c]pyridine-1-carboxylate;
tert-butyl-6-(2-chloro-4-fluorophenylamino)-2-(1-methyl-1H-pyrazol-4-yl)-1H-pyrrolo [3,2-c]pyridine-1-carboxylate;
tert-butyl-6-(2-chloro-4-(1H-1,2,4-triazol-1-yl)phenylamino)-2-(1-methyl-1H-pyrazol-4-yl)-1H-pyrrolo[3,2-c]pyridine-1-carboxylate;
tert-butyl 2-(1-(difluoromethyl)-1H-pyrazol-4-yl)-6-(2-methoxyphenylamino)-1H-pyrrolo [3,2-c]pyridine-1-carboxylate;
or a pharmaceutically acceptable salt or solvate thereof.

15. A pharmaceutical composition comprising (a) a compound, or a pharmaceutically acceptable salt or solvate thereof, as defined in claim 1, and (b) a pharmaceutically acceptable diluent or carrier.

16. A method of treating a proliferative disorder in a patient in need of such treatment, said method comprising administering to said patient a therapeutically effective amount of a compound of formula I

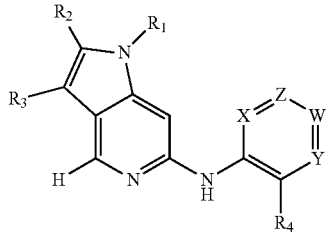

Formula I wherein:
R$_1$, R$_2$, R$_3$, W, X, Y, and Z is are as defined in claim 1 and
R$_4$ is H, cyano, (1-3C)alkyl, (1-3C)fluoroalkyl, (1-3C)alkoxy, (1-3C)perfluoroalkoxy, halo, (1-3C)alkanoyl, C(O)NR$^i$R$^j$, or S(O)$_2$NR$^i$R$^j$; wherein R$^i$ and R$^j$ are each independently selected from H or (1-3C)alkyl;
or a pharmaceutically acceptable salt or solvate thereof.

17. The method of claim 16, wherein the proliferative disorder is a cancer.

18. A method of synthesizing a compound of the formula I, or a pharmaceutically acceptable salt or solvate thereof, as claimed in claim 1, the method comprising:
a) reacting an intermediate of formula A:

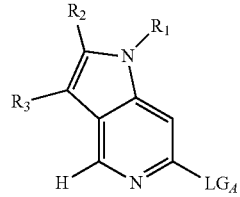

Formula A wherein R$_1$, R$_2$, and R$_3$ each have any one of the meanings as defined in claim 1, and LG$_A$ is a suitable leaving group;
with an intermediate of formula B:

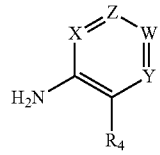

Formula B wherein R$_4$, X, Z, W, and Y have any one of the definitions set out in claim 1; and
b) optionally thereafter, and if necessary:
i) removing any protecting groups present;
ii) converting the compound formula I into another compound of formula I; and/or
iii) forming a pharmaceutically acceptable salt or solvate thereof.

* * * * *